United States Patent
Hershkovitz et al.

(10) Patent No.: US 11,976,106 B2
(45) Date of Patent: May 7, 2024

(54) LONG-ACTING COAGULATION FACTORS AND METHODS OF PRODUCING SAME

(71) Applicant: OPKO BIOLOGICS LTD., Kiryat Gat (IL)

(72) Inventors: Oren Hershkovitz, Kibbutz Revadim (IL); Laura Moschcovich, Givat Shmuel (IL)

(73) Assignee: OPKO BIOLOGICS LTD., Kiryat Gat (IL)

( * ) Notice: Subject to any disclaimer, the term of this patent is extended or adjusted under 35 U.S.C. 154(b) by 174 days.

(21) Appl. No.: 16/317,283

(22) PCT Filed: Jul. 11, 2017

(86) PCT No.: PCT/IL2017/050784
§ 371 (c)(1),
(2) Date: Jan. 11, 2019

(87) PCT Pub. No.: WO2018/011799
PCT Pub. Date: Jan. 18, 2018

(65) Prior Publication Data
US 2020/0354430 A1 Nov. 12, 2020

Related U.S. Application Data

(60) Provisional application No. 62/360,767, filed on Jul. 11, 2016.

(51) Int. Cl.
*A61K 38/00* (2006.01)
*A61K 47/64* (2017.01)
*C07K 14/745* (2006.01)

(52) U.S. Cl.
CPC ............ *C07K 14/745* (2013.01); *A61K 47/64* (2017.08); *A61K 38/00* (2013.01)

(58) Field of Classification Search
CPC ...... C07K 14/59; C07K 14/61; C07K 14/745; C07K 2319/31; A61K 38/00; A61K 47/64; A61K 38/36; A61P 7/04
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | Macconnel |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,400,316 A | 8/1983 | Katsuragi et al. |
| 4,666,828 A | 5/1987 | Gusella |
| 4,683,202 A | 7/1987 | Mullis |
| 4,801,531 A | 1/1989 | Frossard |
| 4,853,332 A | 8/1989 | Mark et al. |
| 4,873,316 A | 10/1989 | Meade et al. |
| 4,879,219 A | 11/1989 | Wands et al. |
| 4,911,691 A | 3/1990 | Aniuk et al. |
| 5,011,771 A | 4/1991 | Bellet et al. |
| 5,118,666 A | 6/1992 | Habener |
| 5,177,193 A | 1/1993 | Boime et al. |
| 5,192,659 A | 3/1993 | Simons |
| 5,272,057 A | 12/1993 | Smulson et al. |
| 5,281,521 A | 1/1994 | Trojanowski et al. |
| 5,338,835 A | 8/1994 | Boime |
| 5,405,945 A | 4/1995 | Boime et al. |
| 5,464,764 A | 11/1995 | Capecchi et al. |
| 5,487,992 A | 1/1996 | Capecchi et al. |
| 5,585,345 A | 12/1996 | Boime |
| 5,597,797 A | 1/1997 | Clark |
| 5,643,575 A | 7/1997 | Martinez et al. |
| 5,681,567 A | 10/1997 | Martinez et al. |
| 5,705,478 A | 1/1998 | Boime |
| 5,759,818 A | 6/1998 | Boime |

(Continued)

FOREIGN PATENT DOCUMENTS

| | | |
|---|---|---|
| CA | 2641342 | 8/2007 |
| CA | 2843672 | 2/2013 |

(Continued)

OTHER PUBLICATIONS

Chevreux et al. (Glycobiology. Dec. 2013; 23(12): 1531-1546). N-/O-glycosylation analysis of human FVIIa produced in the milk of transgenic rabbits (Year: 2013).*

(Continued)

*Primary Examiner* — Aradhana Sasan
*Assistant Examiner* — Mercy H Sabila
(74) *Attorney, Agent, or Firm* — Mark S. Cohen; Pearl Cohen Zedek Latzer Baratz, LLP

(57) ABSTRACT

Polypeptides comprising at least one carboxy-terminal peptide (CTP) of chorionic gonadotropin attached to the carboxy terminus but not to the amino terminus of a coagulation factor and polynucleotides encoding the same are disclosed. Pharmaceutical compositions and pharmaceutical formulations comprising the polypeptides and polynucleotides of the disclosure and methods of using and producing same are also disclosed.

29 Claims, 18 Drawing Sheets

Specification includes a Sequence Listing.

(56) References Cited

U.S. PATENT DOCUMENTS

| | | |
|---|---|---|
| 5,792,460 A | 8/1998 | Boime |
| 5,824,642 A | 10/1998 | Attie et al. |
| 5,919,455 A | 7/1999 | Greenwald et al. |
| 5,929,028 A | 7/1999 | Skrabanja et al. |
| 5,932,447 A | 8/1999 | Siegall |
| 5,935,924 A | 8/1999 | Bunting et al. |
| 5,958,737 A | 9/1999 | Boime et al. |
| 6,028,177 A | 2/2000 | Boime |
| 6,083,725 A | 7/2000 | Selden et al. |
| 6,103,501 A | 8/2000 | Boime et al. |
| 6,113,906 A | 9/2000 | Greenwald et al. |
| 6,225,449 B1 | 5/2001 | Boime |
| 6,238,890 B1 | 5/2001 | Boime |
| 6,242,580 B1 | 6/2001 | Boime et al. |
| 6,306,654 B1 | 10/2001 | Boime et al. |
| 6,310,183 B1 | 10/2001 | Johannessen et al. |
| 6,340,742 B1 | 1/2002 | Burg et al. |
| 6,514,729 B1 | 2/2003 | Bentzien |
| 6,897,039 B2 | 5/2005 | Graversen et al. |
| 7,081,446 B2 | 7/2006 | Lustbader |
| 7,091,326 B2 | 8/2006 | Lee et al. |
| 7,094,566 B2 | 8/2006 | Medlock et al. |
| 7,141,547 B2 | 11/2006 | Rosen et al. |
| 7,202,215 B2 | 4/2007 | Lustbader |
| 7,217,689 B1 | 5/2007 | Elliot et al. |
| 7,371,372 B2 | 5/2008 | Chaturvedi et al. |
| 7,371,373 B2 | 5/2008 | Shirley et al. |
| 7,425,539 B2 | 9/2008 | Donovan et al. |
| 7,442,684 B2 | 10/2008 | Lustbader et al. |
| 7,459,429 B2 | 12/2008 | Klima et al. |
| 7,459,435 B2 | 12/2008 | Lehmann et al. |
| 7,459,436 B2 | 12/2008 | Lehmann et al. |
| 7,553,940 B2 | 6/2009 | Fares et al. |
| 7,553,941 B2 | 6/2009 | Fares et al. |
| 7,585,837 B2 | 9/2009 | Shechter et al. |
| 7,649,084 B2 | 1/2010 | Ferguson |
| 7,666,835 B2 | 2/2010 | Bloom et al. |
| 7,795,210 B2 | 9/2010 | Defrees et al. |
| 8,008,454 B2 | 8/2011 | Lee et al. |
| 8,048,846 B2 | 11/2011 | Chahal et al. |
| 8,048,848 B2 | 11/2011 | Fares et al. |
| 8,048,849 B2 | 11/2011 | Fares et al. |
| 8,063,015 B2 | 11/2011 | Defrees et al. |
| 8,097,435 B2 | 1/2012 | Fares et al. |
| 8,110,376 B2 | 2/2012 | Fares et al. |
| 8,114,836 B2 | 2/2012 | Fares et al. |
| 8,129,330 B2 | 3/2012 | Martinez et al. |
| 8,304,386 B2 | 11/2012 | Fares et al. |
| 8,426,166 B2 | 4/2013 | Fares et al. |
| 8,450,269 B2 | 5/2013 | Fares et al. |
| 8,465,958 B2 | 6/2013 | Lopez De Leon et al. |
| 8,476,234 B2 | 7/2013 | Fima et al. |
| 8,759,292 B2 | 6/2014 | Fima et al. |
| 8,946,155 B2 | 2/2015 | Fares et al. |
| 9,249,407 B2 | 2/2016 | Fima et al. |
| 9,458,444 B2 | 10/2016 | Fima et al. |
| 9,828,417 B2 | 11/2017 | Fima et al. |
| 9,884,901 B2 | 2/2018 | Fima et al. |
| 10,119,132 B2 | 10/2018 | Fima et al. |
| 10,144,921 B2 | 12/2018 | Fima et al. |
| 2001/0007757 A1 | 7/2001 | Boime et al. |
| 2001/0028895 A1 | 10/2001 | Bisgaier et al. |
| 2002/0127652 A1 | 9/2002 | Schambye et al. |
| 2002/0160944 A1 | 10/2002 | Boime et al. |
| 2003/0113871 A1 | 6/2003 | Lee et al. |
| 2003/0143694 A1 | 7/2003 | Lustbader |
| 2003/0216313 A1 | 11/2003 | Lustbader et al. |
| 2004/0009902 A1 | 1/2004 | Boime et al. |
| 2004/0018240 A1 | 1/2004 | Ohmachi et al. |
| 2004/0053370 A1 | 3/2004 | Glaesner et al. |
| 2004/0057996 A1 | 3/2004 | Takada et al. |
| 2004/0115774 A1 | 6/2004 | Kochendoerfer |
| 2004/0138227 A1 | 7/2004 | Nishiyama et al. |
| 2004/0209804 A1 | 10/2004 | Govardhan et al. |
| 2005/0234221 A1 | 10/2005 | Medlock et al. |
| 2006/0073571 A1 | 4/2006 | Saxena et al. |
| 2006/0088595 A1 | 4/2006 | Asakawa et al. |
| 2006/0160177 A1 | 7/2006 | Okkels et al. |
| 2006/0171920 A1 | 8/2006 | Shechter et al. |
| 2007/0184530 A1 | 8/2007 | Fares et al. |
| 2007/0190610 A1 | 8/2007 | Fares et al. |
| 2007/0190611 A1 | 8/2007 | Fares et al. |
| 2007/0298041 A1 | 12/2007 | Tomlinson |
| 2008/0064856 A1 | 3/2008 | Warne et al. |
| 2008/0206270 A1 | 8/2008 | Minev et al. |
| 2008/0221032 A1* | 9/2008 | Turecek ............... A61P 43/00 514/20.1 |
| 2009/0053185 A1 | 2/2009 | Schulte et al. |
| 2009/0087411 A1 | 4/2009 | Fares et al. |
| 2009/0130060 A1 | 5/2009 | Weimer et al. |
| 2009/0221037 A1 | 9/2009 | Lee et al. |
| 2009/0221485 A1 | 9/2009 | James |
| 2009/0270489 A1 | 10/2009 | Fares et al. |
| 2009/0275084 A1 | 11/2009 | Fares et al. |
| 2009/0286733 A1 | 11/2009 | Fares et al. |
| 2009/0312254 A1 | 12/2009 | Fares et al. |
| 2010/0006156 A1 | 1/2010 | Schilp et al. |
| 2010/0081614 A1 | 4/2010 | Fares et al. |
| 2010/0144617 A1 | 6/2010 | Sinha Roy et al. |
| 2010/0310546 A1 | 12/2010 | Schuster et al. |
| 2010/0317585 A1* | 12/2010 | Fima ............... C07K 14/59 514/13.7 |
| 2011/0004172 A1 | 1/2011 | Eckstein et al. |
| 2011/0034374 A1 | 2/2011 | Bloom et al. |
| 2011/0065660 A1 | 3/2011 | Baron et al. |
| 2011/0152181 A1 | 6/2011 | Alsina-Fernandez et al. |
| 2011/0166063 A1 | 7/2011 | Bossard et al. |
| 2011/0223151 A1 | 9/2011 | Behrens et al. |
| 2011/0286967 A1 | 11/2011 | Fares et al. |
| 2012/0004286 A1 | 1/2012 | Fares et al. |
| 2012/0015437 A1 | 1/2012 | Fares et al. |
| 2012/0035101 A1 | 2/2012 | Fares et al. |
| 2012/0048878 A1 | 3/2012 | Burger et al. |
| 2012/0087908 A1 | 4/2012 | Bardat et al. |
| 2012/0114651 A1 | 5/2012 | Wildt et al. |
| 2012/0208759 A1 | 8/2012 | Fima et al. |
| 2012/0231999 A1 | 9/2012 | Alagarsamy et al. |
| 2013/0184207 A1 | 7/2013 | Fares et al. |
| 2013/0243747 A1 | 9/2013 | Fima et al. |
| 2013/0295072 A1 | 11/2013 | Fima et al. |
| 2014/0113860 A1 | 4/2014 | Fima et al. |
| 2014/0170728 A1 | 6/2014 | DeFrees et al. |
| 2014/0316112 A1 | 10/2014 | Hershkovitz et al. |
| 2014/0371144 A1 | 12/2014 | Fares et al. |
| 2015/0038413 A1 | 2/2015 | Fares et al. |
| 2015/0072924 A1 | 3/2015 | Fima et al. |
| 2015/0079063 A1 | 3/2015 | Fima et al. |
| 2015/0158926 A1 | 6/2015 | Fares et al. |
| 2015/0203558 A1 | 7/2015 | Fares et al. |
| 2015/0216951 A1 | 8/2015 | Bardat et al. |
| 2015/0258208 A1 | 9/2015 | Fima et al. |
| 2015/0307865 A1 | 10/2015 | Stennicke et al. |
| 2015/0368630 A9 | 12/2015 | Fima et al. |
| 2016/0076018 A1* | 3/2016 | Fima ............... C12N 9/644 424/94.64 |
| 2016/0168588 A1 | 6/2016 | Hershkovitz et al. |

FOREIGN PATENT DOCUMENTS

| | | |
|---|---|---|
| CN | 1528787 | 9/2004 |
| CN | 1528894 | 3/2006 |
| CN | 102639144 | 8/2012 |
| CN | 104010650 | 8/2014 |
| CN | 104427994 | 3/2015 |
| EP | 0167825 B1 | 1/1986 |
| EP | 0264166 B1 | 4/1988 |
| EP | 0374257 A1 | 6/1990 |
| EP | 01319712 A2 | 6/2003 |
| EP | 2532674 A1 | 12/2012 |
| EP | 2420251 A2 | 3/2013 |
| EP | 2822576 B1 | 1/2018 |
| JP | 2015163650 * | 9/2015 ............... 514/13.7 |
| KR | 20030037598 A | 5/2003 |
| KR | 10-2118729 | 6/2020 |

(56) References Cited

FOREIGN PATENT DOCUMENTS

| | | | |
|---|---|---|---|
| TW | 201638105 A | * 11/2016 | ........... C07K 14/505 |
| WO | WO 1989/010756 | 11/1989 | |
| WO | WO 1993/006844 | 4/1993 | |
| WO | WO 1994/024148 | 10/1994 | |
| WO | WO 2000/023472 | 4/2000 | |
| WO | WO 2002/036169 A2 | 5/2002 | |
| WO | WO 2002/048194 A1 | 6/2002 | |
| WO | WO 2002/066511 | 8/2002 | |
| WO | WO 2003/038100 A1 | 5/2003 | |
| WO | WO 2003/046013 A1 | 6/2003 | |
| WO | WO 2003/048210 A1 | 6/2003 | |
| WO | WO 2002/085311 A2 | 10/2003 | |
| WO | WO 2004/006756 A2 | 1/2004 | |
| WO | WO 2005/080544 A2 | 3/2004 | |
| WO | WO 2004/089280 A2 | 10/2004 | |
| WO | WO 2004/111242 A1 | 12/2004 | |
| WO | WO 2005/035761 A1 | 4/2005 | |
| WO | WO 2006/051288 A2 | 5/2006 | |
| WO | WO 2006/134340 A2 | 12/2006 | |
| WO | WO 2007/092252 A1 | 8/2007 | |
| WO | WO 2007/094985 A2 | 8/2007 | |
| WO | WO 2007/149406 A2 | 12/2007 | |
| WO | WO 2010/007622 A2 | 1/2010 | |
| WO | WO 2010/042145 | 4/2010 | |
| WO | WO 2010/097077 A1 | 9/2010 | |
| WO | WO 2010/099746 | 9/2010 | |
| WO | WO 2011/004361 A2 | 1/2011 | |
| WO | WO 2011/087672 A1 | 7/2011 | |
| WO | WO 2012/011752 A2 | 5/2012 | |
| WO | WO 2012/167251 A1 | 12/2012 | |
| WO | WO 2012/173422 A1 | 12/2012 | |
| WO | WO 2013/018098 A2 | 2/2013 | |
| WO | WO 2013/096386 | 6/2013 | |
| WO | WO 2013/100704 | 7/2013 | |
| WO | WO 2013/0121416 A1 | 8/2013 | |
| WO | WO 2013/157002 A1 | 10/2013 | |
| WO | WO 2013/183052 A1 | 12/2013 | |
| WO | WO 2014/080401 A2 | 5/2014 | |
| WO | WO 2016/092549 | 6/2016 | |
| WO | WO 2016/092550 | 6/2016 | |
| WO | WO 2016/203482 | 12/2016 | |

OTHER PUBLICATIONS

Alberts et al. "Molecular biology of the cell", 5th ed.(Garland Science, 2008). 2002, p. 367.
Ameredes et al. "Growth Hormone Improves Body Mass Recovery with Refeeding after Chronic Undernutrition-Induced Muscle Atrophy in Aging Male Rats" Journal of Nutrition. 129:2264-2270 (1999).
Amirizahdeh et al. "Expression of biologically active recombinant B-domain-deleted human VIII in mammalian cells" Journal of Science, Islamic Republic of Iran. Abstract. 16(2):103-112, (2005).
Anonymous "Prolor Biotech Announces Positive Results of its Obesity/Diabetes Drug Candidate in Preclinical Weight Loss Study", Apr. 17, 2012, pp. 1-2; Retrieved from the Internet: URL;http://web.archive.org/web/20120526154526/uttp://www.prolor-biotech.com/_Uploads/dbsAttachedFiles/NewsPROLORAnnouncesObesityDiabetesStudyResults.pdf.
Anonymous "Prolor Biotech Receives New U.S. Patent Allowance Covering Broad Applications of its CTP Platform for Long Acting Therapeutic Proteins", Jul. 11, 2011, pp. 1-2; Retrieved from the Internet: URL;http://web.archive.org/web/20110725053527/http://www.prolor-biotech.com/_Uploads/dbsAttachedFiles/NewsPROLORAnnouncesAllowanceOfNewCTPPlatformPatentByUSPatentOffice.pdf.
Anonymous "Corporate Presentation—Lazard Capital Markets Healthcare Conference", Nov. 15, 2011, pp. 1-19; Retrieved from the Internet: URL:http://web.archive.org/web/20110628023057/http://www.prolor-biotech.com/_Uploads/dbsAttachedFiles/prolorInvestorsNov2011.pdf.
Anonymous "Corporate Presentation", Jun. 1, 2011, pp. 1-35; Retrieved from the Internet: URL;http://web.archive.org/web/20110628023057/http://www.prolor-biotech.com/_Uploads/dbsAttachedFiles/prolorPresentationJune2011Investors.pdf.
Anonymous "PROLOR and Yeda enter definitive license agreement for Reversible PEGylation technology", Jan. 18, 2011, pp. 1-3; Retrieved from the Internet: URL;http://web.archive.org/web/20110123063420/http://www.news-medical.net/news/20110118/PROLOR-and-Yeda-enter-definitive-license-agreemen-for-Reversible-PEGYlation-technology.aspx.
Anson et al. "The gene structure of human anti-haemophilic factor IX", The EMBO Journal (1984) 3(5):1053-1060.
Askoy et al., "A study of the intracellular and secreted forms of the MUC2 mucin from the PC/AA intestinal cell line." Glycobiology 9.7: 739-746 (1999).
Banerji et al. "A lymphocyte-specific cellular enhancer is located downstream of the joining region in immunoglobulin heavy chain genes" Cell 33:729-740 (1983).
Barker et al. "An immunomagnetic-base method for the purification of ovarian cancer cells from patient-derived ascites"(Gynecologic Oncology 82, 57-63, 2001).
Beeley, Glycoprotein and proteoglycan techniques. Elsevier: 69-72 (1985).
Bengtsson et al. "Treatment of adults with growth hormone (GH) deficiency with recombinant human GH" J Clin Endocrinol Metab. Feb. 1993;76(2):309-17.
Berntorp et al. "The pharmacokinetics of clotting factor therapy"; Haemophilia (2003) 9:353-359.
Biller et al. Effects of once-weekly sustained-release growth hormone: a double-blind, placebo-controlled study in adult growth hormone deficiency. The Journal of Clinical Endocrinology & Metabolism. Mar. 16, 2011;96(6):1718-26.
Bitter et al. "Expression and secretion vectors for yeast" (1987) Methods in Enzymol. 153:516-544.
Bjorkman et al. Pharmacokinetics of Coagulation Factors Clinical Relevance for Patients with Haemophilia. Clin Pharmacokinet vol. 40 (11): 815-832 (2001).
Bohl et al. "Improvement of erythropoiesis in b-thalassemic mice by continuous erythropoietin delivery from muscle" Blood 95:2793-2798 (2000).
Boissel et al. "Erythropoietin structure-function relationships" The Journal of Biological Chemistry 268(21):15983-15993 (1993).
Booth et al. "The use of a 'universal' yeast expression vector to produce an antigenic protein of *Mycobacterium leprae*" Immunol. Lett. 19:65-70 (1988).
Bouloux et al. "First human exposure to FSH-CTP in hypogonadotrophic hypogonadal males" Human Reproduction. Aug. 1, 2001;16(8):1592-7.
Brisson et al. "Expression of a bacterial gene in plants by using a viral vector" Nature, 310:511-514 (1984).
Broglie et al. "Light-Regulated Expression of a Pea Ribulose-1,5-Bisphosphat Carboxylase Small Subunit Gene in Transformed Plant Cells" Science 224:838-843 (1984).
Brunetti-Pierri et al. "Bioengineered factor IX molecules with increased catalytic activity improve the therapeutic index of gene therapy vectors for hemophilia B." Human Gene Therapy 20.5: 479-485 (2009).
Buchwald et al. "Long-term, continuous intravenous heparin administration by an implantable infusion pump in ambulatory patients with recurrent venous thrombosis" Surgery 88:507-516 (1980).
Butler et al., "The beta-subunit of human chorionic gonadotrophin exists as a homodimer." Journal of Molecular Endocrinology 22.2: 185-192 (1999).
Byrne et al. "Multiplex gene regulation: A two-tiered approach to transgene regulation in transgenic mice" Proc. Natl. Acad. Sci USA 86:5473-5477 (1989).
Calame et al. "Transcriptional Controlling Elements in the Immunoglobulin and T Cell Receptor Loci" Adv. Immunol 43:235-275 (1988).
Carles-Bonnet et al. "H-Lys-Arg-Asn-Lys-Asn-Asn-OH is the minimal active structure of oxyntomodulin" Peptides. Dec. 31, 1996;17(3):557-61.
Cawley et al. "Developing long-acting growth hormone formulations", Clinical Endocrinology (2013) 79, 305-309.

(56) References Cited

OTHER PUBLICATIONS

Chan et al. "Plasma Insulin-Like Growth Factor-I and Prostate Cancer Risk: A Prospective Study", Science vol. 279:563-566, Jan. 1998.

Chen et al. "Recombinant carbohydrate variant of human choriogonadotropin beta-subunit (hCG beta) descarboxyl terminus (115-145). Expression and characterization of carboxyl-terminal deletion mutant of hCG beta in the baculovirus system." Journal of Biological Chemistry 266.10: 6246-6251 (1991).

Chen et al., "Glycoengineering Approach to Half-Life Extension of Recombinant Biotherapeutics." Bioconjugate Chemistry 23.8: 1524-1533 (2012).

Chen et al., "Modulating antibody pharmacokinetics using hydrophilic polymers." Expert Opinion on Drug Delivery 8.9: 1221-1236 (2011).

Chihara K. "Clinical aspect of growth hormone deficiency in adults" Nihon Naika Gakkai zasshi. The Journal of the Japanese Society of Internal Medicine. Sep. 10, 2000;89(9):2010; with English Abstract.

Claxton et al., "A systematic review of the associations between dose regimens and medication compliance." Clinical Therapeutics 23.8: 1296-1310 (2001).

Cohen et al. "Oxyntomodulin suppresses appetite and reduces food intake in humans", J Clin Endocrinol Metab. Oct. 2003;88(10):4696-701.

Coleman et al., "Dosing frequency and medication adherence in chronic disease." Journal of managed care pharmacy: JMCP 18.7: 527-539 (2012).

Coruzzi et al. "Tissue-specific and light-regulated expression of a pea nuclear gene encoding the small subunit of ribulose-1,5-bisphosphate carboxylase" The EMBO Journal 3:1671-1680 (1984).

Cutfield et al., "Non-compliance with growth hormone treatment in children is common and impairs linear growth." PLoS One 6.1: e16223 (2011).

Dalton et al. "Over-expression of secreted proteins from mammalian cell lines" Protein Science. May 1, 2014;23(5):517-25.

Database Geneseq [Online] Apr. 7, 2005, "Human interferon beta (without signal peptide)." XP002664024 retrieved from EBI accession No. GSP: ADW02285, Database accession No. ADW02285.

Davis CG et al. "Deletion of clustered O-linked carbohydrates does not impair function of low density lipoprotein receptor in transfected fibroblasts" J Biol Chem. 261(6):2828-38, Feb. 25, 1986.

Diao et al. "The molecular design and drug development of recombinant long-acting follicle stimulating hormone" Acta pharmaceutica Sinica. Apr. 2012;47(4):421-6; Abstract.

Diederichs et al., "Liposome in kosmetika und arzneimitteln." Pharmazeutische Industrie 56.3: 267-275 (1994).

Diness, et al. Lund-Hansen, and U. Hedner. "Effect of recombinant human FVIIA on warfarin-induced bleeding in rats." Thrombosis research 59.6 (1990): 921-929.

Dong et al. "The prolonged half-lives of new erythropoietin derivatives via peptide addition" Biochemical Research Communications, 339(1):380-385 (Jan. 6, 2006).

Drake et al. "Optimizing GH therapy in adults and children" Endocr Rev. Aug. 2001;22(4):425-50. Review.

Edlund et al. "Cell-Specific Expression of the Rat Insulin Gene: Evidence for Role of Two Distinct 5' Flanking Elements" Science 230:912-916 (1985).

Edmunds et al. "Plasma erythropoietin levels and acquired cystic disease of the kidney in patients receiving regular haemodialysis treatment" Br J Haematol. Jun. 1991;78(2):275-7.

Eschbach et al. "Correction of the Anemia of End-Stage Rental Disease with Recombinant Human Erythropoietin", The New England Journal of Medicine Jan. 8, 1987, vol. 316 No. 2, pp. 73-78.

European Search Report for European Application No. 16187710.5 dated Oct. 14, 2016.

European Search Report for European Application No. 12150722.2 dated Jun. 4, 2012.

European Search Report for European Application No. 12179805.2 dated Nov. 9, 2011.

European Search Report for European Application No. 12179821.9 dated Nov. 12, 2012.

European Search Report for European Application No. 14196333.0 dated Mar. 2, 2015.

European Search Report for European Application No. 14197286.9 dated Mar. 2, 2015.

European Search Report for European Application No. 17161199.9 dated Aug. 7, 2017.

European Search Report for European Patent Application No. 18150731.0 dated Feb. 27, 2018.

Fares "The role of O-linked and N-linked oligosaccharides on the structure-function of glycoprotein hormones: Development of agonists and antagonists", Biochimica et Biophysica Acta (BBA)—General Subjects 1760.4: 560-567 (2006).

Fares et al. "Design of a long-acting follitropin agonist by fusing the C-terminal sequence of the chorionic gonadotropin beta subunit to the follitropin beta subunit" Proc Natl Acad Sci U S A., 89(10): 4304-4308, May 15, 1992.

Fares et al. "Designing a long-acting human growth hormone (hGH) by fusing the carboxy-terminal peptide of human chorionic gonadotropin B-subunit to the coding sequence of hGH" Endocrinology 151(9):4410-4417 (2010).

Fares et al. "Growth hormone (GH) retardation of muscle damage due to immobilizationin old rats. Possible intervention with a new long-acting recombinant GH" Ann N Y Acad Sci. 786:430-43 (Jun. 15, 1996).

Fares et al. "Designing a Long Acting Erythropoietin by Fusing Three Carboxyl-Terminal Peptides of Human Chorionic Gondotropin [beta] Subunit to the N-Terminal and C-Terminal Coding Sequence", International Journal of Cell Biology, vol. 9, No. 11, Jan. 1, 2011, pp. 2021-2027.

Fares et al., "Development of a long-acting erythropoietin by fusing the carboxyl-terminal peptide of human chorionic gonadotropin β-subunit to the coding sequence of human erythropoietin." Endocrinology 148.10: 5081-5087 (2007).

Fayad et al. "Update of the M. D. Anderson Cancer Center experience with hyper-CVAD and rituximab for the treatment of mantle cell and Burkitt-type lymphomas" Clin Lymphoma Myeloma. Dec. 2007;8 Suppl 2:S57-62.

Fingl et al., "General Principles." The Pharmacological Basis of Therapeutics (ed. Goodman, LS & Gilman, A,): 1-46 (1975).

Fogarty, Patrick F. "Biological rationale for new drugs in the bleeding disorders pipeline." ASH Education Program Book 2011.1 (2011): 397-404.

Freshney "Culture of animal cells: A manual of basic technique" (Culture of Animal Cells, A Manual of Basic Technique, Alan R. Liss, Inc., 1983, New York, p. 4).

Fuentes-Prior et al. "Structural basis for the anticoagulant activity of the thrombin-thrombomodulin complex" Nature. Mar. 30, 2000; 404 (6777):518-25.

Furuhashi et al. "Fusing the carboxy-terminal peptide of the chorionic gonadotropin (CG)-subunit to the common alpha-submit:: Retention of O-linked glycosylation and enhanced in vivo bioactivity of chimeric human CG" Molecular Endocrinology 9(1):54-63 (1995).

Furuhashi et al. "Processing of O-linked glycosylation in the chimera consisting of alpha-subunit and carboxyl-terminal peptide of the human chorionic gonadotropin beta-subunit is affected by dimer formation with follicle-stimulating hormone beta-subunit" Endocrine Journal 51(1):53-59 (2004).

Gao et al., "Erythropoietin gene therapy leads to autoimmune anemia in macaques" Blood 103(9):3300-3302 (2004).

Garcia-Campayo et al. "Unmasking a new recognition signal for *O*-linked glycosylation in the chorionic gonadotropin β subunit" Molecular and Cellular Endocrinology 194.1: 63-70 (2002).

Gardella et al. "Expression of Human Parathyroid Hormone-( I-84) in *Escherichia coli* as a Factor X-cleavable Fusion Protein" J. Biol. Chem. 265:15854-15859 (1990).

Gellerfors et al. "Characterisation of a secreted form of recombinant derived human growth hormone, expressed in *Escherichia coli* cells", J Pharm Biomed Anal 7(2):173-83 (1989).

Genbank Accession No. NP 002045 (version 1), Sep. 6, 2014.

Ghosh et al., "Activity and regulation of factor VIIa analogs with increased potency atthe endothelial cell surface." Journal of Thrombosis and Haemostasis 5.2: 336-346 (2007).

(56) References Cited

OTHER PUBLICATIONS

Gilboa et al., "Transfer and Expression of Cloned Genes Using Retroviral Vectors", Biotechniques, vol. 4:504-512, (1986).
Goodson, in "Medical applications of controlled release." vol. 2: 115-138 (1984).
Guitton et al., "Influence of in vitro non-enzymatic glycosylation on the physicochemical parameters of type I collagen." Collagen and Related Research 4.4: 253-264 (1984).
Gurley et al. "Upstream Sequences Required for Efficient Expression of a Soybean Heat Shock Gene" Mol.Cell.Biol 6:559-565 (1986).
Hacke et al. "Intravenous thrombolysis with recombinant tissue plasminogen activator for acute hemispheric stroke. The European Cooperative Acute Stroke Study (ECASS)" JAMA. 1995;274(13):1017-1025.
Hammerling et al. "In vitro bioassay for human erythropoietin based on proliferative stimulation of an erythroid cell line and analysis of carbohydrate-dependent microheterogeneity" Journal of Pharm. Biomed. Analysis 14(11):1455-1469 (1996).
Havron et al. "OR2, 8 Phase I PK&PD profile of long acting bio-better CTP modified hGH (MOD-4023) in healthy volunteers" Growth Hormone & IGF Research. Jan. 1, 2010;20:S4-5.
Heffernan et al., "Effects of oral administration of a synthetic fragment of human growth hormone on lipid metabolism." American Journal of Physiology-Endocrinology and Metabolism 279.3: E501-E507 (2000).
Houdebine, L., "The methods to generate transgenic animals and to control transgene expression" Journal of Biotechnology 98:145-160 (2002).
Huston et al. "Protein engineering of antibody binding sites: Recovery of specific activity in an anti-digoxin single-chain Fv analogue produced in *Escherichia coli*" Proc. Natl. Acad. Sci. USA vol. 85, pp. 5879-5883, Biochemistry, Aug. 1988.
International Search Report for Application No. PCT/IL2010/000532 mailed on Apr. 11, 2011.
International Search Report for Application No. PCT/US2007/002767 mailed on Feb. 15, 2008.
International Search Report for Application No. PCT/US20070/03014 mailed on Sep. 22, 2008.
International Search Report for Application No. PCT/IL2009/000700 mailed on Sep. 22, 2008.
International Search Report for Application No. PCT/IL2012/050288 mailed on Jan. 28, 2013.
International Search Report for Application No. PCT/IL2013/050107 mailed on Jul. 10, 2013.
International Search Report for Application No. PCT/IL2014/050910 mailed on Jan. 25, 2015.
International Search Report for Application No. PCT/IL2016/050645 mailed on Jan. 19, 2017.
International Search Report for Application No. PCT/IL2017/050645 mailed on Sep. 21, 2017.
International Search Report for Application No. PCT/IL2017/050784 mailed on Sep. 22, 2017.
Isgaard et al. "Effects of local administration of GH and IGF-1 on longitudinal bone growth in rats" Am J Physiol. Apr. 1986;250(4 Pt 1):E367-72.
Jarrousse et al. "Oxyntomodulin (glucagon-37) and its C-terminal octapeptide inhibit gastric acid secretion", FEBS Lett. Aug. 19, 1985; 188(1): 81-4.
Joshi et al. "Recombinant thyrotropin containing a beta-subunit chimera with the human chorionic gonadotropin-beta carboxy-terminus is biologically active, with a prolonged plasma half-life: role of carbohydrate in bioactivity and metabolic clearance" Endocrinology. Sep. 1995;136(9):3839-48.
Kanda et al. "Genetic Fusion of an a-subunit Gene to the Follicle-Stimulating Hormone and Chorionic Gonadotropin-b Subunit Genes: Production of a Bifunctional Protein", Molecular Endocrinolog, vol. 13, No. 11, p. 1873-1881, Nov. 1999.

Kelly et al. "Outcomes of patients with Burkitt lymphoma older than age 40 treated with intensive chemotherapeutic regimens." Clin Lymphoma Myeloma. Aug. 2009;9(4):307-10.
Kessler et al. "Structure and location of the O-glycosidic carbohydrate units of human chorionic gonadotropin" J Biol Chem. 25;254(16):7909-14 , Aug. 1979.
Kessler et al., "Structures of N-Glycosidic Carbohydrate Units of Human Chorionic Gonadotropin" J Biol Chem. Aug. 25, 1979;254(16):7901-8.
Kicman et al., "Human chorionic gonadotrophin and sport." British Journal of Sports Medicine 25.2 : 73-80 (1991).
Kieffer et al. "Distribution of glucagon receptors on hormone-specific endocrine cells of rat pancreatic islets" Endocrinology. Nov. 1996;137(11):5119-25.
Knudsen et al. "Small-molecule agonists for the glucagon-like peptide 1 receptor", PNAS, Jan. 16, 2007, vol. 104, No. 3, 937-942.
Kontermann, "Half-Life Modulating Strategies—An Introduction." Therapeutic Proteins: Strategies to Modulate Their Plasma Half-Lives : 1-21 (2012).
Kontermann, "Strategies for extended serum half-life of protein therapeutics." Current opinion in Biotechnology 22.6: 868-876 (2011).
Kotler et al., "Effects of growth hormone on abnormal visceral adipose tissue accumulation and dyslipidemia in HIV-infected patients." JAIDS Journal of Acquired Immune Deficiency Syndromes 35.3: 239-252 (2004).
Krantz et al. "Specific binding of erythropoietin to spleen cells infected with the anemia strain of Friend virus" Proc Natl Acad Sci U S A. Dec. 1984;81(23):7574-8.
Langer Robert "New Methods of Drug Delivery" Science 249:1527-1533 (1990).
Larsen et al., "Accumulation of magnetic iron oxide nanoparticles coated with variably sized polyethylene glycol in murine tumors." Nanoscale 4.7: 2352-2361 (2012).
Le et al., "Improved Vancomycin Dosing in Children Using Area Under the Curve Exposure." Pediatr Infect Dis J vol. 32, pp. e155-e163 (2013).
Lentz et al., "Posttranslational modification of the carboxy-terminal region of the. beta.subunit of human chorionic gonadotropin." Biochemistry 23.22: 5330-5337 (1984).
Li et al. "Bioassay of hGH .I. Weight gain of hypophysectomized rats". Abstract, Yaowu Fenxi Zazhi 15(2), 3-7 (1995).
Lippin et al. "Human erythropoietin gene therapy for patients with chronic renal failure" Blood 106(7):2280-2286 (2005).
Littlewood, T.J. "Erythropoietin for the treatment of anemia associated with hematological malignancy" Hematol Oncol. Mar. 2001;19(1):19-30.
Lo et al. "The effects of recombinant human growth hormone on body composition andglucose metabolism in HIV-infected patients with fat accumulation" J Clin Endocrinol Metab. Aug. 2001;86(8):3480-7. PubMed PMID: 11502767.
Lopez-Berestein et al. "Treatment of systemic fungal infections with liposomalamphotericin B." Liposomes in the therapy of infectious diseases and cancer. (1989): 317-327.
Lopez-Berestein et al. "Treatment of systemic fungal infections with liposomal amphotericin B." Arch Intern Med. Nov. 1989;149(11):2533-6.
Maheshwari et al., "Manipulation of Electrostatic and Saccharide Linker Interactions in the Design of Efficient Glycopolypeptide-Based Cholera Toxin Inhibitors." Macromolecular bioscience 10.1: 68-81 (2010).
Maston et al., "Chorionic gonadotropin beta subunit [*Homo sapiens*]" NCBI Accession No. AAL69705.1 (Apr. 3, 2002).
Matsumoto et al. The measurement of low levels of factor VIII or factor IX in hemophilia A and hemophilia B plasma by clot waveform analysis and thrombin generation assay. Journal of Thrombosis and Haemostasis vol. 4:377-384 (2006).
Matsuo et al. "Thrombolysis by human tissue plasminogen activator and urokinase in rabbits with experimental pulmonary embolus" Nature. Jun. 18, 1981;291(5816):590-1.
Maun et al., "Disulfide locked variants of factor VIIa with a restricted β-strand conformation have enhanced enzymatic activity." Protein Science 14.5: 1171-1180 (2005).

(56) References Cited

OTHER PUBLICATIONS

McAlister et al. "NMR analysis of the N-terminal SRCR domain of human CD5: engineering of a glycoprotein for superior characteristics in NMR experiments." Protein Engineering 11.10: 847-853 (1998).
McNeil C. "No rest for fatigue researchers. Journal of the National Cancer Institute" Aug. 20, 2008;100(16):1129.
Medlock et al. "Epogen signal peptide", Jan. 6, 2005, XP002685292.
Meulien et al., "Increased biological activity of a recombinant factor IX variant carrying alanine at position+ 1." Protein Engineering 3.7: 629-633 (1990).
Milton et al. The delineation of a decapeptide gonadotropin-releasing sequence in the carboxyl-terminal extension of the human gonadotropin-releasing hormone precursor J Biol Chem. Dec. 25, 1986; 261(36):16990-7.
Morel L. "Mouse models of human autoimmune diseases: essential tools that require the proper controls," PLoS biology. Aug. 17, 2004;2(8):e241.
Morgan et al. "The amino acid sequence of human chorionic gonadotropin. The alpha subunit and beta subunit", J Biol Chem. Jul. 10, 1975;250(13):5247-58.
Muleo et al. Small doses of recombinant factor VIIa in acquired deficiencies of vitamin K dependent factors. Blood Coagulation & Fibrinolysis Abstract, 10(8), 521-522 (1999).
Murray et al. "Dose titration and patient selection increases the efficacy of GH replacement in severely GH deficient adults", Clinical Endocrinology (1999) 50, pp. 749-757.
Musto "The role of recombinant erythropoietin for the treatment of anemia in multiple myeloma" Leuk Lymphoma. Apr. 1998;29(3-4):283-91.
Mutter et al. "A New Base-Labile Anchoring Group for Polymer-Supported Peptide Synthesis." Helvetica chimica acta 67.7 (1984): 2009-2016.
Mutter et al. "Evolution versus design: template-directed self-assembly of peptides to artificial proteins (TASP)." CHIMIA International Journal for Chemistry 54.10 (2000): 552-557.
NCBI GenBank Accession No. AAL69702 (Apr. 3, 2002).
Nezu et al. "Treatment of idiopathic pituitary dwarfism with human growth hormone", Journal of Nara Medical Association 40.1(1989): 16-22; with English Abstract.
Ngo et al. "Computational Complexity, Protein Structure Protein Prediction and the Levinthal Paradox" in Birkhauser the Protein Folding Problem and Tertiary Structure Prediction, pp. 433-440 and 492-495 (1994).
Office Action for Japanese Application No. 2014-523441 dated May 24, 2016.
Ogle et al. "Renal effects of growth hormone. I. Renal function and kidney growth", Pediatr. Nephrol. vol. 6:394-398, 1992.
Oosterhof et al. Regulation of whole body energy homeostasis with growth hormone replacement therapy and endurance exercise Physiol Genomics. Jun. 28, 2011;43(12):739-48. doi: 10.1152/physiolgenomics. 00034.2010. Epub Mar. 29, 2011.
Pedrosa et al., "Selective neoglycosylation increases the structural stability of vicilin, the 7S storage globulin from pea seeds." Archives of Biochemistry and Biophysics 382.2: 203-210 (2000).
Persson et al. "Recombinant coagulation factor VIIa—from molecular to clinical aspects of a versatile haemostatic agent", Thrombosis Research (2010) 125:483-489.
Persson et al., "Rational design of coagulation factor VIIa variants with substantially increased intrinsic activity." Proceedings of the National Academy of Sciences 98.24: 13583-13588 (2001).
Philips A. "The challenge of gene therapy and DNA delivery" J Pharm. Pharmacology 53:1169-1174 (2001).
Pierce et al. "Glycoprotein hormones: structure and function." Annual review of biochemistry 50.1: 465-495 (1981).
Pinkert et al. "An albumin enhancer located 10 kb upstream functions along with its promoter to direct liver-specific expression in transgenic mice" Genes Dev. 1:268-277 (1987).

Pocai et al. "Glucagon-Like Peptide 1/Glucagon Receptor Dual Agonism Reverses Obesity in Mice", Diabetes, vol. 58, Oct. 2009, pp. 2258-2266.
Polizzotti et al. "Effects of saccharide spacing and chain extension on toxin inhibition by glycopolypeptides of well-defined architecture", Macromolecules 40.20: 7103-7110 (2007).
Poreddy et al., "Exogenous fluorescent tracer agents based on pegylated pyrazine dyes for real-time point-of-care measurement of glomerular filtration rate." Bioorganic & Medicinal Chemistry 20.8: 2490-2497 (2012).
Puett et al. "Structure-Function Relationships of the Luteinizing Hormone Receptor" Annals of the New York Academy of Sciences. Dec. 1, 2005;1061(1):41-54.
Rebois et al., "Hydrodynamic properties of the gonadotropin receptor from a murine Leydig tumor cell line are altered by desensitization." Biochemistry 26.20: 6422-6428 (1987).
Reichel "Sarcosyl-Page: a new electrophoretic method for the separation and immunological detection of PEGylated proteins." Protein Electrophoresis. Humana Press 65-79 (2012).
Reiter et al. "A multicenter study of the efficacy and safety of sustained release GH in the treatment of naive pediatric patients with GH deficiency" J Clin Endocrinol Metab. 86(10):4700-6 (Oct. 2001).
Riddick et al. "A stepwise increase in recombinant human growth hormone dosing during puberty achieves improved pubertal growth: a National Cooperative Growth Study report" Journal of Pediatric Endocrinology and Metabolism. 2009;22(7):623-8.
Ronzi et al. Optimisation of a freeze-drying process of high purity Factor VIII and Factor IX concentrates. Chemical Engineering and Processing. vol. 42:751-757 (2003).
Rosario PW. "Normal values of serum IGF-1 in adults: results from a Brazilian population" Arquivos Brasileiros de Endocrinologia & Metabologia. 2010;54(5):477-81.
Rudman et al. "Effects of human growth hormone in men over 60 years old" N Engl J Med. Jul. 5, 1990;323(1):1-6.
Runge et al. "Different domains of the glucagon and glucagon-like peptide-1 receptors provide the critical determinants of ligand selectivity", British Journal of Pharmacology (2003) 138, 787-794.
Russell et al. "Local injections of human or rat growth hormone or of purified humansomatomedin-C stimulate unilateral tibial epiphyseal growth in hypophysectomized rats" Endocrinology. Jun. 1985;116(6):2563-7.
Sambrook et al. "Molecular cloning: a laboratory manual." Cold Spring Harbor Laboratory Press, Cold Spring Harbor, New York 2 (2001).
Saudek et al. "A preliminary trial of the programmable implantable medication system for insulin delivery" N Engl J Med. 321:574 (1989).
Schein, Catherine H. "The shape of the messenger: Using protein structure informationto design novel cytokine-based therapeutics" Abstract; Current Pharmaceutical Design 8(24):2113-2129 (2002).
Scheuttrumpf et al., "Factor IX variants improve gene therapy efficacy for hemophilia B." Blood 105.6: 2316-2323 (2005).
Schneider KH "GMP Requirements for master and working cell bank" Pharmazeutische Industrie. Jan. 1, 2005;67(11):1366-9.
Schulte "Half-life extension through albumin fusion technologies", Thrombosis Research (2009) 124 Suppl. 2;S6-S8.
Sefton, "Implantable pumps." Critical Reviews in Biomedical Engineering 14.3: 201-240 (1986).
Shechter et al. "Reversible PEGylation of peptide YY3-36 prolongs its inhibition of food intake in mice", FEBS Lett. Apr. 25, 2005;579(11):2439-44.
Sheffield et al. "Effects of genetic fusion of factor IX to albumin on in vivo clearancein mice and rabbits", Blackwell Publishing Ltd, British Journal of Haematology (2004) 126:565-573.
Silverman et al. "A long-acting human growth hormone (Nutropin Depot): Efficacy and safety following two years of treatment in children with growth hormone deficiency" J Pediatr Endocrinol Metab. 15 Suppl 2:715-22. (May 2002).
Smeland et al. "Treatment of Burkitt's/Burkitt-like lymphoma in adolescents and adults: a 20-year experience from the Norwegian Radium Hospital with the use of three successive regimens."Ann Oncol. Jul. 2004;15(7):1072-8.

(56) References Cited

OTHER PUBLICATIONS

Speiser et al. "Optimization of spray-dried and -congealed lipid micropellets and characterization of their surface morphology." Pharm. Res. 8:47-54 (1991).
Srour et al. "Regulation of human factor IX expression using doxycycline-inducible gene expression system" Thromb Haemost 90:398-405 (2003).
Stuart et al. "Polycythemia vera" Am Fam Physician. May 1, 2004;69(9):2139-44.
Studier F.W. et al."Use of T7 RNA Polymerase to Direct Expression of Cloned Genes" Methods in Enzymol. 185:60-89 (1990).
Su et al. "Curcumin Inhibits Human Lung Cell Carcinoma Cancer Tumour Growth in a Murine Xenograft Model" (Phytother. Res. 24:189-191, 2010).
Sugahara et al. "Characterization of the O-glycosylation sites in the chorionic gonadotropin β subunit in vivo using site-directed mutagenesis and gene transfer." Journal of Biological Chemistry 271.34: 20797-20804 (1996).
Supplementary European Search Report for European Application No. 10796803.4 dated Feb. 28, 2013.
Supplementary European Search Report for European Application No. 07749922.6 dated Oct. 8, 2009.
Supplementary European Search Report for European Application No. 09797630.2 dated Dec. 5, 2011.
Supplementary European Search Report for European Application No. 12819794.4 dated Feb. 24, 2015.
Supplementary European Search Report for European Application No. 13749077.7 dated Oct. 22, 2015.
Supplementary European Search Report for European Application No. 14856666.4 dated May 3, 2017.
Supplementary European Search Report for European Application No. 16811146.6 dated Jan. 8, 2019.
Takamatsu et al. "Expression of bacterial chloramphenicol acetyltransferase gene in tobacco plants mediated by TMV-RNA" EMBO J 6:307-311 (1987).
Takeya et al. "Bovine factor VII. Its purification and complete amino acid sequence". Journal of Biological Chemistry. Oct. 15, 1988;263(29):14868-77.
Tape et al. "Apolipoprotein AI and apolipoprotein SAA half-lives during acute inflammation and amyloidogenesis" Biochimica et Biophysica Acta (BBA)—Lipids and Lipid Metabolism. Apr. 17, 1990;1043(3):295-300.
The Merck Index: An Encyclopedia of Chemicals, Drugs, and Biologicals. Fifteenth Edition, (2013) Item No. 4561. Gonadotropin. pp. 835-836.
Tharakan et al. "Emerging therapies in the treatment of 'diabesity': beyond GLP-1" Trends Pharmacol Sci. Jan. 2011;32(1):8-15.
Treat et al. "Liposome Encapsulated Doxorubicin—Preliminary Results of Phase I andPhase II Trials" in: G Lopez-Berestein, IJ Fidler (Eds.) Liposomes in the Therapy of Infectious Diseases and Cancer. Alan R. Liss, New York; 1989: 353-365.
Uenalp et al. "Factor VII deficiency associated with valproate treatment" Pediatrics International 50(3):403-405 Abstract (2008).
Venn et al. "Biosynthesis and metabolism in vivo of intervertebral-disc proteoglycans in the mouse." Biochem. J 215: 217-225 (1983).
Verhoef et al. "Recombinant human erythropoietin for the treatment of anemia in the myelodysplastic syndromes: a clinical and erythrokinetic assessment" Ann Hematol. Jan. 1992;64(1):16-21.
Weiss et al. "Noncompliance in Neurologic Patients" Current Treatment Options in Neurology 7:419-425 (2005).
Weissbach and Weissbach, "Methods for Plant Molecular Biology." Selected Methods in Enzymology (USA) Section VIII: 421-463 (1988).
Wells, J.A, "Additivity of Mutational Effects in Proteins" Biochemistry 29:8509-8517 (1990).
White et al. "Mammalian Recombinant Coagulation Proteins: Structure and Function", Transfus. Sci. (1998) 19(2):177-189.
Wildt et al., "The humanization of N-glycosylation pathways in yeast." Nature Reviews Microbiology 3.2: 119-128 (2005).
Wilken et al. "A novel four-amino acid determinant defines conformational freedom within chorionic gonadotropin β-subunits." Biochemistry 46.14: 4417-4424 (2007).
Wilson et al. "Assessing annotation transfer for genomics: quantifying the relations between protein sequence, structure and function through traditional and probabilistic scores" Journal of molecular biology. Mar. 17, 2000;297(1):233-49.
Winoto et al. "A novel, inducible and T cell-specific enhancer located at the 3' end of the T cell receptor alpha locus" EMBO J. 8:729-733 (1989).
Wynne et al. "Subcutaneous oxyntomodulin reduces body weight in overweight and obese subjects a double-blind, randomized, controlled trial" Diabetes 54.8 (2005): 2390-2395.
Yefenof & McConnell "Interferon amplifies complement activation by Burkitt's lymphoma cells" Nature. Feb. 21-27, 1985;313(6004):68.
Yin et al. "Recombinant human growth hormone replacement therapy in HIV-associated wasting and visceral adiposity". Exper. Rev. Anti-Infect. Ther. 3(5):727-736 (2005).
Zheng, K., Bantog, C., & Bayer, R. (Nov. 2011). "The impact of glycosylation on monoclonal antibody conformation and stability". In MAbs (vol. 3, No. 6, pp. 568-576). Taylor & Francis.
Zhong et al. "The N-terminal epidermal growth factor-like domain in factor IX and factor X represents an important recognition motif for binding to tissue factor" J. Biol. Chem. (2002) 277(5):3622-31.
Zhong et al. "Biological insights Into therapeutic protein modifications throughout trafficking and their biopharmaceutical applications" International journal of cell biology. Apr. 18, 2013;2013.
Japanese Office Action with English translation dated Mar. 5, 2019 for Japanese Application No. 2017-565796.
Calo Doron, et al. "Enhancing the longevity and in vivo potency of therapeutic proteins: the power of CTP." Precision Medicine 1 (2015), pp. 1-8.
Dacambra, et al., "Structural Determinants for Activity of Glucagon-like Peptide-2", Biochemistry (2000), Jul. 6, 2000, pp. 8888-8894.
European Search Report for European Application No. 21151437.7 dated Jun. 8, 2021.
International Search Report and Written Opinion dated Sep. 22, 2020 from International Application No. PCT/IL2020/050769.
Lee D.E. et al. "The prolonged half-lives of new erythropoietin derivatives via peptide addition", Biochemical and Biophysical Research Communications 339 (2006), pp. 380-385.
Naguib, Rania, et al. "Development and Validation of an IGF-1-Modified Child-Pugh Score to Risk-Stratify Hepatocellular Carcinoma Patients", Egyptian Journal of Obesity, Diabetes and Endocrinology, vol. 1, No. 1, Jan. 1, 2015, pp. 14-20.
Pearlman, Rodney, et al. "Formulation, characterization, and stability of protein drugs", vol. 9., Springer Science & Business Media, 1996, pp. 247-274.
Yong, et al., "The Molecular Design and Drug Development of Recombinant Long-Acting Follicle Stimulating Hormone", Acta Pharmaceutica Sinica 2012, 47 (4): pp. 421-426.
Binder et al. "Mod-5014, a Long-Acting FVIIa-CTP, Proposing a Novel Prophylactic Treatment Supporting Less Frequent Subcutaneous or Intravenous Injections with a Similar Mechanism of Action to rFVIIa: Proof-of-Concept in Hemophilic Animal Models" Blood. Dec. 3, 2015;126(23):4670.
Package Insert(s) for NovoSeven® HI 1/2/5 mg for intravenous injection, 2013.
Peter et al. "Pharmacokinetic and pharmacodynamic profile of a new sustained-release GH formulation, LB03002, in children with GH deficiency" European journal of endocrinology. Mar. 2009;160(3):349-55.
Quade-Lyss et al. "Engineered factor VII, factor IX, and factor X variants for hemophilia gene therapy" J Genet Syndr Gene Ther. Dec. 2012;2012:S1.

\* cited by examiner

MOD-5000

MOD-5014

| Purification Step | Charged N-Glycans (%) |
|---|---|
| Harvest | NA |
| Viral Inactivation<br><br>+<br><br>VII Affinity Chromatography | 80.01 |
| Multimodel or mixed-mode Chromatography | 79.4 |
| UF/DF2 | 78.5 |
| UF/DF3 | 79.5 |

FIGURE 19

| Purification Step | RP-HPLC(%) | | |
|---|---|---|---|
| | Main Peak | Oxidized Forms | Other Related Forms |
| Harvest | NA | NA | NA |
| Viral Inactivation + VII Affinity Chromatography | 89.10 | 4.66 | 6.23 |
| Multimodel or mixed-mode Chromatography | 91.31 | 4.38 | 4.31 |
| Hydrophobic Interaction Chromatography (HIC) | 94.03 | 2.68 | 3.29 |
| Anion exchange Chromatography | 94.69 | 2.48 | 2.83 |

FIGURE 20

| Purification Step | Gamma Carboxylated (%) |
|---|---|
| Harvest | NA |
| Viral Inactivation<br><br>+<br><br>VII Affinity Chromatography | 95.4 |
| Multimodel or mixed-mode Chromatography | 100 |

FIGURE 21

| Purification Step | Sialic acid (mol/ mol of product) |
|---|---|
| Harvest | NA |
| Viral Inactivation<br><br>+<br><br>VII Affinity Chromatography | 15.25 |
| CHT | 16.6 |
| UF/DF2 | 16.6 |
| UF/DF3 | 16.4 |

LONG-ACTING COAGULATION FACTORS AND METHODS OF PRODUCING SAME

FIELD OF DISCLOSURE

Polypeptides comprising at least one carboxy-terminal peptide (CTP) of chorionic gonadotropin attached to the carboxy terminus of a coagulation factor and polynucleotides encoding the same are disclosed. Pharmaceutical compositions and pharmaceutical formulations comprising the polypeptides and polynucleotides of the disclosure and methods of using and producing same are also disclosed.

BACKGROUND

The development of coagulation factor replacement therapy has transformed the lives of many individuals with hemophilia. Hemophilia is a group of hereditary genetic disorders that impair the body's ability to control blood clotting or coagulation. Patients with hemophilia do not produce adequate amounts of Factor VIII or Factor IX proteins, which are necessary for effective blood clotting. In severe hemophiliacs even a minor injury can result in blood loss that continues for days or weeks, and complete healing may not occur, leading to the potential for debilitating permanent damage to joints and other organs, and premature death.

Hemophilia is an inherited, X-chromosome-linked hemorrhagic disorder caused by defects in, or the absence of, critical factors in the coagulation cascade. In hemophilia patients, thrombin generation and fibrin clot formation are severely compromised, leading to spontaneous bleeding episodes most commonly in joints and internal organs, and excessive bleeding during and following surgery or trauma. Frequent bleeding can also cause joint swelling, joint damage, severe deformity, frequent infections, and reduced mobility in hemophilia patients (Mayo Clinic). Hemophilia A is caused by defects in or lack of Factor VIII expression, while hemophilia B is caused by defects in or lack of Factor IX expression.

Hemophilia B results in a deficiency of the procoagulant activity of FIX. Hemophilia B patients have spontaneous soft tissue hemorrhages and recurrent hemarthroses that often lead to a crippling arthopathy. Current treatment for these patients includes an intravenous administration of recombinant FIX. However issues of cost and relatively rapid clearance of FIX from the circulation make developing a long-acting FIX a challenging task. Commercial availability of FVIII and FIX has led to improved control of life-threatening bleedings episodes. Many patients receive prophylactic therapy, which reduces the risk of bleeding and its associated complications. However, a significant proportion of patients (10-30%) develop inhibitory antibodies to exogenously administered FVIII and FIX. Administration of FVIIa, which is a bypassing product, can induce homeostasis and provide an effective treatment for patients with inhibitory Abs.

Recombinant FVIIa (NovoSeven®) is commercially available and was approved in 1996 for treatment of bleeding episodes in hemophilia patients with inhibitors. However, rFVIIa is rapidly cleared with a terminal half-life of 2.5 hours. As a result, patients generally require multiple, frequent infusions (2-3 doses given in 2-3 hour intervals) to achieve adequate homeostasis following a mild to moderate bleed. Consequently, there is much interest in developing a long-acting form of FVIIa that would prolong the duration of haemostatic activity following a single dose and allow much less frequent dosing. A long-acting FVIIa would also increase the feasibility of long-term prophylactic therapy.

Various technologies are being developed for prolonging the half-life of FVIIa. However, there remains a need to achieve a prolonged half-life of this protein while preserving its biological activity and ensuring that the modifications do not induce significant immunogenicity. The present invention addresses this need by attaching gonadotropin carboxy terminal peptides (CTPs) to FVIIa, thereby modifying it to prolong its half-life and biological activity.

SUMMARY OF THE DISCLOSURE

In one aspect, disclosed is a method of manufacturing a human chorionic gonadotropin carboxy terminal peptide (CTP)-modified human factor VII (FVII) polypeptide, wherein said polypeptide comprises three CTP molecules attached in tandem on the C-terminal end of FVII, the method comprising the steps of: stably transfecting a predetermined number of cells with an expression vector comprising a coding portion encoding said CTP-modified FVII, wherein said transfected cells express and secrete said CTP-modified FVII; obtaining cell clones that overexpress said CTP-modified FVII; expanding said clones in solution to a predetermined scale; harvesting said solution containing said clones; filtering said solution containing said clones to obtain a clarified harvest solution; and, purifying said polypeptide from said clarified harvest solution to obtain a purified protein solution having a desired concentration of the CTP-modified FVII; thereby manufacturing a CTP-modified FVII, wherein the amino acid sequence of the manufactured CTP-modified FVII is set forth in SEQ ID NO: 7.

In another aspect, disclosed is a method of manufacturing a human chorionic gonadotropin carboxy terminal peptide (CTP)-modified human active factor VII (FVIIa) polypeptide, wherein said polypeptide comprises three CTP molecules attached in tandem on the C-terminal end of the FVII, the method comprising the steps of: stably transfecting a predetermined number of cells with an expression vector comprising a coding portion encoding a CTP-modified FVII, wherein said transfected cells express and secrete said CTP-modified FVII; obtaining cell clones that overexpress said CTP-modified FVII; expanding said clones in solution to a predetermined scale; harvesting said solution containing said clones; filtering said solution containing said clones to obtain a clarified harvest solution; and, purifying and activating said polypeptide from said clarified harvest solution to obtain the purified protein solution having a desired concentration of the CTP-modified FVIaI; thereby manufacturing a CTP-modified FVIIa, wherein the amino acid sequence of the manufactured CTP-modified to FVIIa is set forth in SEQ ID NO: 7.

In another aspect, disclosed is a human chorionic gonadotropin carboxy terminal peptide (CTP)-modified human Factor VII (FVII) polypeptide comprising three CTP molecules attached in tandem to the C-terminal end of the FVII, wherein said CTP-modified FVII is manufactured by a method comprising the steps of: stably transfecting a predetermined number of cells with an expression vector comprising a coding portion encoding said CTP-modified FVII, wherein said transfected cells express and secrete said CTP-modified FVII; obtaining cell clones that overexpress said CTP-modified FVII; expanding said clones in solution to a predetermined scale; harvesting said solution containing said clones; filtering said solution containing said clones to obtain a clarified harvest solution; and, purifying said polypeptide from said clarified harvest solution to obtain a purified protein solution having a desired concentration of a CTP-modified FVII; wherein said manufactured CTP-modified FVII comprises the amino acid sequence set forth in SEQ ID NO: 7.

In another aspect, disclosed is a human chorionic gonadotropin carboxy terminal peptide (CTP)-modified human activated Factor VII (FVIIa) polypeptide comprising three CTP molecules attached in tandem to the C-terminal end of the FVII, wherein said CTP-modified FVIIa is manufactured by a method comprising the steps of: stably transfecting a predetermined number of cells with an expression vector comprising a coding portion encoding said CTP-modified FVII, wherein said transfected cells express and secrete said CTP-modified FVII; obtaining cell clones that overexpress said CTP-modified FVII; expanding said clones in solution to a predetermined scale; harvesting said solution containing said clones; filtering said solution containing said clones to obtain a clarified harvest solution; and, purifying and activating said polypeptide from said clarified harvest solution to obtain a purified protein solution having a desired concentration of a CTP-modified FVIIa; wherein said manufactured CTP-modified FVIIa comprises the amino acid sequence set forth in SEQ ID NO: 7.

In a related aspect, the manufactured human chorionic gonadotropin carboxy terminal peptide (CTP)-modified human Factor VII (FVII) polypeptide is highly glycosylated. In another related aspect, the glycosylation pattern of the manufactured CTP-modified FVII comprises glycosylation of at least 4 O-linked glycosylation sites per CTP. In another related aspect, said CTP-modified FVII comprises a high percent of charged N-glycans. In another related aspect, the manufactured human chorionic gonadotropin carboxy terminal peptide (CTP)-modified human Factor VII (FVII) polypeptide is highly sialylated.

In a related aspect, the manufactured human chorionic gonadotropin carboxy terminal peptide (CTP)-modified human Factor VII (FVII) polypeptide comprises a high percentage of carboxylated glutamic acid residues.

In a related aspect, expanding clones comprises expanding clones obtained from a working cell bank (WCB) or from a master cell bank (MCB). In another related aspect, said clones express and secrete CTP-modified FVII at a level of at least 600 mg/L. In another related aspect, said clones are expanded in solution through a series of sub-cultivating steps up to production bioreactor level. In another related aspect, a bioreactor comprises a disposable bioreactor or a stainless steel bioreactor. In another related aspect, said bioreactor is run as a fed-batch mode bioreactor.

In a related aspect, at least 60% of the purified human chorionic gonadotropin carboxy terminal peptide (CTP)-modified human Factor VII (FVII) polypeptide from said clarified harvest comprises a high glycosylation form of CTP-modified FVII. In a related aspect, at least 60% of the purified human chorionic gonadotropin carboxy terminal peptide (CTP)-modified human Factor VII (FVII) polypeptide from said clarified harvest comprises a high percentage of carboxylated glutamic acid residues.

In a related aspect, purification comprises sequentially performing steps comprising passing said clarified harvest through an affinity column, a multimodel or mixed mode column, a hydrophobic interaction column, and an anion exchange column; inactivating viruses present in the clarified harvest or in the eluate collect following column chromatography, or any combination thereof, wherein inactivating viruses comprises incubation in a solution toxic to said viruses or nanofilitration, or any combination thereof; and wherein the anion exchange eluate undergoes an ultrafiltration/diafiltration step.

In a related aspect, the (CTP)-modified human Factor VII (FVII) polypeptide manufactured comprises an active CTP-modified FVII polypeptide (CTP-modified FVIIa polypeptide).

In a related aspect, the manufacturing method achieves at least a 20% recovery rate of highly glycosylated CTP-modified FVII.

In another aspect, a composition comprises a manufactured CTP-modified FVII, and a pharmaceutically acceptable carrier.

In another aspect, disclosed herein is a human chorionic gonadotropin carboxy terminal peptide (CTP)-modified human active Factor VII (FVIIa) polypeptide comprising three CTP molecules attached in tandem to the C-terminal end of FVIIa, wherein said CTP-modified FVIIa polypeptide is in a substantially pure and active form, said CTP-modified FVIIa polypeptide comprising: (a) a high sialic acid content; (b) a low oxidized form; (c) a high glycosylation form; (d) a high percentage of carboxylated glutamic acid residues; (e) a high percentage of charged N-glycans; and (f) a high potency; or any combination thereof wherein said CTP-modified FVIIa comprises the amino acid sequence set forth in SEQ ID NO: 7.

In a related aspect, the high sialic acid content consists of at least 15 mol/mol. In another related aspect, the high glycosylation form comprises an O-glycan content of at least 10 mol/mol. In another related aspect, the substantially pure and active form comprises at least 60% of a high glycosylation form of said active CTP-modified FVIIa. In another related aspect, at least 60% of the substantially pure and CTP-modified FVIIa form comprises a high percentage of carboxylated glutamic acid (Gla) residues. In another related aspect, the high percentage of carboxylated glutamic acid (Gla) residues consists of at least 90% Gla residues. In another related aspect, the low percentage of oxidized form consists of less than 5%. In another related aspect, the purity of said substantially pure and active CTP-modified FVII polypeptide is at least 90%. In a further related aspect, the purity percentage is selected from the group consisting of 97.3%, 97.6%, 97.4% and 97.0%. In another related aspect, the potency of said substantially pure and active CTP-modified FVII polypeptide is at least 10,500 U/mg. In further related aspect, the potency is selected from the group consisting of 15,563 U/mg 16,720 U/mg, 22,478 U/mg and 23,608 U/mg.

In another aspect, disclosed herein is a composition comprising the CTP-modified FVIIa comprising: (a) a high sialic acid content; (b) a low oxidized form; (c) a high glycosylation form; (d) a high percentage of carboxylated glutamic acid residues; (e) a high percentage of charged N-glycans; and (f) a high potency; or any combination thereof, wherein said CTP-modified FVIIa comprises the amino acid sequence set forth in SEQ ID NO: 7, and a pharmaceutically acceptable carrier.

Other features and advantages will become apparent from the following detailed description, examples and figures. It should be understood, however, that the detailed description and the specific examples while indicating preferred embodiments of the disclosure are given by way of illustration only, since various changes and modification within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 19. Shows that the percentage of charged N-Glycans out of the total N-Glycans was consistent during the purification process, the initial charged N-Glycans percentage is effected from upstream cell culture process.

FIG. 20. Presents the content of oxidized forms and other related forms is reduced throughout the purification process. The Multimodel and HIC columns are the purification steps with the most significant effect on the reduction of oxidized forms and related forms.

FIG. 21. Presents the removal of non-Gamma carboxylated protein by the Multimodel column. The CHT column enriches the Gamma carboxylated fraction by removing the non-Gamma carboxylated protein FIG. 22. Presents the conctent content of Sialic acid throughout the purification process. The Sialic acid content was consistent during the purification process, the initial Sialic acid content is effected from upstream cell culture process.

DETAILED DESCRIPTION

Figure 1:
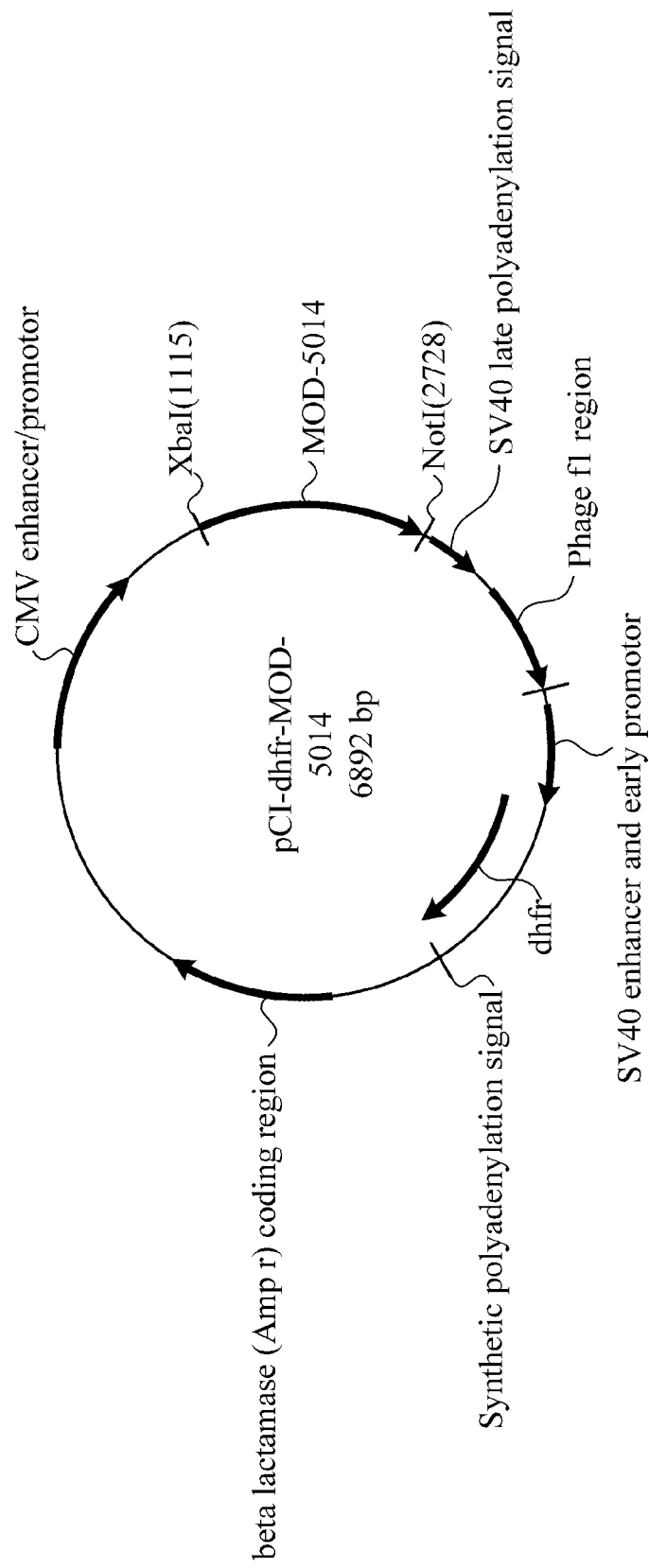
FIG. 1. Shows map of pCI-dhfr-MOD-5014 plasmid.

In one embodiment, disclosed is a method of manufacturing a human chorionic gonadotropin carboxy terminal peptide (CTP)-modified human factor VII (FVII) polypeptide, wherein said FVII comprises three CTP molecules attached in tandem on its C-terminal end, the method comprising the steps of: stably transfecting a predetermined number of cells with an expression vector comprising a coding portion encoding said CTP-modified FVII, wherein said transfected cells express and secrete said CTP-modified FVII; obtaining cell clones that overexpress said CTP-modified FVII; expanding said clones in solution to a predetermined scale; harvesting said solution containing said clones; filtering said solution containing said clones to obtain a clarified harvest solution; and, purifying said clarified harvest solution to obtain a purified protein solution having a desired concentration of the CTP-modified FVII; thereby manufacturing a CTP-modified FVII, wherein the amino acid sequence of the manufactured CTP-modified FVII is set forth in SEQ ID NO: 7.

In one embodiment, disclosed is a human chorionic gonadotropin carboxy terminal peptide (CTP)-modified human Factor VII (FVII) comprising three CTP molecules attached in tandem to its C-terminal end, wherein said CTP-modified FVII is manufactured by a method comprising the steps of: stably transfecting a predetermined number of cells with an expression vector comprising a coding portion encoding said CTP-modified FVII, wherein said transfected cells express and secrete said CTP-modified FVII; obtaining cell clones that overexpress said CTP-modified FVII; expanding said clones in solution to a predetermined scale; harvesting said solution containing said clones; filtering said solution containing said clones to obtain a clarified harvest solution; and, purifying said clarified harvest solution to obtain a purified protein solution having a desired concentration of a CTP-modified FVII; wherein said manufactured CTP-modified FVII comprises the amino acid sequence set forth in SEQ ID NO: 7.

In one embodiment, disclosed is a composition comprising a human chorionic gonadotropin carboxy terminal peptide (CTP)-modified human Factor VII (FVII) comprising three CTP molecules attached in tandem to its C-terminal end. In another embodiment, the CTP-modified FVII comprises an activated CTP-modified FVII (CTP-modified FVIIa).

Human Chorionic Gonadotropin Carboxy Terminal Peptide (CTP)-Modified Factor VII Polypeptide Coagulation Factor VII (FVII) is a 444 amino acid glycoprotein (50 KDa) secreted by hepatocytes into the bloodstream as an inactive pro-enzyme (zymogen). Upon tissue injury and exposure to circulating blood, FVII forms a complex with Tissue Factor (TF) which is a true receptor protein to FVII and is expressed by various cells localized in the deeper layers of the vessel wall. The formation of this FVII-TF complex leads to activation of FVII. Activated FVII (FVIIa) initiates the extrinsic coagulation pathway by activating Factor IX and Factor X. FVII belong to a group of Vitamin K-dependent glycoproteins associated with the coagulation system. FVII is synthesized as a precursor with an N-terminal propeptide followed by a mature amino acid sequence. The propeptide contains a docking site for gammacarboxylase which converts glutamic acid residues (Glu) into gamma carboxy glutamic acid residues (Gla). Carboxyglutamic acid (Gla) is an uncommon amino acid introduced into proteins by a post-translational carboxylation of glutamic acid residues. This modification introduces an affinity for calcium ions, wherein vitamin K is required to introduce gamma-carboxylation of clotting factors, including factor FVII. The Gla domain is responsible for the high-affinity binding of calcium ions, which has an important role to play in coagulation. This domain is followed by two epidermal growth factor-like (EGF) domains, a connecting region (CR) and a C-terminal serine protease domain Prior to secretion, FVII propeptide is cleaved, wherein the signal peptide is removed, forming a 406 amino acid single chain zymogen FVII glycoprotein. After secretion, the protein can be activated into a disulfide-linked two chain heterodimer, FVIIa, by cleavage in the CR. The plasma concentration of FVII is 10 nM and approximately 1% circulates in the active form in healthy individuals.

In one embodiment, provided herein is a method of extending the biological half-life or a method of improving the area under the curve (AUC) of FVII or FVIIa, comprising the step of attaching three CTPs to the carboxy terminus of FVII or FVIIa, thereby extending the biological half-life or improving the AUC of FVII or FVIIa.

In another embodiment, disclosed herein is a method of reducing the dosing frequency of a Factor VIIa (FVIIa) polypeptide, comprising the step of attaching three chorionic gonadotropin carboxy terminal peptides (CTPs) to the carboxy terminus of said FVIIa polypeptide, thereby reducing the dosing frequency of said FVIIa polypeptide.

In another embodiment, disclosed herein is a method of reducing the clearance rate of a Factor VIIa (FVIIa) polypeptide, comprising the step of attaching three chorionic gonadotropin carboxy terminal peptides (CTPs) to the carboxy terminus of said FVIIa polypeptide, thereby reducing the clearance rate of said FVIIa polypeptide.

In one embodiment, disclosed herein is a method of producing an activated CTP-modified Factor VII (FVIIa) polypeptide, comprising the step of attaching three chorionic gonadotropin carboxy terminal peptides (CTPs) to the carboxy terminus of said FVIIa polypeptide, thereby producing a CTP-modified FVIIa polypeptide.

In another embodiment, a coagulation factor of the disclosure is a protein. In another embodiment, a coagulation factor of the disclosure is a peptide. In another embodiment, a coagulation factor of the disclosure is a polypeptide. In another embodiment, the coagulation factor is an enzyme. In another embodiment, the coagulation factor is a serine protease. In another embodiment, the coagulation factor is a glycoprotein. In another embodiment, the coagulation factor is a vitamin K-dependent glycoprotein. In another embodiment, the coagulation factor is a vitamin K-independent glycoprotein. In another embodiment, the coagulation factor is a transglutaminase. In another embodiment, the coagulation factor is an inactive zymogen. In another embodiment, the coagulation factor is any coagulation factor known to one of skill in the art. In another embodiment, the coagulation factor is Factor VIIa (FVIIa).

In another embodiment, the coagulation factor is a recombinant protein. In another embodiment, the coagulation factor is a recombinant glycoprotein. In another embodiment, the coagulation factor is a recombinant FVII. In another embodiment, the coagulation factor is a recombinant FVIIa. In another embodiment, the coagulation factor comprises a signal peptide. In another embodiment, a recombinant coagulation factor does not comprise a signal peptide. In another embodiment, an activated coagulation factor does not comprise a signal peptide.

In another embodiment, a coagulation factor comprises 3 CTP repeats attached to the C-terminus and no CTPs attached to the N-terminus.

In another embodiment, disclosed herein is a CTP-modified Factor VIIa (FVIIa) polypeptide consisting of a FVIIa polypeptide and three gonadotropin carboxy terminal peptides (CTPs) attached to the carboxy terminus of said FVIIa.

In another embodiment, the coagulation factor is a coagulation factor comprising a domain organization similar or identical to the domain organization of FVII. In another embodiment, the coagulation factor is synthesized as a precursor with an N-terminal propeptide (signal sequence). In another embodiment, the coagulation factor described herein is in an inactive pro-enzyme form. In another embodiment, the coagulation factor, as described herein is an inactive zymogen, which has been secreted from a cell and is lacking the N-terminal signal sequence. In another embodiment, the coagulation factor, described herein is an activated coagulation factor. In another embodiment, the CTP-modified FVII described herein is in an inactive pro-enzyme form until it is activated. In another embodiment, the CTP-modified FVII, as described herein is an inactive zymogen, which has been secreted from a cell and is lacking the N-terminal signal sequence. In another embodiment, the CTP-modified FVII, described herein is an activated coagulation factor. In another embodiment, the coagulation factor is produced in hepatocytes. In another embodiment, the coagulation factor comprises a docking site for gammacarboxylase which converts glutamic acids (Glu) into gamma carboxy glutamic acids (Gla). In another embodiment, the coagulation factor as used herein is a commercially available coagulation factor.

In one embodiment, disclosed herein is a human chorionic gonadotropin carboxy terminal peptide (CTP)-modified human active Factor VII (FVIIa) polypeptide comprising three CTP molecules attached in tandem to the C-terminal end of FVIIa, wherein said CTP-modified FVIIa polypeptide is in a substantially pure and active form, said CTP-modified FVIIa polypeptide comprising: (a) a high sialic acid content; (b) a low oxidized form; (c) a high glycosylation form; (d) a high percentage of carboxylated glutamic acid residues; (e) a high percentage of charged N-glycans; and (f) a high potency; or any combination thereof wherein said CTP-modified FVIIa comprises the amino acid sequence set forth in SEQ ID NO: 7.

In one embodiment, disclosed herein is a human chorionic gonadotropin carboxy terminal peptide (CTP)-modified human active Factor VII (FVIIa) polypeptide comprising three CTP molecules attached in tandem to the C-terminal end of FVIIa, wherein said CTP-modified FVIIa polypeptide is in a substantially pure and active form, said CTP-modified FVIIa polypeptide comprising: (a) a high sialic acid content; (b) a low oxidized form; (c) a high glycosylation form; (d) a high percentage of carboxylated glutamic acid residues; (e) a high percentage of charged N-glycans; and (f) a potency of at least 10 U/mg; or any combination thereof wherein said CTP-modified FVIIa comprises the amino acid sequence set forth in SEQ ID NO: 7.

In a related embodiment, the high sialic acid content consists of at least 15 mol/mol. In another related aspect, the high glycosylation form comprises an O-glycan content of at least 10 mol/mol. In another related aspect, the substantially pure and active form comprises at least 60% of a high glycosylation form of said active CTP-modified FVIIa. In another related aspect, at least 60% of the substantially pure and CTP-modified FVIIa form comprises a high percentage of carboxylated glutamic acid (Gla) residues. In another related aspect, the high percentage of carboxylated glutamic acid (Gla) residues consists of at lest 90% Gla residues. In another related aspect, the low percentage of oxidized form consists of less than 5%. In another related aspect, the purity of said substantially pure and active CTP-modified FVII polypeptide is at least 90%. In a further related aspect, the purity percentage is selected from the group consisting of 97.3%, 97.6%, 97.4% and 97.0%. In another related aspect, the potency of said substantially pure and active CTP-modified FVII polypeptide is at least 10,500 U/mg. In further related aspect, the potency is selected from the group consisting of 15,563 U/mg 16,720 U/mg, 22,478 U/mg and 23,608 U/mg.

In another embodiment, disclosed herein is a composition comprising the CTP-modified FVIIa comprising: (a) a high sialic acid content; (b) a low oxidized form; (c) a high glycosylation form; (d) a high percentage of carboxylated glutamic acid residues; (e) a high percentage of charged N-glycans; and (f) a high potency; or any combination thereof, wherein said CTP-modified FVIIa comprises the amino acid sequence set forth in SEQ ID NO: 7, and a pharmaceutically acceptable carrier.

In another embodiment, disclosed herein is a composition comprising the CTP-modified FVIIa comprising: (a) a high sialic acid content; (b) a low oxidized form; (c) a high glycosylation form; (d) a high percentage of carboxylated glutamic acid residues; (e) a high percentage of charged N-glycans; and (f) a potency of at least 10,500 U/mg; or any combination thereof, wherein said CTP-modified FVIIa comprises the amino acid sequence set forth in SEQ ID NO: 7, and a pharmaceutically acceptable carrier.

In another embodiment, disclosed herein is a composition comprising the CTP-modified FVIIa, wherein said CTP-modified FVIIa polypeptide is in a substantially pure and active form, said CTP-modified FVIIa polypeptide comprising:
  a. a high sialic acid content;
  b. a high glycosylation form; wherein said CTP-modified FVIIa further comprises at least one of the following:
  c. a low oxidized form;
  d. a high percentage of carboxylated glutamic acid residues;
  e. at least 60% charged N-glycans; or
  f. a potency of at least 10,500 U/mg;
  or any combination thereof; and,
  wherein said CTP-modified FVIIa comprises the amino acid sequence set forth in SEQ ID NO: 7.

In another embodiment, disclosed herein is a composition comprising the CTP-modified FVIIa, wherein said CTP-modified FVIIa polypeptide is in a substantially pure and active form, said CTP-modified FVIIa polypeptide comprising:
  a. a high sialic acid content;
  b. a high glycosylation form; wherein said CTP-modified FVIIa further comprises at least one of the following:
  c. a low oxidized form;
  d. a high percentage of carboxylated glutamic acid residues;
  e. at least 60% charged N-glycans; or
  f. a potency of at least 10,500 U/mg;
  or any combination thereof; and,
  wherein said CTP-modified FVIIa comprises the amino acid sequence set forth in SEQ ID NO: 7, wherein the amino acid sequence of said CTP-modified FVIIa is structurally present as a disulfide-linked two chain heterodimer comprising a disulfide (S—S) bridge between cysteine residue 135 and cysteine residue 262 of SEQ ID NO: 7, and wherein said two chains comprise a light chain comprising amino acids 1-152 and a heavy chain comprising amino acids 153-490 of SEQ ID NO: 7.

In one embodiment, the nucleic acid sequence encoding Factor VII comprises the following nucleic acid sequence:

```
                                      (SEQ ID NO: 1)
ctcgaggacatggtctcccaggccctcaggctcctctgccttctgct tgggcttcagggctgcctggctgcagtcttcgtaacccaggaggaag cccacggcgtcctgcaccggcgccggcgcgccaacgcgacctggagg agctgcggccgggctccctggagagggagtgcaaggaggagcagtgc tcatcgaggaggcccgggagatatcaaggacgcggagaggacgaagc tgactggatacttacagtgatggggaccagtgtgcctcaagtccatg ccagaatgggggctcctgcaaggaccagctccagtcctatatctgat ctgcctccctgccttcgagggccgaactgtgagacgcacaaggatg accagctgatctgtgtgaacgagaacggcggctgtgagcagtactgc agtgaccacacgggcaccaagcgctcctgtcggtgccacgagggta ctctctgctggcagacggggtgtcctgcacacccacagttgaatatc
```

```
                                      -continued
catgtggaaaaatacctattctagaaaaaagaaatgccagcaaaccc caaggccgaattgtggggggcaaggtgtgccccaaaggggagtgtcc atggcaggtcctgagaggtgaatggagctcagagtgtgggggggaccc tgatcaacaccatctgggtggtctccgcggcccactgatcgacaaaa tcaagaactggaggaacctgatcgcggtgctgggcgagcacgacctc agcgagcacgacgggatgagcagagccggcgggtggcgcaggtcat catcccagcacgtacgtcccgggcaccaccaaccacgacatcgcgc tgctccgcctgcaccagcccgtggtcctcactgaccatgtggtgccc ctctgcctgcccgaacggacgactctgagaggacgctggccacgtgc gcttctcattggtcagcggctggggccagctgctggaccgtggcgcc acggccctggagctcatggtcctcaacgtgccccggctgatgaccca ggactgcctgcagcagtcacggaaggtgggagactcccaaatatca cggagtacatgttctgtgccggctactcggatggcagcaaggactcc tgcaaggggacagtggaggcccacatgccacccactaccggggcac gtggtacctgacgggcatcgtcagctggggccagggctgcgcaaccg tgggccactaggggtgtacaccagggtctcccagtacatcgagtggc tgcaaaagctcatgcgctcagagccacgcccaggagtcctcctgcga gccccatttccctgaggatgcggccgc.
```

In another embodiment, the amino acid sequence of Factor VII comprises the following amino acid sequence:

```
                                      (SEQ ID NO: 2)
MVSQALRLLCLLLGLQGCLAAVFVTQEEAHGVLHRRRRANAFLEEL

RPGSLERECKEEQCSFEEAREIFKDAERTKLFWISYSDGDQCASSP

CQNGGSCKDQLQSYICFCLPAFEGRNCETHKDDQLICVNENGGCEQ

YCSDHTGTKRSCRCHEGYSLLADGVSCTPTVEYPCGKIPILEKRNA

SKPQGRIVGGKVCPKGECPWQVLLLVNGAQLCGGTLINTIWVVSAA

HCFDKIKNWRNLIAVLGEHDLSEHDGDEQSRRVAQVIIPSTYVPGT

TNHDIALLRLHQPVVLTDHVVPLCLPERTFSERTLAFVRFSLVSGW

GQLLDRGATALELMVLNVPRLMTQDCLQQSRKVGDSPNITEYMFCA

GYSDGSKDSCKGDSGGPHATHYRGTWYLTGIVSWGQGCATVGHFGV

YTRVSQYIEWLQKLMRSEPRPGVLLRAPFP.
```

In another embodiment, the amino acid sequence of Factor VII comprises the following amino acid sequence:

```
                                      (SEQ ID NO: 3)
MVSQALRLLCLLLGLQGCLAAVFVTQEEAHGVLHRRRRANAFLEEL

RPGSLERECKEEQCSFEEAREIFKDAERTKLFWISYSDGDQCASSP

CQNGGSCKDQLQSYICFCLPAFEGRNCETHKDDQLICVNENGGCEQ

YCSDHTGTKRSCRCHEGYSLLADGVSCTPTVEYPCGKIPILEKRNA

SKPQGRIVGGKVCPKGECPWQVLLLVNGAQLCGGTLINTIWVVSAA

HCFDKIKNWRNLIAVLGEHDLSEHDGDEQSRRVAQVIIPSTYVPGT
```

-continued
TNHDIALLRLHQPVVLTDHVVPLCLPERTFSERTLAFVRFSLVSGW

GQLLDRGATALELMVLNVPRLMTQDCLQQSRKVGDSPNITEYMFCA

GYSDGSKDSCKGDSGGPHATHYRGTWYLTGIVSWGQGCATVGHFGV

YTRVSQYIEWLQKLMRSEPRPGVLLRAPFPGCGR.

In another embodiment, the nucleic acid sequence encoding Factor VII-CTP-CTP-CTP (attached to the carboxy terminus) comprises the following nucleic acid sequence:

(SEQ ID NO: 4)
ctcgaggacatggtctcccaggccctcaggctcctctgccttctgcttgg gcttcagggctgcctggctgcagtcttcgtaacccaggaggaagcccacg gcgtcctgcaccggcgccggcgcgccaacgcgacctggaggagctgcggc cgggctccctggagagggagtgcaaggaggagcagtgctcatcgaggagg cccgggagatatcaaggacgcggagaggacgaagctgactggatacttac agtgatggggaccagtgtgcctcaagtccatgccagaatggggctcctg caaggaccagctccagtcctatatctgatctgcctccctgccttcgaggg ccggaactgtgagacgcacaaggatgaccagctgatctgtgtgaacgaga acggcggctgtgagcagtactgcagtgaccacacgggcaccaagcgctcc tgtcggtgccacgagggggtactctctgctggcagacggggtgtcctgcac acccacagttgaatatccatgtggaaaaatacctattctagaaaaaagaa atgccagcaaaccccaaggccgaattgtgggggggcaaggtgtgccccaaa ggggagtgtccatggcaggtcctgagaggtgaatggagctcagagtgtgg ggggaccctgatcaacaccatctgggtggtctccgcggcccactgatcga caaaatcaagaactggaggaacctgatcgcggtgctgggcgagcacgacc tcagcgagcacgacggggatgagcagagccggcgggtggcgcaggtcatc atccccagcacgtacgtcccgggcaccaccaaccacgacatcgcgctgct ccgcctgcaccagcccgtggtcctcactgaccatgtggtgcccctctgcc tgcccgaacggacgactctgagaggacgctggccacgtgcgcttctcatt ggtcagcggctggggccagctgctggaccgtggcgccacggccctggagc tcatggtcctcaacgtgccccggctgatgacccaggactgcctgcagcag tcacggaaggtgggagactccccaaatatcacggagtacatgttctgtgc cggctactcggatggcagcaaggactcctgcaaggggggacagtggaggcc cacatgccacccactaccggggcacgtggtacctgaccggcatcgtgagc tggggccagggctgcgccaccgtgggccacttcggcgtgtacaccagggt gtcccagtacatcgagtggctgcagaaactgatgagaagcgagcccagac ccggcgtgctgctgagagcccccttccccagcagcagctccaaggcccct cccctagcctgcccagccctagcagactgcctgggcccagtgacacccc tatcctgcctcagtccagctccagcaaggcccaccccctagcctgccac tccactcggctgcctggccccagcgatactccaattctgccccagtcctc cagcagtaaggctcccctccatctctgccatccccagcagactgccag gcccactgatacacccatcctcccacagtgatgaggatccgcggccgctt aattaa.

In another embodiment, the amino acid sequence of Factor VII-CTP-CTP-CTP (attached to the carboxy terminus) comprises the following amino acid sequence:

(SEQ ID NO: 5)
MVSQALRLLCLLLGLQGCLAAVFVTQEEAHGVLHRRRRANAFLEELRP

GSLERECKEEQCSFEEAREIFKDAERTKLFWISYSDGDQCASSPCQNG

GSCKDQLQSYICFCLPAFEGRNCETHKDDQLICVNENGGCEQYCSDHT

GTKRSCRCHEGYSLLADGVSCTPTVEYPCGKIPILEKRNASKPQGRIV

GGKVCPKGECPWQVLLLVNGAQLCGGTLINTIWVVSAAHCFDKIKNWR

NLIAVLGEHDLSEHDGDEQSRRVAQVIIPSTYVPGTTNHDIALLRLHQ

PVVLTDHVVPLCLPERTFSERTLAFVRFSLVSGWGQLLDRGATALELM

VLNVPRLMTQDCLQQSRKVGDSPNITEYMFCAGYSDGSKDSCKGDSGG

PHATHYRGTWYLTGIVSWGQGCATVGHFGVYTRVSQYIEWLQKLMRSE

PRPGVLLRAPFPSSSKAPPPSLPSPSRLPGPSDTPILPQSSSSKAPPP

SLPSPSRLPGPSDTPILPQSSSSKAPPPSLPSPSRLPGPSDTPILPQ.

In another embodiment, amino acids 1-38 of SEQ ID NO: 5 comprise a signal sequence. In another embodiment, the amino acid sequence of the signal sequence comprises MVSQALRLLCLLLGLQGCLAAVFVTQEE-AHGVLHRRRR (SEQ ID NO: 6).

In another embodiment, the amino acid sequence of Factor VII-CTP-CTP-CTP (attached to the carboxy terminus) lacking a signal peptide comprises the following amino acid sequence:

(SEQ ID NO: 7)
ANAFLEELRP GSLERECKEE QCSFEEAREI FKDAERTKLF

WISYSDGDQC ASSPCQNGGS CKDQLQSYIC FCLPAFEGRN

CETHKDDQLI CVNENGGCEQ YCSDHTGTKR SCRCHEGYSL

LADGVSCTPT VEYPCGKIPI LEKRNASKPQ GRIVGGKVCP

KGECPWQVLL LVNGAQLCGG TLINTIWVVS AAHCFDKIKN

WRNLIAVLGE HDLSEHDGDE QSRRVAQVII PSTYVPGTTN

HDIALLRLHQ PVVLTDHVVP LCLPERTFSE RTLAFVRFSL

VSGWGQLLDR GATALELMVL NVPRLMTQDC LQQSRKVGDS

PNITEYMFCA GYSDGSKDSC KGDSGGPHAT HYRGTWYLTG

IVSWGQGCAT VGHFGVYTRV SQYIEWLQKL MRSEPRPGVL

LRAPFPSSSS KAPPPSLPSP SRLPGPSDTP ILPQSSSSKA

PPPSLPSPSR LPGPSDTPIL PQSSSSKAPP SLPSPSRLP

GPSDTPILPQ.

In another embodiment, the amino acid sequence of activated Factor VII-CTP-CTP-CTP (attached to the carboxy terminus) (FVIIa-CTP$_3$) lacks a signal peptide and comprises the amino acid sequence as put forth in SEQ ID NO: 7. In another embodiment, FVIIa-CTP$_3$ lacks a signal peptide and comprises a homolog of SEQ ID NO: 7. In another embodiment, FVIIa-CTP$_3$ lacks a signal peptide and comprises a variant of SEQ ID NO: 7. In another embodiment, the amino acid sequence of FVIIa-CTP$_3$ is cleaved between arginine (R) at residue 152 and isoleucine (I) at residue 153. In another embodiment, the amino acid sequence of FVIIa-CTP$_3$ is structurally present as a disulfide-linked two chain heterodimer comprising a disulfide S—S bridge between cysteine residues present on each of the chains. In another embodiment, the amino acid sequence of FVIIa-CTP$_3$ is structurally present as a heterodimer comprising a light-chain and a heavy-chain linked by a disulfide —S—S— bond between a cysteine residue present in the light-chain and a cysteine residue present in the heavy chain. In another embodiment, the light chain comprises an N-terminal fragment of the FVIIa-CTP3 amino acid sequence and the heavy chain comprises a C-terminal fragment of the FVIIa-CTP3 amino acid sequence. In another embodiment, the cysteine residues may be any cysteine residue in either chain. In another embodiment, the amino acid sequence of FVIIa-CTP$_3$ is structurally present as a disulfide-linked two chain heterodimer comprising an S—S bridge between cysteine residue 135 and cysteine residue 262 of SEQ ID NO: 7, wherein said two chains comprise a light chain comprising amino acids 1-152 and a heavy chain comprising amino acids 153-490 of SEQ ID NO: 7.

In another embodiment, a light chain migrates at about 25 kDA in an SDS-PAGE under denaturing conditions. In another embodiment, a heavy chain migrates at about 50 kDA in an SDS-PAGE under denaturing conditions. In another embodiment, a heavy chain migrates at about 60 kDA in an SDS-PAGE under denaturing conditions.

In another embodiment, the light chain of an activated FVII modified by attacing 3 CTPs on its C-terminal (FVIIa-CTP-CTP-CTP) comprises SEQ ID NO: 8

```
                                          (SEQ ID NO: 8)
ANAFLEELRPGSLERECKEEQCSFEEAREIFKDAERTKLFWISYSDGD

QCASSPCQNGGSCKDQLQSYICFCLPAFEGRNCETHKDDQLICVNENG

GCEQYCSDHTGTKRSCRCHEGYSLLADGVSCTPTVEYPCGKIPILEKR

NASKPQGR.
```

In another embodiment, the heavy chain of an activated FVII modified by attacing 3 CTPs on its C-terminal (FVIIa-CTP-CTP-CTP) comprises SEQ ID NO: 9

```
                                          (SEQ ID NO: 9)
IVGGKVCPKGECPWQVLLLVNGAQLCGGTLINTIWVVSAAHCFDKIK

NWRNLIAVLGEHDLSEHDGDEQSRRVAQVIIPSTYVPGTTNHDIALL

RLHQPVVLTDHVVPLCLPERTFSERTLAFVRFSLVSGWGQLLDRGAT

ALELMVLNVPRLMTQDCLQQSRKVGDSPNITEYMFCAGYSDGSKDSC

KGDSGGPHATHYRGTWYLTGIVSWGQGCATVGHFGVYTRVSQYIEWL

QKLMRSEPRPGVLLRAPFPSSSSKAPPPSLPSPSRLPGPSDTPILPQ

SSSSKAPPPSLPSPSRLPGPSDTPILPQSSSSKAPPPSLPSPSRLPG

PSDTPILPQ
```

In another embodiment, furin is added to a cell expressing the coagulation factor-CTP of the disclosure. In another embodiment, furin increases the production efficiency of a coagulation factor-CTP of the disclosure in a cell. In another embodiment, furin is co-transfected with the vector comprising the coding sequence of the coagulation factor-CTP of the disclosure. In another embodiment, furin is encoded by a separate vector. In another embodiment, furin and a coagulation factor-CTP are encoded by one vector. In another embodiment, the coding sequence of furin is inserted into pCI-DHFR. In another embodiment, the coding sequence of furin is engineered in pCI-dhfr/smaI+NotI, Furin/AsisI F.I.+NotI.

In another embodiment, the nucleic acid sequence encoding furin comprises the following nucleic acid sequence:

```
                                         (SEQ ID NO: 10)
tctagagtcgacccgccatggagctgaggccctggagctatgggtg gtagcagcaacaggaaccaggtcctgctagcagctgatgctcagggc cagaaggtcttcaccaacacgtgggctgtgcgcatccctggaggccc agcggtggccaacagtgtggcacggaagcatgggacctcaacctggg ccagatatcggggactattaccacactggcatcgaggagtgacgaag cggtccctgtcgcctcaccgcccgcggcacagccggctgcagaggga gcctcaagtacagtggctggaacagcaggtggcaaagcgacggacta aacgggacgtgtaccaggagcccacagaccccaagtacctcagcagt ggtacctgtctggtgtcactcagcgggacctgaatgtgaaggcggcc tgggcgcagggctacacagggcacggcattgtggtctccattctgga cgatggcatcgagaagaaccacccggacttggcaggcaattatgatc ctggggccagattgatgtcaatgaccaggaccctgaccccagcctc ggtacacacagatgaatgacaacaggcacggcacacggtgtgcgggg gaagtggctgcggtggccaacaacggtgtctgtggtgtaggtgtggc ctacaacgcccgcattggaggggtgcgcatgctggatggcgaggtga cagatgcagtggaggcacgctcgctgggcctgaaccccaaccacatc cacatctacagtgccagctggggccccgaggatgacggcaagacagt ggatgggccagcccgcctcgccgaggaggccacttccgtggggttag ccagggccgagggggctgggctccatctagtctgggcctcggggaa cgggggccgggaacatgacagctgcaactgcgacggctacaccaaca gtatctacacgctgtccatcagcagcgccacgcagtaggcaacgtgc cgtggtacagcgaggcctgctcgtccacactggccacgacctacagc agtggcaaccagaatgagaagcagatcgtgacgactgacttgcggca gaagtgcacggagtctcacacgggcacctcagcctctgccccttag cagccggcatcattgctctcaccctggaggccaataagaacctcaca tggcgggacatgcaacacctggtggtacagacctcgaagccagccca cctcaatgccaacgactgggccaccaatggtgtgggccggaaagtga gccactcatatggctacgggcttaggacgcaggcgccatggtggccc tggcccagaattggaccacagtggccccccagcggaagtgcatcatc gacatcctcaccgagcccaaagacatcgggaaacggctcgaggtgcg gaagaccgtgaccgcgtgcctgggcgagcccaaccacatcactcggc tggagcacgctcaggcgcggctcaccctgtcctataatcgccgtggc gacctggccatccacctggtcagcccatgggcacccgctccaccct gctggcagccaggccacatgactactccgcagatgggataatgactg ggcatcatgacaactcattcctgggatgaggatccctctggcgagtg ggtcctagagattgaaaacaccagcgaagccaacaactatgggacgc tgaccaagttcaccctcgtactctatggcaccgccctgagggctg
```

```
cccgtacctccagaaagcagtggctgcaagaccctcacgtccagtca ggcctgtgtggtgtgcgaggaaggcttctccctgcaccagaagagct gtgtccagcactgccctccaggcttcgcccccaagtcctcgatacg cactatagcaccgagaatgacgtggagaccatccgggccagcgtctg cgcccctgccacgcctcatgtgccacatgccaggggccggccctga cagactgcctcagctgcccagccacgcctccaggaccctgtggagc agacttgctcccggcaaagccagagcagccgagagtccccgccacag cagcagccacctcggctgccccggaggtggaggcggggcaacggct gcgggcagggctgctgccctcacacctgcctgaggtggtggccggcc tcagctgcgccttcatcgtgctggtcttcgtcactgtcttcctggtc ctgcagctgcgctctggctttagttttcgggggggtgaaggtgtacac catggaccgtggcctcatctcctacaaggggctgcccctgaagcct ggcaggaggagtgcccgtctgactcagaagaggacgagggccggggc gagaggaccgccatatcaaagaccagagcgccctctgaacgcggccg c.
```

In another embodiment, the amino acid sequence of furin comprises the following amino acid sequence:

```
                                          (SEQ ID NO: 11)
MELRPWLLWVVAATGTLVLLAADAQGQKVFTNTWAVRIPGGPAVAN

SVARKHGFLNLGQIFGDYYHFWHRGVTKRSLSPHRPRHSRLQREPQ

VQWLEQQVAKRRTKRDVYQEPTDPKFPQQWYLSGVTQRDLNVKAAW

AQGYTGHGIVVSILDDGIEKNHPDLAGNYDPGASFDVNDQDPDPQP

RYTQMNDNRHGTRCAGEVAAVANNGVCGVGVAYNARIGGVRMLDGE

VTDAVEARSLGLNPNHIHIYSASWGPEDDGKTVDGPARLAEEAFFR

GVSQGRGGLGSIFVWASGNGGREHDSCNCDGYTNSIYTLSISSATQ

FGNVPWYSEACSSTLATTYSSGNQNEKQIVTTDLRQKCTESHTGTS

ASAPLAAGIIALTLEANKNLTWRDMQHLVVQTSKPAHLNANDWATN

GVGRKVSHSYGYGLLDAGAMVALAQNWTTVAPQRKCIIDILTEPKD

IGKRLEVRKTVTACLGEPNHITRLEHAQARLTLSYNRRGDLAIHLV

SPMGTRSTLLAARPHDYSADGFNDWAFMTTHSWDEDPSGEWVLEIE

NTSEANNYGTLTKFTLVLYGTAPEGLPVPPESSGCKTLTSSQACVV

CEEEGFSLHQKSCVQHCPPGFAPQVLDTHYSTENDVETIRASVCAPC

HASCATCQGPALTDCLSCPSHASLDPVEQTCSRQSQSSRESPPQQQ

PPRLPPEVEAGQRLRAGLLPSHLPEVVAGLSCAFIVLVFVTVFLVL

QLRSGFSPRGVKVYTMDRGLISYKGLPPEAWQEECPSDSEEDEGRG

ERTAFIKDQSAL.
```

In one embodiment, the term coagulation factor further includes a homologue of a known coagulation factor. In one embodiment, the homologue has a coagulating activity. In some embodiments, homology according to the present invention also encompasses deletion, insertion, or substitution variants, including an amino acid substitution, thereof and biologically active polypeptide fragments thereof. In one embodiment, the variant comprises conservative substitutions, or deletions, insertions, or substitutions that do not significantly alter the three dimensional structure of the coagulation factor. In another embodiment, the deletion, insertion, or substitution does not alter the function of interest of the coagulation factor, which in one embodiment, is binding to a particular binding partner.

In another embodiment, the disclosure includes a homologue of a coagulation factor. In another embodiment, the disclosure includes a homologue of a coagulation factor having a coagulation activity. In another embodiment, the disclosure includes a homologue of a coagulation factor having functional binding. In another embodiment, the disclosure includes homologues of a coagulation factor as described herein having a coagulation activity. In another embodiment, the disclosure includes homologues of a coagulation factor as described herein having functional binding. In another embodiment, homologues e.g., polypeptides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to a coagulation factor as determined using BlastP software of the National Center of Biotechnology Information (NCBI) using default parameters.

In another embodiment, a [(CTP)n>1-coagulation factor] as described herein comprises a full length coagulation factor or an active fragment thereof connected via a peptide bond on its carboxy terminus to at least one CTP unit with no CTPs on its amino terminus. In another embodiment, a [(CTP)n>1-coagulation factor] as described herein comprises a coagulation factor or an active fragment thereof connected via a peptide bond to at least one CTP unit which is connected to an additional CTP unit via a peptide bond with no CTPs on its amino terminus. In another embodiment, one nucleic acid molecule encodes an engineered coagulation factor comprising at least one CTP attached to its C-terminus and no CTPs on its amino terminus.

In another embodiment, the CTP is attached to the coagulation factor via a linker. In another embodiment, the linker which connects the CTP sequence to the coagulation factor is a covalent bond. In another embodiment, the linker which connects the CTP sequence to the coagulation factor is a peptide bond. In another embodiment, the linker which connects the CTP sequence to the coagulation factor is a substituted peptide bond. In another embodiment, the CTP sequence comprises: DPRFQDSSSSKAPPPSLPSPSRLPGPSDTPIL (SEQ ID NO: 12). In another embodiment, the CTP sequence comprises: SSSSKAPPPSLPSPSRLPGPSDTPILPQ (SEQ ID NO: 13). In another embodiment, the CTP sequence comprises an amino acid sequence selected from the sequences set forth in SEQ ID NO: 12 and SEQ ID NO: 13.

In another embodiment, the carboxy terminal peptide (CTP) peptide disclosed herein comprises the amino acid sequence from amino acid 112 to position 145 of human chorionic gonadotropin, as set forth in SEQ ID NO: 12. In another embodiment, the CTP sequence disclosed herein comprises the amino acid sequence from amino acid 118 to position 145 of human chorionic gonadotropin, as set forth in SEQ ID NO: 13. In another embodiment, the CTP sequence also commences from any position between positions 112-118 and terminates at position 145 of human chorionic gonadotropin. In some embodiments, the CTP sequence peptide is 28, 29, 30, 31, 32, 33 or 34 amino acids long and commences at position 112, 113, 114, 115, 116, 117 or 118 of the CTP amino acid sequence.

In another embodiment, the CTP peptide is a variant of chorionic gonadotropin CTP which differs from the native CTP by 1-5 conservative amino acid substitutions as described in U.S. Pat. No. 5,712,122, which is incorporated herein by reference. In another embodiment, the CTP peptide is a variant of chorionic gonadotropin CTP which differs from the native CTP by 1 conservative amino acid substitution. In another embodiment, the CTP peptide is a variant of chorionic gonadotropin CTP which differs from the native CTP by 2 conservative amino acid substitutions. In another embodiment, the CTP peptide is a variant of chorionic gonadotropin CTP which differs from the native CTP by 3 conservative amino acid substitutions. In another embodiment, the CTP peptide is a variant of chorionic gonadotropin CTP which differs from the native CTP by 4 conservative amino acid substitutions. In another embodiment, the CTP peptide is a variant of chorionic gonadotropin CTP which differs from the native CTP by 5 conservative amino acid substitutions.

In another embodiment, the CTP peptide amino acid sequence disclosed herein is at least 70% homologous to the native CTP amino acid sequence or a peptide thereof. In another embodiment, the CTP peptide amino acid sequence disclosed herein is at least 80% homologous to the native CTP amino acid sequence or a peptide thereof. In another embodiment, the CTP peptide amino acid sequence disclosed herein is at least 90% homologous to the native CTP amino acid sequence or a peptide thereof. In another embodiment, the CTP peptide amino acid sequence disclosed herein is at least 95% homologous to the native CTP amino acid sequence or a peptide thereof. In another embodiment, the CTP peptide amino acid sequence disclosed herein is at least 98% homologous to the native CTP amino acid sequence or a peptide thereof.

In another embodiment, the polynucleotide encoding the CTP peptide disclosed herein is at least 70% homologous to the native human CTP DNA sequence or a peptide thereof. In another embodiment, the polynucleotide encoding the CTP peptide disclosed herein is at least 80% homologous to the native human CTP DNA sequence or a peptide thereof. In another embodiment, the polynucleotide encoding the CTP peptide disclosed herein is at least 90% homologous to the native CTP DNA sequence or a peptide thereof. In another embodiment, the polynucleotide encoding the CTP peptide disclosed herein is at least 95% homologous to the native CTP DNA sequence or a peptide thereof. In another embodiment, the polynucleotide encoding the CTP peptide disclosed herein is at least 98% homologous to the native CTP DNA sequence or a peptide thereof.

In one embodiment, at least one of the chorionic gonadotropin CTP amino acid sequences is truncated. In another embodiment, both of the chorionic gonadotropin CTP amino acid sequences are truncated. In another embodiment, 2 of the chorionic gonadotropin CTP amino acid sequences are truncated. In another embodiment, 3 of the chorionic gonadotropin CTP amino acid sequences are truncated. In another embodiment, 4 of the chorionic gonadotropin CTP amino acid sequences are truncated. In another embodiment, 5 of the chorionic gonadotropin CTP amino acid sequences are truncated. In another embodiment, 2 or more of the chorionic gonadotropin CTP amino acid sequences are truncated. In another embodiment, all of the chorionic gonadotropin CTP amino acid sequences are truncated. In one embodiment, the truncated CTP comprises the first 10 amino acids of SEQ ID NO: 14. In another embodiment, SEQ ID NO: 14 comprises the following amino acid (AA) sequence: SSSSKAPPPSLP. In another embodiment, the first 10 amino acids of SEQ ID NO: 14 are set for in SEQ ID NO: 15: SSSSKAPPPS.

In one embodiment, the truncated CTP comprises the first 10 amino acids of SEQ ID NO: 13.

In one embodiment, the truncated CTP comprises the first 11 amino acids of SEQ ID NO: 13. In one embodiment, the truncated CTP comprises the first 12 amino acids of SEQ ID NO: 13. In one embodiment, the truncated CTP comprises the first 8 amino acids of SEQ ID NO: 13 or SEQ ID NO: 14. In one embodiment, the truncated CTP comprises the first 13 amino acids of SEQ ID NO: 13. In one embodiment, the truncated CTP comprises the first 14 amino acids of SEQ ID NO: 13. In one embodiment, the truncated CTP comprises the first 6 amino acids of SEQ ID NO: 13 or SEQ ID NO: 14. In one embodiment, the truncated CTP comprises the first 5 amino acids of SEQ ID NO: 13 or SEQ ID NO: 14.

In one embodiment, at least one of the chorionic gonadotropin CTP amino acid sequences is glycosylated. In another embodiment, 2 of the chorionic gonadotropin CTP amino acid sequences are glycosylated. In another embodiment, 3 of the chorionic gonadotropin CTP amino acid sequences are glycosylated. In another embodiment, 4 of the chorionic gonadotropin CTP amino acid sequences are glycosylated. In another embodiment, 5 of the chorionic gonadotropin CTP amino acid sequences are glycosylated. In another embodiment, 2 or more of the chorionic gonadotropin CTP amino acid sequences are glycosylated. In another embodiment, all of the chorionic gonadotropin CTP amino acid sequences are glycosylated.

In one embodiment, the CTP sequence disclosed herein comprises at least one glycosylation site. In one embodiment, the CTP sequence disclosed herein comprises 2 glycosylation sites. In one embodiment, the CTP sequence disclosed herein comprises 3 glycosylation sites. In one embodiment, the CTP sequence disclosed herein comprises 4 glycosylation sites. In one embodiment, one or more of the chorionic gonadotropin CTP amino acid sequences is fully glycosylated. In another embodiment, one or more of the chorionic gonadotropin CTP amino acid sequences is partially glycosylated. In one embodiment, partially glycosylated indicates that one of the CTP glycosylation sites is glycosylated. In another embodiment, two of the CTP glycosylation sites are glycosylated. In another embodiment, three of the CTP glycosylation sites are glycosylated.

In some embodiments, the CTP sequence modification is advantageous in permitting the usage of lower dosages. In some embodiments, the CTP sequences modification is advantageous in permitting fewer dosages. In some embodiments, the CTP sequences modification is advantageous in permitting a safe, long-acting effect.

In some embodiments, "polypeptide", "engineered coagulation factor", or "protein" as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which have, in some embodiments, modifications rendering the polypeptides comprising a coagulation factor even more stable while in a body or more capable of penetrating into cells.

In some embodiments, modifications include, but are limited to C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

In some embodiments, polypeptide bonds (—CO—NH—) within the polypeptide are substituted. In some embodiments, the polypeptide bonds are substituted by N-methylated bonds (—N(CH3)-CO—). In some embodiments, the polypeptide bonds are substituted by ester bonds (—C(R)H—C—O—O—C(R)—N—). In some embodiments, the polypeptide bonds are substituted by ketomethylen bonds (—CO—CH2-). In some embodiments, the polypeptide bonds are substituted by α-aza bonds (—NH—N(R)—CO—), wherein R is any alkyl, e.g., methyl, carba bonds (—CH2-NH—). In some embodiments, the polypeptide bonds are substituted by hydroxyethylene bonds (—CH(OH)—CH2-). In some embodiments, the polypeptide bonds are substituted by thioamide bonds (—CS—NH—). In some embodiments, the polypeptide bonds are substituted by olefinic double bonds (—CH=CH—). In some embodiments, the polypeptide bonds are substituted by retro amide bonds (—NH—CO—). In some embodiments, the polypeptide bonds are substituted by polypeptide derivatives (—N(R)—CH2-CO—), wherein R is the "normal" side chain, naturally presented on the carbon atom. In some embodiments, these modifications occur at any of the bonds along the polypeptide chain and in one embodiment at several (2-3 bonds) at the same time.

In some embodiments, natural aromatic amino acids of the polypeptide such as Trp, Tyr and Phe, are substituted for synthetic non-natural acid such as Phenylglycine, TIC, naphthylelanine (Nol), ring-methylated derivatives of Phe, halogenated derivatives of Phe or o-methyl-Tyr. In some embodiments, the polypeptides disclosed herein include one or more modified amino acid or one or more non-amino acid monomers (e.g. fatty acid, complex carbohydrates etc).

In some embodiments, the natural amino acid, glutamic acid (Glu), is post-translationally carboxylated, resulting in the presence of carboxyglutamic acid (Gla) in a CTP-modified FVII or CTP-modified FVIIa described herein.

In one embodiment, "amino acid" or "amino acid sequence" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acids.

In some embodiments, the polypeptides disclosed herein are utilized in therapeutics which requires the polypeptides comprising a coagulation factor to be in a soluble form. In some embodiments, the polypeptides disclosed herein include one or more non-natural or natural polar amino acid, including but not limited to serine and threonine which are capable of increasing polypeptide solubility due to their hydroxyl-containing side chain.

In some embodiments, the engineered coagulation factor disclosed herein is utilized in a linear form, although it will be appreciated by one skilled in the art that in cases where cyclicization does not severely interfere with engineered coagulation factors characteristics, cyclic forms of the engineered coagulation factors can also be utilized.

In some embodiments, the engineered coagulation factors disclosed herein are biochemically synthesized such as by using standard solid phase techniques. In some embodiments, these biochemical methods include exclusive solid phase synthesis, partial solid phase synthesis, fragment condensation, or classical solution synthesis.

In some embodiments, recombinant protein techniques are used to generate the engineered coagulation factors disclosed herein. In some embodiments, recombinant protein techniques are used for the generation of relatively long polypeptides (e.g., longer than 18-25 amino acids). In some embodiments, recombinant protein techniques are used for the generation of large amounts of the engineered coagulation factors disclosed herein. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463, which are incorporated herein by reference in their entirety.

In another embodiment, the disclosure provides a polynucleotide molecule comprising the coding portion of a gene encoding a polypeptide comprising a coagulation factor and gonadotropin carboxy terminal peptides attached to the carboxy terminus of the coagulation factor, as described hereinabove. In another embodiment, the disclosure provides a polynucleotide molecule consisting of the coding portion of a gene encoding a polypeptide comprising a coagulation factor and gonadotropin carboxy terminal peptides attached to the carboxy terminus of the coagulation factor, as described hereinabove. In another embodiment, the disclosure provides a polynucleotide molecule consisting essentially of the coding portion of a gene encoding a polypeptide comprising a coagulation factor and gonadotropin carboxy terminal peptides attached to the carboxy terminus of the coagulation factor, as described hereinabove.

In another embodiment, the disclosure provides a polynucleotide encoding a polypeptide comprising a coagulation factor and three gonadotropin carboxy terminal peptides attached to the carboxy terminus of the coagulation factor, as described hereinabove. In another embodiment, the disclosure provides a polynucleotide encoding a polypeptide consisting of a coagulation factor and three gonadotropin carboxy terminal peptides attached to the carboxy terminus of the coagulation factor, as described hereinabove. In another embodiment, the disclosure provides a polynucleotide encoding a polypeptide consisting essentially of a coagulation factor and three gonadotropin carboxy terminal peptides attached to the carboxy terminus of the coagulation factor, as described hereinabove. In one embodiment, the polynucleotide is a polynucleotide sequence. In one embodiment, the polynucleotide is a polynucleotide molecule.

In another embodiment, the disclosure provides an expression vector comprising a polynucleotide molecule as described herein. In another embodiment, disclosed herein is an expression vector comprising a polynucleotide encoding a CTP-modified polypeptide consisting of a Factor VII polypeptide and three gonadotropin carboxy terminal peptides (CTPs) attached to the carboxy terminus of said FVII polypeptide. In another embodiment, the CTP-modified FVII expressed from an expression vector described herein, may be activated at some time point following expression, resulting in CTP-modified FVIIa.

In another embodiment, the disclosure provides a cell comprising the expression vector as described herein. In another embodiment, disclosed herein is a cell comprising an expression vector comprising a polynucleotide encoding a CTP-modified polypeptide consisting of a Factor VII (FVII) polypeptide and three gonadotropin carboxy terminal peptides (CTPs) attached to the carboxy terminus of said FVIIa polypeptide. In another embodiment, a CTP-FVII expressed from an expression vector described herein and comprised within a cell, may be activated following secretion from the cell.

In another embodiment, the disclosure provides a composition comprising the expression vector as described herein. In another embodiment, disclosed herein is a composition comprising an expression vector comprising a polynucleotide encoding a CTP-modified polypeptide consisting of a Factor VII (FVII) polypeptide and three gonadotropin carboxy terminal peptides (CTPs) attached to the carboxy terminus of said FVIIa polypeptide.

In another embodiment, the disclosure provides a composition comprising the cell as described herein. In another embodiment, the cell is a eukaryotic cell. In another embodiment, the cell is a prokaryotic cell.

In one embodiment, disclosed herein is a method of producing a CTP-modified FVII, comprising the step of attaching three chorionic gonadotropin carboxy terminal peptides (CTPs) to the carboxy terminus of said FVII, thereby producing a CTP-modified FVII.

In another embodiment, the engineered coagulation factors disclosed herein are synthesized using a polynucleotide molecule encoding a polypeptide as disclosed herein. In some embodiments, the polynucleotide molecule encoding the engineered coagulation factors is ligated into an expression vector, comprising a transcriptional control of a cis-regulatory sequence (e.g., promoter sequence). In some embodiments, the cis-regulatory sequence is suitable for directing constitutive expression of an engineered coagulation factor disclosed herein. In some embodiments, the cis-regulatory sequence is suitable for directing tissue-specific expression of the engineered coagulation factors. In some embodiments, the cis-regulatory sequence is suitable for directing inducible expression of the engineered coagulation factors.

In some embodiment, tissue-specific promoters suitable for use with the present disclosure include sequences which are functional in one or more specific cell populations. Examples include, but are not limited to, promoters such as albumin that is liver-specific [Pinkert et al., (1987) Genes Dev. 1:268-277], lymphoid-specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166). Inducible promoters suitable for use with the present invention include, for example, the tetracycline-inducible promoter (Srour, M. A., et al., 2003. Thromb. Haemost. 90: 398-405).

In one embodiment, the phrase "a polynucleotide molecule" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

In one embodiment, a "complementary polynucleotide sequence" refers to a sequence, which results from reverse transcription of messenger RNA using a reverse transcriptase or any other RNA-dependent DNA polymerase. In one embodiment, the sequence can be subsequently amplified in vivo or in vitro using a DNA polymerase.

In one embodiment, a "genomic polynucleotide sequence" refers to a sequence derived (isolated) from a chromosome and thus it represents a contiguous portion of a chromosome.

In one embodiment, a "composite polynucleotide sequence" refers to a sequence, which is at least partially complementary and at least partially genomic. In one embodiment, a composite sequence can include some exonal sequences required to encode the polypeptide disclosed herein, as well as some intronic sequences interposing therebetween. In one embodiment, the intronic sequences can be of any source, including of other genes, and typically will include conserved splicing signal sequences. In one embodiment, intronic sequences include cis-acting expression regulatory elements.

In one embodiment, following expression and prior to secretion, the signal peptides are cleaved from the precursor engineered coagulation factors resulting in the mature engineered coagulation factors lacking a signal peptide. In another embodiment, following secretion said mature engineered coagulation factor is activated.

In some embodiments, polynucleotides disclosed herein are prepared using PCR techniques, or any other method or procedure known to one skilled in the art. In some embodiments, the procedure involves the ligation of two different DNA sequences (See, for example, "Current Protocols in Molecular Biology", eds. Ausubel et al., John Wiley & Sons, 1992).

In one embodiment, polynucleotides disclosed herein which encode the engineered coagulation factors are inserted into expression vectors (i.e., a nucleic acid construct) to enable expression of the recombinant polypeptide. In one embodiment, the expression vector disclosed herein includes additional sequences which render this vector suitable for replication and integration in prokaryotes. In one embodiment, the expression vector disclosed herein includes additional sequences which render this vector suitable for replication and integration in eukaryotes. In one embodiment, the expression vector disclosed herein includes a shuttle vector which renders this vector suitable for replication and integration in both prokaryotes and eukaryotes. In some embodiments, cloning vectors comprise transcription and translation initiation sequences (e.g., promoters, enhances) and transcription and translation terminators (e.g., polyadenylation signals).

In one embodiment, a variety of prokaryotic or eukaryotic cells can be used as host-expression systems to express the coagulation factors disclosed herein. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In some embodiments, non-bacterial expression systems are used (e.g. mammalian expression systems such as CHO cells) to express the coagulation factors disclosed herein. In one embodiment, the expression vector used to express polynucleotides disclosed herein in mammalian cells is pCI-DHFR vector comprising a CMV promoter and a neomycin resistance gene. Construction of the pCI-dhfr vector is described, according to one embodiment, in International Application No. PCT/IL2016/050645, which is incorporated herein in full.

In some embodiments, in bacterial systems disclosed herein, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion proteins are engineered with a specific cleavage site to aid in recovery of the polypeptide. In one embodiment, vectors adaptable to such manipulation include, but are not limited to, the pET series of E. coli expression vectors [Studies et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447, which is incorporated by reference herein in its entirety. In another embodiment, vectors which promote integration of foreign DNA sequences into the yeast chromosome are used.

In one embodiment, the expression vector disclosed herein can further include additional polynucleotide sequences that allow, for example, the translation of several proteins from a single mRNA such as an internal ribosome entry site (IRES) and sequences for genomic integration of the promoter-chimeric polypeptide.

In some embodiments, recombinant viral vectors are useful for in vivo expression of the coagulation factors disclosed herein since they offer advantages such as lateral infection and targeting specificity. In one embodiment, lateral infection is inherent in the life cycle of, for example, a retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector disclosed herein into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992, incorporated herein by reference, for positive-negative selection methods.

In some embodiments, introduction of nucleic acid by viral infection offers several advantages over other methods such as lipofection and electroporation, since higher transfection efficiency can be obtained due to the infectious nature of viruses.

In one embodiment, it will be appreciated that the engineered coagulation factors disclosed herein can also be expressed from a nucleic acid construct administered to the individual employing any suitable mode of administration, described hereinabove (i.e., in vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex vivo gene therapy).

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct disclosed herein can also include sequences engineered to optimize stability, production, purification, yield or activity of the expressed polypeptide.

In some embodiments, transformed cells are cultured under effective conditions, which allow for the expression of high amounts of recombinant engineered coagulation factors. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide disclosed herein. In some embodiments, a medium typically includes an aqueous solution having assimilable carbon, nitrogen and phosphate sources, and appropriate salts, minerals, metals and other nutrients, such as vitamins. In some embodiments, cells disclosed herein can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, the determination of culturing conditions are within the expertise of one of ordinary skill in the art.

In some embodiments, depending on the vector and host system used for production, resultant engineered coagulation factors disclosed herein either remain within the recombinant cell, are secreted into the fermentation medium, are secreted into a space between two cellular membranes, such as the periplasmic space in *E. coli*; or are retained on the outer surface of a cell or viral membrane.

In one embodiment, following a predetermined time in culture, recovery of the recombinant engineered coagulation factor is effected.

In one embodiment, the phrase "recovering the recombinant engineered coagulation factor" used herein refers to collecting the whole fermentation medium containing the polypeptide and need not imply additional steps of separation or purification.

In one embodiment, engineered coagulation factors disclosed herein are purified using a variety of standard protein purification techniques, such as, but not limited to, affinity chromatography, ion exchange chromatography, filtration, electrophoresis, hydrophobic interaction chromatography (HIC), gel filtration chromatography, reverse phase chromatography, concanavalin A chromatography, chromatofocusing and differential solubilization.

In one embodiment, a type of hydrophobic interaction column is Capto Phenil Impress (CIP) column.

In one embodiment, to facilitate recovery, the expressed coding sequence can be engineered to encode the engineered coagulation factor disclosed herein and fused cleavable moiety. In one embodiment, a fusion protein can be designed so that the polypeptide can be readily isolated by affinity chromatography; e.g., by immobilization on a column specific for the cleavable moiety. In one embodiment, a cleavage site is engineered between the engineered coagulation factor and the cleavable moiety and the polypeptide can be released from the chromatographic column by treatment with an appropriate enzyme or agent that specifically cleaves the fusion protein at this site [e.g., see Booth et al., Immunol. Lett. 19:65-70 (1988); and Gardena et al., J. Biol. Chem. 265:15854-15859 (1990)].

In one embodiment, the engineered coagulation factor disclosed herein is retrieved in "substantially pure" form. In another embodiment, a substantially pure engineered coagulation factor may further comprise the active form of the coagulation factor. In another embodiment, a substantially pure form is at least 90% pure. In another embodiment, a substantially pure form is at least 95-99% pure.

In one embodiment, the engineered coagulation factor disclosed herein can also be synthesized using in vitro expression systems. In one embodiment, in vitro synthesis methods are well known in the art and the components of the system are commercially available.

In some embodiments, the recombinant engineered coagulation factors are synthesized and purified; their therapeutic efficacy can be assayed either in vivo or in vitro. In one embodiment, the binding activities of the recombinant engineered coagulation factors disclosed herein can be ascertained using various assays as known to one of skill in the art.

It is to be understood that the polypeptides, compositions, formulations and methods disclosed herein comprising the elements or steps as described herein may, in another embodiment, consist of those elements or steps, or in another embodiment, consist essentially of those elements or steps. In some embodiments, the term "comprise" refers to the inclusion of the indicated active agent, such as the CTP-modified coagulation factor, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

In another embodiment, disclosed herein are a polynucleotide encoding a CTP-modified polypeptide consisting of a Factor VII (FVII) polypeptide and three gonadotropin carboxy terminal peptides (CTPs) attached to the carboxy terminus of said FVII polypeptide. In another embodiment, disclosed herein is a composition comprising an expression vector comprising a polynucleotide encoding a Factor VII (FVII) polypeptide and three gonadotropin carboxy terminal peptides (CTPs) attached to the carboxy terminus of said FVIIa polypeptide. In one embodiment, the CTP-modified FVII includes a signal peptide. In another embodiment, the CTP-modified FVII does not include a signal peptide.

In one embodiment, disclosed herein is a recombinant coagulation factor as described hereinabove. In one embodiment, disclosed herein is an engineered coagulation factor as described hereinabove. In one embodiment, the engineered coagulation factor as described hereinabove is referred to as a CTP-modified coagulation factor.

In one embodiment, the CTPs that are attached to the carboxy terminus of the coagulation factor are attached in tandem to the carboxy terminus.

In one embodiment, an engineered coagulation factor as described herein has equivalent or improved biological activity compared to the non-CTP-modified coagulation factor. In another embodiment, an engineered coagulation factor as described herein has equivalent or improved pharmacological measurements compared to the non-CTP-modified coagulation factor. In another embodiment, an engineered coagulation factor as described herein has equivalent or improved pharmacokinetics compared to the non-CTP-modified coagulation factor. In another embodiment, an engineered coagulation factor as described herein has equivalent or improved pharmacodynamics compared to the non-CTP-modified coagulation factor.

In another embodiment, the terms "CTP peptide," "carboxy terminal peptide" and "CTP sequence" are used interchangeably herein. In another embodiment, the carboxy terminal peptide is a full-length CTP.

In other embodiments, the term engineered coagulation factor refers to the amino acid sequence of a matured coagulation factor. In other embodiments, the term engineered coagulation factor refers to the amino acid sequence of the coagulation factor including its signal sequence or signal peptide.

In another embodiment, "signal sequence" and "signal peptide" are used interchangeably herein having all the same qualities and meanings. In another embodiment, "sequence" when in reference to a polynucleotide molecule can refer to a coding portion. In another embodiment, an engineered coagulation factor comprising at least one CTP as described herein has enhanced in vivo biological activity compared the same coagulation factor without at least one CTP. In one embodiment, the enhanced biological activity stems from the longer half-life of the engineered coagulation factor while maintaining at least some biological activity. In another embodiment, the enhanced biological activity stems from enhanced biological activity resulting from the CTP modification. In another embodiment, the enhanced biological activity stems from both a longer half-life and from enhanced functionality of the CTP-modified coagulation factor.

In some embodiments, at least one CTP sequence at the carboxy terminal end of the coagulation factor provides enhanced protection against degradation of a coagulation factor. In some embodiments, at least one CTP sequence at the carboxy terminal end of the coagulation factor provides enhanced protection against clearance. In some embodiments, at least one CTP sequence at the carboxy terminal end of the coagulation factor provides prolonged clearance time. In some embodiments, at least one CTP sequence at the carboxy terminal end of the coagulation factor enhances its Cmax. In some embodiments, at least one CTP sequence at the carboxy terminal end of the coagulation factor enhances its Tmax. In some embodiments, at least one CTP sequence at the carboxy terminal end of the coagulation factor prolongs its T½.

In another embodiment, a conjugated coagulation factor of this invention is used in the same manner as an unmodified conjugated coagulation factor. In another embodiment, a conjugated coagulation factor of this invention has an increased circulating half-life and plasma residence time, decreased clearance, and increased clinical activity in vivo. In another embodiment, due to the improved properties of the conjugated coagulation factor as described herein, this conjugate is administered less frequently than the unmodified form of the same coagulation factor.

In another embodiment, decreased frequency of administration will result in improved treatment strategy, which in one embodiment, will lead to improved patient compliance leading to improved treatment outcomes, as well as improved patient quality of life. In another embodiment, compared to conventional conjugates of coagulation factors, it has been found that conjugates having the molecular weight and linker structure of the conjugates of this invention have an improved potency, improved stability, elevated AUC levels, and enhanced circulating half-life.

Compositions and Methods of Use

In another embodiment, the engineered coagulation factor disclosed herein can be provided to the individual per se. In one embodiment, the engineered coagulation factor disclosed herein can be provided to the individual as part of a pharmaceutical composition where it is mixed with a pharmaceutically acceptable carrier.

In one embodiment, a "pharmaceutical composition" or a "pharmaceutical formulation" refers to a preparation of one or more of the active ingredients described herein with other chemical components such as physiologically suitable carriers and excipients. The purpose of a pharmaceutical composition or a "pharmaceutical formulation" is to facilitate administration of a compound to an organism. In certain embodiments, a "pharmaceutical composition" or a "pharmaceutical formulation" provides the pharmaceutical dosage form of a drug. "Pharmaceutical compositions" or "pharmaceutical formulations" in certain embodiments include slow release technologies, transdermal patches, or any known dosage form in the art.

In another embodiment, "active ingredient" refers to the polypeptide sequence of interest, which is accountable for the biological effect.

In another embodiment, any of the compositions disclosed herein will comprise at least one CTP sequence bound only to the carboxy terminus of an engineered coagulation factor of interest, in any form. In one embodiment, disclosed herein is combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In another embodiment, disclosed herein is a pharmaceutical composition or a pharmaceutical formulation comprising a CTP-modified Factor VIIa (FVIIa) polypeptide consisting of a FVIIa polypeptide and three gonadotropin carboxy terminal peptides (CTPs) attached to the carboxy terminus of said FVIIa.

In another embodiment, provided herein is a composition comprising a conjugated coagulation factor as described herein. In another embodiment, provided herein is a pharmaceutical composition comprising the conjugated coagulation factor as described herein. In another embodiment, provided herein is a pharmaceutical composition comprising a therapeutically effective amount of the conjugated coagulation factor as described herein. In one embodiment, a therapeutically effective amount of a conjugated coagulation factor is determined according to factors such as the specific condition being treated, the condition of the patient being treated, as well as the other ingredients in the composition.

In one embodiment, the disclosure provides a pharmaceutical formulation for use in compositions, formulations, and methods of the disclosure. In another embodiment, the disclosure provides a pharmaceutical formulation comprising a polypeptide consisting of a coagulation factor and three chorionic gonadotropin carboxy terminal peptides attached to the carboxy terminus of the coagulation factor. In another embodiment, the pharmaceutical formulation further comprises a buffer and a tonicity agent. In another embodiment, the buffer is 20 mM citrate and 13.3 mM Glycine, and the tonicity agent is 150 mM NaCl. In another embodiment, the formulation is at about a pH of 6.4. In another embodiment, the buffer is 20 mM citrate and 13.3 mM Glycine, and the tonicity agent is 150 mM NaCl, and the pH is 6.4. In another embodiment, the buffer is 20 mM citrate, 100 mM Arginine, 2% Trehalose, and the pH is 6.2. In another embodiment, the formulation is a liquid formulation. In another embodiment, the formulation is a lyophilized formulation. In another embodiment, the liquid formulation may be formed using a lyophilized CTP-modified coagulation factor. In another embodiment, the CTP-modified coagulation factor is FVII-CTP3. In another embodiment, the CTP-modified coagulation factor is FVIIa-CTP3.

In another embodiment, provided herein is a once weekly dosage form comprising the pharmaceutical formulation provided herein. In another embodiment, provided herein is a once daily dosage form comprising the pharmaceutical formulation provided herein. In another embodiment, provided herein is an every other day dosage form comprising the pharmaceutical formulation provided herein. In another embodiment, provided herein is an every third day dosage form comprising the pharmaceutical formulation provided herein. In another embodiment, provided herein is a twice weekly dosage form comprising the pharmaceutical formulation provided herein. In another embodiment, provided herein is twice weekly dosage form comprising the pharmaceutical formulation provided herein. In another embodiment, provided herein is a weekly dosage form comprising the pharmaceutical formulation provided herein. In another embodiment, provided herein is a bi-weekly (every two weeks) dosage form comprising the pharmaceutical formulation provided herein.

In another embodiment, disclosed herein is a formulation comprising a polypeptide consisting of a coagulation factor and three chorionic gonadotropin CTPs attached to the carboxy terminus of said coagulation factor, and wherein said polypeptide optionally consists of a signal peptide, wherein said formulation has increased stability. In one embodiment, the formulation is stable for at least one year. In another embodiment, the formulation is stable for at least two years.

In one embodiment, a coagulation factor modified by CTPs is formulated in a liquid formulation. In another embodiment, a Factor VII modified by CTPs is formulated in a liquid formulation. In another embodiment, a Factor VIIa modified by CTPs is formulated in a liquid formulation. In another embodiment, coagulation factor modified by CTPs is formulated in an intranasal dosage form. In another embodiment, coagulation factor modified by CTPs is formulated in an injectable dosage form.

In another embodiment, the methods of the disclosure include increasing the compliance in the use of coagulation factor therapy, comprising providing to a subject in need thereof, a coagulation factor modified by CTPs, thereby increasing compliance in the use of coagulation factor therapy.

In another embodiment, a coagulation factor modified by CTPs is administered to a subject once a day. In another embodiment, a polypeptide comprising a coagulation factor modified by CTPs is administered to a subject once every two days. In another embodiment, a coagulation factor modified by CTPs is administered to a subject once every three days. In another embodiment, a coagulation factor modified by CTPs is administered to a subject once every four days. In another embodiment, a coagulation factor modified by CTPs is administered to a subject once every five days. In another embodiment, a coagulation factor modified by CTPs is administered to a subject once every six days. In another embodiment, a coagulation factor modified by CTPs is administered to a subject once every week. In another embodiment, a coagulation factor modified by CTPs is administered to a subject once every 7-14 days. In another embodiment, a coagulation factor modified by CTPs is administered to a subject once every 10-20 days. In another embodiment, a coagulation factor modified by CTPs is administered to a subject once every 5-15 days. In another embodiment, a coagulation factor modified by CTPs is administered to a subject once every 15-30 days.

In one embodiment, the preparation disclosed herein is formulated in liquid formulations for injection via a syringe or Pen device.

In one embodiment, the formulations provided herein also comprise preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise local anesthetics or other actives. The compositions can be used as sprays, mists, drops, and the like.

In one embodiment, a coagulation factor as described herein is a human coagulation factor.

In another embodiment, a conjugated coagulation factor as described herein is useful in the treatment of subjects afflicted with a coagulation or clotting disorder. In another embodiment, the coagulation or clotting disorder is Hemophilia. In another embodiment, a conjugated coagulation factor as described herein is useful in the prophylactic therapy of Hemophilia thus reducing the risk of bleeding and associated complications. In another embodiment, reducing the risk of bleeding and associated complications reduces the risk of spontaneous bleeding. In another embodiment, reducing the risk of bleeding and associated complications reduces the risk of excessive bleeding. In another embodiment, a conjugated coagulation factor as described herein is useful in the treatment of subjects afflicted with Hemophilia while reducing the risk of developing inhibitory antibodies to exogenously administered coagulation factors. In another embodiment, a conjugated coagulation factor as described herein is useful in the treatment of subjects afflicted with Hemophilia thus inducing to homeostasis.

In one embodiment, a CTP-modified coagulation factor disclosed herein has therapeutic uses. In another embodiment, a CTP-modified coagulation factor disclosed herein has prophylactic uses.

In another embodiment, a conjugated coagulation factor as described herein is useful in the treatment of subjects experiencing excessive bleeding or bruising or having a prolonged Prothrombin Time (PT) or Partial Thromboplastin Time (PTT). In another embodiment, a conjugated coagulation factor as described herein is useful in the treatment of subjects having an acquired condition that is causing bleeding, such as vitamin K deficiency or liver disease. In another embodiment, a conjugated coagulation factor as described herein is useful in the treatment of subjects having deficiencies in coagulation factors that are acquired (due to other diseases) or inherited, mild or severe, permanent or temporary. In another embodiment, a conjugated coagulation factor as described herein is useful in the treatment of subjects afflicted with hemophilia A. In another embodiment, a conjugated coagulation factor as described herein is useful in the treatment of subjects afflicted with hemophilia B. In another embodiment, a conjugated coagulation factor as described herein is useful in the treatment of subjects having acquired deficiencies due to chronic diseases, such as liver disease or cancer; to an acute condition such as disseminated intravascular coagulation (DIC), which uses up clotting factors at a rapid rate; or to a deficiency in vitamin K or treatment with a vitamin K antagonist like warfarin (the production of factors II, VII, IX, and X require vitamin K). In another embodiment, a conjugated coagulation factor as described herein is useful in the treatment of subjects afflicted with a disease in which causes clotting imbalances such as but not limited to: a liver disease, uremia, a cancer, a bone marrow disorder, an exposure to snake venom, a vitamin K deficiency, an anticoagulation therapy, an accidental ingestion of the anticoagulant warfarin, multiple blood transfusions (stored units of blood lose some of their clotting factors), or a combination thereof. In another embodiment, disclosed herein is a method of treating deep vein thrombosis in a subject comprising administering a CTP-modified coagulation factor disclosed herein. In another embodiment, disclosed herein is a method of preventing uncontrolled bleeding in a subject with hemophilia comprising administering a CTP-modified coagulation factor disclosed herein. In another embodiment, disclosed herein is a method of preventing bleeding episodes in a subject with hemophilia comprising administering a CTP-modified coagulation factor disclosed herein. In another embodiment, disclosed herein is a method of controlling bleeding episodes in a subject with hemophilia B (congenital factor IX deficiency).

In one embodiment, a composition of this invention comprises a formulation as described herein. In another embodiment, a method of this invention comprises administering a formulation as described herein. In another embodiment, a method of this invention comprises administering a composition comprising a formulation as described herein.

In one embodiment, disclosed herein is a method of preventing or treating a clotting or coagulation disorder. In another embodiment, disclosed herein is a method of preventing or treating hemophilia in a subject comprising administering a CTP-modified coagulation factor disclosed herein. In another embodiment, disclosed herein is a method of preventing and treating hemophilia in a subject comprising administering a CTP-modified coagulation factor disclosed herein. In another embodiment, disclosed herein is a method of treating hemophilia in a subject comprising administering a CTP-modified Factor VIIa disclosed herein.

In one embodiment, hemophilia is hemophilia A. In another embodiment, hemophilia is hemophilia B. In another embodiment, methods of this invention for prevention or treating a clotting or coagulation disorder prevent or treat hemophilia in patients having hemophilia A or B with inhibitors to FVIII or FIX, respectively. In another embodiment, methods of this invention are for preventing or treating patients with acquired hemophilia (hemophilia without inhibitors). In another embodiment, methods of this invention for prevention or treating a clotting or coagulation disorder prevent or treat hemophilia A or B without inhibitors. In another embodiment, hemophilia is severe hemophilia. In another embodiment, hemophilia is moderate hemophilia. In another embodiment, hemophilia is moderate to severe hemophilia with or without inhibitors. It will be appreciated by a skilled artisan that the term "moderate to severe hemophilia" refers to a subject having less than or equal to 3% FVIII or FIX. In another embodiment, severe hemophila may encompass coagulation factor levels equal to about 0-1%. In another embodiment, the hemophilia is moderate hemophilia, which in another embodiment, describes hemophilia in which the coagulation factor levels are 1-5%. In another embodiment, the hemophilia is mild hemophilia, which in another embodiment, describes hemophilia in which the coagulation factor levels are 5-50%.

In another embodiment, disclosed herein is a method of preventing or treating a clotting or coagulation disorder in a subject comprising administering a CTP-modified Factor VII (FVII) polypeptide comprising a FVIIa polypeptide and three chorionic gonadotropin carboxy terminal peptides (CTPs) attached to the carboxy terminus of said FVIIa polypeptide to said subject, thereby preventing or treating a clotting or coagulation disorder in said subject.

In another embodiment, disclosed herein is a method of preventing or treating hemophilia in a subject comprising administering a CTP-modified Factor VIIa (FVIIa) polypeptide comprising a FVIIa polypeptide and three chorionic gonadotropin carboxy terminal peptides (CTPs) attached to the carboxy terminus of said FVIIa polypeptide to said subject, thereby preventing or treating hemophilia in said subject.

In another embodiment, disclosed herein is a method of treating hemophilia in a subject comprising administering one or more CTP-modified coagulation factors as described herein to said subject. Thus, in one embodiment, disclosed herein is a method of treating hemophilia in a subject comprising administering a CTP-modified Factor VIIa (FVIIa) polypeptide comprising a FVIIa polypeptide and three chorionic gonadotropin carboxy terminal peptides (CTPs) attached to the carboxy terminus of said FVIIa polypeptide to said subject, thereby treating hemophilia in said subject. In one embodiment, the CTP-modified FVIIa are administered in the same composition at the same time. In another embodiment, and the CTP-modified FVIIa are administered in separate compositions at the same time. In another embodiment, the CTP-modified FVIIa are administered in separate compositions at separate times.

In another embodiment, disclosed herein is a method of preventing or treating hemophilia in a subject comprising administering a FVIIa polypeptide and three chorionic gonadotropin carboxy terminal peptides (CTPs) attached to the carboxy terminus of said FVIIa polypeptide to said subject, thereby preventing or treating hemophilia in said subject.

In another embodiment, disclosed herein is a method of preventing or treating hemophilia in a subject comprising subcutaneously or intravenously administering a CTP-modified Factor VIIa polypeptide comprising a FVIIa polypeptide and three chorionic gonadotropin carboxy terminal peptides (CTPs) attached to the carboxy terminus of said FVIIa polypeptide to said subject, thereby preventing or treating hemophilia in said subject. In some embodiments, provided herein is a method of preventing or treating a hemophilia in a subject, the method comprising the step of administering to the subject a CTP-modified coagulation factor, comprising three to five chorionic gonadotropin carboxy terminal peptides (CTPs) attached to the carboxy terminus of said coagulation factor polypeptide, wherein the sequence of said CTP-modified coagulation factor is selected from the group consisting of SEQ ID NO: 5 or 7, thereby preventing hemophilia in said subject. In another embodiment, said CTP-modified coagulation factor is selected from the group consisting of SEQ ID NO: 5 or 7. In another embodiment, said CTP-modified coagulation factor consists of SEQ ID NO: 7. In another embodiment, said CTP-modified coagulation factor consisting of SEQ ID NO: 7 comprises an activated FVII (FVIIa).

In another embodiment, disclosed herein is a method of treating hemophilia in a subject comprising administering an activated CTP-modified Factor VII (FVIIa) polypeptide comprising a FVIIa polypeptide and three chorionic gonadotropin carboxy terminal peptides (CTPs) attached to the carboxy terminus of said FVIIa polypeptide to said subject, thereby treating hemophilia in said subject.

In another embodiment, subcutaneous (SC) administration results in higher bioavailability of CTP-modified FVII as compared to recombinant FVII. In another embodiment, half-life is longer and bioavailability (AUC SC/AUC IV) is higher following FVIIa-CTP3 SC administration when compared to SC administration of NovoSeven®. In another embodiment, subcutaneously injected MOD-5014 shows improved mice survival in comparison to recombinant FVII (NovoSeven®).

In one embodiment, MOD-5014 is FVIIa-CTP$_3$ (having three CTP peptides attached at the C-terminus end). In one embodiment, MOD-5014 provides a long-acting coagulation factor. In one embodiment, MOD-5014 provides a more sustained and prolonged blood clotting response compared with recombinant human FVIIa. It will be appreciated by a skilled artisan that the terms MOD-5014 or FVIIa-CTP$_3$ may be used interchangeably having all the same qualities and meanings, and refer in one embodiment, to a disulfide-linked two chain heterodimer structure comprising the amino acid SEQ ID NO: 7. Further, a skilled artisan would appreciate that in describing coagulation factors or CTP-modified coagulation factors herein, for example FVII-CTP$_3$, the term FVII-CTP$_3$ may in certain instances refer to the inactive form of FVII-CTP$_3$. The skilled artisan would certainly recognize which form is being referred to based on associated details such as activity. Similarly, while the term MOD-5014 is interchangeable with the term FVIIa-CTP$_3$, i.e., represents the active form of the CTP-modified coagulation factor, in certain instances the term MOD-5014 may be used to denote an active form of FVII or a nucleotide sequence encoding a FVII-CTP$_3$, which will then be expressed and secreted from a cell, and purified and activated in vitro, resulting in the active form of FVIIa being present in a MOD-5014 molecule.

In one embodiment, deactivation of MOD-5014 by tissue factor pathway inhibitor (TFPI) is dose-dependent. In one embodiment, deactivation of MOD-5014 by TFPI shows a similar dose-dependent deactivation pattern to that of recombinant FVIIa (NovoSeven®) by TFPI. In one embodiment, MOD-5014 is inhibited by anti-thrombin III. In one embodiment, inhibition of MOD-5014 by anti-thrombin III is augmented in the presence of heparin. In one embodiment, inhibition of MOD-5014 by anti-thrombin III shows similar inhibition pattern to that of recombinant FVIIa (NovoSeven®), in the presence or absence of heparin.

In one embodiment, MOD-5014 generates thrombin in a dose-dependent manner. In one embodiment, MOD-5014 decreases lag phase of thrombin generation. In one embodiment, MOD-5014 decreases blood clotting time. In one embodiment, MOD-5014 increases efficiency of blood clot formation. In one embodiment, administration of MOD-5014 decreases blood clotting time in a subject. In one embodiment, administration of MOD-5014 increases efficiency of blood clot formation in a subject. In one embodiment, the generation of thrombin by MOD-5014 is similar to that produced by recombinant FVIIa (NovoSeven®). In one embodiment, decrease of lag-phase of thrombin generation by MOD-5014 is similar to that produced by recombinant FVIIa (NovoSeven®). In one embodiment, decrease blood clotting time by MOD-5014 is similar to that produced by recombinant FVIIa (NovoSeven®). In one embodiment, increased efficiency of blood clot formation by MOD-5014 is similar to that produced by recombinant FVIIa (NovoSeven®).

As provided herein, CTP attachments to blood clotting factors, for example factor FVII, increases the half-life of the blood clotting factor. Examples show that CTP attachments, for example three CTPs attached to FVIIA, do not appear to affect blood clotting activities. In one embodiment, CTP attachments to FVII do not interfere with blood clot formation. In one embodiment, CTP attachments to FVII do not interfere with increased efficiency of blood clot formation. In one embodiment, CTP attachments to FVII do not interfere with decreased in blood clotting time. In one embodiment, binding of phospholipid to FVII is maintained following attachment of CTPs to the blood clotting factor. In one embodiment, CTP attachments to FVIIA do not interfere with blood clot formation. In one embodiment, CTP attachments to FVIIA do not interfere with increased efficiency of blood clot formation. In one embodiment, CTP attachments to FVIIA do not interfere with decreased blood clot formation. In one embodiment, binding of phospholipid to FVIIA is maintained following attachment of CTPs to the blood clotting factor.

In another embodiment, disclosed herein is a method of treating hemophilia in a subject comprising administering a CTP-modified coagulation factors described herein to said subject.

In other embodiments, the engineered coagulation factor is for the treatment of hemophilia B patients. Results of administering MOD-5014 to a large mammal (dogs). MOD-5014 administration provided an effective and safe long-acting FVIIa for blood coagulation (See International Application No. PCT/IL2016/050645, which is incorporated herein in full. Treatment using MOD-5014 may be prophylactic or on-demand. In one embodiment, disclosed herein is a method of treating hemophilia in a subject comprising administering MOD-5014 to said subject, thereby treating hemophilia in said subject. In one embodiment, disclosed herein is a method of preventing excess bleeding in a subject comprising administering MOD-5014 to said subject, thereby preventing excess bleeding in said subject. In one embodiment, disclosed herein is a method of prophylactically treating hemophilia in a subject comprising administering MOD-5014 to said subject, thereby prophylactically treating hemophilia in said subject.

In one embodiment, treating hemophilia in a subject with MOD-5014 comprises a reduced frequency of administration of MOD-5014, as compared with recombinant FVIIa (NovoSeven®). In one embodiment, prophylactically treating hemophilia in a subject with MOD-5014 comprises a reduced frequency of administration of MOD-5014, as compared with recombinant FVIIa (NovoSeven®). In one embodiment, preventing excess bleeding in a subject with MOD-5014 comprises a reduced frequency of administration of MOD-5014, as compared with recombinant FVIIa (NovoSeven®).

In one embodiment, coagulation Factor VII comprising 3 CTPs in tandem in its carboxy terminus exhibits an improved PK profile while maintaining its coagulation activity vs. NovoSeven®.

In another embodiment, the compositions, formulations and methods disclosed herein are for the treatment of bleeding episodes in hemophilia A or B patients with inhibitors to FVIII or FIX and in patients with acquired hemophilia; prevention of bleeding in surgical interventions or invasive procedures in hemophilia A or B patients with inhibitors to FVIII or FIX and in patients with acquired hemophilia; treatment of bleeding episodes in patients with congenital FVII deficiency and prevention of bleeding in surgical interventions or invasive procedures in patients with congenital FVII deficiency. Acquired hemophilia is a spontaneous autoimmune disorder in which patients with previously normal hemostasis develop autoantibodies against clotting factors, most frequently FVIII. The development of autoantibodies against FVIII leads to FVIII deficiency, which results in insufficient generation of thrombin by factor IXa and the factor VIIIa complex through the intrinsic pathway of the coagulation cascade. The following conditions may be associated with acquired hemophilia A: idiopathic, pregnancy, autoimmune disorders, inflammatory bowel disease, ulcerative colitis, dermatologic disorders (eg, psoriasis, pemphigus), respiratory diseases (eg, asthma, chronic obstructive pulmonary disease), allergic drug reactions, diabetes, acute hepatitis B infection, acute hepatitis C infection, malignancies-solid tumors (prostate, lung, colon, pancreas, stomach, bile duct, head and neck, cervix, breast, melanoma, kidney), hematologic malignancies. It will be appreciated by the skilled artisan that autoimmune disorders may include rheumatoid arthritis, systemic lupus erythematosus, multiple sclerosis, temporal arteritis, sjögren syndrome, autoimmune hemolytic anemia, goodpasture syndrome, myasthenia gravis, graves' disease, autoimmune hypothyroidism. It will be appreciated by the skilled artisan that allergic reactions may occur from a subject being administered penicillin and its derivatives, sulfamides, phenytoin, chloramphenicol, methyldopa, depot thioxanthene, interferon alfa, fludarabine, bacille calmette-guérin (BCG) vaccination, desvenlafaxine. It will be appreciated by the skilled artisan that hematologic malignancies may include chronic lymphocytic leukemia, non-Hodgkin lymphoma, multiple myeloma, waldenstrom macroglobulinemia, myelodysplastic syndrome, myelofibrosis, and erythroleukemia. Hence, and in one embodiment, provided herein is a method for treating acquired hemophilia in a subject, comprising administering to the subject any of the compositions provided herein.

In another embodiment, the compositions, formulations, and methods disclosed herein are for the treatment or prevention of muscle bleeds. In another embodiment, the compositions, formulations, and methods disclosed herein are for the treatment or prevention of joint bleeds. In another embodiment, the compositions, formulations, and methods disclosed herein provide therapeutic or prophylactic treatment of epistaxis and gum bleeding, mucous membrane bleeding, bleeding into the central nervous system. In another embodiment, the compositions, formulations, and methods disclosed herein provide therapeutic or prophylactic treatment of gastrointestinal or cerebral bleeding. In another embodiment, the compositions, formulations, and methods disclosed herein provide therapeutic or prophylactic treatment of low frequency mild bleeds. In another embodiment, the compositions, formulations, and methods disclosed herein provide therapeutic or prophylactic treatment of low frequency moderate bleeds. In another embodiment, the compositions, formulations, and methods disclosed herein provide therapeutic or prophylactic treatment of high frequency mild bleeds. In another embodiment, the compositions, formulations, and methods disclosed herein provide therapeutic or prophylactic treatment of high frequency moderate bleeds.

In one embodiment, the compositions, formulations, and methods disclosed herein provide therapeutic or prophylactic treatment of asymptomatic hemophilia. In another embodiment, the compositions, formulations, and methods disclosed herein provide therapeutic or prophylactic treatment of mild to moderate hemophilia. In another embodiment, the compositions, formulations, and methods disclosed herein provide therapeutic or prophylactic treatment of severe hemophilia.

In one embodiment, the compositions, formulations, and methods disclosed herein provide therapeutic or prophylactic treatment of hemorrhage, which in one embodiment, is uncontrollable hemorrhage, and, in another embodiment, intracerebral hemorrhage. In another embodiment, the compositions, formulations, and methods disclosed herein provide therapeutic or prophylactic treatment of neonatal coagulopathies; severe hepatic disease; high-risk surgical procedures; traumatic blood loss; bone marrow transplantation; thrombocytopenias and platelet function disorders; urgent reversal of oral anticoagulation; congenital deficiencies of factors V, VII, X, and XI; or von Willebrand disease, in one embodiment, von Willebrand disease with inhibitors to von Willebrand factor.

In one embodiment, a CTP-modified coagulation factor disclosed herein is for the treatment of hemophilia or a related disease as described herein in a subject. In one embodiment, the subject is human. In another embodiment, the subject is a human child. In another embodiment, the subject is a domesticated animal. In another embodiment, the subject is a mammal. In another embodiment, the subject is a farm animal. In another embodiment, the subject is a monkey. In another embodiment, the subject is a horse. In another embodiment, the subject is a cow. In another embodiment, the subject is a mouse. In another embodiment, the subject is a rat. In another embodiment, the subject is canine. In another embodiment, the subject is feline. In another embodiment, the subject is bovine, ovine, porcine, equine, murine, or cervine. In one embodiment, the subject is male. In another embodiment, the subject is female. In one embodiment, the subject is a child, in another embodiment, an adolescent, in another embodiment, an adult or, in another embodiment, an elderly subject. In another embodiment, the subject is a pediatric subject, in another embodiment, a geriatric subject.

In another embodiment, the phrases "physiologically acceptable carrier" and "pharmaceutically acceptable carrier" which are interchangeably used refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media.

In another embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, PA, latest edition, which is incorporated herein by reference.

Various embodiments of dosage ranges are contemplated by this invention. The dosage of the engineered coagulation factor disclosed herein, in one embodiment, is in the range of 0.005-100 mg/day. In another embodiment, the dosage is in the range of 0.005-5 mg/day. In another embodiment, the dosage is in the range of 0.01-50 mg/day. In another embodiment, the dosage is in the range of 0.1-20 mg/day. In another embodiment, the dosage is in the range of 0.1-10 mg/day. In another embodiment, the dosage is in the range of 0.01-5 mg/day. In another embodiment, the dosage is in the range of 0.001-0.01 mg/day. In another embodiment, the dosage is in the range of 0.001-0.1 mg/day. In another embodiment, the dosage is in the range of 0.1-5 mg/day. In another embodiment, the dosage is in the range of 0.5-50 mg/day. In another embodiment, the dosage is in the range of 0.2-15 mg/day. In another embodiment, the dosage is in the range of 0.8-65 mg/day. In another embodiment, the dosage is in the range of 1-50 mg/day. In another embodiment, the dosage is in the range of 5-10 mg/day. In another embodiment, the dosage is in the range of 8-15 mg/day. In another embodiment, the dosage is in a range of 10-20 mg/day. In another embodiment, the dosage is in the range of 20-40 mg/day. In another embodiment, the dosage is in a range of 60-120 mg/day. In another embodiment, the dosage is in the range of 12-40 mg/day. In another embodiment, the dosage is in the range of 40-60 mg/day. In another embodiment, the dosage is in a range of 50-100 mg/day. In another embodiment, the dosage is in a range of 1-60 mg/day. In another embodiment, the dosage is in the range of 15-25 mg/day. In another embodiment, the dosage is in the range of 5-10 mg/day. In another embodiment, the dosage is in the range of 55-65 mg/day.

In another embodiment, the dosage is in a range of 50-500 mg/day. In another embodiment, the dosage is in a range of 50-150 mg/day. In another embodiment, the dosage is in a range of 100-200 mg/day. In another embodiment, the dosage is in a range of 150-250 mg/day. In another embodiment, the dosage is in a range of 200-300 mg/day. In another embodiment, the dosage is in a range of 250-400 mg/day. In another embodiment, the dosage is in a range of 300-500 mg/day. In another embodiment, the dosage is in a range of 350-500 mg/day.

In one embodiment, the dosage is 20 mg/day. In one embodiment, the dosage is 30 mg/day. In one embodiment, the dosage is 40 mg/day. In one embodiment, the dosage is 50 mg/day. In one embodiment, the dosage is 0.01 mg/day. In another embodiment, the dosage is 0.1 mg/day. In another embodiment, the dosage is 1 mg/day. In another embodiment, the dosage is 0.530 mg/day. In another embodiment, the dosage is 0.05 mg/day. In another embodiment, the dosage is 50 mg/day. In another embodiment, the dosage is 10 mg/day. In another embodiment, the dosage is 20-70 mg/day. In another embodiment, the dosage is 5 mg/day.

In one embodiment, the dosage of the CTP-modified coagulation factor is 1-5 mg/day. In one embodiment, the dosage of the CTP-modified coagulation factor is 1-3 mg/day. In another embodiment, the dosage of the CTP-modified coagulation factor is 2 mg/day.

In another embodiment, the dosage is 1-90 mg/day. In another embodiment, the dosage is 1-90 mg/2 days. In another embodiment, the dosage is 1-90 mg/3 days. In another embodiment, the dosage is 1-90 mg/4 days. In another embodiment, the dosage is 1-90 mg/5 days. In another embodiment, the dosage is 1-90 mg/6 days. In another embodiment, the dosage is 1-90 mg/week. In another embodiment, the dosage is 1-90 mg/9 days. In another embodiment, the dosage is 1-90 mg/11 days. In another embodiment, the dosage is 1-90 mg/14 days.

In another embodiment, the coagulation factor dosage is 10-50 mg/day. In another embodiment, the dosage is 10-50 mg/2 days. In another embodiment, the dosage is 10-50 mg/3 days. In another embodiment, the dosage is 10-50 mg/4 days. In another embodiment, the dosage is 10-50 micrograms mg/5 days. In another embodiment, the dosage is 10-50 mg/6 days. In another embodiment, the dosage is 10-50 mg/week. In another embodiment, the dosage is 10-50 mg/9 days. In another embodiment, the dosage is 10-50 mg/11 days. In another embodiment, the dosage is 10-50 mg/14 days.

In another embodiment, a polypeptide comprising a coagulation factor and at least one CTP unit is formulated in an intranasal dosage form. In another embodiment, a polypeptide comprising a coagulation factor and at least one CTP unit is formulated in an injectable dosage form. In another embodiment, a polypeptide comprising a coagulation factor and at least one CTP unit is administered to a subject in a dose ranging from 0.0001 mg to 0.6 mg. In another embodiment, a polypeptide comprising a coagulation factor and at least one CTP unit is administered to a subject in a dose ranging from 0.001 mg to 0.005 mg. In another embodiment, a polypeptide comprising a coagulation factor and at least one CTP unit is administered to a subject in a dose ranging from 0.005 mg to 0.01 mg. In another embodiment, a polypeptide comprising a coagulation factor and at least one CTP unit is administered to a subject in a dose ranging from 0.01 mg to 0.3 mg. In another embodiment, a polypeptide comprising a coagulation factor and at least one CTP unit is administered to a subject in a dose in a dose ranging from 0.2 mg to 0.6 mg. In another embodiment, the coagulation factor is free of CTPs on its amino terminus.

In another embodiment, a polypeptide comprising a coagulation factor and at least one CTP unit is administered to a subject in a dose ranging from 1-100 micrograms. In another embodiment, a polypeptide comprising a coagulation factor and at least one CTP unit is administered to a subject in a dose ranging from 10-80 micrograms. In another embodiment, a polypeptide comprising a coagulation factor and at least one CTP unit is administered to a subject in a dose ranging from 20-60 micrograms. In another embodiment, a polypeptide comprising a coagulation factor and at least one CTP unit is administered to a subject in a dose ranging from 10-50 micrograms. In another embodiment, a polypeptide comprising a coagulation factor and at least one CTP unit is administered to a subject in a dose ranging from 40-80 micrograms. In another embodiment, a polypeptide comprising a coagulation factor and at least one CTP unit is administered to a subject in a dose ranging from 10-30 micrograms. In another embodiment, a polypeptide comprising a coagulation factor and at least one CTP unit is administered to a subject in a dose ranging from 30-60 micrograms.

In another embodiment, a polypeptide comprising a coagulation factor and at least one CTP unit is administered to a subject in a dose ranging from 0.2 mg to 2 mg. In another embodiment, a polypeptide comprising a coagulation factor and at least one CTP unit is administered to a subject in a dose ranging from 2 mg to 6 mg. In another embodiment, a polypeptide comprising a coagulation factor and at least one CTP unit is administered to a subject in a dose ranging from 4 mg to 10 mg. In another embodiment, a polypeptide comprising a coagulation factor and at least one CTP unit is administered to a subject in a dose ranging from 5 mg and 15 mg.

In one embodiment, coagulation factor modified by CTPs is administered to a subject in a dose ranging from 10 µg/kg-1000 µg/kg. In another embodiment, coagulation factor modified by CTPs is administered to a subject in a dose ranging from 25 µg/kg-600 µg/kg. In another embodiment, coagulation factor modified by CTPs is administered to a subject in a dose ranging from 50 µg/kg-400 µg/kg. In another embodiment, coagulation factor modified by CTPs is administered to a subject in a dose of about 25 µg/kg. In another embodiment, coagulation factor modified by CTPs is administered to a subject in a dose of about 50 µg/kg. In another embodiment, coagulation factor modified by CTPs is administered to a subject in a dose of about 100 µg/kg. In another embodiment, coagulation factor modified by CTPs is administered to a subject in a dose of about 200 µg/kg. In another embodiment, coagulation factor modified by CTPs is administered to a subject in a dose of about 300 µg/kg. In another embodiment, coagulation factor modified by CTPs is administered to a subject in a dose of about 400 µg/kg. In another embodiment, coagulation factor modified by CTPs is administered to a subject in a dose of about 500 µg/kg. In another embodiment, coagulation factor modified by CTPs is administered to a subject in a dose of about 600 µg/kg.

In one embodiment, the dosage of the CTP-modified FVIIa comprises 50% of the amount of FVIIa administered in the recommended dosage of recombinant FVIIa (e.g., NovoSeven®) to patients over the same period of time. In one embodiment, the dosage of the CTP-modified FVII comprises 50% of the amount of FVII administered in the recommended dosage of recombinant FVII to patients over the same period of time. For example, if NovoSeven® is given at a dose of 90 mcg/kg every two hours to a patient pre- or post-operatively (i.e., 7.65 mg every two hours or 45.9 mg in six doses over a 12 hour period, for an 85 kg patient), a CTP-modified coagulation factor disclosed herein may be given at a dose that is 50% of the patient's 12-hour dose of recombinant FVIIa (i.e., at a dose of 23 mg given once over a 12-hour period).

In another embodiment, the dosage of CTP-modified coagulation factor is such that it contains 45% of the amount of the coagulation factor than that administered using the non-CTP-modified coagulation factor. In another embodiment, the dosage of CTP-modified coagulation factor is such that it contains 10% of the amount of the coagulation factor than that administered using the non-CTP-modified coagulation factor. In another embodiment, the dosage of CTP-modified coagulation factor is such that it contains 25% of the amount of the coagulation factor than that administered using the non-CTP-modified coagulation factor. In another embodiment, the dosage of CTP-modified coagulation factor is such that it contains 35% of the amount of the coagulation factor than that administered using the non-CTP-modified coagulation factor. In another embodiment, the dosage of CTP-modified coagulation factor is such that it contains 75% of the amount of the coagulation factor than that administered using the non-CTP-modified coagulation factor. In another embodiment, the dosage of CTP-modified coagulation factor is such that it contains 100% of the amount of the coagulation factor than that administered using the non-CTP-modified coagulation factor. However, even if the dosage contains the same amount of coagulation factor (e.g. FIX) as non-CTP-modified coagulation factor, it is still advantageous to subjects in that it will be administered less frequently because of its increased half-life compared to recombinant coagulation factors.

In another embodiment, a therapeutically effective amount of a conjugated coagulation factor is between 10 µg/Kg-500 µg/Kg for FVIIa. In another embodiment, a therapeutically effective amount of a conjugated coagulation factor is 150-250 IU per kg body weight, administered once a day. In another embodiment, a pharmaceutical composition comprising a conjugated coagulation factor is formulated at a strength effective for administration by various means to a human patient.

In one embodiment, the CTP-modified coagulation factor is administered to a subject on a weekly basis. In another embodiment, the CTP-modified coagulation factor is administered to a subject twice a week. In another embodiment, the CTP-modified coagulation factor is administered to a subject on a fortnightly (once every two weeks) basis. In another embodiment, the CTP-modified coagulation factor is administered to a subject twice a month. In another embodiment, the CTP-modified coagulation factor is administered to a subject once a month. In another embodiment, the CTP-modified coagulation factor is administered to a subject on a daily basis. In another embodiment, the CTP-modified coagulation factor is administered to a subject every two days. In another embodiment, a polypeptide comprising a coagulation factor and at least one CTP unit is administered to a subject once every three days. In another embodiment, a polypeptide comprising a coagulation factor and at least one CTP unit is administered to a subject once every four days. In another embodiment, a polypeptide comprising a coagulation factor and at least one CTP unit is administered to a subject once every five days. In another embodiment, a polypeptide comprising a coagulation factor and at least one CTP unit is administered to a subject once every six days. In another embodiment, a polypeptide comprising a coagulation factor and at least one CTP unit is administered to a subject once every 7-14 days. In another embodiment, a polypeptide comprising a coagulation factor and at least one CTP unit is administered to a subject once every 10-20 days. In another embodiment, a polypeptide comprising a coagulation factor and at least one CTP unit is administered to a subject once every 5-15 days. In another embodiment, a polypeptide comprising a coagulation factor and at least one CTP unit is administered to a subject once every 15-30 days.

In another embodiment, the methods of the disclosure include increasing the compliance in the use of coagulation factor therapy, comprising providing to a subject in need thereof, a polypeptide comprising a coagulation factor and at least one chorionic gonadotropin carboxy terminal peptide (CTP) attached to the carboxy terminus of the coagulation factor, thereby increasing compliance in the use of coagulation factor therapy.

In another embodiment, the methods of the disclosure include increasing the compliance of patients afflicted with chronic illnesses that are in need of a coagulation factor therapy. In another embodiment, the methods of the disclosure enable reduction in the dosing frequency of a coagulation factor by modifying the coagulation factor with CTPs as described hereinabove.

In another embodiment, the term compliance comprises adherence. In another embodiment, the methods of the disclosure include increasing the compliance of patients in need of a coagulation factor therapy by reducing the frequency of administration of the coagulation factor. In another embodiment, reduction in the frequency of administration of the coagulation factor is achieved due to the CTP modifications which render the CTP-modified coagulation factor more stable. In another embodiment, reduction in the frequency of administration of the coagulation factor is achieved as a result of increasing T½ of the coagulation factor. In another embodiment, reduction in the frequency of administration of the coagulation factor is achieved as a result of increasing the clearance time or reducing the clearance rate of the coagulation factor.

In another embodiment, reduction in the frequency of administration of the coagulation factor is achieved as a result of increasing the AUC measure of the coagulation factor.

In another embodiment, provided herein is a method of reducing the dosing frequency of a coagulation factor, comprising the step of attaching one to ten CTPs to the carboxy terminus of the coagulation factor, thereby reducing a dosing frequency of the coagulation factor. In another embodiment, provided herein is a method of reducing the dosing frequency of a coagulation factor, comprising the step of attaching one to five CTPs to the carboxy terminus of the coagulation factor, thereby reducing a dosing frequency of the coagulation factor. In another embodiment, provided herein is a method of reducing the dosing frequency of a coagulation factor, comprising the step of attaching three CTPs to the carboxy terminus of the coagulation factor, thereby reducing a dosing frequency of the coagulation factor. In another embodiment, provided herein is a method of reducing the dosing frequency of a coagulation factor, comprising the step of attaching three to five CTPs to the carboxy terminus of the coagulation factor, thereby reducing a dosing frequency of the coagulation factor.

In another embodiment, provided herein is a method of increasing compliance in the use of coagulation factor therapy, comprising providing to a subject in need thereof, a polypeptide comprising a coagulation factor and one to ten chorionic gonadotropin carboxy terminal peptides attached to the carboxy terminus of a coagulation factor, thereby increasing compliance in the use of coagulation factor therapy. In another embodiment, provided herein is a method of increasing compliance in the use of coagulation factor therapy, comprising providing to a subject in need thereof, a polypeptide comprising a coagulation factor and one to five chorionic gonadotropin carboxy terminal peptides attached to the carboxy terminus of a coagulation factor, thereby increasing compliance in the use of coagulation factor therapy. In another embodiment, provided herein is a method of increasing compliance in the use of coagulation factor therapy, comprising providing to a subject in need thereof, a polypeptide comprising a coagulation factor and three chorionic gonadotropin carboxy terminal peptides attached to the carboxy terminus of a coagulation factor, thereby increasing compliance in the use of coagulation factor therapy. In another embodiment, provided herein is a method of increasing compliance in the use of coagulation factor therapy, comprising providing to a subject in need thereof, a polypeptide comprising a coagulation factor and three to five chorionic gonadotropin carboxy terminal peptides attached to the carboxy terminus of a coagulation factor, thereby increasing compliance in the use of coagulation factor therapy.

In another embodiment, provided herein is a method of preventing or treating a blood clotting or coagulation disorder in a subject, comprising providing to said subject a polypeptide comprising a coagulation factor and one to ten chorionic gonadotropin carboxy terminal peptides attached to the carboxy terminus of a coagulation factor, thereby treating a blood clotting or coagulation disorder in said subject. In another embodiment, provided herein is a method of preventing or treating a blood clotting or coagulation disorder in a subject, comprising providing to a subject in need thereof, a polypeptide comprising a coagulation factor and one to five chorionic gonadotropin carboxy terminal peptides attached to the carboxy terminus of a coagulation factor, thereby preventing or treating a blood clotting or coagulation disorder in said subject. In another embodiment, provided herein is a method of preventing or treating a blood clotting or coagulation disorder in a subject, comprising providing to a subject in need thereof, a polypeptide comprising a coagulation factor and three chorionic gonadotropin carboxy terminal peptides attached to the carboxy terminus of a coagulation factor, thereby preventing or treating a blood clotting or coagulation disorder in said subject.

In another embodiment, provided herein is a method of preventing hemophilia in a subject, comprising providing to a subject in need thereof, a polypeptide comprising a coagulation factor and three chorionic gonadotropin carboxy terminal peptides attached to the carboxy terminus of a coagulation factor, thereby preventing hemophilia in said subject. In another embodiment, provided herein is a method of preventing hemophilia in a subject, comprising providing to a subject in need thereof, a polypeptide comprising a coagulation factor and three to five chorionic gonadotropin carboxy terminal peptides attached to the carboxy terminus of a coagulation factor, thereby preventing hemophilia in said subject.

In another embodiment, the compositions provided herein are surprisingly more effectively absorbed into the bloodstream after SC administration (see PCT/IL2016/050645, which is incorporated by reference herein in its entirety). To be able to administer FVIIa subcutaneously serves as an advantage as it can be used for prophylactic applications. Subcutaneous injections are also much easier for patients to self-inject, and are advantage when the patients are very young and their veins are small and difficult to find.

In another embodiment, provided herein is a method of treating hemophilia in a subject, comprising providing to said subject a polypeptide comprising a coagulation factor and one to ten chorionic gonadotropin carboxy terminal peptides attached to the carboxy terminus of a coagulation factor, thereby treating hemophilia in said subject. In another embodiment, provided herein is a method of treating hemophilia in a subject, comprising providing to a subject in need thereof, a polypeptide comprising a coagulation factor and one to five chorionic gonadotropin carboxy terminal peptides attached to the carboxy terminus of a coagulation factor, thereby treating hemophilia in said subject. In another embodiment, provided herein is a method of treating hemophilia in a subject, comprising providing to a subject in need thereof, a polypeptide comprising a coagulation factor and three chorionic gonadotropin carboxy terminal peptides attached to the carboxy terminus of a coagulation factor, thereby treating hemophilia in said subject. In another embodiment, provided herein is a method of treating hemophilia in a subject, comprising providing to a subject in need thereof, a polypeptide comprising a coagulation factor and three to five chorionic gonadotropin carboxy terminal peptides attached to the carboxy terminus of a coagulation factor, thereby treating hemophilia in said subject.

Oral administration, in one embodiment, comprises a unit dosage form comprising tablets, capsules, lozenges, chewable tablets, suspensions, emulsions and the like. Such unit dosage forms comprise a safe and effective amount of the desired coagulation factor of the disclosure, each of which is in one embodiment, from about 0.7 or 3.5 mg to about 280 mg/70 kg, or in another embodiment, about 0.5 or 10 mg to about 210 mg/70 kg. The pharmaceutically-acceptable carriers suitable for the preparation of unit dosage forms for peroral administration are well-known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form disclosed herein comprises an extended release tablets, capsules, lozenges or chewable tablets. In one embodiment, the oral dosage form disclosed herein comprises a slow release tablets, capsules, lozenges or chewable tablets. In one embodiment, the oral dosage form disclosed herein comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.001% to about 0.933% of the desired compound or compounds, or in another embodiment, from about 0.01% to about 10%.

In some embodiments, compositions for use in the methods of this invention comprise solutions or emulsions, which in some embodiments are aqueous solutions or emulsions comprising a safe and effective amount of the compounds disclosed herein and optionally, other compounds, intended for topical intranasal administration. In some embodiments, h compositions comprise from about 0.001% to about 10.0% w/v of a subject compound, more preferably from about 00.1% to about 2.0, which is used for systemic delivery of the compounds by the intranasal route.

In another embodiment, a polypeptide comprising a coagulation factor and at least one CTP unit is injected into the muscle (intramuscular injection). In another embodiment, a polypeptide comprising a coagulation factor and at least one CTP unit is injected below the skin (subcutaneous injection). In another embodiment, a polypeptide comprising a coagulation factor and at least one CTP unit is injected into the muscle. In another embodiment, a polypeptide comprising a coagulation factor and at least one CTP unit is injected into the skin. In another embodiment, a coagulation factor as described herein is administered via systemic administration. In another embodiment, a coagulation factor as described herein is administered by intravenous injection. In another embodiment, administration can be parenteral, pulmonary, oral, topical, intradermal, intramuscular, intraperitoneal, intravenous, subcutaneous, intranasal, transnasal, intraocular, ophthalmic, epidural, buccal, rectal, transmucosal, intestinal or parenteral delivery, including intramedullary injections as well as intrathecal or direct intraventricular administration.

In another embodiment, the preparation is administered in a local rather than systemic manner, for example, via injection of the preparation directly into a specific region of a patient's body.

In one embodiment, the route of administration may be enteral. In another embodiment, the route may be conjunctival, transdermal, intradermal, intra-arterial, vaginal, rectal, intratumoral, parcanceral, transmucosal, intramuscular, intravascular, intraventricular, intracranial, intra-nasal, sublingual, or a combination thereof.

In another embodiment, the pharmaceutical compositions and pharmaceutical formulations are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions and pharmaceutical formulations are administered intravenously, and are thus formulated in a form suitable for intravenous administration. In another embodiment, the pharmaceutical compositions and pharmaceutical formulations are administered intra-arterially, and are thus formulated in a form suitable for intra-arterial administration. In another embodiment, the pharmaceutical compositions and pharmaceutical formulations are administered intramuscularly, and are thus formulated in a form suitable for intramuscular administration.

Further, in another embodiment, the pharmaceutical compositions and pharmaceutical formulations are administered topically to body surfaces, and are thus formulated in a form suitable for topical administration. Suitable topical formulations include gels, ointments, creams, lotions, drops and the like. For topical administration, the compounds disclosed herein are combined with an additional appropriate therapeutic agent or agents, prepared and applied as solutions, suspensions, or emulsions in a physiologically acceptable diluent with or without a pharmaceutical carrier.

In one embodiment, pharmaceutical compositions and pharmaceutical formulations disclosed herein are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions and pharmaceutical formulations for use in accordance with the present invention are formulated in a conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables of the disclosure are formulated in aqueous solutions. In one embodiment, injectables of the disclosure are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions and pharmaceutical formulations for parenteral administration include aqueous solutions of the active preparation in water-soluble form. Additionally, suspensions of the active ingredients, in some embodiments, are prepared as appropriate oil or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contains suitable stabilizers or agents which increase the solubility of the active ingredients to allow for the preparation of highly concentrated solutions.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; J. E. Diederichs and al., Pharm./nd. 56 (1994) 267-275).

In another embodiment, the pharmaceutical composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

In some embodiments, the active ingredient is in powder form for constitution with a suitable vehicle, e.g., sterile, pyrogen-free water based solution, before use. Compositions are formulated, in some embodiments, for atomization and inhalation administration. In another embodiment, compositions are contained in a container with attached atomizing means.

In one embodiment, the preparation disclosed herein is formulated in rectal compositions such as suppositories or retention enemas, using, e.g., conventional suppository bases such as cocoa butter or other glycerides.

In some embodiments, pharmaceutical compositions and pharmaceutical formulations suitable for use in context disclosed herein include compositions wherein the active ingredients are contained in an amount effective to achieve the intended purpose. In some embodiments, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered. If the subject compound is to be injected, in one embodiment, the pharmaceutically-acceptable carrier is sterile, physiological saline, with a blood-compatible suspending agent, the pH of which has been adjusted to about 7.4.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the active material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the disclosure are particulate compositions coated with polymers (e.g. poloxamers or poloxamines) and the compound coupled to antibodies directed against tissue-specific receptors, ligands or antigens or coupled to ligands of tissue-specific receptors.

In some embodiments, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified compounds exhibit substantially longer half-lives in blood following intravenous injection than do the corresponding unmodified compounds. In one embodiment, modifications also increase the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation disclosed herein formulated in a compatible pharmaceutical carrier are also prepared, placed in an appropriate container, and labeled for treatment of an indicated condition.

In another embodiment, a coagulation factor as described herein is lyophilized (i.e., freeze-dried) preparation in combination with complex organic excipients and stabilizers such as nonionic surface active agents (i.e., surfactants), various sugars, organic polyols and/or to human serum albumin. In another embodiment, a pharmaceutical composition comprises a lyophilized coagulation factor as described in sterile water for injection. In another embodiment, a pharmaceutical composition comprises a lyophilized coagulation factor as described in sterile PBS for injection. In another embodiment, a pharmaceutical composition comprises a lyophilized coagulation factor as described in sterile 0.9% NaCl for injection.

In another embodiment, the pharmaceutical composition comprises a coagulation factor as described herein and complex carriers such as human serum albumin, polyols, sugars, and anionic surface active stabilizing agents. In another embodiment, the pharmaceutical composition comprises a coagulation factor as described herein and lactobionic acid and an acetate/glycine buffer. In another embodiment, the pharmaceutical composition comprises a coagulation factor as described herein and amino acids, such as arginine or glutamate that increase the solubility of interferon compositions in water. In another embodiment, the pharmaceutical composition comprises a lyophilized coagulation factor as described herein and glycine or human serum albumin (HSA), a buffer (e g. acetate) and an isotonic agent (e.g NaCl). In another embodiment, the pharmaceutical composition comprises a lyophilized coagulation factor as described herein and phosphate buffer, glycine and HSA.

In another embodiment, the pharmaceutical composition comprising a coagulation factor as described herein is stabilized when placed in buffered solutions having a pH between about 4 and 7.2. In another embodiment, the pharmaceutical composition comprising a coagulation factor is in a buffered solution having a pH between about 4 and 8.5. In another embodiment, the pharmaceutical composition comprising a coagulation factor is in a buffered solution having a pH between about 6 and 7. In another embodiment, the pharmaceutical composition comprising a coagulation factor is in a buffered solution having a pH of about 6.5. In another embodiment, the pharmaceutical composition comprising a coagulation factor is in a buffered solution having a pH of about 6.4. In another embodiment, the pharmaceutical composition comprising a coagulation factor as described herein is stabilized with an amino acid as a stabilizing agent and in some cases a salt (if the amino acid does not contain a charged side chain).

In another embodiment, the pharmaceutical composition comprising a coagulation factor as described herein is a liquid composition comprising a stabilizing agent at between about 0.3% and 5% by weight which is an amino acid.

In another embodiment, the pharmaceutical composition comprising a coagulation factor as described herein provides dosing accuracy and product safety. In another embodiment, the pharmaceutical composition comprising a coagulation factor as described herein provides a biologically active, stable liquid formulation for use in injectable applications. In another embodiment, the pharmaceutical composition comprises a non-lyophilized coagulation factor as described herein.

In another embodiment, the pharmaceutical composition comprising a coagulation factor as described herein provides a liquid formulation permitting storage for a long period of time in a liquid state facilitating storage and shipping prior to administration.

In another embodiment, the pharmaceutical composition comprising a coagulation factor as described herein comprises solid lipids as matrix material. In another embodiment, the injectable pharmaceutical composition comprising a coagulation factor as described herein comprises solid lipids as matrix material. In another embodiment, the production of lipid microparticles by spray congealing was described by Speiser (Speiser and al., Pharm. Res. 8 (1991) 47-54) followed by lipid nanopellets for peroral administration (Speiser EP 0167825 (1990)). In another embodiment, lipids, which are used, are well tolerated by the body (e. g. glycerides composed of fatty acids which are present in the emulsions for parenteral nutrition).

In another embodiment, the pharmaceutical composition comprising a coagulation factor as described herein comprises polymeric microparticles. In another embodiment, the pharmaceutical composition comprising a coagulation factor as described herein comprises nanoparticles. In another embodiment, the pharmaceutical composition comprising a coagulation factor as described herein comprises liposomes. In another embodiment, the pharmaceutical composition comprising a coagulation factor as described herein comprises lipid emulsion. In another embodiment, the pharmaceutical composition comprising a coagulation factor as described herein comprises microspheres. In another embodiment, the pharmaceutical composition comprising a coagulation factor as described herein comprises lipid nanoparticles. In another embodiment, the pharmaceutical composition comprising a coagulation factor as described herein comprises lipid nanoparticles comprising amphiphilic lipids. In another embodiment, the pharmaceutical composition comprising a coagulation factor as described herein comprises lipid nanoparticles comprising a drug, a lipid matrix and a surfactant. In another embodiment, the lipid matrix has a monoglyceride content which is at least 50% w/w.

In one embodiment, compositions disclosed herein are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, it will be appreciated that the coagulation factors disclosed herein can be provided to the individual with additional active agents to achieve an improved therapeutic effect as compared to treatment with each agent by itself. In another embodiment, measures (e.g., dosing and selection of the complementary agent) are taken to avoid adverse side effects which are associated with combination therapies.

Manufacturing

In one embodiment, disclosed is a method of manufacturing a human chorionic gonadotropin peptide (CTP)-modified Factor VIIa polypeptide, the method comprising the steps of: (a) stably transfecting a predetermined number of cells with an expression vector comprising a coding portion encoding said CTP-modified Factor VII, wherein said transfected cell expresses and optionally secretes said CTP-modified Factor VII; (b) obtaining cell clones that overexpress said CTP-modified Factor VII; (c) expanding said clones in solution to a predetermined scale; (d) harvesting said solution containing said clones; (e) filtering said solution containing said clones to obtain a clarified harvest solution; and, (f) purifying and activating said clarified harvest solution to obtain a purified protein solution having a desired concentration of a CTP-modified Factor VIIa, thereby manufacturing a human chorionic gonadotropin peptide (CTP)-modified Factor VIIa polypeptide. In another embodiment, the CTP-modified Factor VII is secreted. In another embodiment, the CTP-modified Factor VII is not secreted. In the manufacturing of CTP-modified Factor VII transfection is an early step. Once the final high expressing clone is selected, each production includes thawing of a master cell bank (MCB), expansion, harvest and purification. (See Example 3, steps 1-5 describing clone expansion through harvest; steps 6-14 describing purification and activation). In one embodiment, disclosed is a method of manufacturing a human chorionic gonadotropin carboxy terminal peptide (CTP)-modified human active factor VII (FVIIa) polypeptide, wherein said polypeptide comprises three CTP molecules attached in tandem to the C-terminal end of FVII, the method comprising the steps of: stably transfecting a predetermined number of cells with an expression vector comprising a coding portion encoding said CTP-modified FVII, wherein said transfected cells express and secrete said CTP-modified FVII; obtaining cell clones that overexpress said CTP-modified FVII; expanding said clones in solution to a predetermined scale; harvesting said solution containing said clones; filtering said solution containing said clones to obtain a clarified harvest solution containing said CTP-modified FVII; and, purifying and activating CTP-modified FVII from said clarified harvest solution to obtain a purified protein solution having a desired concentration of the CTP-modified FVIIa; wherein said manufactured CTP-modified FVIIa comprises at least one of the following:
  a. a low oxidized form;
  b. a high percentage of carboxylated glutamic acid residues;
  c. at least 60% charged N-glycans; or
  d. a potency of at least 10,500 U/mg;
thereby manufacturing a CTP-modified FVIIa, and wherein the amino acid sequence of the manufactured CTP-modified FVIIa is set forth in SEQ ID NO: 7.

In one embodiment, polynucleotides disclosed herein are inserted into expression vectors (i.e., a nucleic acid construct) to enable expression of the recombinant polypeptide. In one embodiment, the expression vector disclosed herein includes additional sequences which render this vector suitable for replication and integration in prokaryotes. In one embodiment, the expression vector disclosed herein includes additional sequences which render this vector suitable for replication and integration in eukaryotes. In one embodiment, the expression vector disclosed herein includes a shuttle vector which renders this vector suitable for replication and integration in both prokaryotes and eukaryotes. In some embodiments, cloning vectors comprise transcription and translation initiation sequences (e.g., promoters, enhancer) and transcription and translation terminators (e.g., polyadenylation signals).

In one embodiment, a method of manufacture of a CTP-modified FVIIa polypeptide, comprises a step comprising the use of an expression vector, wherein said expression vector comprises a promoter, a coding sequence for a CTP-modified FVII polypeptide, and a polyadenylation sequence. In another embodiment the polyadenylation sequence is a simian virus (SV) 40 polyadenylation sequence.

In one embodiment, a variety of prokaryotic or eukaryotic cells can be used as host-expression systems to express the polypeptides disclosed herein. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In one embodiment, non-bacterial expression systems are used (e.g. mammalian expression systems such as CHO cells or cells derived from CHO cells) to express the polypeptide disclosed herein. In one embodiment, the expression vector used to express polynucleotides disclosed herein in mammalian cells is pCI-DHFR vector comprising a CMV promoter and a neomycin resistance gene.

In one embodiment, the expression vector disclosed herein can further include additional polynucleotide sequences that allow, for example, the translation of several proteins from a single mRNA such as an internal ribosome entry site (IRES) and sequences for genomic integration of the promoter-chimeric polypeptide.

In some embodiments, mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by methods disclosed herein. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In one embodiment, various methods can be used to introduce the expression vector encoding the CTP-modified Factor VII disclosed herein into cells. "Transfection" of eukaryotic host cells with a polynucleotide or expression vector, resulting in genetically modified cells or transgenic cells, can be performed by any method well known in the art and described, e.g., Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, and electroporation. In addition, see U.S. Pat. Nos. 5,464,764 and 5,487,992 for positive-negative selection methods. Transfection methods further include but are not limited to liposome-mediated transfection, calcium phosphate co-precipitation, electroporation, polycation (such as DEAE-dextran)-mediated transfection, protoplast fusion, viral infections (including recombinant viral infections) and microinjection. Preferably, the transfection is a stable transfection. The transfection method that provides optimal transfection frequency and expression of the heterologous genes encoding the peptide of interest disclosed herein in the particular host cell line and type is favored. Suitable methods can be determined by routine procedures. For stable transfectants the constructs are either integrated into the host cell's genome or an artificial chromosome/mini-chromosome or located episomally so as to be stably maintained within the host cell.

The practice disclosed herein will employ, unless otherwise indicated, conventional techniques of cell biology, molecular biology, cell culture, immunology and the like which are in the skill of one in the art. These techniques are fully disclosed in the current literature. See e.g. Sambrook et al., Molecular Cloning: A Laboratory Manual, 2$^{nd}$ Ed., Cold Spring Harbor Laboratory Press, Cold Spring Harbor, N.Y. (1989); Ausubel et al., Current Protocols in Molecular Biology (1987, updated); Brown ed., Essential Molecular Biology, IRL Press (1991); Goeddel ed., Gene Expression Technology, Academic Press (1991); Bothwell et al. eds., Methods for Cloning and Analysis of Eukaryotic Genes, Bartlett Publ. (1990); Wu et al., eds., Recombinant DNA Methodology, Academic Press (1989); Kriegler, Gene Transfer and Expression, Stockton Press (1990); McPherson et al., PCR: A Practical Approach, IRL Press at Oxford University Press (1991); Gait ed., Oligonucleotide Synthesis (1984); Miller & Calos eds., Gene Transfer Vectors for Mammalian Cells (1987); Butler ed., Mammalian Cell Biotechnology (1991); Pollard et al., eds., Animal Cell Culture, Humana Press (1990); Freshney et al., eds., Culture of Animal Cells, Alan R. Liss (1987); Studzinski, ed., Cell Growth and Apoptosis, A Practical Approach, IRL Press at Oxford University Press (1995); Melamed et al., eds., Flow Cytometry and Sorting, Wiley-Liss (1990); Current Protocols in Cytometry, John Wiley & Sons, Inc. (updated); Wirth & Hauser, Genetic Engineering of Animals Cells, in: Biotechnology Vol. 2, Paler ed., VCH, Weinheim 663-744; the series Methods of Enzymology (Academic Press, Inc.), and Harlow et al., eds., Antibodies: A Laboratory Manual (1987).

A heterologous gene of interest encoding the CTP-modified Factor VII may be introduced into the cell disclosed herein by various methods, for example by viral transformation, transfection or microinjection. The heterologous gene of interest may be introduced into the cell as linear DNA or as part of an expression vector. A number of eukaryotic expression vectors are known which allow multiple cloning sites for the insertion of one or more heterologous genes and their expression. Commercial suppliers include among others companies such as Stratagene, La Jolla, Calif., USA; Invitrogen, Carlsbad, Calif., USA; Promega, Madison, Wis., USA or BD Biosciences Clontech, Palo Alto, Calif., USA. The transfection of the cells with a DNA or an expression vector which code(s) for one or more genes of interest is carried out by conventional methods as described for example in Sambrook et al., 1989 or Ausubel et al., 1994. Suitable methods of transfection include for example liposome-mediated transfection, calcium phosphate co-precipitation, electroporation, polycation- (e.g. DEAE dextran)-mediated transfection, protoplast fusion, microinjection and viral infections. Preferably, stable transfection is carried out in which the DNA molecules are either integrated into the genome of the host cell or an artificial chromosome/minichromosome, or are episomally contained in stable manner in the host cell. The transfection method which gives the optimum transfection frequency and expression of one or more heterologous genes of interest in the host cell in question is preferred.

In some embodiments, introduction of nucleic acid by viral infection offers several advantages over other methods such as lipofection and electroporation, since higher transfection efficiency can be obtained due to the infectious nature of viruses.

In one embodiment, it will be appreciated that the polypeptides disclosed herein can also be expressed from a nucleic acid construct administered to the individual employing any suitable mode of administration, described hereinabove (i.e., in-vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

The heterologous gene of interest is usually functionally linked to a promoter which enables the transcription of the gene of interest, and to other regulatory elements which allow transcription and translation (expression) of the gene of interest or increase its efficiency.

A skilled artisan would appreciate that the term "promoter" may encompass a polynucleotide sequence which enables and controls transcription of the genes or sequences functionally linked to it. A promoter contains recognition sequences for binding RNA polymerase and the initiation site for transcription (transcription initiation site). In order to express a desired sequence in a certain cell type or a host cell a suitable functional promoter must be chosen. The skilled man will be familiar with a variety of promoters from various sources, including to constitutive, inducible and repressible promoters. They are deposited in databanks such as GenBank, for example, and may be obtained as separate elements or elements cloned within polynucleotide sequences from commercial or individual sources. In inducible promoters the activity of the promoter may be reduced or increased in response to a signal. One example of an inducible promoter is the tetracycline (tet) promoter. This contains tetracycline operator sequences (tetO) which can be induced by a tetracycline-regulated transactivator protein (tTA). In the presence of tetracycline the binding of tTA to tetO is inhibited. Examples of other inducible promoters are the jun, fos, metallothionein and heat shock promoter (see also Sambrook, J., Fritsch, E. F. & Maniatis, T., Molecular Cloning: A Laboratory Manual Cold Spring Harbor Laboratory, Cold Spring Harbor, N.Y., 1989; Gossen, M. et al., Curr Opi Biotech 1994, 5, 516-520). Of the promoters which are particularly suitable for high expression in eukaryotes, there are for example the ubiquitin/S27a promoter of the hamster (WO 97/15664), SV 40 early promoter, adenovirus major late promoter, mouse metallothionein-1 promoter, the long terminal repeat region of Rous Sarcoma Virus and the early promoter of human Cytomegalovirus. Examples of other heterologous mammalian promoters are the actin, immunoglobulin or heat shock promoter(s).

For example, the promoter may be functionally linked to enhancer sequences in order to increase the transcriptional activity. For this, one or more enhancers and/or several copies of an enhancer sequence may be used, e.g. a CMV or SV40 enhancer. For example, the promoter may be functionally linked to enhancer sequences in order to increase the transcriptional activity. For this, one or more enhancers and/or several copies of an enhancer sequence may be used, e.g. a CMV or SV40 enhancer.

A skilled artisan would appreciate that the term enhancer may encompass a polynucleotide sequence which in the cis location acts on the activity of a promoter and thus stimulates the transcription of a gene functionally connected to this promoter. Unlike promoters the effect of enhancers is independent of position and orientation and they can therefore be positioned in front of or behind a transcription unit, within an intron or even within the coding region. The enhancer may be located both in the immediate vicinity of the transcription unit and at a considerable distance from the promoter. It is also possible to have a physical and functional overlap with the promoter. The skilled artisan will be aware of a number of enhancers from various sources (and deposited in databanks such as GenBank, e.g. SV40 enhancers, CMV enhancers, polyoma enhancers, adenovirus enhancers) which are available as independent elements or elements cloned within polynucleotide sequences (e.g. deposited at the ATCC or from commercial and individual sources). A number of promoter sequences also contain enhancer sequences such as the frequently used CMV promoter. The human CMV enhancer is one of the strongest enhancers identified hitherto. One example of an inducible enhancer is the metallothionein enhancer, which can be stimulated by glucocorticoids or heavy metals.

Basically, the regulatory elements include promoters, enhancers, termination and polyadenylation signals and other expression control elements. Both inducible and constitutively regulatory sequences are known for the various cell types. "Transcription-regulatory elements" generally comprise a promoter upstream of the gene sequence to be expressed, transcription initiation and termination sites and a polyadenylation signal.

A skilled artisan would appreciate that the term "transcription initiation site" may encompass a nucleic acid in the construct which corresponds to the first nucleic acid which is incorporated in the primary transcript, i.e. the mRNA precursor. The transcription initiation site may overlap with the promoter sequences.

A skilled artisan would appreciate that the term "transcription termination site" may encompass a nucleotide sequence which is normally at the 3' end of the gene of interest or of the gene section which is to be transcribed, and which brings about the termination of transcription by RNA polymerase.

A skilled artisan would appreciate that the term "polyadenylation signal" may encompass a signal sequence which causes cleavage at a specific site at the 3' end of the eukaryotic mRNA and posttranscriptional incorporation of a sequence of about 100-200 adenine nucleotides (polyA tail) at the cleaved 3'-end. The polyadenylation signal comprises the sequence AATAAA about 10-30 nucleotides upstream of the cleavage site and a sequence located downstream. Various polyadenylation elements are known such as tk polyA, SV40 late and early polyA or BGH polyA (described for example in U.S. Pat. No. 5,122,458).

"Translation regulatory elements" comprise a translation initiation site (AUG), a stop codon and a polyA signal for each polypeptide to be expressed. For optimum expression it may be advisable to remove, add or change 5'- and/or 3'-untranslated regions of the nucleic acid sequence which is to be expressed, in order to eliminate any potentially unsuitable additional translation initiation codons or other sequences which might affect expression at the transcription or expression level. In order to promote expression, ribosomal consensus binding sites may alternatively be inserted immediately upstream of the start codon. In order to produce a secreted polypeptide the gene of interest usually contains a signal sequence which codes for a signal precursor peptide which transports the synthesized polypeptide to and through the ER membrane. The signal sequence is often but not always located at the amino terminus of the secreted protein and is cleaved by signal peptidases after the protein has been filtered through the ER membrane. The gene sequence will usually but not necessarily contain its own signal sequence. If the native signal sequence is not present a heterologous signal sequence may be introduced in known manner. Numerous signal sequences of this kind are known to the skilled artisan and deposited in sequence databanks such as GenBank and EMBL.

A skilled artisan would appreciate that the terms "polypeptides", "polypeptide" or grammatical equivalents thereof, may be used interchangeably to encompass amino acid sequences or proteins and may encompass polymers of amino acids of any length. This term also includes proteins which have been modified post-translationally by reactions such as glycosylation, phosphorylation, acetylation or protein processing. The structure of the polypeptide may be modified, for example, by substitutions, deletions or insertions of amino acids and fusion with other proteins while retaining its biological activity.

In order to produce one or more gene products of interest in the cells, the cells may be grown in a serum-free culture medium and in suspension culture under conditions which allow expression of the gene of interest. If for example the gene of interest is under the control of a constitutive promoter, there is no need to add special inducers. If the expression of the gene of interest is under the control of an inducible promoter, for example, a corresponding inducer must be added to the cell culture medium in a sufficient but non-toxic concentration. The cells can be expanded as desired by multiple subpassaging and transferred into suitable cell culture vessels. The gene product(s) is or are produced as either a cellular, membrane-bound or secretory product.

In one embodiment, a step of manufacturing a CTP-modified Factor Vita comprises stably transfecting a predetermined number of cells with an expression vector comprising a coding portion encoding a CTP-modified Factor VII. In another embodiment, a step of manufacturing a CTP-modified Factor VIIa comprises stably transfecting cells with an expression vector comprising a coding portion encoding said CTP-modified Factor VII. In one embodiment, cells are CHO cells. In another embodiment, cells are DG44 cells. In another embodiment, cells are any cells known in the art suitable for expression and secretion of CTP-modified Factor VII. In one embodiment, the CTP-modified FVII expressed is a FVII-CTP3 zymogen lacking a signal peptide. In another embodiment, the amino acid sequence of the CTP-modified FVII expressed is set forth in SEQ ID NO: 7

A skilled artisan would appreciate that while a CTP-modified FVII may be expressed as a zymogen in an inactive state, the zymogen may be activated during or after a purification process. The term "CTP-modified FVII" may be used interchangeable with "CTP-modified FVII/FVIIa" and may encompass both the inactive and active forms of the CTP-modified FVII polypeptide. Similarly, individual CTP-modified Factor VII polypeptides, for example, FVII/FVIIa-CTP$_3$ may also use the nomenclature FVII/FVIIa to represent either the inactive or active forms or both. In one embodiment, the CTP-modified polypeptide comprising an activated FVIIa-CTP$_3$ comprises a light chain and a heavy chain linked by a disulfide bond.

In another embodiment, the transfected cells express CTP-modified Factor VII. In another embodiment, the FVII/FVIIa-CTP3 being expressed and manufactured consists of two CTP attached to the carboxy terminus of said Factor VII/VIIa, and one chorionic gonadotropin carboxy terminal peptide attached to the amino terminus of said Factor VII/VIIa. In another embodiment, the CTP-modified Factor VII/VIIa being expressed and manufactured and expressed consists of one chorionic gonadotropin carboxy terminal peptide attached to the carboxy terminus of said Factor VII/FVIIa. In other embodiment, the expression of CTP-modified Factor VII is at a high expression level. In another embodiment, said CTP-modified Factor VII/VIIa is highly glycosylated. In another embodiment, said CTP-modified Factor VII/VIIa is highly sialated. In another embodiment, said CTP-modified Factor VII/VIIa has a high O-glycan content. In another embodiment, said CTP-modified Factor VII/VIIa has a high N-glycan content. In another embodiment, said CTP-modified Factor VII/VIIa has a high charged N-glycan content. In another embodiment, said CTP-modified Factor VII/VIIa has a high percentage of carboxy-glutamic acid. As described herein detail, CTP-modified Factor VIIa may have different glycosylation content and patterns. A CTP-modified Factor VIIa manufactured by the methods disclosed herein may include any of the glycosylation patterns and content as disclosed herein. In general, method of manufacture presented here, provide a CTP-modified Factor VIIa having a high glycosylation content and a high percentage of glycosylation sites glycosylated.

In another embodiment, said high O-glycan content of CTP-modified Factor VII/VIIa is at least 2 mol/mol. In another embodiment, said high O-glycan content of CTP-modified Factor VII/VIIa is at least 4 mol/mol. In another embodiment, said high O-glycan content of CTP-modified Factor VII/VIIa is at least 5 mol/mol. In another embodiment, said high O-glycan content of CTP-modified Factor VII/VIIa is at least 6 mol/mol. In another embodiment, said high O-glycan content of CTP-modified Factor VII/VIIa is at least 8 mol/mol. In another embodiment, said high O-glycan content of CTP-modified Factor VII/VIIa is at least 10 mol/mol. In another embodiment, said high O-glycan content of CTP-modified Factor VII/VIIa is at least 12 mol/mol. In another embodiment, said high O-glycan content of CTP-modified Factor VII/VIIa is at least 14 mol/mol. In another embodiment, said high O-glycan content of CTP-modified Factor VII/VIIa is at least 16 mol/mol.

In one embodiment, the high level or content of O-glycan is driven by the upstream process in the manufacturing process disclosed herein. In another embodiment, the high level or content of O-glycan is driven by the clone in the manufacturing process disclosed herein. In another embodiment, the high O-glycan content or levels are maintained until the final drug substance is obtained.

In another embodiment, the CTP-modified Factor VII/VIIa has a high sicalic acid content. In another embodiment, said high Sialic acid content of CTP-modified Factor VII/VIIa is at least 4 mol/mol. In another embodiment, said high Sialic acid content of CTP-modified Factor VII/VIIa is at least 6 mol/mol. In another embodiment, said high Sialic acid content of CTP-modified Factor VII/VIIa is at least 8 mol/mol. In another embodiment, said high Sialic acid content of CTP-modified Factor VII/VIIa is at least 10 mol/mol. In another embodiment, said high Sialic acid content of CTP-modified Factor VII/VIIa is at least 12 mol/mol. In another embodiment, said high Sialic acid content of CTP-modified Factor VII/VIIa is at least 14 mol/mol. In another embodiment, said high Sialic acid content of CTP-modified Factor VII/VIIa is at least 15 mol/mol. In another embodiment, said high Sialic acid content of CTP-modified Factor VII/VIIa is at least 17 mol/mol. In another embodiment, said high Sialic acid content of CTP-modified Factor VII/VIIa is at least 18 mol/mol. In another embodiment, said high Sialic acid content of CTP-modified Factor VII/VIIa is at least 20 mol/mol. In another embodiment, said high Sialic acid content of CTP-modified Factor VII/VIIa is at least 22 mol/mol. In another embodiment, said high Sialic acid content of CTP-modified Factor VII/VIIa is at least 25 mol/mol. In another embodiment, said high Sialic acid content of CTP-modified Factor VII/VIIa is at least 27 mol/mol. In another embodiment, said high Sialic acid content of CTP-modified Factor VII/VIIa is at least 30 mol/mol.

In another embodiment, said high percent carboxy-glutamic acid of CTP-modified Factor VII/VIIa is at least 40%. In another embodiment, said high percent carboxy-glutamic acid of CTP-modified Factor VII/VIIa is at least 50%. In another embodiment, said high percent carboxy-glutamic acid of CTP-modified Factor VII/VIIa is at least 60%. In another embodiment, said high percent carboxy-glutamic acid of CTP-modified Factor VII/VIIa is at least 70%. In another embodiment, said high percent carboxy-glutamic acid of CTP-modified Factor VII/VIIa is at least 80%. In another embodiment, said high percent carboxy-glutamic acid of CTP-modified Factor VII/VIIa is at least 85%. In another embodiment, said high percent carboxy-glutamic acid of CTP-modified Factor VII/VIIa is at least 90%. In another embodiment, said high percent carboxy-glutamic acid of CTP-modified Factor VII/VIIa is at least 91%. In another embodiment, said high percent carboxy-glutamic acid of CTP-modified Factor VII/VIIa is at least 92%. In another embodiment, said high percent carboxy-glutamic acid of CTP-modified Factor VII/VIIa is at least 93%. In another embodiment, said high percent carboxy-glutamic acid of CTP-modified Factor VII/VIIa is at least 94%. In another embodiment, said high percent carboxy-glutamic acid of CTP-modified Factor VII/VIIa is at least 95%. In another embodiment, said high percent carboxy-glutamic acid of CTP-modified Factor VII/VIIa is at least 96%. In another embodiment, said high percent carboxy-glutamic acid of CTP-modified Factor VII/VIIa is at least 97%. In another embodiment, said high percent carboxy-glutamic acid of CTP-modified Factor VII/VIIa is at least 98%. In another embodiment, said high percent carboxy-glutamic acid of CTP-modified Factor VII/VIIa is at least 99%. A skilled artisan would appreciate that percent of carboxy-glutamic acid residue may be expressed inversely as the % carboxy-glutamic acid residue domainless (Gla domainless), wherein, for example if high percent Gla is 40% then Gla domainless is 60%.

In one embodiment, a step of manufacturing a CTP-modified Factor VIIa comprises obtaining cell clones that overexpress the CTP-modified Factor VII. In another embodiment, expression of CTP-modified Factor VII is optimal. In another embodiment, the level of expression is between 30-1500 mg/L. In another embodiment, the level of expression is at least 30 mg/L. In another embodiment, the level of expression is at least 40 mg/L. In another embodiment, the level of expression is at least 50 mg/L. In another embodiment, the level of expression is at least 60 mg/L. In another embodiment, the level of expression is at least 70 mg/L. In another embodiment, the level of expression is between 50-70 mg/L. In another embodiment, the level of expression is at least 200 mg/L. In another embodiment, the level of expression is at least 300 mg/L. In another embodiment, the level of expression is at least 400 mg/L. In another embodiment, the level of expression is at least 500 mg/L. In another embodiment, the level of expression is at least 600 mg/L. In another embodiment, the level of expression is at least 700 mg/L. In another embodiment, the level of expression is at least 800 mg/L. In another embodiment, the level of expression is at least 900 mg/L. In another embodiment, the level of expression is at least 1000 mg/L. In another embodiment, the level of expression is at least 1100 mg/L. In another embodiment, the level of expression is at least 1200 mg/L. In another embodiment, the level of expression is at least 1300 mg/L. In another embodiment, the level of expression is at least 1400 mg/L. In another embodiment, the level of expression is at least 1500 mg/L. In another embodiment, the clones are propagated in medium to form a master cell bank (MCB) and a working cell bank (WCB). In one embodiment, clones at step (c) are obtained from a MCB. In another embodiment, clones are obtained from a WCB.

The CTP-modified FVII is obtained from the cell culture medium as a secreted gene product. If a protein or polypeptide is expressed without a secretion signal, however, the gene product may also be isolated from cell lysates. In order to obtain a pure homogeneous product which is substantially free from other recombinant proteins and host cell proteins, conventional purification procedures are carried out. First of all, cells and cell debris are frequently removed from the culture medium or lysate. The desired gene product can then be freed from contaminating to soluble proteins, polypeptides and nucleic acids, e.g. by fractionation on immunoaffinity and ion exchange columns, affinity columns, ethanol precipitation, reversed phase HPLC or chromatography on Sephadex, hydroxyapatite, silica or cation exchange resins such as DEAE (see Examples herein). General methodologies known in the art and which result in the purification of a heterologous protein expressed by recombinant host cells are known to the skilled man and described in the literature, e.g. by Harris et al. (Harris et al., Protein Purification: A Practical Approach, Pickwood and Hames, eds., IRL Press, Oxford, 1995) and Scopes (Scopes, R., Protein Purification, Springer Verlag, 1988). These methods may be employed in whole or in part in the methods disclosed herein.

In another embodiment, disclosed herein is a method of preparing a CTP-modified FVII in mammalian cells under serum-free conditions, characterized in that (i) mammalian cells contain a gene which codes for the CTP-modified FVII; (ii) the mammalian cells are grown under serum-free conditions which allow replication of the mammalian cells; (iii) in each case at least one (1) of these mammalian cell(s) are deposited in a cell culture vessel under serum-free conditions; (iv) the suitably deposited mammalian cells are replicated under serum-free conditions; (v) the replicated cells are cultivated under serum-free conditions in which the CTP-modified FVII is expressed; and (vi) the CTP-modified FVII product is then isolated from the cells or culture supernatant and purified and activated. In another embodiment of this process the mammalian cell is a transfected mammalian cell into which the gene for CTP-modified FVII has been introduced. Accordingly, methods disclosed herein also relates to a method of preparing recombinant gene products, characterized in that before step (i) of the process described above the mammalian cells are transfected with a nucleic acid which at least codes for a CTP-modified FVII. Stable transfection of the corresponding mammalian cell is preferred.

Examples of serum-free, protein-free or chemically defined media include for example the commercially obtainable media Ham's F12 (Sigma, Deisenhofen, DE), RPMI 1640 (Sigma), Dulbecco's Modified Eagle's medium (DMEM; Sigma), Minimal Essential medium (MEM; Sigma), Iscove's Modified Dulbecco's medium (IMDM; Sigma), CDCHO (Invitrogen, Carlsbad, Calif., USA), CHO-S-SFMII (Invitrogen), serum-free CHO medium (Sigma), CD-PowerCHO2 medium (Lonza) and protein-free CHO medium (Sigma). Each of these media can if desired be supplemented with various compounds such as hormones and/or other growth factors (e.g. insulin, transferrin, epidermal growth factor, insulin-like growth factor), salts (e.g. sodium chloride, calcium, magnesium, phosphate), buffers (e.g. HEPES), nucleosides (e.g. adenosine, thymidine), glutamine, glucose or other equivalent nutrients, antibiotics and/or trace elements or commercially available Feed such as Power Feed A (Lonza) If the replicable cells are recombinant cells which express one or more selectable markers, one or more suitable selection agents such as antibiotics may also be added to the medium.

It will be appreciated that other than containing the necessary elements for the transcription and translation of the inserted coding sequence (encoding the polypeptide), the expression construct disclosed herein can also include sequences engineered to optimize stability, production, purification, yield or activity of the expressed polypeptide. In one embodiment, the nucleotide sequence encoding the CTP-modified FVII is set forth in SEQ ID NO: 4.

In some embodiments, transformed cells are cultured under effective conditions, which allow for the expression of high amounts of recombinant polypeptide. In some embodiments, effective culture conditions include, but are not limited to, effective media, bioreactor, temperature, pH and oxygen conditions that permit protein production. A skilled artisan would appreciate that the term "an effective medium" may encompass any medium in which a cell is cultured to produce the recombinant polypeptide disclosed herein. In some embodiments, a medium typically includes an aqueous solution having assimilable carbon, nitrogen and phosphate sources, and appropriate salts, minerals, metals and other nutrients, such as vitamins. In some embodiments, cells disclosed herein can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In one embodiment, culture conditions comprised dissolved oxygen (DO) content at about 20-80%. In another embodiment, DO content is at about 20-30%. In another embodiment, DO content is at about 30-40%. In another embodiment, DO content is at about 40-50%. In another embodiment, DO content is at about 50-60%. In another embodiment, DO content is at about 60-70%. In another embodiment, DO content is at about 70-80%.

In one embodiment, culture conditions comprise pH starting at one temperature and shifting to another during the manufacture. In another embodiment, pH starts at about 7.3 and shifts to about 6.7 during bioreactor incubation. In another embodiment, pH starts at about 7.3, about 7.2 or about 7.1 and shifts to about 6.7, about 6.8, about 6.9 or about 7.0 during bioreactor incubation.

In some embodiments, depending on the vector and host system used for production, resultant polypeptides disclosed herein either remain within the recombinant cell, or are secreted into the medium.

In one embodiment, following a predetermined time in culture, recovery of the recombinant polypeptide is effected.

A skilled artisan would appreciate that the phrase "recovering the recombinant polypeptide" used herein may encompass collecting the whole medium containing the polypeptide and can imply additional steps of separation or purification.

In one embodiment, polypeptides disclosed herein are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, hydroxyapatite chromatography, chromatofocusing and differential solubilization.

In one embodiment, each column can be run under controlled or non-controlled temperature.

In one embodiment, all chromatography steps are conducted in down flow mode. In another embodiment, all chromatography steps are run in an upflow mode.

In one embodiment, to facilitate recovery, the expressed coding sequence can be engineered to encode the polypeptide disclosed herein and fused to a cleavable moiety. In one embodiment, a fusion protein can be designed so that the polypeptide can be readily isolated by affinity chromatography; e.g., by immobilization on a column specific for the cleavable moiety. In one embodiment, a cleavage site is engineered between the polypeptide and the cleavable moiety and the polypeptide can be released from the chromatographic column by treatment with an appropriate enzyme or agent that specifically cleaves the fusion protein at this site [e.g., see Booth et al., Immunol. Lett. 19:65-70 (1988); and Gardena et al., J. Biol. Chem. 265:15854-15859 (1990)].

In one embodiment, the polypeptide disclosed herein is retrieved in "substantially pure" form. A skilled artisan would appreciate that the phrase "substantially pure" may encompass a purity that allows for the effective use of the protein in the applications described herein. Such a form may also include highly glycosylated (O-glycan and/or N-glycan) and highly sialylated forms as also disclosed herein. In another embodiment, such a form may include forms with a high percentage carboxylated glutamic acid residues, and/or a low percent of oxidized form. In yet another embodiment, a CTP-modified FVII polypeptide disclosed herein may comprise a substantially pure and active form of the polypeptide.

In another embodiment, the percent oxidation of a CTP-modified FVII/FVIIa described herein is below 20% oxidized. In another embodiment, the percent oxidation of a CTP-modified FVII/FVIIa described herein is below 15% oxidized. In another embodiment, the percent oxidation of a CTP-modified FVII/FVIIa described herein is below 10% oxidized. In another embodiment, the percent oxidation of a CTP-modified FVII/FVIIa described herein is below 8% oxidized In another embodiment, the percent oxidation of a CTP-modified FVII/FVIIa described herein is to below 5% oxidized. In another embodiment, the percent oxidation of a CTP-modified FVII/FVIIa described herein is below 4% oxidized. In another embodiment, the percent oxidation of a CTP-modified FVII/FVIIa described herein is below 3% oxidized.

In one embodiment, the reduction in oxidized forms and the control over the level of oxidized forms is performed throughout the whole manufacturing process, from upstream to final drub substance.

In another embodiment, the purity of said substantially pure and active CTP-modified FVII polypeptide is at least 40%. In another embodiment, the purity of said substantially pure and active CTP-modified FVII polypeptide is at least 50%. In another embodiment, the purity of said substantially pure and active CTP-modified FVII polypeptide is at least 60%. In another embodiment, the purity of said substantially pure and active CTP-modified FVII polypeptide is at least 70%. In another embodiment, the purity of said substantially pure and active CTP-modified FVII polypeptide is at least 75%. In another embodiment, the purity of said substantially pure and active CTP-modified FVII polypeptide is at least 80%. In another embodiment, the purity of said substantially pure and active CTP-modified FVII polypeptide is at least 85%. In another embodiment, the purity of said substantially pure and active CTP-modified FVII polypeptide is at least 90%. In another embodiment, the purity of said substantially pure and active CTP-modified FVII polypeptide is at least 91%. In another embodiment, the purity of said substantially pure and active CTP-modified FVII polypeptide is at least 92%. In another embodiment, the purity of said substantially pure and active CTP-modified FVII polypeptide is at least 93%. In another embodiment, the purity of said substantially pure and active CTP-modified FVII polypeptide is at least 94%. In another embodiment, the purity of said substantially pure and active CTP-modified FVII polypeptide is at least 95%. In another embodiment, the purity of said substantially pure and active CTP-modified FVII polypeptide is at least 96%. In another embodiment, the purity of said substantially pure and active CTP-modified FVII polypeptide is at least 97%. In another embodiment, the purity of said substantially pure and active CTP-modified FVII polypeptide is at least 98%. In another embodiment, the purity of said substantially pure and active CTP-modified FVII polypeptide is at least 99%. In a further embodiment, the purity percentage is selected from the group consisting of 97.3%, 97.6%, 97.4% and 97.0%.

In one embodiment, a subject disclosed herein, is a human subject. In another embodiment, the subject is a domesticated animal. In another embodiment, the subject is a pet. In another embodiment, the subject is a mammal. In another embodiment, the subject is a farm animal. In another embodiment, the subject is a monkey. In another embodiment, the subject is a horse. In another embodiment, the subject is a cow. In another embodiment, the subject is a mouse. In another embodiment, the subject is a rat. In another embodiment, the subject is canine. In another embodiment, the subject is feline. In another embodiment, the subject is bovine, ovine, porcine, equine, murine, or cervine. In one embodiment, the subject is male. In another embodiment, the subject is female. In one embodiment, the subject is a child, in another embodiment, an adolescent, in another embodiment, an adult or, in another embodiment, an elderly subject. In another embodiment, the subject is a pediatric subject, in another embodiment, a geriatric subject.

In one embodiment, the CTP-modified FVII polypeptide disclosed herein is synthesized using in vitro expression systems. In one embodiment, in vitro synthesis methods are well known in the art and the components of the system are commercially available.

In one embodiment, production of a Factor Vita modified by CTPs using recombinant DNA technology is performed.

In some embodiments, the recombinant polypeptides are synthesized and purified; their therapeutic efficacy can be assayed either in vivo or in vitro. In one embodiment, the binding activities of the recombinant a Factor VII/VIIa modified by CTPs disclosed herein can be ascertained using various assays.

In one embodiment, a method of manufacturing CTP-modified Factor VIIa comprises a step for obtaining clones that optimally express said CTP-modified Factor VII from said WCB, and expanding said clones. In another embodiment, a method of manufacturing CTP-modified Factor VIIa comprises a step for obtaining clones that optimally express said CTP-modified Factor VII from said MCB, and expanding said clones. In another embodiment, the cell clones are expanded in solution through a series of sub-cultivation steps up to production bioreactor level. In another embodiment, the solution containing said sub-cultivated clones is seeded in a bioreactor. In another embodiment, the bioreactor is a disposable bioreactor. In another embodiment, the bioreactor comprises a stainless steel bioreactor, a rocking motion bioreactor such as Wave system from GE, a perfusion bioreactor, or any other bioreactor system known in the art. In one embodiment, removal of cells from a bioreactor is accomplished by use of a disposable filter system. If a large scale manufacture is performed, continuous centrifugation could be used prior to use of a filtering system.

In one embodiment, the cell clones are expanded further or up-scaled by serially culturing said cells in increasing sizes of the bioreactor until a desired scale is reached. In another embodiment, a bioreactor is run in a fed-batch mode. In another embodiment, a bioreactor is run in a batch mode. In another embodiment, a bioreactor is run in a repeated-batch mode. In another embodiment, a bioreactor is run in a perfusion mode.

Peak viable cell densities differ depending on the type of bioreactor employed. In one embodiment, the peak viable cell density of a bioreactor used in methods of manufacturing disclosed herein is about $0.2 \times 10^6$-$1.4 \times 10^6$ cells/ml. In another embodiment, the peak viable cell density of a bioreactor used in methods of manufacturing disclosed herein is about $0.05 \times 10^6$-$100 \times 10^6$. In another embodiment, the peak viable cell density of a bioreactor is about $0.05 \times 10^6$-$0.5 \times 10^6$. In another embodiment, the peak viable cell density of a bioreactor is about $0.5 \times 10^6$-$5 \times 10^6$. In another embodiment, the peak viable cell density of a bioreactor is about $5.0 \times 10^6$-$50 \times 10^6$. In another embodiment, the peak viable cell density of a bioreactor is about $50 \times 10^6$-$100 \times 10^6$.

Feed schemes for bioreactor use could be different, e.g. repeated daily feeding from a certain day, or fixed in several days, in addition % of feed added could be different from few % up to even 50% or more.

DMSO may be added to a bioreactor at different concentrations as is known in the art. In one embodiment, 0.1-3% DMSO is added to a bioreactor during its use. In another embodiment, 0.1-0.5% DMSO is added. In another embodiment, 0.5-1.0% DMSO is added. In another embodiment, 1.0-1.5% DMSO is added. In another embodiment, 1.5-2.0% DMSO is added. In another embodiment, 2.0-2.5% DMSO is added. In another embodiment, 2.5-3.0% DMSO is added.

In one embodiment, a method of manufacturing a CTP-modified Factor VIIa comprises the step of purifying and activating a clarified harvest solution in order to obtain a purified active CTP-modified FVII solution. In another embodiment, a purified protein solution manufactured using methods presented herein, comprises at least 5-95% CTP-modified Factor VII/VIIa. In another embodiment, a purified protein solution manufactured using methods presented herein, comprises at least 5% CTP-modified Factor VII/VIIa. In another embodiment, a purified protein solution manufactured using methods presented herein, comprises at least 10% CTP-modified Factor VII/VIIa. In another embodiment, a purified protein solution manufactured using methods presented herein, comprises at least 20% CTP-modified Factor VII/VIIa. In another embodiment, a purified protein solution manufactured using methods presented In another embodiment, a purified protein solution manufactured using methods presented herein, comprises at least 30% CTP-modified Factor VII/VIIa, comprises at least 40% CTP-modified Factor VII/VIIa. In another embodiment, a purified protein solution comprises at least 50% CTP-modified Factor VII/VIIa. In another embodiment, a purified protein solution comprises at least 60% CTP-modified Factor VII/VIIa. In another embodiment, a purified protein solution comprises at least 70% CTP-modified Factor VII/VIIa. In another embodiment, a purified protein solution comprises at least 80% CTP-modified Factor VII/VIIa. In another embodiment, a purified protein solution comprises at least 90% CTP-modified Factor VII/VIIa. In another embodiment, a purified protein solution manufactured using methods presented herein, comprises at least 95% CTP-modified Factor VII/VIIa.

In one embodiment, a clarified harvest is held up to 24 hours at 2-25° C. In another embodiment, the clarified harvest is stored at least 5° C. for up to one month.

In one embodiment, the clarified harvest obtained in step is tested for bioburden, bacterial endotoxin, specific protein content, residual DNA, viruses, virus-like particles, and/or *Mycoplasma*, or any combination thereof.

In one embodiment, the purification of the clarified harvest is accomplished by sequentially performing the steps comprising: (g) concentrating, diafiltering and purifying said clarified harvest solution, wherein said concentration, diafiltration and purifying is accomplished by hollow fiber cassette or tangential flow cassette sequentially passing said clarified harvest solution through an anion exchange column and a hydrophobic interaction column; (h) obtaining said clarified harvest obtained following step; (i) and inactivating viruses present in said clarified harvest by incubating in a solution toxic to said viruses; (j) obtaining said clarified harvest solution from (h) and concentrating, diafiltering and purifying said clarified harvest solution, wherein said concentration, diafiltration, activation and purification is followed by sequentially passing said clarified harvest solution through an affinity column, a Multimodel or Mixed-Mode column, a hydrophobic interaction column (HIC), and an anion exchange column; (j) obtaining said clarified harvest solution following step (i) and physically removing said clarified harvest solution from viruses by nanofiltration; (k) obtaining said clarified harvest solution following step (j) and concentrating, diafiltering and purifying said clarified harvest solution to arrive at a maximally purified clarified harvest containing said a highly glycosylated form of CTP-modified FVII/FVIIa.

In one embodiment, the CTP-modified FVII is activated during purification. In an alternative embodiment, the CTP-modified FVII is activated following purification. In another embodiment, the CTP-modified FVII is activated concurrent with any step of purification.

In one embodiment, ultrafiltration and diafiltration to concentrate and filter a clarified harvest may be performed using a hollow fiber cartridge, or equivalent TFF based UFDF step. The cartridge nominal molecular weight cutoff size is 10,000 kDa. In another embodiment, a membrane cartridge could comply PES/PS/RC membranes with a cut-off of 3 kDa to 30 kDa. In another embodiment, the UFDF step may be performed between chromatography steps. In another embodiment, the UFDF step may be performed prior to use of the anion exchange column. In another embodiment, the UFDF step may be performed prior to the use of Hydrophobic Interaction Chromatography (HIC). In another embodiment, the UFDF step may be performed following the use of Hydrophobic Interaction Chromatography (HIC). In yet another embodiment, UFDF may be performed at multiple steps, for example UFDF may be performed following harversing, between chromatographic steps, or as a step following viral removal by nanofiltration, or any combination thereof.

In another embodiment, the anion exchange column of is a DEAE-Sepharose Fast Flow column. In another embodiment, the DEAE column purifies the highly glycosylated form of said CTP-modified Factor VII/VIIa. In one embodiment, the higher the glycosylation the better the pharmacodynamics of the CTP-modified Factor VII/VIIa. In another embodiment, an anion exchange column may comprise other anion exchange columns known in the art, for example a Capto DEAE anion exchange column or other resins such as Eshmuno Q.

In one embodiment, the hydrophobic column of is a Phenyl Hydrophobic Interaction Chromatography (HIC) column. The number of cycles of use for phenyl HIC may range between about 1-10. In one embodiment, 1-3 cycles are performed. In another embodiment, 1-5 cycles are performed. In another embodiment, 1-6 cycles are performed. In another embodiment, 1-7 cycles are performed. In another embodiment, 1-8 cycles are performed. In another embodiment, 1-9 cycles are performed. In another embodiment, 1-10 cycles are performed. In another embodiment, buffers known in the art are used for washing and elution. In one embodiment, an elution buffer comprises Ammonium Sulfate with propylene glycol. In one embodiment, an elution buffer comprises Ammonium Sulfate with ethylene glycol.

In one embodiment, a Hydroxyapatite Mixed-Mode column comprises a ceramic hydroxyapatite Mixed-Mode column (CHT). The number of cycles of use for CHT may range between about 1-10. In one embodiment, 1-3 cycles are performed. In another embodiment, 1-5 cycles are performed. In another embodiment, 1-6 cycles are performed. In another embodiment, 1-7 cycles are performed. In another embodiment, 1-8 cycles are performed. In another embodiment, 1-9 cycles are performed. In another embodiment, 1-10 cycles are performed. Elution from a CHT column may be performed with between about 3-10 column volumes (CV). In one embodiment, elution is performed with about 3 CV. In another embodiment, elution is performed with about 4 CV. In another embodiment, elution is performed with about 5 CV. In another embodiment, elution is performed with about 6 CV. In another embodiment, elution is performed with about 7 CV. In another embodiment, elution is performed with about 8 CV. In another embodiment, elution is performed with about 9 CV. In another embodiment, elution is performed with about 10 CV.

In one embodiment, viruses that could be present in the clarified harvest due to contamination are inactivated in the clarified harvest. In another embodiment, the viruses are inactivated using a 1% Triton-X 100 solution. In another embodiment, the viruses are inactivated using a 0.2 to 2% Triton-X 100 solution. In another embodiment, the viruses are inactivated using 0.5% Triton-X 100 solution. In another embodiment, the viruses are inactivated using a 1-4% Triton-X 100 solution. In another embodiment, the viruses are inactivated using a 0.2-0.5% Triton-X 100 solution. In another embodiment, the viruses are inactivated using a 0.5-1.0% Triton-X 100 solution. In another embodiment, the viruses are inactivated using a 2% Triton-X 100 solution. In another embodiment, the viruses are inactivated using a 3% Triton-X 100 solution. In another embodiment, the viruses are inactivated using a 4% Triton-X 100 solution. In another embodiment, the viruses are inactivated using a 5-10% Triton-X 100 solution. In another embodiment, viral inactivation in a Triton-X 100 solution is for about 0.5 to 24 hours. In another embodiment, viral inactivation in a Triton-X solution is for about 0.5 to 1 hours. In another embodiment, viral inactivation in a Triton-X solution is for about 1 to 2 hours. In another embodiment, viral inactivation in a Triton-X solution is for about 2 to 3 hours. In another embodiment, viral inactivation in a Triton-X solution is for about 3 to 4 hours. In another embodiment, viral inactivation in a Triton-X solution is for about 4 to 6 hours. In another embodiment, viral inactivation in a Triton-X solution is for about 6 to 8 hours. In another embodiment, viral inactivation in a Triton-X solution is for about 8 to 10 hours. In another embodiment, viral inactivation in a Triton-X solution is for about 10 to 12 hours. In another embodiment, viral inactivation in a Triton-X solution is for about 12 to 24 hours.

It will be appreciated by the skilled artisan that other concentrations or other solutions available in the art and that are toxic to these viruses, including but not limited to, sodium cholate and Tween 80 may be used in methods disclosed herein. In another embodiment, a mixture of Tri-n-butyl phosphate (TNBP) and Polysorbate 80 (Tween 80) is used to inactivate the virus in step (h).

In one embodiment, viruses are physically removed by using nanofiltration. It will be appreciated by the skilled artisan that any filter known in the art for removing viruses may be applied in methods disclosed herein. In another embodiment, nanofiltration is carried out using a Planova or Planova type filter cartridge (1-60 mm$^2$). Such methods are followed by confirmation of viral clearance from the clarified harvest using methods known in the art.

In one embodiment, the methods disclosed herein achieve at least a 20% recovery rate of highly glycosylated CTP-modified Factor VII/VIIa. In another embodiment, the methods achieve a recovery rate of at least 5%, at least 10%, at least 15%, 20%, at least 25%, at least 30%, at least 40%, at least 50%, at least 60%, at least 70%, at least 80%, at least 90%, at least 95%, at least 96%, at least 97%, at least 98%, at least 99%, at least 99.9% recovery rate of highly glycosylated CTP-modified Factor VII/VIIa.

In one embodiment, following purification of highly glycosylated CTP-modified Factor VII/VIIa, the methods disclosed herein further comprise characterizing said CTP-modified polypeptide. In another embodiment, the purity of the CTP-modified Factor VII/VIIa is determined. In another embodiment, glycosylation content is determined. In another embodiment, glycosylation site occupancy is determined. In one embodiment, purity, glycosylation content and glycosylation site occupancy are determined in the manufactured CTP-modified Factor VII/VIIa.

In another embodiment, the cell clones utilized in methods disclosed herein are stored in a frozen cell bank. In another embodiment, the cell clones are stored in a lyophilized cell bank.

In another embodiment, the cell bank of methods and compositions disclosed herein is a master cell bank. In another embodiment, the cell bank is a working cell bank. In another embodiment, the cell bank is Good Manufacturing Practice (GMP) cell bank. In another embodiment, the cell bank is intended for production of clinical-grade material. In another embodiment, the cell bank conforms to regulatory practices for human use. In another embodiment, the cell bank is any other type of cell bank known in the art.

"Good Manufacturing Practices" are defined, in another embodiment, by (21 CFR 210-211) of the United States Code of Federal Regulations. In another embodiment, "Good Manufacturing Practices" are defined by other standards for production of clinical-grade material or for human consumption; e.g. standards of a country other than the United States. Each possibility represents a separate embodiment disclosed herein.

In another embodiment, the medium used for propagating cells contains methotrexate (MXT). In another embodiment, the medium is methotrexate-free medium. In another embodiment, the concentration of MXT present in a medium is between about 0.1-2 uM. In another embodiment, the concentration of MXT present in the medium is about 0.1-0.5 uM. In another embodiment, the concentration of MXT present in the medium is about 0.5-1.0 uM. In another embodiment, the concentration of MXT present in the medium is about 1.0-1.5 uM. In another embodiment, the concentration of MXT present in the medium is about 1.5-2.0 uM. It will be well appreciated that the term "medium" may encompass a liquid or gel or powder that is suitable for growth or culture of the cells comprising the CTP-modified Factor VII disclosed herein. Such medium may be alternatively referred to as "growth medium" or "culture medium" and may include but is not limited to, nutrient media, enriched media, minimal media, differential media, transport media, or selective media. In a further aspect, selective medium may be suitable for selecting a particular group of cells during the manufacturing process.

In one embodiment, the purified protein solution contains at least 5-95% CTP-modified to Factor VII/VIIa. In another embodiment, the purified protein solution contains at least 5% CTP-modified Factor VII/VIIa. In another embodiment, the purified protein solution contains at least 10% CTP-modified Factor VII/VIIa. In another embodiment, the purified protein solution contains at least 15% CTP-modified Factor VII/VIIa. In another embodiment, a purified protein solution contains at least 20% CTP-modified Factor VII/VIIa. In another embodiment, the purified protein solution contains at least 30% CTP-modified Factor VII/VIIa. In another embodiment, the purified protein solution contains at least 40% CTP-modified Factor VIIa. In another embodiment, the purified protein solution contains at least 50% CTP-modified Factor VII/VIIa. In another embodiment, the purified protein solution contains at least 60% CTP-modified Factor VIIa. In another embodiment, the purified protein solution contains at least 70% CTP-modified Factor VII/VIIa. In another embodiment, the purified protein solution contains at least 80% CTP-modified Factor VII/VIIa. In another embodiment, the purified solution contains at least 90-95% CTP-modified Factor VII/VIIa. In another embodiment, the purified solution contains 95.1-99.9% CTP-modified Factor VII/VIIa. In another embodiment, the purified solution contains 100% CTP-modified Factor VII/VIIa.

In one embodiment, a CTP-modified coagulation factor manufactured comprises a high % gammacarboxylation. A skilled artisan would appreciate that the percent (%) gamma carboxylation of a coagulation factor may have a direct relationship to the potency of the CTP-modified coagulation factor. In one embodiment, the % gamma carboxylation of FVII-CTP3 or FVIIa-CTP3 comprises at least 50% gamma carboxylation. In another embodiment, the % gamma carboxylation of FVII-CTP3 or FVIIa-CTP3 comprises at least 60% gamma carboxylation. In another embodiment, the % gamma carboxylation of FVII-CTP3 or FVIIa-CTP3 comprises at least 70% gamma carboxylation. In another embodiment, the % gamma carboxylation of FVII-CTP3 or FVIIa-CTP3 comprises at least 80% gamma carboxylation. In another embodiment, the % gamma carboxylation of FVII-CTP3 or FVIIa-CTP3 comprises at least 90% gamma carboxylation. In another embodiment, the % gamma carboxylation of FVII-CTP3 or FVIIa-CTP3 comprises at least 92% gamma carboxylation. In another embodiment, the % gamma carboxylation of FVII-CTP3 or FVIIa-CTP3 comprises at least 93% gamma carboxylation. In another embodiment, the % gamma carboxylation of FVII-CTP3 or FVIIa-CTP3 comprises at least 94% gamma carboxylation. In another embodiment, the % gamma carboxylation of FVII-CTP3 or FVIIa-CTP3 comprises at least 95% gamma carboxylation. In another embodiment, the % gamma carboxylation of FVII-CTP3 or FVIIa-CTP3 comprises at least 96% gamma carboxylation. In another embodiment, the % gamma carboxylation of FVII-CTP3 or FVIIa-CTP3 comprises at least 97% gamma carboxylation. In another embodiment, the % gamma carboxylation of FVII-CTP3 or FVIIa-CTP3 comprises at least 98% gamma carboxylation. In another embodiment, the % gamma carboxylation of FVII-CTP3 or FVIIa-CTP3 comprises at least 99% gamma carboxylation. In another embodiment, the % gamma carboxylation of FVII-CTP3 or FVIIa-CTP3 comprises 100% gamma carboxylation.

In another embodiment, the % gamma carboxylation of FVII-CTP3 or FVIIa-CTP3 comprises between 40-50% gamma carboxylation. In another embodiment, the % gamma carboxylation of FVII-CTP3 or FVIIa-CTP3 comprises between 50-60% gamma carboxylation. In another embodiment, the % gamma carboxylation of FVII-CTP3 or FVIIa-CTP3 comprises between 60-70% gamma carboxylation. In another embodiment, the % gamma carboxylation of FVII-CTP3 or FVIIa-CTP3 comprises between 70-80% gamma carboxylation. In another embodiment, the % gamma carboxylation of FVII-CTP3 or FVIIa-CTP3 comprises between 80-85% gamma carboxylation. In another embodiment, the % gamma carboxylation of FVII-CTP3 or FVIIa-CTP3 comprises between 85-90% gamma carboxylation. In another embodiment, the % gamma carboxylation of FVII-CTP3 or FVIIa-CTP3 comprises between 90-92% gamma carboxylation. In another embodiment, the % gamma carboxylation of FVII-CTP3 or FVIIa-CTP3 comprises between 90-95% gamma carboxylation. In another embodiment, the % gamma carboxylation of FVII-CTP3 or FVIIa-CTP3 comprises between 95-97% gamma carboxylation. In another embodiment, the % gamma carboxylation of FVII-CTP3 or FVIIa-CTP3 comprises between 95-100% gamma carboxylation.

Figure 17:
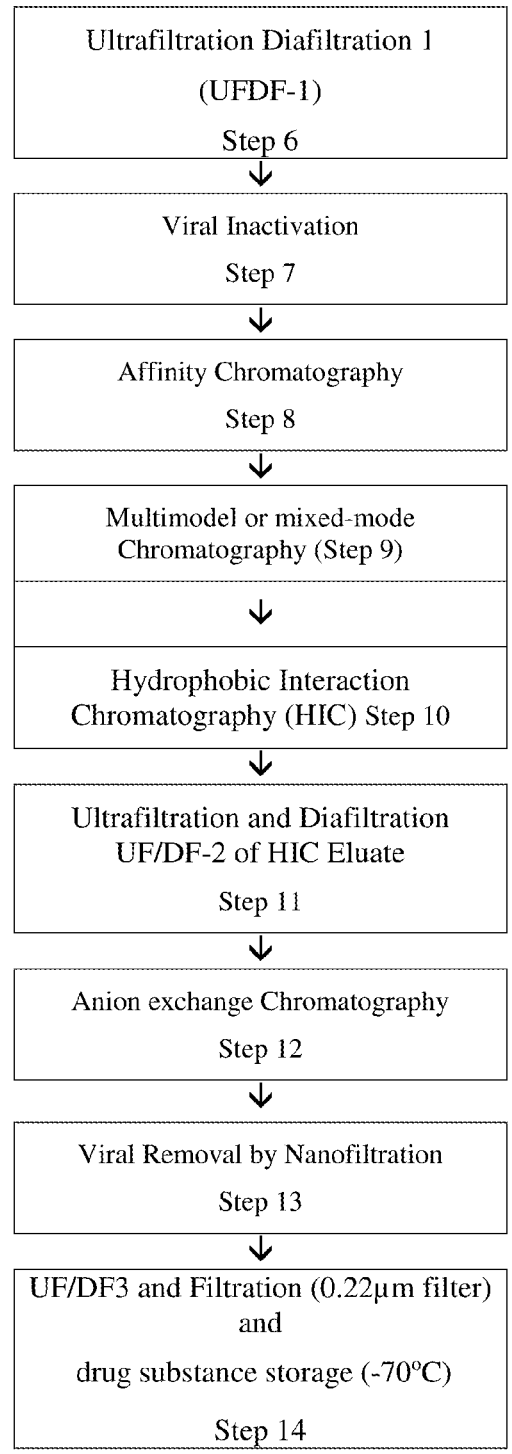
FIG. 17. Presents a flow chart of the purification process of CTP-modified FVII-CTP$_3$.

In one embodiment, the removal of the low gamma carboxylated is performed in the Multimodel or mixed-mode Chromatography step of the manufacturing process disclosed herein (see Step 9, FIG. 17).

In one embodiment, the CTP-modified Factor VII/VIIa manufactured is highly glycosylated. It will be well appreciated by the skilled artisan that the term "highly glycosylated" when in reference to a CTP-modified Factor VII/VIIa, may encompass a glycosylation level of about 70-80% of total CTP-modified Factor VII/VIIa polypeptide. In another embodiment, highly glycosylated CTP-modified Factor VII/VIIa a has a glycosylation level of at least 70%. In another embodiment, highly glycosylated CTP-modified Factor VII/VIIa a has a glycosylation level of at least 80%. In another embodiment, the term may encompass a glycosylation level of about 81-90% of the total CTP-modified Factor VII/VIIa polypeptide. In another embodiment, highly glycosylated CTP-modified Factor VII/VIIa has a glycosylation level of at least 90%. In another embodiment, the term may encompass a glycosylation level of about 91-95% of the total CTP-modified Factor VIIa polypeptide. In another embodiment, the term may encompass a glycosylation level of about 95.1-99% of the total CTP-modified Factor VII/VIIa polypeptide. In another embodiment, the term may encompass a glycosylation level of 100% of the total CTP-modified Factor VII/VIIa polypeptide. Highly glycosylated CTP-modified Factor VII/VIIa polypeptides may have beneficial properties in methods of use for a long-acting Factor VII/VIIa, supporting reduced frequency of administration. The high glycosylation levels contribute to the significant increased hydrodynamic volume of a CTP-modified Factor VII/VIIa, for example a CTP-modified Factor VIIa, as compared to recombinant Factor VII/VIIa. This may result in an elongated circulating time of CTP-modified Factor VIIa.

In one embodiment, the number of O-glycans per CTP is at least 4-6. In another embodiment, the number of O-glycans per CTP is between 4-6. In another embodiment, the number of O-glycans per CTP is at least 4-8. In another embodiment, the number of O-glycans per CTP is between 4-8. In one embodiment, the number of O-glycans per CTP is at least 6-8. In one embodiment, the number of O-glycans per CTP is between 6-8. In another embodiment, the number of O-glycans per CTP is at least 4. In another embodiment, the number of O-glycans per CTP is at least 5. In another embodiment, the number of O-glycans per CTP is at least 6. In another embodiment, the number of O-glycans per CTP is at least 7. In another embodiment, the number of O-glycans per CTP is 8.

In one embodiment, the number of O-glycans per CTP-modified Factor VII/VIIa polypeptide having one CTP attached is at least 4-6. In another embodiment, the number of O-glycans per CTP-modified Factor VII/VIIa polypeptide having one CTP attached is at least 6-8. In another embodiment, the number of O-glycans per CTP-modified Factor VII/VIIa polypeptide having one CTP attached is at least 4-8. In another embodiment, the number of O-glycans per CTP-modified Factor VII/VIIa polypeptide having two CTP units attached is at least 8-12. In another embodiment, the number of O-glycans per CTP-modified Factor VII/VIIa polypeptide having two CTP units attached is at least 12-16. In another embodiment, the number of O-glycans per CTP-modified Factor VII/VIIa polypeptide having two CTP units attached is at least 8-16. In another embodiment, the number of O-glycans per CTP-modified Factor VII/VIIa polypeptide having three CTP units attached is at least 12-18. In another embodiment, the number of O-glycans per CTP-modified Factor VII/VIIa polypeptide having three CTP units attached is at least 18-24. In another embodiment, the number of O-glycans per CTP-modified Factor VII/VIIa polypeptide having three CTP units attached is at least 12-24. In another embodiment, the number of O-glycans per CTP-modified Factor VII/VIIa polypeptide having four CTP units attached is at least 16-24. In another embodiment, the number of O-glycans per CTP-modified Factor VII/VIIa polypeptide having four CTP units attached is at least 24-32. In another embodiment, the number of O-glycans per CTP-modified Factor VII/VIIa polypeptide having four CTP units attached is at least 16-32. In another embodiment, the number of O-glycans per CTP-modified Factor VII/VIIa polypeptide having five CTP units attached is at least 20-30. In another embodiment, the number of O-glycans per CTP-modified Factor VII/VIIa polypeptide having five CTP units attached is at least 30-40. In another embodiment, the number of O-glycans per CTP-modified Factor VII/VIIa polypeptide having five CTP units attached is at least 20-40. In another embodiment, the number of O-glycans per CTP-modified Factor VII/VIIa polypeptide having six CTP units attached is at least 24-36. In another embodiment, the number of O-glycans per CTP-modified Factor VII/VIIa polypeptide having six CTP units attached is at least 36-48. In another embodiment, the number of O-glycans per CTP-modified Factor VII/VIIa polypeptide having six CTP units attached is at least 24-48. In another embodiment, the number of O-glycans per CTP-modified Factor VII/VIIa polypeptide having seven CTP units attached is at least 28-35. In another embodiment, the number of O-glycans per CTP-modified Factor VII/VIIa polypeptide having seven CTP units attached is at least 42-56. In another embodiment, the number of O-glycans per CTP-modified Factor VII/VIIa polypeptide having seven CTP units attached is at least 28-56. In another embodiment, the number of O-glycans per CTP-modified Factor VII/VIIa polypeptide having eight CTP units attached is at least 32-48. In another embodiment, the number of O-glycans per CTP-modified Factor VII/VIIa polypeptide having eight CTP units attached is at least 48-64. In another embodiment, the number of O-glycans per CTP-modified Factor VII/VIIa polypeptide having eight CTP units attached is at least 32-64. In another embodiment, the number of O-glycans per CTP-modified Factor VII/VIIa polypeptide having nine CTP units attached is at least 36-54. In another embodiment, the number of O-glycans per CTP-modified Factor VII/VIIa polypeptide having nine CTP units attached is at least 54-72. In another embodiment, the number of O-glycans per CTP-modified Factor VII/VIIa polypeptide having nine CTP units attached is at least 36-72. In another embodiment, the number of O-glycans per CTP-modified Factor VII/VIIa polypeptide having ten CTP units attached is at least 40-60. In another embodiment, the number of O-glycans per CTP-modified Factor VII/VIIa polypeptide having ten CTP units attached is at least 60-80. In another embodiment, the number of O-glycans per CTP-modified Factor VII/VIIa polypeptide having five CTP units attached is at least 40-80.

In one embodiment, O-glycan occupancy per CTP is at least 70%. In another embodiment, O-glycan occupancy per CTP is at least 80%. In another embodiment, O-glycan occupancy per CTP is at least 90%. In another embodiment, O-glycan occupancy per CTP is 100%.

In one embodiment, a high percentage of N-glycans per CTP-modified FVII/FVIIa are charged. In another embodiment, the percent of N-glycans per CTP-modified FVII/FVIIa that are charged comprises at least 40%. In another embodiment, the percent of N-glycans per CTP-modified FVII/FVIIa that are charged comprises at least 50%. In another embodiment, the percent of N-glycans per CTP-modified FVII/FVIIa that are charged comprises at least 60%. In another embodiment, the percent of N-glycans per CTP-modified FVII/FVIIa that are charged comprises at least 70%. In another embodiment, the percent of N-glycans per CTP-modified FVII/FVIIa that are charged comprises at least 80%. In another embodiment, the percent of N-glycans per CTP-modified FVII/FVIIa that are charged comprises at least 85%. In another embodiment, the percent of N-glycans per CTP-modified FVII/FVIIa that are charged comprises at least 90%. In another embodiment, the percent of N-glycans per CTP-modified FVII/FVIIa that are charged comprises at least 95%. In another embodiment, the percent of N-glycans per CTP-modified FVII/FVIIa that are charged comprises 100%.

In another embodiment, the percent of N-glycans per CTP-modified FVII/FVIIa that are charged comprises about 40%. In another embodiment, the percent of N-glycans per CTP-modified FVII/FVIIa that are charged comprises about 50%. In another embodiment, the percent of N-glycans per CTP-modified FVII/FVIIa that are charged comprises about 60%. In another embodiment, the percent of N-glycans per CTP-modified FVII/FVIIa that are charged comprises about 70%. In another embodiment, the percent of N-glycans per CTP-modified FVII/FVIIa that are charged comprises about 80%. In another embodiment, the percent of N-glycans per CTP-modified FVII/FVIIa that are charged comprises about 85%. In another embodiment, the percent of N-glycans per CTP-modified FVII/FVIIa that are charged comprises about 90%. In another embodiment, the percent of N-glycans per CTP-modified FVII/FVIIa that are charged comprises about 95%. In another embodiment, the percent of N-glycans per CTP-modified FVII/FVIIa that are charged comprises about 100%.

In another embodiment, the percent of N-glycans per CTP-modified FVII/FVIIa that are charged comprises between about 10% and 30%. In another embodiment, the percent of N-glycans per CTP-modified FVII/FVIIa that are charged comprises between about 20% and 40%. In another embodiment, the percent of N-glycans per CTP-modified FVII/FVIIa that are charged comprises between about 30% and 40%. In another embodiment, the percent of N-glycans per CTP-modified FVII/FVIIa that are charged comprises between about 20% and 50%. In another embodiment, the percent of N-glycans per CTP-modified FVII/FVIIa that are charged comprises between about 40% and 50%. In another embodiment, the percent of N-glycans per CTP-modified FVII/FVIIa that are charged comprises between about 30% and 60%. In another embodiment, the percent of N-glycans per CTP-modified FVII/FVIIa that are charged comprises between about 50% and 60%. In another embodiment, the percent of N-glycans per CTP-modified FVII/FVIIa that are charged comprises between about 40% and 70%. In another embodiment, the percent of N-glycans per CTP-modified FVII/FVIIa that are charged comprises between about 60% and 70%. In another embodiment, the percent of N-glycans per CTP-modified FVII/FVIIa that are charged comprises between about 50% and 80%. In another embodiment, the percent of N-glycans per CTP-modified FVII/FVIIa that are charged comprises between about 70% and 80%. In another embodiment, the percent of N-glycans per CTP-modified FVII/FVIIa that are charged comprises between about 55% and 85%. In another embodiment, the percent of N-glycans per CTP-modified FVII/FVIIa that are charged comprises between about 80% and 85%. In another embodiment, the percent of N-glycans per CTP-modified FVII/FVIIa that are charged comprises between about 60% and 90%. In another embodiment, the percent of N-glycans per CTP-modified FVII/FVIIa that are charged comprises between about 85% and 90%. In another embodiment, the percent of N-glycans per CTP-modified FVII/FVIIa that are charged comprises between about 65% and 95%. In another embodiment, the percent of N-glycans per CTP-modified FVII/FVIIa that are charged comprises between about 90% and 95%. In another embodiment, the percent of N-glycans per CTP-modified FVII/FVIIa that are charged comprises between about 95% and 100%.

In one embodiment, the high level of N-glycans that are charged is driven by the upstream process in the manufacturing process disclosed herein. In another embodiment, more that 60% of charged N-glycans are reached at early DSP stage and this level is maintained until the final drug substance is obtained.

In one embodiment, the high level of N-glycans that are charged is driven by the upstream process in the manufacturing process disclosed herein. In another embodiment, more that 60% of charged N-glycans are reached at early DSP stage and this level is maintained until the final drug substance is obtained.

In one embodiment, the CTP-modified Factor VII/VIIa is highly sialylated. It will be appreciated by the skilled artisan that the term "highly sialylated" when in reference to a CTP-modified Factor VII/VIIa, may encompass a sialylation level of about 70-80% of total CTP-modified Factor Vita polypeptide. In another embodiment, the term may encompass a sialylation level of about 80-90% of the total CTP-modified Factor VII/VIIa polypeptide. In another embodiment, the term may encompass a sialylation level of about 90-95% of the total CTP-modified Factor VII/VIIa polypeptide. In another embodiment, the term may encompass a sialylation level of about 95.1-99% of the total CTP-modified Factor VII/VIIa polypeptide. In another embodiment, the term may encompass a sialylation level of 100% of the total CTP-modified Factor VII/VIIa polypeptide. In another embodiment, an O-glycan structure in a CTP-modified Factor VIIa comprises a mono-sialylated core 1.

In one embodiment, the high percentage of sialylation and O-linked glycan content of a CTP-modified FVII/FVIIa described herein, increases the potency of the CTP-modified FVII/FVIIa. In another embodiment, the high percentage of sialylation and O-linked glycan content of a CTP-modified FVII/FVIIa described herein, increases the hydrodynamic volume of the CTP-modified FVII/FVIIa.

In one embodiment, a CTP-modified FVII/FVIIa described herein has potency. In another embodiment, the CTP-modified FVII/FVIIa is substantially pure and active CTP-modified FVII polypeptide. In another embodiment, the CTP-modified FVII/FVIIa is manufactured using a method described herein. In another embodiment, the potency is at least 5,000 U/mg. In another embodiment, the potency is at least 7,500 U/mg. In another embodiment, the potency is at least 10,000 U/mg. In another embodiment, the potency is at least 10,500 U/mg. In another embodiment, the potency is at least 15,000 U/mg. In another embodiment, the potency is at least 20,000 U/mg. In another embodiment, the potency is at least 25,000 U/mg. In another embodiment, the potency is at least 27,500 U/mg. In another embodiment, the potency is at least 30,000 U/mg. In another embodiment, the potency is at least 35,000 U/mg. In another embodiment, the potency is at least 40,000 U/mg. In further embodiment, the potency is selected from the group consisting of 15,563 U/mg 16,720 U/mg, 22,478 U/mg and 23,608 U/mg.

In one embodiment, the CTP-modified Factor VII/VIIa polypeptide consists of two CTP attached to the carboxy terminus of said Factor VII/VIIa, and one chorionic gonadotropin carboxy terminal peptide attached to the amino terminus of said Factor VII/VIIa. In another embodiment, the CTP-modified Factor VII/VIIa a polypeptide consists of one chorionic gonadotropin carboxy terminal peptide attached to the carboxy terminus of said Factor VII/VIIa.

In one embodiment, the expression vector comprising a coding portion encoding said CTP-modified Factor VII/VIIa also comprises a promoter, a coding sequence for said CTP-modified polypeptide, and a polyadenylation sequence. In one embodiment, the polyadenylation sequence is a simian virus (SV) 40 polyadenylation sequence.

In one embodiment, the CTP-modified Factor VII is expressed at a level of between 30-1500 mg/L. In another embodiment, the CTP-modified Factor VII is expressed at a level of at least 30 mg/L. In another embodiment, the CTP-modified Factor VII is expressed at a level of at least 40 mg/L. In another embodiment, the CTP-modified Factor VII is expressed at a level of at least 50 mg/L. In another embodiment, the CTP-modified Factor VII is expressed at a level of at least 60 mg/L. In another embodiment, the CTP-modified Factor VII is expressed at a level of at least 70 mg/L. In another embodiment, the CTP-modified Factor VII is expressed at a level of at least 50-70 mg/L. In another embodiment, the CTP-modified Factor VII is expressed at a level of at least 80 mg/L. In another embodiment, the CTP-modified Factor VII is expressed at a level of at least 90 mg/L. In another embodiment, the CTP-modified Factor VII is expressed at a level of at least 70-100 mg/L. In another embodiment, the CTP-modified Factor VII is expressed at a level of at least 100 mg/L. In another embodiment, the CTP-modified Factor VII is expressed at a level of at least 200 mg/L. In another embodiment, the CTP-modified Factor VII is expressed at a level of at least 100-200 mg/L. In another embodiment, the CTP-modified Factor VII is expressed at a level of at least 300 mg/L. In another embodiment, the CTP-modified Factor VII is expressed at a level of at least 200-300 mg/L. In another embodiment, the CTP-modified Factor VII is expressed at a level of at least 400 mg/L. In another embodiment, the CTP-modified Factor VII is expressed at a level of at least 300-400 mg/L. In another embodiment, the CTP-modified Factor VII is expressed at a level of at least 500 mg/L. In another embodiment, the CTP-modified Factor VII is expressed at a level of at least 500-600 mg/L. In another embodiment, the CTP-modified Factor VII is expressed at a level of at least 600 mg/L. In another embodiment, the CTP-modified Factor VII is expressed at a level of at least 600-700 mg/L. In another embodiment, the CTP-modified Factor VII is expressed at a level of at least 700 mg/L. In another embodiment, the CTP-modified Factor VII is expressed at a level of at least 701-800 mg/L. In another embodiment, the CTP-modified Factor VII is expressed at a level of at least 800 mg/L. In another embodiment, the CTP-modified Factor VII is expressed at a level of at least 801-900 mg/L. In another embodiment, the CTP-modified Factor VII is expressed at a level of at least 900 mg/L. In another embodiment, the CTP-modified Factor VII is expressed at a level of at least 901-1000 mg/L. In another embodiment, the CTP-modified Factor VII is expressed at a level of at least 1000 mg/L. In another embodiment, the CTP-modified Factor VII is expressed at a level of at least 1001-1100 mg/L. In another embodiment, the CTP-modified Factor VII is expressed at a level of at least 1100 mg/L. In another embodiment, the CTP-modified Factor VII is expressed at a level of at least 1101-1200 mg/L. In another embodiment, the CTP-modified Factor VII is expressed at a level of at least 1200 mg/L. In another embodiment, the CTP-modified Factor VII is expressed at a level of at least 1201-1300 mg/L. In another embodiment, the CTP-modified Factor VII is expressed at a level of at least 1300 mg/L. In another embodiment, the CTP-modified Factor VII is expressed at a level of at least 1301-1400 mg/L. In another embodiment, the CTP-modified Factor VII is expressed at a level of at least 1400 mg/L. In another embodiment, the CTP-modified Factor VII is expressed at a level of at least 1401-1500 mg/L. In another embodiment, the CTP-modified Factor VII is expressed at a level of at least 1500 mg/L.

It will be appreciated by the skilled artisan that the term "expression" may encompass transcription and/or translation of a heterologous nucleic acid sequence within a host cell. The level of expression of a desired product/protein of interest in a host cell may be determined on the basis of either the amount of corresponding mRNA or cDNA that is present in the cell, or the amount of the desired polypeptide/protein of interest encoded by the selected sequence as in the present examples. For example, mRNA transcribed from a selected sequence can be quantitated by Northern blot hybridization, ribonuclease RNA protection, in situ hybridization to cellular RNA or by PCR (see Sambrook et al., 1989; Ausubel et al., 1987 updated). Proteins encoded by a selected sequence can be quantitated by various methods, e.g. by ELISA, by Western blotting, by radioimmunoassays, by immunoprecipitation, by assaying for the biological activity of the protein, by immunostaining of the protein followed by FACS analysis (see Sambrook et al., 1989; Ausubel et al., 1987 updated) or by homogeneous time-resolved fluorescence (HTRF) assays. In one embodiment, quantitation of the CTP-modified Factor VIIa comprises use of a reverse phase high performance liquid chromatography (RP-HPLC). In another embodiment, the RP-HPLC comprises a C-18 column. In another embodiment, the RP-HPLC comprises a C-8 column. In another embodiment, methods disclosed herein use an RP-HPLC to quantitate a CTP-modified Factor VII in the harvest (See Example 3 steps 2 to 5). In another embodiment, methods disclosed herein use an RP-HPLC to quantitate a CTP-modified Factor VII during purification.

In another embodiment, a cell bank, or frozen stock disclosed herein exhibits viability upon thawing of greater than 90%. In another embodiment, the storage is for an indefinite amount of time.

In another embodiment, the storage is for 2 weeks. In another embodiment, the storage is for 3 weeks. In another embodiment, the storage is for 1 month. In another embodiment, the storage is for 2 months. In another embodiment, the storage is for 3 months. In another embodiment, the storage is for 5 months. In another embodiment, the storage is for 6 months. In another embodiment, the storage is for 9 months. In another embodiment, the storage is for 1 year.

In another embodiment, a cell bank, or frozen stock disclosed herein is cryopreserved by a method that comprises growing a culture of the cells in a defined media disclosed herein, freezing the culture in a solution comprising glycerol, and storing the cell clones at below −20 degrees Celsius. In another embodiment, the temperature is about −70 degrees Celsius. In another embodiment, the temperature is about −70-−80 degrees Celsius. In another embodiment, any defined media disclosed herein may be used in this method. Each defined media represents a separate embodiment disclosed herein.

In another embodiment of methods and compositions disclosed herein, the culture is inoculated from a cell bank. In another embodiment, the culture is inoculated from a frozen stock. In another embodiment, the culture is inoculated from a starter culture. In another embodiment, the culture is inoculated from a colony. In another embodiment, the culture is inoculated at mid-log growth phase. In another embodiment, the culture is inoculated at approximately mid-log growth phase. In another embodiment, the culture is inoculated at another growth phase.

In another embodiment of methods and compositions disclosed herein, the solution used for freezing comprises DMSO in an amount of 2-20%. In another embodiment, the amount is 2%. In another embodiment, the amount is 20%. In another embodiment, the amount is 1%. In another embodiment, the amount is 1.5%. In another embodiment, the amount is 3%. In another embodiment, the amount is 4%. In another embodiment, the amount is 5%. In another embodiment, the amount is 2%. In another embodiment, the amount is 2%. In another embodiment, the amount is 7%. In another embodiment, the amount is 7.5%. In another embodiment, the amount is 9%. In another embodiment, the amount is 10%. In another embodiment, the amount is 12%. In another embodiment, the amount is 14%. In another embodiment, the amount is 16%. In another embodiment, the amount is 18%. In another embodiment, the amount is 22%. In another embodiment, the amount is 25%. In another embodiment, the amount is 30%. In another embodiment, the amount is 35%. In another embodiment, the amount is 40%.

In another embodiment, the additive is sucrose. In another embodiment, the additive is any other colligative additive or additive with anti-freeze properties that is known in the art. Each possibility represents a separate embodiment disclosed herein.

In one embodiment, a freezing solution used in the methods and for the compositions disclosed herein comprises conditioned media and DMSO. In one embodiment, a freezing solution used in the methods and for the compositions disclosed herein comprises about 46.255% conditioned media and 7.5% DMSO.

In one embodiment, the cell culture is grown by techniques routine in the art. In another embodiment, a constant pH is maintained during growth of the cell culture. In another embodiment, the pH is maintained at about 7.0. In another embodiment, the pH is about 6. In another embodiment, the pH is about 6.5. In another embodiment, the pH is about 7.5. In another embodiment, the pH is about 8. In another embodiment, the pH is 6.5-7.5. In another embodiment, the pH is 6-8. In another embodiment, the pH is 6-7. In another embodiment, the pH is 7-8.

In another embodiment, a constant temperature is maintained during growth of the culture. In another embodiment, the temperature is maintained at about 37° C. In another embodiment, the temperature is 37° C. In another embodiment, the temperature is 25° C. In another embodiment, the temperature is 27° C. In another embodiment, the temperature is 28° C. In another embodiment, the temperature is 30° C. In another embodiment, the temperature is 32° C. In another embodiment, the temperature is 34° C. In another embodiment, the temperature is 35° C. In another embodiment, the temperature is 36° C. In another embodiment, the temperature is 38° C. In another embodiment, the temperature is 39° C.

In another embodiment, a constant dissolved oxygen concentration is maintained during growth of the culture. In another embodiment, the dissolved oxygen concentration is maintained at 20% of saturation. In another embodiment, the concentration is 15% of saturation. In another embodiment, the concentration is 16% of saturation. In another embodiment, the concentration is 18% of saturation. In another embodiment, the concentration is 22% of saturation. In another embodiment, the concentration is 25% of saturation. In another embodiment, the concentration is 30% of saturation. In another embodiment, the concentration is 35% of saturation. In another embodiment, the concentration is 40% of saturation. In another embodiment, the concentration is 45% of saturation. In another embodiment, the concentration is 50% of saturation. In another embodiment, the concentration is 55% of saturation. In another embodiment, the concentration is 60% of saturation. In another embodiment, the concentration is 65% of saturation. In another embodiment, the concentration is 70% of saturation. In another embodiment, the concentration is 75% of saturation. In another embodiment, the concentration is 80% of saturation. In another embodiment, the concentration is 85% of saturation. In another embodiment, the concentration is 90% of saturation. In another embodiment, the concentration is 95% of saturation. In another embodiment, the concentration is 100% of saturation. In another embodiment, the concentration is near 100% of saturation.

In another embodiment of methods and compositions disclosed herein, the culture is grown in media having a maximum volume of 2 liters (L) per vessel. In another embodiment, the media has a maximum volume of 200 ml per vessel. In another embodiment, the media has a maximum volume of 300 ml per vessel. In another embodiment, the media has a maximum volume of 500 ml per vessel. In another embodiment, the media has a maximum volume of 750 ml per vessel. In another embodiment, the media has a maximum volume of 1 L per vessel. In another embodiment, the media has a maximum volume of 1.5 L per vessel. In another embodiment, the media has a maximum volume of 2.5 L per vessel. In another embodiment, the media has a volume of 3 L per vessel. In another embodiment, the media has a volume of 5 L per vessel. In another embodiment, the media has a volume of at least 5 L per vessel. In another embodiment, the media has a volume of at least 10 L per vessel.

In another embodiment, the media has a minimum volume of 2 L per vessel. In another embodiment, the media has a minimum volume of 500 ml per vessel. In another embodiment, the media has a minimum volume of 750 ml per vessel. In another embodiment, the media has a minimum volume of 1 L per vessel. In another embodiment, the media has a minimum volume of 1.5 L per vessel. In another embodiment, the media has a minimum volume of 2.5 L per vessel. In another embodiment, the media has a minimum volume of 3 L per vessel. In another embodiment, the media has a minimum volume of 4 L per vessel. In another embodiment, the media has a minimum volume of 5 L per vessel. In another embodiment, the media has a minimum volume of 6 L per vessel. In another embodiment, the media has a minimum volume of 8 L per vessel. In another embodiment, the media has a minimum volume of 10 L per vessel.

In another embodiment, the step of freezing is performed when the culture has a density of $1\times10^6$ viable cells (VC)/ml. In another embodiment, the biomass is $1.5\times10^6$ VC/ml. In another embodiment, the biomass is $1.5\times10^6$ VC/ml. In another embodiment, the biomass is $2\times10^6$ VC/ml. In another embodiment, the biomass is $3\times10^6$ VC/ml. In another embodiment, the biomass is $4\times10^6$ VC/ml. In another embodiment, the biomass is $5\times10^6$ VC/ml. In another embodiment, the biomass is $7\times10^6$ VC/ml. In another embodiment, the biomass is $9\times10^6$ VC/ml. In another embodiment, the biomass is $10\times10^6$ VC/ml. In another embodiment, the biomass is $12\times10^6$ VC/ml. In another embodiment, the biomass is $15\times10^6$ VC/ml. In another embodiment, the biomass is $20\times10^7$ VC/ml. In another embodiment, the biomass is $25\times10^6$ VC/ml. In another embodiment, the biomass is $30\times10^7$ VC/ml. In another embodiment, the biomass is $33\times10^6$ VC/ml. In another embodiment, the biomass is $40\times10^6$ VC/ml. In another embodiment, the biomass is $50\times10^6$ VC/ml. In another embodiment, the biomass is more than $50\times10^6$ VC/ml.

In another embodiment of methods and compositions disclosed herein, the cell culture is flash-frozen in liquid nitrogen, followed by storage at the final freezing temperature. In another embodiment, the culture is frozen in a more gradual manner; e.g. by placing in a vial of the culture in the final storage temperature. In another embodiment, the culture is frozen by any other method known in the art for freezing cell cultures.

It will be understood by the skilled artisan that the terms "cell culture" and "tissue culture" may be used interchangeably and denote the maintenance of cells in vitro, in suspension culture in a liquid medium or on surface such as glass, plastic or agar provided with liquid medium. In general, "cell culture" necessitates a medium that is buffered to maintain a constant suitable pH. Media used in cell culture are generally formulated to include an adequate supply of necessary nutrients and can be osmotically tailored to the particular cells being maintained, with temperature and gas phase also being controlled within suitable limits. Cell culture techniques are well known in the art. See, e.g., Morgan et al. 1993 Animal Cell Culture, BIOS Scientific Publishers, Oxford, UK; and Adams, R. L. P. 1990 Cell Culture for Biochemists, Second Edition, Elsevier.

It will be appreciated by the skilled artisan that the term "passage" may encompass the act of subculturing a cell population. A skilled artisan would appreciate that the term "subculture" may encompass a cell culture established by the inoculation of sterile medium, which in one embodiment is a fresh sterile medium, with a sample from a previous culture.

It will also be appreciated by the skilled artisan that the term "cell strain" may encompass a population of cells derived from a primary culture using subcultivation techniques. Thus, a primary culture can be subcultured into two or more new cultures and the subculturing repeated at periodic intervals for several months to maintain the cell strain. Subculturing can be carried out using established cell culture techniques.

In one embodiment, passaged cell strains, and immortalized cell lines can be characterized by their expression of specific functional markers such as keratins, hormonal and growth factor receptors and the like.

In some aspects, cultures may be carried out in serum-free defined media with added growth factors. In other aspects the media contains serum with or without added growth factors. Such modifications may be empirically determined by the skilled artisan so as to optimize cell proliferation.

It will be appreciated by a skilled artisan that the term "cell line" can encompass a population of cells derived from a single explant which are characterized as having the potential for unlimited proliferation in vitro. A cell line can be isolated from a primary culture based on its ability to survive and continue to grow in culture. Cell lines which have been derived originally from tumor tissue may have been transformed in vivo, although not all neoplastic cell populations have the capacity to grow indefinitely in vitro. Further, cell lines generally retain their differentiated character through many rounds of division.

Suitable cell culture substrates are generally a container that can be sterilized, does not leach toxic factors and does not distort microscopy images. Thus plates formed from glass and plastic are suitable substrates herein. Plastic containers may further be treated to encourage cell attachment using techniques known in the art (Ramsey et al. 1984 In vitro 20:802). Suitable tissue culture media generally consist of an isotonic, buffered, basal nutrient medium which provides an energy source, coupled with inorganic salts, amino acids, vitamins and various supplements. Supplements may include serum (e.g., fetal calf serum, or the like) various antibiotics to prevent contamination or to provide selective conditions, attachment and growth factors, or the like. A number of media formulations are known in the art, such as, but not limited to, minimal essential medium (MEM), Rosewell Park Memorial Institute (RPMI) 1640 or Dulbecco's modified Eagle's medium (DMEM). Suitable tissue culture conditions are also known in the art. See, e.g., Morgan et al. 1993 Animal Cell Culture, BIOS Scientific Publishers Ltd., Oxford, U K, and Adams, R. L. P. 1990 Cell Culture for Biochemists, Second Edition, Elsevier. In another embodiment disclosed herein, methods of manufacture of CTP-modified Factor VIIa is a serum-free process. In another embodiment disclosed herein, methods of manufacture of CTP-modified Factor VIIa is an animal derived-free process.

In another embodiment of methods and compositions disclosed herein, the storage temperature of the culture is between $^-20$ and $^-80$ degrees Celsius (° C.). In another embodiment, the temperature is significantly below $^-20°$ C. In another embodiment, the temperature is not warmer than $^-70°$ C. In another embodiment, the temperature is $^-70°$ C.

In another embodiment, the temperature is about −70° C. In another embodiment, the temperature is −20° C. In another embodiment, the temperature is about −20° C. In another embodiment, the temperature is −30° C. In another embodiment, the temperature is −40° C. In another embodiment, the temperature is −50° C. In another embodiment, the temperature is −60° C. In another embodiment, the temperature is −80° C. In another embodiment, the temperature is −30-−70° C. In another embodiment, the temperature is −40-−70° C. In another embodiment, the temperature is −50-−70° C. In another embodiment, the temperature is −60-−70° C. In another embodiment, the temperature is −30-−80° C. In another embodiment, the temperature is −40-−80° C. In another embodiment, the temperature is −50-−80° C. In another embodiment, the temperature is −60-80° C. In another embodiment, the temperature is −70-−80° C. In another embodiment, the temperature is colder than −70° C. In another embodiment, the temperature is colder than −80° C.

In another embodiment, for cryopreservation, the cells are frozen slowly until they reach a temperature below −70° C. in medium that includes a cryoprotectant and vials are then transferred to a liquid-nitrogen freezer to maintain them at temperatures below −130° C.

In another embodiment of methods and compositions disclosed herein, the cryopreservation, or frozen storage, is for a maximum of 24 hours. In another embodiment, the cryopreservation, or frozen storage is for maximum of 2 days, is for maximum of 3 days, is for maximum of 4 days, is for maximum of 1 week, is for maximum of 2 weeks, is for maximum of 3 weeks, is for maximum of 1 month, is for maximum of 2 months, is for maximum of 3 months, is for maximum of 5 months, is for maximum of 6 months, is for maximum of 9 months, or is for maximum of 1 year. Each possibility listed above is an embodiment disclosed herein.

In another embodiment, the cryopreservation, or frozen storage is for a minimum of 1 week, is for minimum of 2 weeks, is for minimum of 3 weeks, is for minimum of 1 month, is for minimum of 2 months, is for minimum of 3 months, is for minimum of 5 months, is for minimum of 6 months, is for minimum of 9 months, is for minimum of 1 year, is for minimum of 1.5 years, is for minimum of 2 years, is for minimum of 3 years, is for minimum of 5 years, is for minimum of 7 years, is for minimum of 10 years, or is for longer than 10 years. Each possibility listed above is an embodiment disclosed herein.

In another embodiment of methods and compositions disclosed herein, the cells exhibit growth after thawing following an extended period of cryopreservation or frozen storage. In another embodiment, the cells exhibit growth within about 15-22 hours after inoculating fresh media with cells from the cell bank or starter culture. In another embodiment, the cells exhibit growth within about 12-20 hours after inoculating fresh media with cells from the cell bank or starter culture. In one embodiment, to ensure viability, genetic stability, and phenotypic stability, cell lines need to be maintained in the exponential growth phase (via subculturing on a regular basis).

An "extended period" of cryopreservation, or frozen storage, is, in another embodiment, 1 month. In another embodiment, the period is 2 months. In another embodiment, the period is 3 months. In another embodiment, the period is 5 months. In another embodiment, the period is 6 months. In another embodiment, the period is 9 months. In another embodiment, the period is 1 year. In another embodiment, the period is 1.5 years. In another embodiment, the period is 2 years. In another embodiment, the period is 2-7 years. In another embodiment, the period is for at least 7 years. In another embodiment, the period is for at least 10 years.

In another embodiment, the cells of the methods and compositions disclosed herein retain a viability of over 90% after thawing following cryopreservation. In another embodiment, the viability upon thawing is close to 100% following the period of cryopreservation. In another embodiment, the viability upon thawing is close to 90%. In another embodiment, the viability upon thawing is at least 90%. In another embodiment, the viability upon thawing is over 80%.

In another embodiment, a cell bank, frozen stock, or batch of vaccine doses disclosed herein is grown in a defined cell culture media. Such media are known in the art and may include, but not limited to Dulbecco's Modified Eagle's Medium (DMEM) (ATCC® No. 30-2002), Iscove's Modified Dulbecco's Medium (IMDM) (ATCC® No. 30-2005), Hybri-Care Medium (ATCC® No. 46-X), McCoy's 5A and RPMI-1640 (ATCC® No. 30-2007), Ham's Nutrient Mixtures (ATCC® CCL-61™), PowerCHO™ Chemically Defined, Serum-free CHO Medium (Lonza Cat. No. 12-771Q); or any other media known in the art. In another embodiment these media may be supplemented in antibiotics or animal sera, as will be empirically determined by the skilled artisan.

In one embodiment, disclosed herein are bioreactors and methods, which allow the cultivation of mammalian cells in large scale volumes. Furthermore, and in another embodiment, said bioreactors and methods, allow the cultivation of mammalian cells under optimal conditions, even if grown in large scale volumes and therefore allow a process performance and product quality independent of the size of the bioreactor. The duration of time of incubation within the bioreactor can vary, just by changing the scale and bioreactor system, for example the duration may be between 8-9, or it may be between 15-16 days. In another embodiment, the duration of incubation in a bioreactor is about 7 days, about 8 days, about 9 days, about 10 days, about 11 days, about 12 days, about 13 days, about 14 days, about 15 days, about 16 days, about 17 days, about 18 days, about 19 days, about 20 days or more. In another embodiment, when a perfusion bioreactor is used, the duration of incubation may be up to 7-120 days.

In another embodiment, disclosed herein are large-scale bioreactors which allow the cultivation of mammalian cells in a homogenous environment with respect to process parameters such as pH, dissolved oxygen tension (DOT) and temperature, maintaining a well-mixed cell suspension and blending nutrient feeds within the bioreactor. In another embodiment, the bioreactor is a disposable bioreactor.

Methods disclosed herein solves the technical problems underlying methods disclosed herein by the provision of bioreactors, bioreactor systems and methods for the cultivation of eukaryotic cells, especially of mammalian cells, according to the claims.

In one embodiment, the bioreactor has a volume of at least 250 liters (L). In another embodiment, the bioreactor has a volume of at least 500 L. In another embodiment the volume is at least 1000 L, at least 2000 L, at least 5,000 L, at least 10,000 L at least 12,000 L or at least 15,000 L.

In another embodiment, the cells are subcultivated in increasing volumes of bioreactors (see Examples).

As is generally known in the art, the modified peptides and proteins of the disclosure may be coupled to labels, drugs, targeting agents, carriers, solid supports, and the like, depending on the desired application. The labeled forms of the modified biologicals may be used to track their metabolic fate; suitable labels for this purpose include, especially, radioisotope labels such as iodine 131, technetium 99, indium 111, and the like. The labels may also be used to mediate detection of the modified proteins or peptides in assay systems; in this instance, radioisotopes may also be used as well as enzyme labels, fluorescent labels, chromogenic labels, and the like. The use of such labels is particularly helpful if the peptide or protein is itself a targeting agent such as an antibody or a receptor ligand.

Similar linking techniques, along with others, may be employed to couple the modified peptides and proteins of the disclosure to solid supports. When coupled, these modified peptides and proteins can then be used as affinity reagents for the separation of desired components with which specific reaction is exhibited.

Finally, the modified peptides and proteins of the disclosure may be used to generate antibodies specifically immunoreactive with these new compounds. These antibodies are useful in a variety of diagnostic and therapeutic applications, depending on the nature of the biological activity of the unmodified peptide or protein. It is to be understood that the disclosure provides antibodies that are immunoreactive with FVII or FVIIa as described herein. In one embodiment, such antibodies may be used to distinguish or identify CTP-modified coagulation factors that were administered from endogenous coagulation factors. In another embodiment, the antibodies may be used to localize administered CTP-modified coagulation factors.

Additional objects, advantages, and novel features disclosed herein will become apparent to one ordinarily skilled in the art upon examination of the following examples, which are not intended to be limiting. Additionally, each of the various embodiments and aspects disclosed herein as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference. Other general references are provided throughout this document.

Example 1

FVII-CTP$_3$ Feasibility Studies in FVIII-Deficient Hemophilic Mice

Studies testing FVII-CTP, FVII-CTP$_2$ and FVII-CTP$_3$ harvest PK profile and coagulation activity vs. a commercial FVII were conducted. FVII-CTP$_3$ exhibited an improved PK profile while maintaining its coagulation activity vs. FVII-CTP and FVII-CTP$_2$ harvests or rhFVII. In order to further characterize FVII-CTP$_3$ in vitro and in vivo properties, a mini stable pool expressing and secreting the protein was generated, and purification and activation processes were developed.

In the current study, the pharmacokinetic and pharmacodynamic properties of FVIIa-CTP$_3$ were tested in FVIII-deficient mice. The PK profile of the protein was evaluated. A FVIIa specific activity-based PK profile was established and compared to commercial product NovoSeven®. In addition, the long-lasting in vivo hemostatic capabilities of FVIIa-CTP$_3$ to induce coagulation in FVIII-deficient mice after a tail vain transection (survival study) were tested.

Study Objectives:

To evaluate the pharmacokinetic and pharmacodynamic parameters of FVIIa-CTP$_3$ vs. commercial rhFVIIa (NovoSeven®) in FVIII-deficient mice following a single IV administration at a similar activity dose.

To determine the in vivo ability of FVIIa-CTP$_3$ to maintain homoeostasis in FVIII-deficient mice by a single IV administration of FVIIa-CTP$_3$ and NovoSeven® at a similar activity dose followed by a challenge of tail vein transection (survival study).

Production of FVII-CTP$_3$ Harvest:

FVII-CTP$_3$ was expressed in-house in Dg44 cells using a pCI-DHFR vector (FIG. 1). Stable transfected pool #71 was grown in shake flasks, in the presence of 25 ng/L of Vitamin K3 (Sigma). Cell suspension was cultured and harvested following viability decline to 60-80%. The harvest was filtered and frozen at −70° C.

Determination of Harvest FVII Antigen Level:

FVII antigen level was determined using human FVII ELISA kit (Zymotest HyPhen) (Table 1). The antigen level was calculated per each pooled harvest batch.

TABLE 1

| | FVII-CTP₃ antigen level | | |
|---|---|---|---|
| | FVII antigen level | | |
| | PK-PD study | | Survival study |
| | harvest 31A | harvest 31B | harvest 38 |
| Av (μg/ml) | 16.0 | 15.9 | 16.6 |
| STD | 1.5 | 0.0 | 0.8 |
| % CV | 9.1 | 0.1 | 4.9 |

Figure 2A:
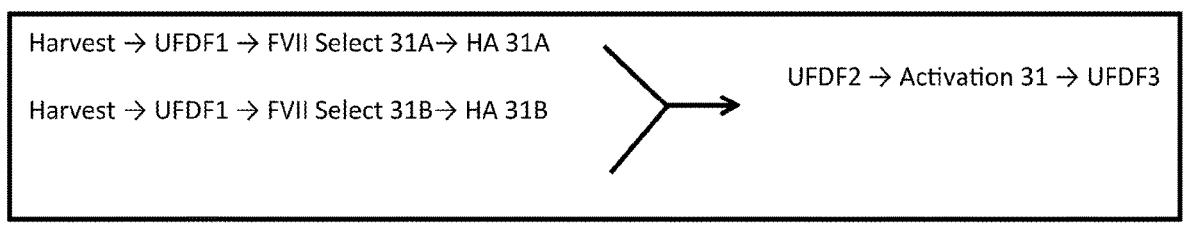
FIG. 2A. Shows a schematic diagram of FVII-CTP$_3$ purification process. Batch 31 was produced for the PK/PD study.
Figure 2B:
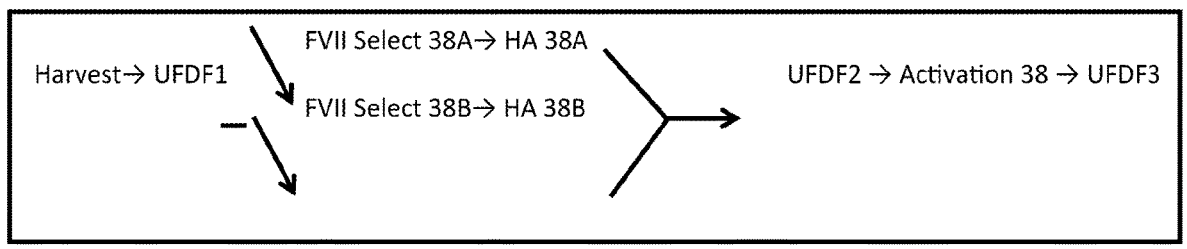
FIG. 2B. Shows a schematic diagram of FVII-CTP$_3$ purification process. Batch 38 was produced for the survival study.
Figures 3A, 3B, 3C, 3D:
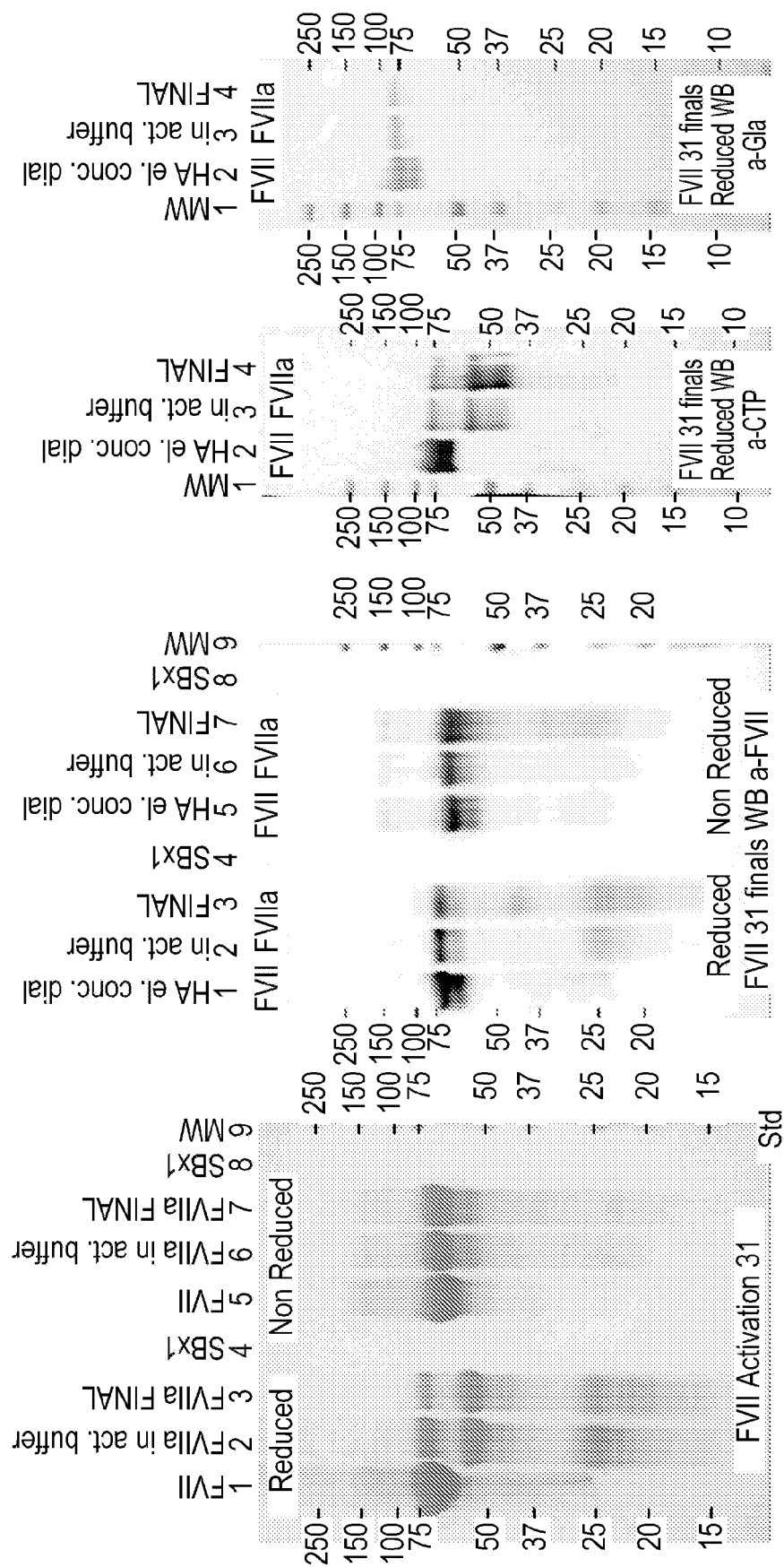
FIG. 3A. Shows an SDS-PAGE and Western blot of Final FVII and FVIIa. 10 μg (Batch 31) or 5 μg (Batch 38) were loaded in each lane of Coomassie stained SDS-PAGE. 1. FVII-CTP$_3$ polypeptide; 2. Heavy chain, including 3×CTP; 3. Light Chain. All three antibodies detect FVII.
FIG. 3B. Shows an SDS-PAGE and Western blot of Final FVII and FVIIa. 10 μg (Batch 31) or 5 μg (Batch 38) were loaded in each lane of Coomassie stained SDS-PAGE 1. FVII-CTP$_3$ polypeptide; 2. Heavy chain, including 3×CTP; 3. Light Chain.
FIG. 3C. Shows an SDS-PAGE and Western blot of Final FVII and FVIIa. 10 μg (Batch 31) or 5 μg (Batch 38) were loaded in each lane of Coomassie stained SDS-PAGE 1. FVII-CTP$_3$ polypeptide; 2. Heavy chain, including 3×CTP; 3. Light Chain.
FIG. 3D. Shows an SDS-PAGE and Western blot of Final FVII and FVIIa. 10 μg (Batch 31) or 5 μg (Batch 38) were loaded in each lane of Coomassie stained SDS-PAGE 1. FVII-CTP$_3$ polypeptide; 2. Heavy chain, including 3×CTP; 3. Light Chain.
Figures 3E, 3F, 3G, 3H:
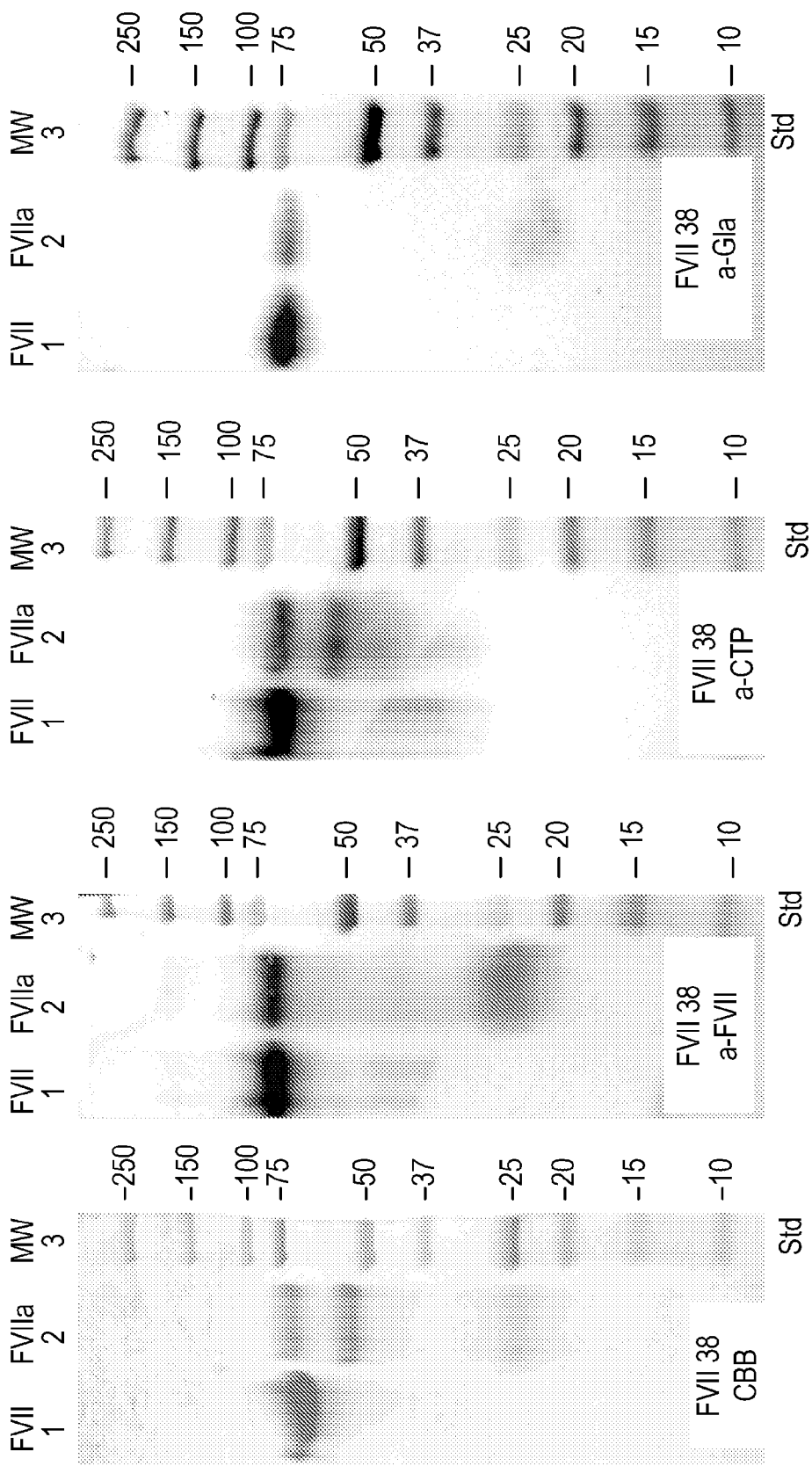
FIG. 3E. Shows an SDS-PAGE and Western blot of Final FVII and FVIIa. 10 μg (Batch 31) or 5 μg (Batch 38) were loaded in each lane of Coomassie stained SDS-PAGE 1. FVII-CTP$_3$ polypeptide; 2. Heavy chain, including 3×CTP; 3. Light Chain.
FIG. 3F. Shows an SDS-PAGE and Western blot of Final FVII and FVIIa. 1 μg protein was loaded in each lane of Western blot. 1. FVII-CTP$_3$ polypeptide; 2. Heavy chain, including 3×CTP; 3. Light Chain. All three antibodies detect FVII. FVIIa light chain is detected with both α-FVII.
FIG. 3G. Shows an SDS-PAGE and Western blot of Final FVII and FVIIa. 1 μg protein was loaded in each lane of Western blot. 1. FVII-CTP$_3$ polypeptide; 2. Heavy chain, including 3×CTP; 3. Light Chain. All three antibodies detect FVII. FVIIa heavy chain was detected by α-CTP.
FIG. 3H. Shows an SDS-PAGE and Western blot of Final FVII and FVIIa. 1 μg protein was loaded in each lane of Western blot. 1. FVII-CTP$_3$ polypeptide; 2. Heavy chain, including 3×CTP; 3. Light Chain. All three antibodies detect FVII. FVIIa heavy chain was detected by α-Gla.

FVII-CTP₃ Purification Process (FIGS. 2A-2B)

Process Outline

Following a short purification study, the following purification process using 2 columns was performed. VII-Select affinity column (GE) and Ceramic Hydroxyapatite type 1 (HA), 40 μm (Bio Rad), FVII-CTP₃ γ-carboxylated enriched protein was purified. Auto-activation was induced by incubation of purified FVII-CTP₃ in the presence of CaCl₂ overnight at 2-8° C. The purification process is in its final developmental stage and is being optimized, thus although most of the purification steps are similar, some part of the purification steps are not identical in the two batches.

Ultra-Filtration/Diafiltration (UFDF) Using 10 kDa Hollow Fiber or Pellicon Cassette Clarified harvest was thawed at 4° C. over the weekend (2-3 days).

In Batch 31, clarified harvest (12 liters) was concentrated 4-fold (in two successive runs) using a hollow fiber cartridge (GE Healthcare Catalog #UFP-10-C-4X2MA) with a 10 KDa molecular weight cut-off. Concentrated harvest was dia-filtrated against 1-2 volumes of TBS (50 mM Tris 150 mM NaCl pH 7.4).

In Batch 38, clarified harvest (8.5 liters) was concentrated 4-fold using a Pellicon 2 (Millipore) cassette with a 10 KDa molecular weight cut-off. Concentrated harvest was directly loaded on VII-Select column.

Both ultra-filtrations were performed on ice with ice cold buffers. UFDF samples were filtered 0.22 μm before loading.

Capture on FVII-Select Column

The UFDF or concentrated harvest was loaded on VII-Select column (XK16/20, CV 18 ml), pre-equilibrated with TBS pH 7.4. The column was washed with 50 mM Tris-HCl, 0.5M NaCl pH 7.5, and FVII-CTP₃ was eluted with 50 mM Tris-HCl, 1M NaCl 50% (v/v), Propylene Glycol pH 7.5. The process was performed in two successive cycles utilizing the same column.

Gamma Carboxylation-Based Separation on a Ceramic Hydroxyapatite Column

The eluted product was diluted 1:10 with 10 mM sodium phosphate pH 6.8 and loaded on ceramic hydroxyapatite columns (XK16/20, CV 24 ml). The column was washed with 59 mM sodium phosphate pH 6.8 and the γ-carboxylated rich fraction of Factor VII was eluted with 500 mM sodium phosphate pH 6.8. This process was performed in two successive cycles on the same column. At each batch, the eluates of the two cycles were pooled and concentrated to 1.7-2 mg/ml and dia-filtered with 20 mM Tris-HCl, 100 mM NaCl pH 8.2 to reduce volume and prepare the material for the activation step.

FVII Activation

Purified FVII-CTP₃ was diluted to 1 mg/ml and incubated in 20 mM Tris-HCl, 100 mM NaCl and 1 mM CaCl₂) pH 8.2 at 2-8° C. for 24 hours. Activation was terminated by buffer exchange (UFDF) to preliminary formulation buffer (20 mM Citric buffer, 240 mM NaCl, 13.3 mM Glycine, pH 6.9).

FVII-CTP₃ and FVIIa-CTP₃ Analytical Properties:

SDS-PAGE and Western Blots

Purified FVII-CTP₃, and FVIIa-CTP₃ were loaded on 12% Tris-Glycine gel using to Precision Plus Dual Color Protein Marker (Bio-Rad). The SDS-PAGE Coomassie analysis was performed by staining the gel with Coomassie brilliant blue reagent (5 or 10 μg of protein/lane). Western blot analysis was performed (1 μg of protein/lane) using anti-human FVII polyclonal Ab (R&D systems; AF2338), anti-human gamma carboxylation monoclonal antibody (American Diagnostics Catalog #499, 3570), and anti-CTP polyclonal Ab. Under reduced conditions, FVII-CTP₃ migrated at 75 KDa, and FVIIa-CTP₃ migrated as two main bands: a heavy chain at 50 kDa, and a light chain at 25 kDa, represented in FIGS. 3A-3H as Bands 2 and 3, respectively.

The purification procedure significantly enriched the FVII-CTP₃ portion while reducing impurities. The purification process yield was 25-30% FVII (according to ELISA). Most of the protein lost during purification had low FVII chromogenic activity or no activity. Based on Coomassie-stained SDS-PAGE, the reduced FVIIa-CTP₃ contains more than the predicted bands. A band migrating to around ~75 kDa represents non-activated FVII (FIGS. 3A-3H, Band 1). This band consists of two bands with minor MW differences, which might reflect different γ-carboxylation content. Additional bands with MW lower than 20 kDa were observed. This was previously reported to be degradation products of the heavy chain.

Figure 4:
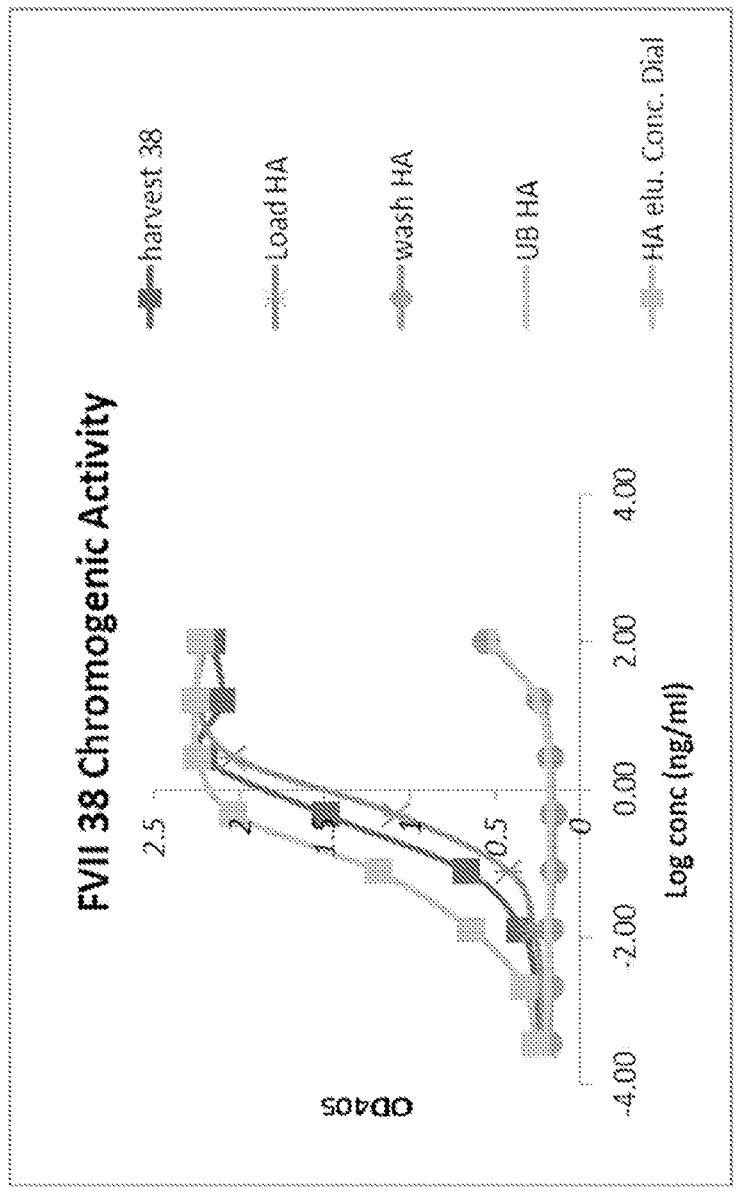
FIG. 4. Shows that FVII-CTP$_3$ chromogenic activity is enhanced as a result of purification on ceramic hydroxyapatite (HA) column. A comparative assessment of the in vitro potency of FVII-CTP$_3$ harvest, in-process fractions, and purified FVII-CTP$_3$ versus human pool normal plasma was performed using a commercially available chromogenic activity test kit, BIOPHEN (Hyphen BioMed 221304). FVII-CTP$_3$ harvest and protein were serially diluted and the potency was assessed by comparing a dose-response curve to a reference preparation of normal human plasma.

FVII-CTP₃ Chromogenic Activity:

A comparative assessment of the in vitro potency of FVII-CTP₃ harvest, in-process fractions, and purified FVII-CTP₃ versus human pool normal plasma was performed using a commercially available chromogenic activity test kit, BIOPHEN (Hyphen BioMed 221304). FVII-CTP₃ harvest and protein were serially diluted and the potency was assessed by comparing a dose-response curve to a reference preparation of normal human plasma. Following FVII-CTP₃ purification, the chromogenic activity was significantly improved, and non-active fractions were separated mainly by HA column (FIG. 4). A strong correlation between FVII chromogenic activity and detection of FVII with monoclonal anti-Gla antibodies in Western blot was observed. The potency of FVII chromogenic activity as reflected by EC50 value in harvest is affected from both carboxylated and non-carboxylated FVII fractions. Following purification and enrichment of FVII-CTP₃ γ-carboxylated fraction, the activity was improved, demonstrating the important contribution of γ-carboxylation to FVII activity (FIG. 4). This parameter is crucial for proper FVII in vivo activity and will be further addressed in a clone development program.

Protein Determination by A280

The theoretical extinction coefficient of FVIIa-CTP₃ and NovoSeven® was calculated using the ProtParam algorithm (http://web.expasy.org/protparam). The calculation is based on amino acid sequence. The calculated extinction coefficients for FVII-CTP$_3$ and NovoSeven® is 1.186 and 1.406, respectively. These values represent the absorbance of 1 g/L at 280 nm.

The extinction coefficient difference between the two proteins derives solely from the increase in molecular weight of FVIIa-CTP$_3$ compared to NovoSeven®, since CTP lacks aromatic and cysteine residues, thus does not contribute to the absorbance.

Protein determination by A280 is used for final FVII, and for purified in-process samples, starting from the elution of VII-Select column.

Determination of FVIIa Antigen Level

FVIIa antigen level was determined using Human FVIIa ELISA kit (IMUBIND, American Diagnostica). The antigen level was calculated per each batch. However, this tool was not useful for the determination of the dose for injection, since it did not represent the amount of active product.

Clotting Assay of FVIIa-Staclot® VIIa-rTF

FVIIa is derived from an intra-chain cleavage of the single-chain FVII. Native tissue factor (TF) is a cofactor of FVIIa. Upon binding to TF, FVII mediates the activation of Factor X to Xa, while itself is transformed to FVIIa. The soluble tissue factor is the extracellular part of native tissue factor. It can no longer activate FVII by auto-activation, but the FVIIa bound to tissue factor can activate FX to FXa.

The recombinant soluble tissue factor (rsTF) used in this assay utilizes the FVIIa specificity to construct a FVIIa clotting test. rsTF, in the presence of FVIIa, calcium and phospholipids leads to coagulation of plasma, without activating FVII to FVIIa.

The observed clotting time in this system has an inverse relationship with the FVIIa content in the tested sample, with no interference of FVII presence in the sample.

The assay was performed by Omri Laboratories (Nes-Ziona, Israel). FVIIa activity was evaluated for both Novo-Seven® following reconstitution and FVIIa-CTP$_3$ prior to each study. NovoSeven® activity did not correlate with the anticipated activity as reported on the vial, but the discrepancy might be due to a different approach for activity evaluation. Table 39 summarizes the FVIIa clotting activity per volume without considering the protein concentration.

TABLE 2

| | FVIIa clotting activity of batch products | | | |
|---|---|---|---|---|
| | PK study | | Survival Study | |
| | FVIIa-3*CTP (FVIIa 31) | NovoSeven® | FVIIa-3*CTP (FVIIa 38) | NovoSeven® |
| Activity (U/ml) | 1.3E+06 | 2.5E+05 | 1.3E+06 | 7.4E+05 |

Specific Activity of FVIIa-CTP$_3$

FVIIa specific activity (which is calculated as the activity/ml divided by protein concentration) was calculated based on A280 and is presented in Table 3. When comparing the specific activity of the two molecules, which differ in MW, compensation must be made in order to normalize the activity (i.e. because of the molecular weight difference, the number of active sites in 1 mg of NovoSeven® is 1.185-fold higher than in FVIIa-CTP$_3$). Calculation of the conversion factor is presented in the following equation:

$$\text{Normalized\_SA} = \frac{SA(FVIa-CTP_3)}{MW.(FVII\ CTP_3)} \times MW(\text{Native\_FVII}) =$$
$$= \frac{SA(FVIIa\ CTP_3)}{53419.5Da} \times 45079.1Da$$
$$= SA(FVIIa-CTP_3) * 1.185$$

TABLE 3

| | | | | | | | Specific Activity | | Fold decrease |
|---|---|---|---|---|---|---|---|---|---|
| | | | | | Prot | | | | |
| Sample | Average A280 | STDV (n = 9) | % CV | Extinction coefficient | conc. (mg/ml) | U/ml | U/mg protein | U/mg FVIIa | from NovoSeven® |
| NovoSeven® | 1.274 | 0.031 | 2.398 | 1.406 | 0.906 | 8.36E+05 | 9.23E+05 | 9.23E+05 | 1.0 |
| FVIIa-CTP$_3$ | 4.396 | 0.092 | 2.094 | 1.186 | 3.706 | 7.23E+05 | 1.95E+05 | 2.31E+05 | 4.0 |

FVIIa-CTP$_3$ PK-PD Study:

Study Outline

FVIIa-CTP$_3$ and rhFVIIa (NovoSeven®, NS) were administered in a single intravenous injection to C57B FVIII-deficient mice at a dose of 6.4E6 U/kg body weight (160,000 U/animal) Blood samples were drawn retro-orbitally from 4 mice alternately at 0.166, 0.5, 2, 4, 8, 12, 24, 34, 48, 58, and 72 hours post-dosing (Table 4). Citrated plasma (0.32%) was prepared immediately after sampling and stored at −20° C. until analysis. FVIIa clotting activity level was evaluated, and a detailed PK analysis was performed. The study was performed by Omri Laboratories (Nes-Ziona, Israel).

TABLE 4

Study outline

| Treated Groups | Test Article | No. of animals/ group/ timepoint | Dose Route | Amount of Units/ animal | Injected Vol. (µl) | Time-Points (hours post-dose) |
|---|---|---|---|---|---|---|
| A | rhFVIIa | 4 | IV | 1.6e5 | 200 | 0 (Pre-dose) 0.166, 0.5, 2, 4, 8, 12, 24, 34, 48, 58, 72 |
| B | FVIIa-CTP$_3$ | 4 | IV | 1.6e5 | 200 | 0 (Pre-dose) 0.166, 0.5, 2, 4, 8, 12, 24, 34, 48, 58, 72 |

FVIIa-CTP$_3$ PK Profile in FVIII-Deficient Mice

Figure 5:
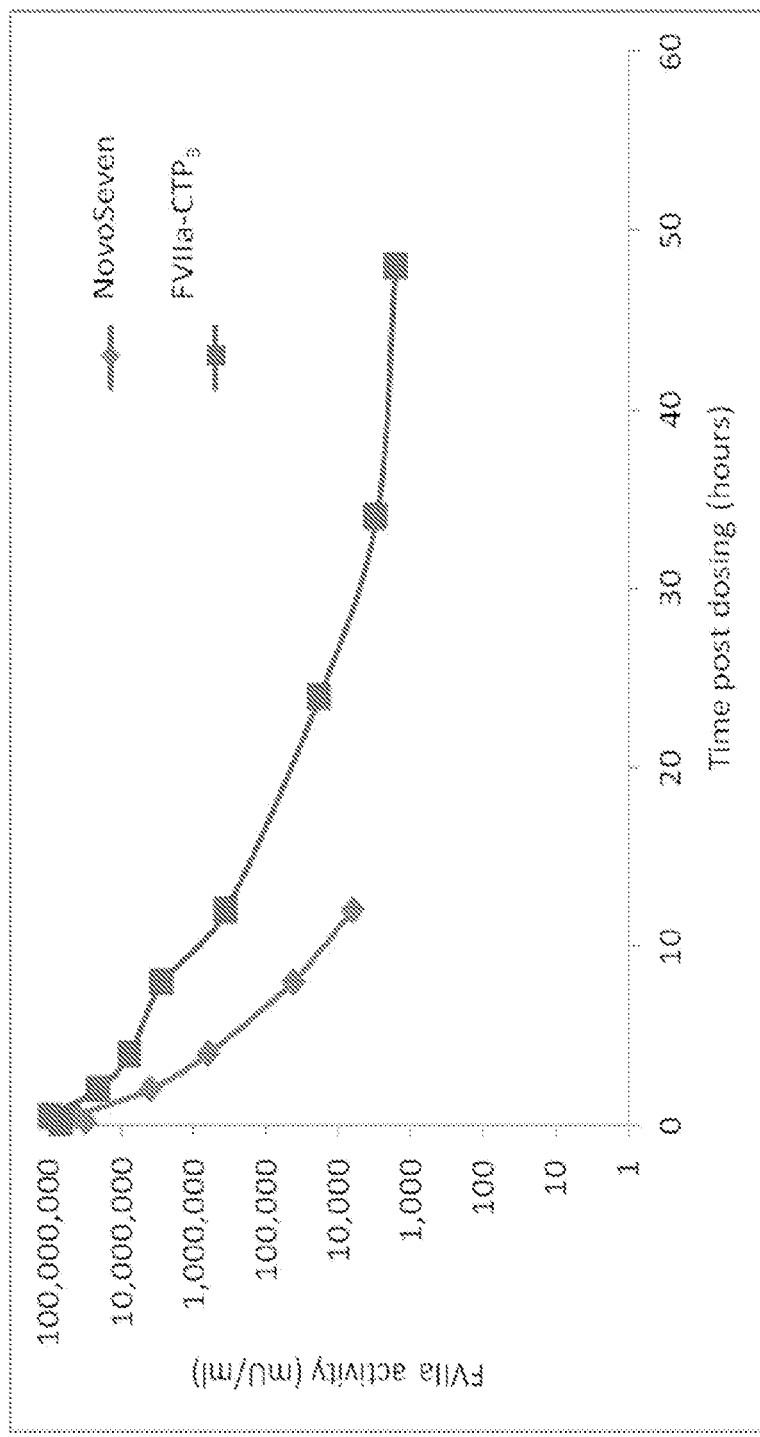
FIG. 5. Shows the PK profile of FVIIa-CTP$_3$ vs. NovoSeven® in FVIII-deficient mice. FVIIa-CTP$_3$ was produced following FVII selection, HA purification process and activation. FVIIa-CTP$_3$ or NovoSeven® was administered in a single intravenous injection to FVIII-/- hemophilic mice. Blood samples were drawn retro-orbitally at 0.083, 0.5 2, 8, 24, 48, and 72 hours post-dosing. Citrated plasma (0.38%) was prepared immediately after sampling and stored at -20° C. until analysis, and a PK profile was established based on FVIIa clotting activity using a STACLOT commercial kit.

FVIIa activity in blood samples was quantitated using a Staclot® VIIa-rTF kit (Stago, Parsippany, NJ). The pharmacokinetic profile was calculated for each protein and represents the mean of 4 animals at each time point. FIG. 5 presents the PK profile of FVIIa throughout the experiment.

FVIIa recovery is presented in Table 6. A summary of the PK parameters is presented in Table 7.

Table 5 summarizes the clotting activity values following administration of either NovoSeven® or FVIIa-CTP$_3$. FVIIa-CTP$_3$ and NovoSeven® reached maximal activity half an hour post-dosing. NovoSeven®'s highest activity value reached only 43% of FVIIa-CTP$_3$'s maximal activity value. FVIIa-CTP$_3$ clotting activity was maintained for a longer period of time, demonstrating elongated activity. Clotting activity for the NovoSeven®-treated mice was undetectable at time points later than 12 hours, while FVII-CTP$_3$ treated mice continued to retain measurable activity at 48 hours post dosing (Table 5 and FIG. 5).

The addition of three tandem CTP copies to FVIIa elevated recovery by 100% (Table 6), as measured by the highest activity post-dosing and compared to the anticipated activity based on in vitro analysis, and increased the half-life and mean resident time (MRT) 5-fold. The exposure time (AUC) was increased 3-fold (Table 7).

TABLE 5

FVIIa clotting activity following single IV injection

| Time after administration | Average FVIIa Clotting Activity (U/ml) | |
|---|---|---|
| (hours) | FVIIa-CTP$_3$ | NovoSeven ® |
| 0.16 | 6.8E+07 | 3.2E+07 |
| 0.5 | 9.7E+07 | 4.3E+07 |
| 2 | 2.1E+07 | 3.9E+06 |
| 4 | 7.7E+06 | 7.3E+05 |
| 8 | 2.7E+06 | 4.2E+04 |
| 12 | 3.7E+05 | 6.2E+03 |
| 24 | 2.4E+04 | BLQ |
| 34 | 4.6E+03 | BLQ |
| 48 | 1.5E+03 | BLQ |

TABLE 6

FVIIa-CTP$_3$ recovery

| Treated. Groups | Test Article | Amount of Units/ animal | Practical administered dose (U/ml) | *Anticipated Cmax (U/ml blood) | Cmax (U/ml) | % Recovery |
|---|---|---|---|---|---|---|
| A | rFVIIa | 1.60E+05 | 1.20E+06 | 1.40E+05 | 4.25E+04 | 30 |
| B | FVIIa-CTP$_3$ | 1.60E+05 | 1.29E+06 | 1.50E+05 | 9.74E+04 | 64.6 |

*anticipated Cmax is derived from administered dose divided in blood volume

TABLE 7

PK parameters of FVIIa-CTP$_3$ vs. NovoSeven ®

| PK Parameters | NovoSeven ® | FVIIa-CTP$_3$ |
|---|---|---|
| Half-life-$\alpha$ (0.5-12 hr) | 0.94 | 1.57 |
| Half-life-$\beta$ (12-48 hr) | NA | 4.62 |
| AUC (mU*hr/ml) | 5.80E+07 | 1.80E+08 |
| Vd/Kg (ml/Kg) | 1408 | 2375 |
| CL/Kg (ml/hr/Kg) | 1034 | 356 |
| MRT (hr) | 1.3 | 6.7 |

FVIII-deficient mice were administered a single intravenous injection of FVIIa-CTP$_3$ or NovoSeven®. The mice were dosed with drug in amounts that provided equivalent FVIIa activity (1.6E05 units, 200 μl), calculated according to the potency of each drug evaluated in the FVIIa clot activity assay (Table 8). The administered doses were 9 mg/kg of NovoSeven®, and 40 mg/kg of FVII-CTP$_3$ due to the reduced activity of FVIIa-CTP$_3$. A control group was injected with 200 μl vehicle.

The tail vein was transected 2.7 cm from the tail tip 15 min (injection 1), 24 hours (injection 2) or 48 hours (injection 3) post-administration, and mice survival was recorded for 24 hours.

TABLE 8

Evaluation of injected samples

| | NovoSeven ® | | | FVIIa-CTP$_3$ | | | |
|---|---|---|---|---|---|---|---|
| Injection No. | protein conc. (mg/ml) | Activity (U/ml) | Specific Activity (U/mg) | protein conc. (mg/ml) | Activity (U/ml) | Specific Activity (U/mg) | Specific Activity (normalized) |
| 1 | 0.91 | 8.0E+05 | 8.8E+05 | 3.63 | 6.6E+05 | 1.8E+05 | 2.2E+05 |
| 2 | 0.92 | 8.3E+05 | 9.0E+05 | 3.81 | 7.8E+05 | 2.0E+05 | 2.4E+05 |
| 3 | 0.89 | 8.8E+05 | 9.9E+05 | 3.68 | 7.3E+05 | 2.0E+05 | 2.3E+05 |

Thrombin Generation Assay (TGA)

Figure 6A:
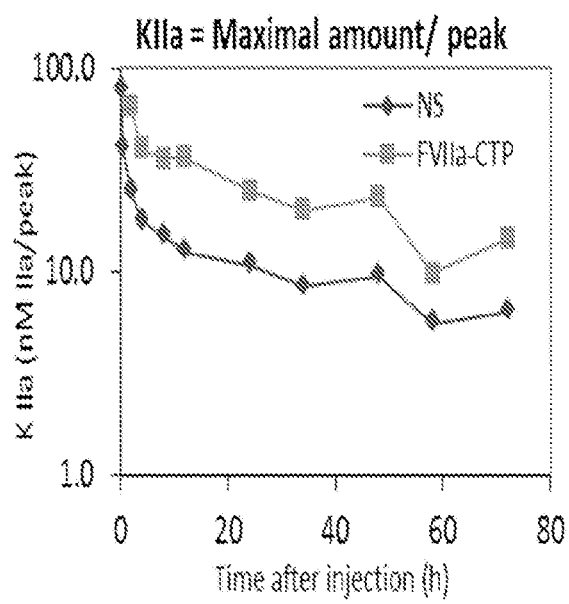
FIG. 6A. Shows that FVIIa-CTP$_3$ was produced following FVII selection, HA purification process and activation. FVIIa-CTP$_3$ or NovoSeven® was administered in a single intravenous injection to FVIII-/- hemophilic mice. Blood samples were drawn retro-orbitally at 0.083, 0.5 2, 8, 24, 48, and 72 hours post-dosing. Citrated plasma (0.38%) was prepared immediately after sampling and stored at -20° C. until analysis. Thrombin generation parameters were evaluated during the PK experiment, and parameters including maximal amount to peak was evaluated.
Figure 6B:
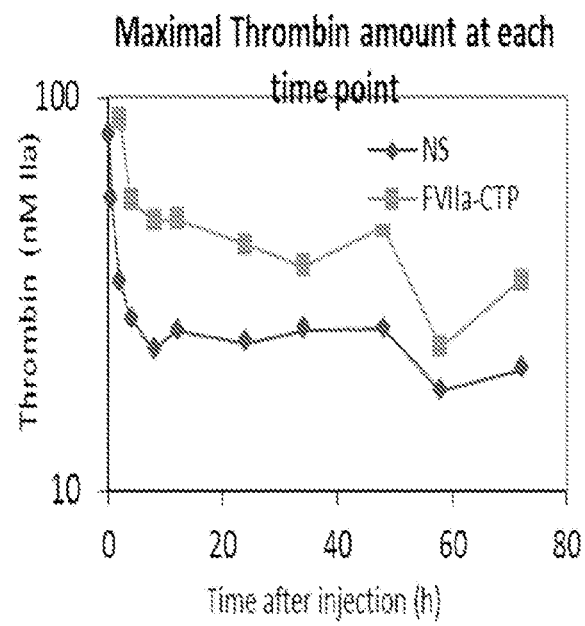
FIG. 6B. Shows that FVIIa-CTP$_3$ was produced following FVII selection, HA purification process and activation. FVIIa-CTP$_3$ or NovoSeven® was administered in a single intravenous injection to FVIII-/- hemophilic mice. Blood samples were drawn retro-orbitally at 0.083, 0.5 2, 8, 24, 48, and 72 hours post-dosing. Citrated plasma (0.38%) was prepared immediately after sampling and stored at -20° C. until analysis. Thrombin generation parameters were evaluated during the PK experiment, and parameters including amount of thrombin to time point was evaluated.
Figure 6C:
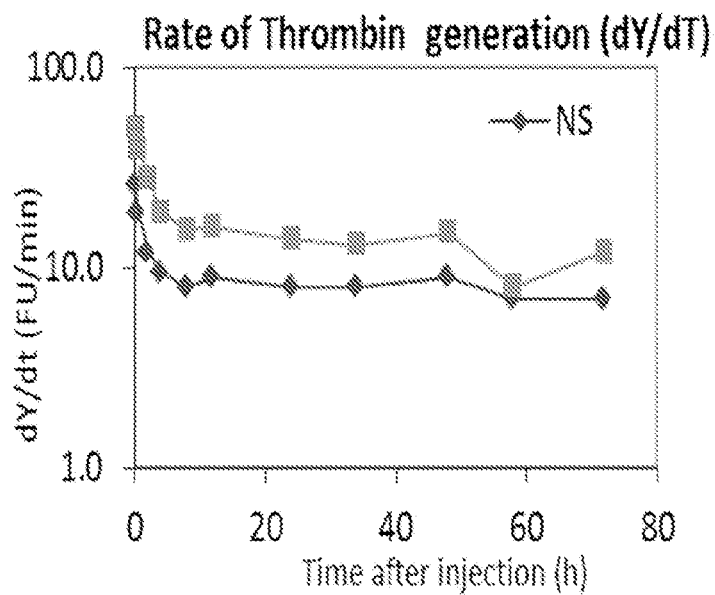
FIG. 6C. Shows that FVIIa-CTP$_3$ was produced following FVII selection, HA purification process and activation. FVIIa-CTP$_3$ or NovoSeven® was administered in a single intravenous injection to FVIII-/- hemophilic mice. Blood samples were drawn retro-orbitally at 0.083, 0.5 2, 8, 24, 48, and 72 hours post-dosing. Citrated plasma (0.38%) was prepared immediately after sampling and stored at -20° C. until analysis. Thrombin generation parameters were evaluated during the PK experiment, and parameters including rate of thrombin generation was evaluated.

The generation of thrombin is a fundamental part of the clotting cascade and as such an estimate of how well a particular individual can generate thrombin may correlate with either a risk of bleeding or thrombosis. Commonly measured variables when analyzing thrombin generation include: the lag time, the time to peak thrombin generation, the peak, the endogenous thrombin potential [ETP] (i.e., the area under the curve and the tail), the time course of the thrombogram ("TG"). After a lag time, a burst of thrombin is observed. However, clotting occurs at the end of the lag time, when more than 95% of all thrombin has not yet formed. The thrombin generation assay was performed at Omri Laboratories, using Thrombinoscope reagents supplemented with human hemophilic plasma. TGA reflects of the clotting ability in mice plasma, derived from injection of NovoSeven® and FVIIa-CTP$_3$. FIGS. 6A-6C presents TGA parameter values for mice plasma following administration of either FVIIa-CTP$_3$ or NovoSeven®. Following FVIIa-CTP$_3$ administration, all three parameters (rate of thrombin generation, maximal amount of generated thrombin and Kik) demonstrate an advantage of FVII-CTP$_3$ over NovoSeven® treatment. This further strengthens the notion of potential long-acting superiority of FVII-CTP$_3$ as compared to NovoSeven®.

FVIIa-CTP$_3$ Tail Vain Transection (TVT) Study:
Study Outline

The data obtained from the PK/PD test for FVIIa-CTP$_3$ provided insight into the functionality of FVIIa-CTP$_3$, and demonstrated that FVIIa-CTP$_3$ had a pharmacokinetic advantage when compared with NovoSeven®. However, the ability of the protein to induce a clot in vivo, after a traumatic event has not yet been demonstrated. In order to evaluate the ability of FVIIa-CTP$_3$ to stop bleeding, the same FVIII-deficient mice model was employed for a bleeding challenge.

Protein concentration was determined by A280.

Results

Data from the vehicle-injected control groups for the three injections (5 animals×3 injections), were summarized and are presented in FIGS. 7A-7D. 30% survival was observed 24 hours after tail vein transection.

NovoSeven® and FVIIa-CTP$_3$-treated mice demonstrated proper hemostatic activity after tail vein transection performed 15 min after FVIIa administration. A 100% survival rate was observed in FVIIa-CTP$_3$ and NovoSeven® treated animals (FIGS. 7A-7D).

The reduced clearance rate of FVII-CTP$_3$ which was demonstrated in the PK/PD study is most clearly appreciated after a tail vein transection performed 24 hours post-administration. A decline in the survival rate of NovoSeven® is observed. Similar to the control group, 50% death is observed within 10 hours. Meanwhile, 90% of FVIIa-CTP$_3$ treated mice survived (FIG. 7A-7D). This result emphasizes the long-lasting efficacy of the FVIIa-CTP$_3$ treatment.

Figure 7A:
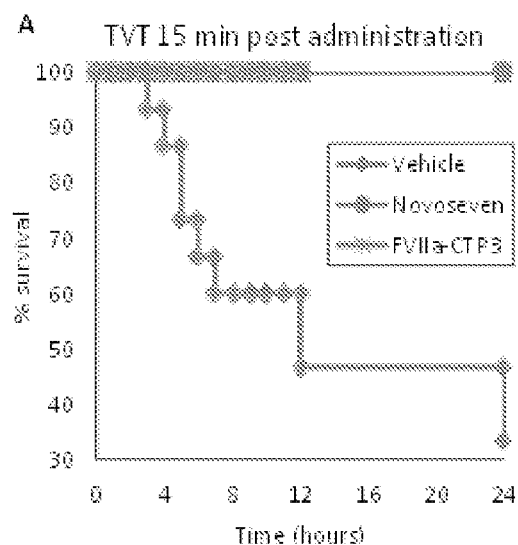
FIG. 7A. Shows hemophilic mice survival curves post tail vain transection (TVT). TVT was performed 15 min post administration. Mice Survival was observed for 24 hours after TVT and recorded every single hour for the first 12 hours, and after 24 hours. Control group data (vehicle) is the sum of the 3 experiments with 5 mice/experiment.
Figure 7B:
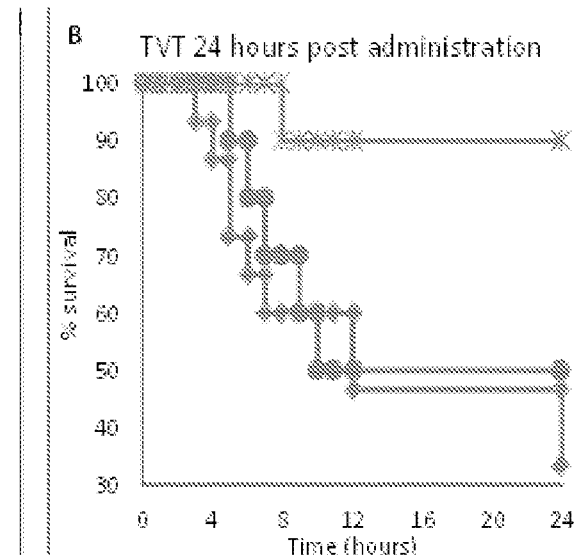
FIG. 7B. Shows hemophilic mice survival curves post tail vain transection (TVT). TVT was performed 24 hours post administration. Mice Survival was observed for 24 hours after TVT and recorded every single hour for the first 12 hours, and after 24 hours. Control group data (vehicle) is the sum of the 3 experiments with 5 mice/experiment.
Figure 7C:
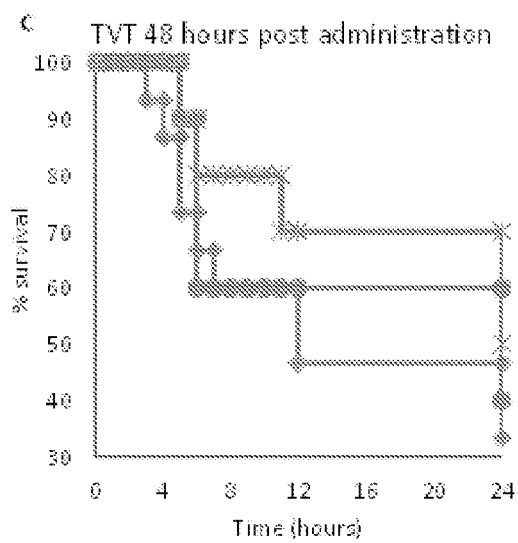
FIG. 7C. Shows hemophilic mice survival curves post tail vain transection (TVT). TVT was performed 48 hours post administration. Mice Survival was observed for 24 hours after TVT and recorded every single hour for the first 12 hours, and after 24 hours. Control group data (vehicle) is the sum of the 3 experiments with 5 mice/experiment.
Figure 7D:
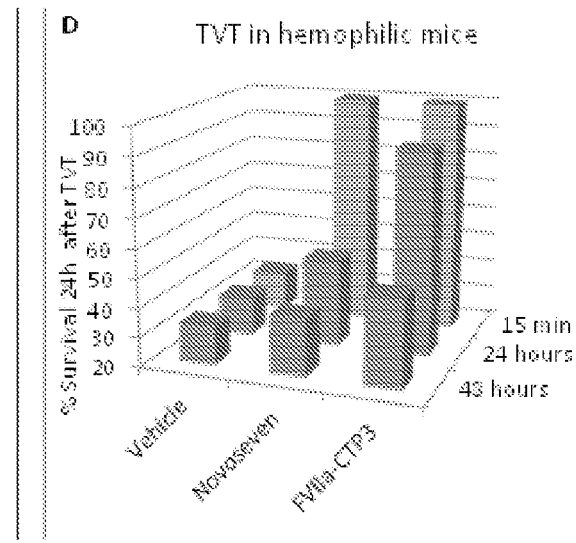
FIG. 7D. Summarizes mouse survival as recorded 24 hours post TVT.

48 hours after administration, a decline in survival rate is demonstrated in groups treated with either FVIIa-CTP$_3$ or NovoSeven® (FIG. 7C). A slight improvement in FVIIa-CTP mice was observed, but the difference did not reach statistical significance.

Discussion

CTP fusion to recombinant proteins extends the circulatory half-life of proteins while maintaining comparable activity. While the mechanism behind the reduced clearance of protein above a threshold size of 70 KDa is well understood with respect to renal clearance, additional protection is achieved following CTP fusion. CTP fusion is believed to sweep around the protein shield and protect it from proteolytic cleavage, to increase its radial molecular weight due to the highly negative charge and to reduce its affinity to hepatic clearance receptors.

The present study was aimed to provide specific insight on the impact of CTP fusion to FVII on protein half-life and clearance and also address the paradigm of its specific activity following this modification. FVIII-deficient mice were administered with a single IV injection of FVIIa-CTP$_3$ or recombinant commercial FVIIa (NovoSeven®) at similar dose (unit based) and a PK activity-based analysis was performed. FVIIa-CTP$_3$ demonstrated a superior longevity as reflected by 5- and 3.5-fold increase in its half-life and AUC, respectively. The specific activity (U/mg) of FVIIa-CTP as calculated by the Staclot® activity kit divided by the protein concentration measured by A280 was shown to be 4-5 times lower than the specific activity of NovoSeven®.

To build on the understanding of how CTP affects the haemostatic effects of FVIIa in vivo, the ability of FVIIa-CTP$_3$ to reduce bleeding was investigated. In the tail vein transection bleeding model in hemophilic mice model, rFVIIa administration can improve the survival rate of challenged animals and avoid their bleeding to death. In the study described herein, animals were administered with FVIIa-CTP$_3$ or NovoSeven®. Both molecules were able to maintain homeostasis when the transection was performed 0.25 hours post-dosing. A significantly prolonged duration of activity was demonstrated for the FVIIa-CTP$_3$-treated group when the tail transection was performed 24 hr post dosing. The vehicle-treated group's survival rate was higher than anticipated and higher than that obtained in previous studies (50% vs. 20% in previous studies, data not shown). The percent survival of treated animals at is further evaluated at earlier time points, including at 36 hr post dosing.

In conclusion, it was demonstrated that FVIIa-CTP$_3$ has an increased duration of activity in hemophilic mice which translates into a longer duration of haemostatic effect when compared to NovoSeven®. The data gathered suggest that fusion of CTP to FVII is a technology with the potential to significantly improve prophylactic treatment in patients with hemophilia.

Example 2

Biochemical Properties of MOD-5014 Relative to Commercial Recombinant hFVIIa-Effect of a Carboxy-Terminal Peptide (CTP) on Factor VIIa Activity
Project Rationale and Summary These studies were designed to assess the biochemical properties of MOD-5014 relative to commercial recombinant hFVIIa, referred to herein as MOD-5000.
The studies examined:
Synthetic substrate cleavage of MOD-5014
Tissue factor (TF) binding of MOD-5014 as measured by synthetic substrate cleavage
TF binding of MOD-5014 as measured by factor X (FX) activation
Kinetics of FX activation by TF-bound MOD-5014
Lipid binding of MOD-5014 as measured by FX activation
Kinetics of factor activation by lipid-bound MOD-5014
Inactivation of MOD-5014 by anti-thrombin (AT)
Inactivation of MOD-5014 by TFPI
Overall the data suggests that, relative to MOD-5000, MOD-5014 has similar mechanism of action with a slightly reduced catalytic activity. These results demonstrated slightly reduced activity of TF-bound MOD-5014 and somewhat more reduced activity, independent of TF.

These effects were reflected mainly by reaction rates rather than the extent of reactions, and reactions for which the entire time course can be measured do go to completion.

The slightly reduced rate of AT inhibition suggests an extension of MOD-5014 half-life in vivo with a proper inhibition response.

Experimental Materials
MOD-5014 GMP-1: 2.5 mg/ml (based on A280)
NovoSeven Lot #CU60430: 0.943 mg/ml (based on A280), referred to as MOD-5000.
Synthetic Substrate Cleavage of Mod-5014

Rationale: Cleavage of synthetic substrate should depend exclusively on the availability of a functional active site.

Methods: MOD-5000 and MOD-5014 were diluted to equal concentrations on a molar basis. The same concentration was then added to a fixed concentration of the substrate Pefachrome FVIIa (methylsul fonyl-D-cyclohexylalanyl-2-aminobutyryl-arginine-p-nitroanilide) and cleavage of the substrate was monitored by the appearance of a yellow color.
Results Concentration: FVIIa 360 nM; Substrate 500 μM Analysis: Absorbance at 405 nm was converted to concentration of p-nitroaniline using the known extinction coefficient. Concentration of p-nitroaniline was plotted vs. time to determine a rate of substrate cleavage. Data was fitted to:

rate=$k_1$[VIIa]

$k_1$=27.5 mol pNA/min/mol VIIa

Figure 8:
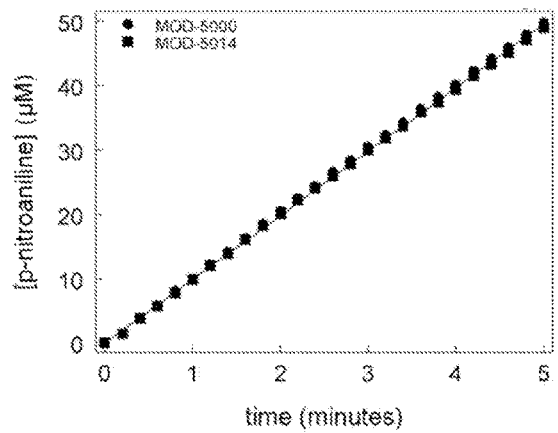
FIG. 8. Shows a comparison of substrate (Pefachrome FVIIa) cleavage activity between FVIIa (NovoSeven) and CTP-modified factor VIIa (MOD-5014).

Conclusion: On a molar basis, MOD-5000 and MOD-5014 have the same rate of substrate cleavage (FIG. 8). For subsequent studies, measurement of substrate cleavage is used as a control for dilutions and pipetting.
Tf Binding of Mod-5014 as Measured by Synthetic Substrate Cleavage Rationale: When factor VIIa binds TF, a conformational change occurs in factor VIIa that results in an increase in the rate of substrate cleavage. This means that increased substrate cleavage can be used to monitor factor VIIa binding to TF.

Methods: Varying concentrations of MOD-5000 and MOD-5014 were added to a fixed concentration of
TF and incubated for 5 minutes. Substrate (Pefachrome FVIIa) was added. Substrate cleavage was monitored at 405 nm by the appearance of yellow color.
Results:

Concentration: FVIIa 0-25 nM; TF 8.7 nM; Substrate 500 μM

Analysis: As the concentration of TF is well above the expected Kd, at low concentrations all of FVIIa should be bound to TF. The rate of substrate cleavage will be that of the VIIa/TF complex. Once the concentration of FVIIa exceeds that of TF, the rate of substrate cleavage should drop to that of free FVIIa. Since FVIIa and TF form a 1:1 molar complex, the concentration of FVIIa at which the change in rate of substrate cleavage occurs is a check on the estimated concentration of FVIIa.

Data was fitted to:

rate=$k_1$[VIIa]+$k_2$[VIIa/TF]

|  | MOD-5000 | MOD-5014 |  |
| --- | --- | --- | --- |
| $k_1$ | 27.5 | 27.5 | mol pNA/min/mol VIIa |
| $k_2$ | 365 | 357 | mol pNA/min/mol VIIa/TF |

Figure 9:
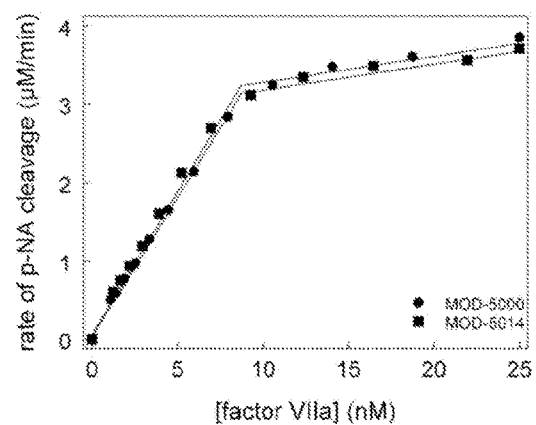
FIG. 9. Shows a comparison of substrate (Pefachrome FVIIa) activity between FVIIa (NovoSeven) and CTP-modified factor VIIa (MOD-5014) when bound to tissue factor.

Conclusion: MOD-5000 (Novoseven) and MOD-5014 show the same inflection point at the expected concentration of TF (8.7 nM) (FIG. 9). This confirms that the molar concentrations of MOD-5000 and MOD-5014 as predicted by substrate cleavage are correct. MOD-5014 had a very slightly lower rate of substrate cleavage when bound to TF (98%) relative to MOD-5000 (FIG. 9).

Tf Binding of Mod-5014 as Measured by Factor x Activation

Rationale: Cleavage of FX by FVIIa is slow relative to cleavage by the FVIIa/TF complex. Therefore, binding of FVIIa to TF can be assessed by measuring the rate of FX activation.

Methods: Varying concentrations of MOD-5000 and MOD-5014 were added to a fixed concentration of TF and the rate of FX activation was measured. Factor X activation was assessed by cleavage of the synthetic substrate Pefachrome FXa (methoxycarbonyl-D-cyclohexylalanyl-glycyl-arginine paranitroanilide). Cleavage of synthetic substrate is converted to FXa concentration by a standard curve. Neither FVIIa nor FVIIa/TF cleaves the FX substrate at an appreciable rate.

Results

Concentration: FVIIa 0-2 nM; TF 10 pM; FX 135 nM; Substrate 500 µM

Factor X concentration in plasma is 8 µg/mL (µ135 nM).

Figure 10:
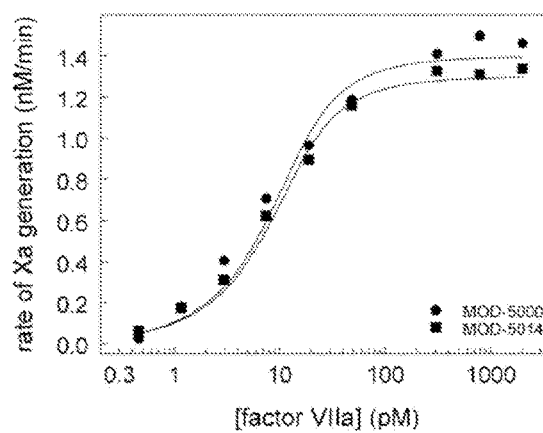
FIG. 10. Shows a comparison of the generation of activated Factor X by FVIIa (NovoSeven) or CTP-modified FVIIa (MOD-5014), in view of Factor VIIa concentration.

Analysis: The rate of FX activation should increase as FVIIa binds to TF. Once all of the TF is saturated with FVIIa, the rate of FX activation will have reached a maximum value (FIG. 10).

Data was fitted to:

$$v = V_{max} \frac{[VIIa]^n + [TF] + K_d^n - \sqrt{([VIIa]^n + [TF] + K_d^n)^2 - 4[VIIa]^n[TF]}}{2[TF]}$$

|  | MOD-5000 | MOD-5014 |  |
| --- | --- | --- | --- |
| $V_{max}$ | 1.40 | 1.30 | nM FXa/min |
| $K_d$ | 3.3 | 3.0 | pM |
| Hill value | 0.93 | 0.91 |  |

Conclusion: There is a very slight negative cooperativity (Hill value <1) in the binding of FVIIa to TF. This is the same for MOD-5000 and MOD-5014. When bound to TF, MOD-5014 has a slightly reduced rate of FX activation (93%) relative to MOD-5000. The affinity of MOD-5014 for TF is equivalent to the affinity of MOD-5000 (FIG. 10).

Rate of FX Activation as a Function of FX Concentration

Rationale: The slightly reduced rate of MOD-5014 activation when bound to TF could be a consequence of reduced affinity for FXa or reduced turnover of FX once it is bound to the complex. Measuring the rate of FX activation as a function of FX concentration established the kinetic parameters of the complex.

Methods: Varying concentrations of FX were incubated with a fixed concentration of FVIIa/TF complex.

Factor X activation was assessed by cleavage of a synthetic substrate (Pefachrome FXa). Cleavage of the synthetic substrate is converted to FXa concentration by a standard curve.

Results

Concentration: FVIIa 1 nM; TF 5 pM; FX 0-1500 nM; Substrate 500 µM

Analysis: As more FX was added, more of the FVIIa/TF complex should have FX bound up to the point where all FVIIa/TF complexes have bound FX. At that point the reaction was limited by the rate at which FX was activated. Therefore, the rate of FX activation should have increased with an increasing concentration of FX, with the shape of the curve asymptotically approaching a maximum rate (FIG. 123).

Data was fitted to:

$$v = V_{max}\left(\frac{[S]}{K_m + [S]}\right)$$

|  | MOD-5000 | MOD-5014 |  |
| --- | --- | --- | --- |
| $V_{max}$ | 1.78 | 1.64 | nM FXa/min |
| $K_m$ | 140 | 120 | nM |

Figure 11:
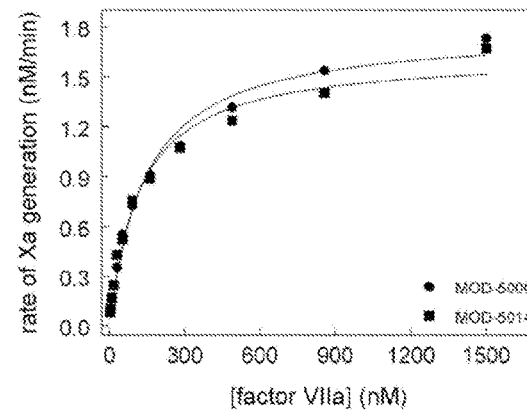
FIG. 11. Shows a comparison of the generation of activated Factor X by FVIIa (NovoSeven) or CTP-modified FVIIa (MOD-5014), in view of Factor X concentration.

Conclusion: When bound to TF, MOD-5014 had a slightly reduced turnover of FX (92%) relative to MOD-5000. The binding of FX to the MOD-5014/TF complex was the same as its binding to the MOD-5000/TF complex (FIG. 11).

Lipid Binding of MOD-5014 as Measured by FX Activation

Rationale: Factor X activation on platelets is thought to contribute to the hemostatic effect of FVIIa. This platelet activity is thought to occur in a low-TF environment, or in the absence of TF. Factor X activation without TF can be studied on lipid vesicles.

Methods: Factor X activation by FVIIa on lipids is a function of binding of both enzyme (FVIIa) and protein substrate (FX). The lipid ratio was PC:PE:PS 41:44:14, designed to mimic the composition of highly activated platelets. The lipids were prepared as large unilamellar vesicles (200 nm). Increasing concentrations of vesicles were added to FVIIa and FX. Factor X activation was assessed by the cleavage of a synthetic substrate (Pefachrome FXa). Cleavage of the synthetic substrate was converted to FXa concentration by a standard curve.

Results

Concentration: FVIIa 20 nM; FX 500 nM; Lipids 0-1000 µM; Substrate 500 µM.

Figure 12A:
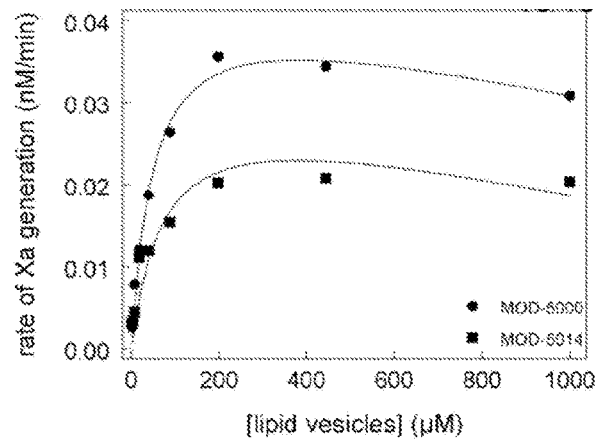
FIGS. 12A and 12B. Shows a comparison of the rate of generation of activated Factor X by FVIIa (NovoSeven) or CTP-modified FVIIa (MOD-5014), in the absence of tissue factor and in view of lipid concentration (FIG. 12A). Show a comparison of the generation of activated Factor X by FVIIa (NovoSeven) or CTP-modified FVIIa (MOD-5014), in the absence of tissue factor and in view of lipid concentration (FIG. 12B).
Figure 12B:
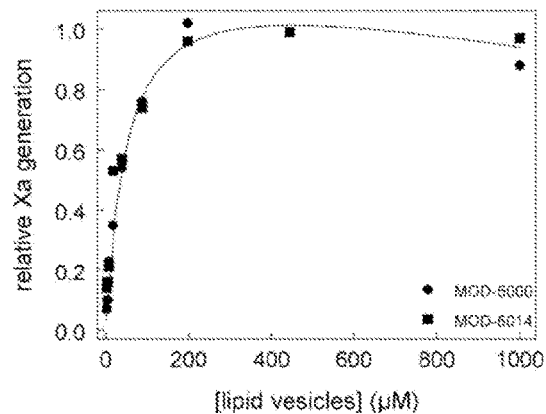

Analysis: The rate of FXa generation was plotted against the concentration of lipid vesicles (FIG. 12A). As expected, FXa generation increased with the increasing concentrations of lipid since more surface area was available for the reaction. At a sufficiently high concentration of lipids, the rate of the reaction decreased as FVIIa and FX were segregated onto different lipid vesicles. This template response is expected for this system. Data was not fitted to an equation and the lines shown are for visual reference only. The difference in the rate of FXa generation between MOD-5000 and MOD-5014 were not due to differences in affinity for the lipids. This is shown in FIG. 12B, where the rate of FXa generation relative to the maximum for each is plotted against lipid concentration.

Conclusion: The rate of FX activation in the absence of TF is lower for MOD-5014 (~60%) relative to MOD-5000. The affinity of MOD-5014 for lipids is the same as for MOD-5000.

Kinetics of FX Activation by Lipid-Bound MOD-5014

Rationale: The reduced rate of FX activation in the absence of TF for MOD-5014 relative to MOD-5000 could be a consequence of reduced affinity for FXa or reduced turnover of FX once it is bound to the enzyme on the lipid surface.

Methods: Varying FX concentrations were incubated with a fixed concentration of FVIIa and lipid vesicles. Factor X activation was assessed by cleavage of a synthetic substrate (Pefachrome FXa). Cleavage of synthetic substrate was converted to FXa concentration by a standard curve.

Results

Concentration: FVIIa 20 nM; FX 0-2500 nM; Lipids 100 μM; Substrate 500 μM.

Figure 13:
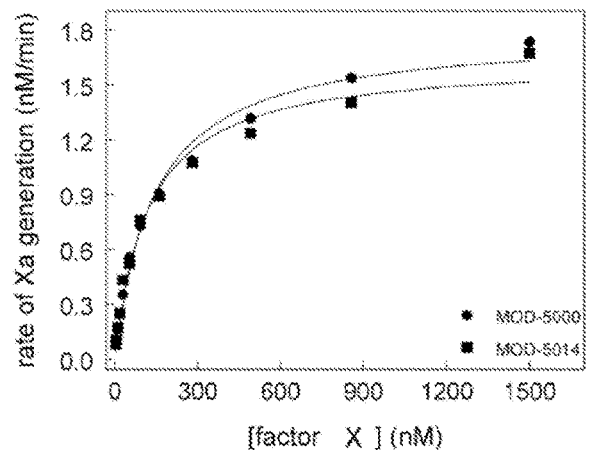
FIG. 13. Show the a comparison of the generation of activated Factor X between FVIIa (NovoSeven) and MOD-5014, in the absence of tissue factor and in view of Factor X concentration.

Analysis: As more FX is added, more of the FVIIa on the lipid surface should have FX bound up to the point where all FVIIa is bound to FX. At that point the reaction is limited by the rate at which FX is activated. Therefore, the rate of FX activation should increase with an increasing concentration of FX, with the shape of the curve asymptotically approaching a maximum rate. As expected, the affinity for FX of FVIIa is reduced (higher Km) in the absence of TF and the rate of FXa generation is reduced in the absence of TF (FIG. 13).

Data was fitted to:

$$v = V_{max}\left(\frac{[S]}{K_m + [S]}\right)$$

|  | MOD-5000 | MOD-5014 |  |
|---|---|---|---|
| $V_{max}$ | 0.253 | 0.115 | nM FXa/min |
| $K_m$ | 878 | 848 | nM FXa/min |

Conclusion: The rate of FX activation on a lipid surface in the absence of TF is lower for MOD-5014 (45%) relative to MOD-5000. The binding of FX to MOD-5014 on the lipid surface was the same as its binding to MOD-5000 (FIG. 13).

Inactivation of MOD-5014 by AT

Rationale: A significant part of FVIIa clearance in vivo is thought to be through formation of a FVIIa complex with AT. The rate of this reaction is measurable in vitro only when FVIIa is bound to TF. To proceed at a measurable rate, the in vitro reaction also requires high concentrations of heparin, which is thought to mimic the effects of a naturally occurring glycosaminoglycan.

Methods: Factor VIIa was incubated with TF to allow formation of the complex. The complex was incubated with AT and heparin. The reaction was stopped at timed intervals by the addition of polybrene (hexadimethrine bromide) to neutralize the heparin. The residual FVIIa/TF activity was measured by the cleavage of a synthetic substrate (Pefachrome FVIIa). At the concentrations used in the assay, polybrene did not alter substrate cleavage.

Results

Concentration: FVIIa 10 nM; TF 11 nM; AT 1 μM; Heparin 5 U/mL; FVIIa/TF 8.2 nM; Polybrene 100 μg/mL; Substrate 500 μM.

Figure 14:
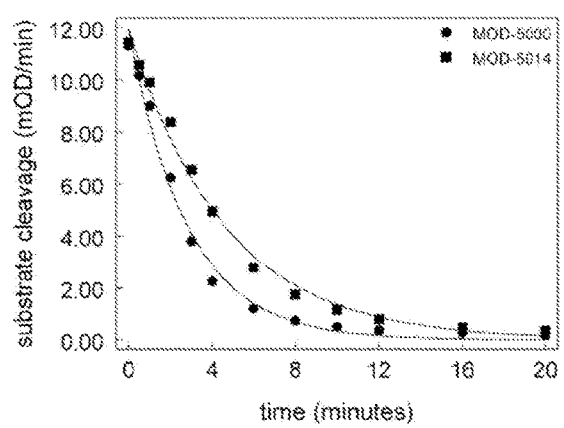
FIG. 14. Show a comparison of the inhibition of substrate (Pefachrome FVIIa) cleavage by FVIIa (NovoSeven) and CTP-modified FVIIa (MOD-5014) in view of polybrene.

Analysis: The concentration of FVIIa/TF, measured as a rate of substrate cleavage, was plotted against the time in minutes (FIG. 14). As expected, AT/heparin inhibited FVIIa, leading to a loss of FVIIa/TF activity.

Data was fitted to:

$$v = V_{t=0} e^{-k*time}$$

|  | MOD-5000 | MOD-5014 |  |
|---|---|---|---|
| $V_0$ | 11.89 | 11.93 |  |
| k | 0.354 | 0.217 | min$^{-1}$ |

Conclusion: Similar values for the activity at T=0 indicate that equal amounts of MOD-5000 and MOD-5014 were present in the reaction. MOD-5014 was inhibited slightly more slowly (62%) than MOD-5000 (FIG. 14). Both reactions proceeded to complete inhibition.

Inactivation of MOD-5014 by TFPI

Rationale: TFPI is the physiologic inhibitor of the FVIIa/TF complex. The K2 domain of TFPI forms an initial complex with FXa. This complex binds FVIIa/TPI, where the K1 domain of TFPI interacts with FVIIa. Therefore, FX activation by FVIIa/TF should lead to inhibited complexes and to shutdown of FVIIa-TFPI.

Methods: Factor VIIa and TF were incubated together to form a complex. The complex was added to TFPI/FX/FXa substrate. Factor X activation was assessed by cleavage of a synthetic substrate (Pefachrome FXa). Cleavage of the synthetic substrate was converted to FXa concentration by a standard curve.

Results

Concentration—inhibition: FVIIa 1 nM; TF 20 pM; FX 135 nM; TFPI 0-5 nM; Substrate 500 μM.

Figure 15B:
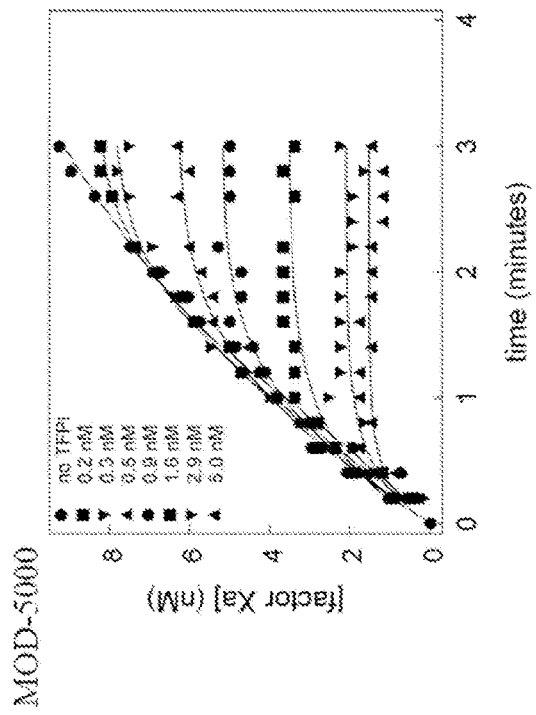
FIGS. 15A-15C. Show a comparison of the inhibition of substrate (Pefachrome FXa) cleavage by FVIIa (Novo-Seven) and CTP-modified FVIIa (MOD-5014) in view of TFPI concentration (FIG. 15A) and duration of TFPI exposure for FVIIa (FIG. 15B) and MOD-5014 (FIG. 15C).
Figure 15C:
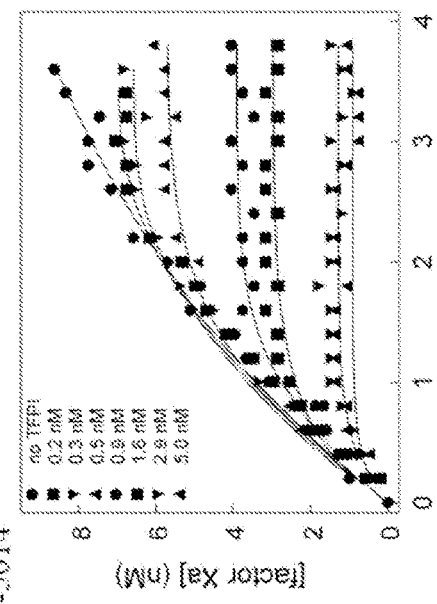
Figure 15A:
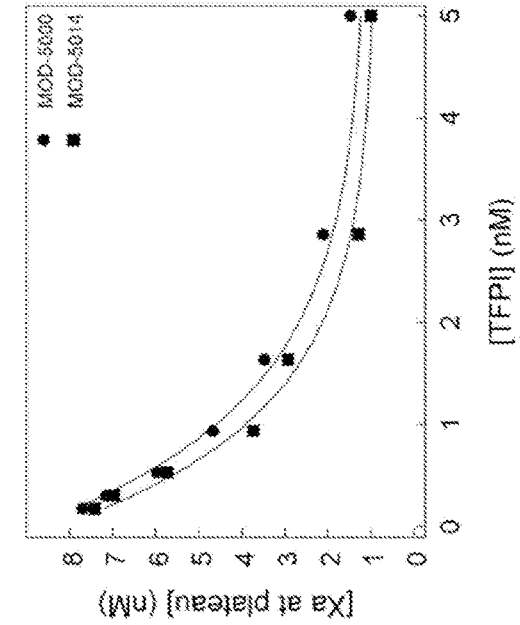

Analysis: As expected, initial FXa generation occurred at the same rate in all reactions (FIG. 15A-C). In the presence of TFPI, the rate of FXa generation slowed as the FVIIa/TFPI complex was inhibited by TFPI/FXa (lower two panels). Shutdown of the TFPI complexes occurred more rapidly at higher concentrations of TFPI (lower two panels). The amount of FXa formed before FVIIa/TFPI was shut down is a measure of TFPI interaction with FVIIa/TF. Since MOD-5014 has a slightly reduced rate of FXa generation which would therefore slow formation of FXa/TFPI complexes, the reaction took longer to reach a plateau with MOD-5014 than with MOD-5000.

Conclusion: As shown in the upper panel, the concentration dependence for TFPI inhibition of MOD-5014/TF generation of FXa is very similar to that of MOD-5000. MOD-5014 might be slightly more sensitive to TFPI inhibition (124%); alternatively, this might be an artifact of the slightly slower rate of FXa generation.

Example 3

Production of CTP-Modified Activated Factor VII

Objective

The objective of the production method was to develop a fed batch upstream process by recombinant DNA technology using CHO cells in a chemically defined medium, followed by a robust and scalable downstream process purifying a highly glycosylated and highly gamma carboxylated MOD-5014. In other words, to produce and purify MOD-5014 with the highest content of gamma carboxylation and effectively remove process and production related impurities. It was important to analyze for O-glycans, N-Glycans, sialic acid percent, oxidative related forms, potency (tested by STA-CLOT analysis), percent of Gla domains (or alternatively the percent of glutamic acid residues not carboxylated, and percent of non-activated FVII.

Production Procedure

Transfection and Stable Clone Selection

The cDNA encoding MOD-5014 was transfected into CHO cells (dhfr-negative CD DG44 cells, which are adapted for growth in protein-free medium and suspension growth) and stable clones were generated by limiting dilution steps. The highest producing clones were amplified and a final clone was selected for further development.

Animal component-free media was used throughout the derivation of the Master and Working Cell Banks (MCB;

WCB). Stable clones were isolated by limiting dilution steps in cell culture. The highest producing clones were amplified with increasing concentrations of the selectable agent. Based on clone population doubling level (PDL), productivity of CTP-modified Factor VII (picogram per cell per day, PCD), and maximum attained cell density in the selected medium, the highest producing clones were isolated and were used to prepare the R&D banks followed by manufacturing of a qualified Master Cell Bank (MCB) and Working Cell Bank (WCB).

Figure 16:
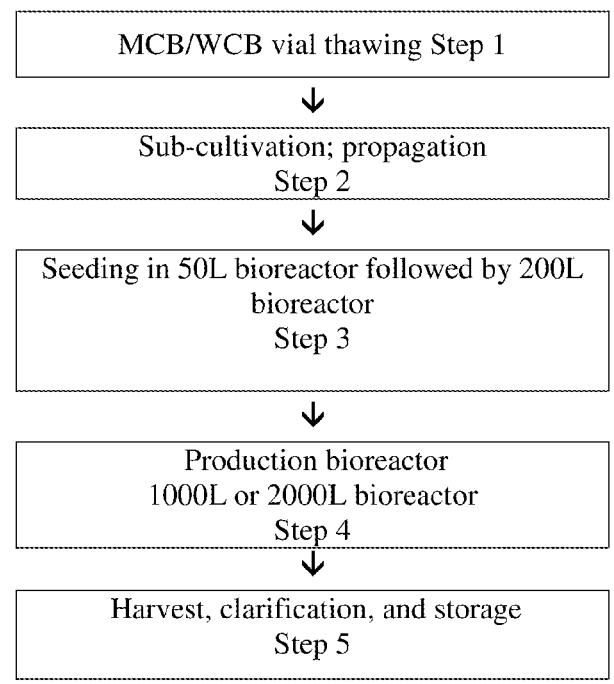
FIG. 16. Shows upstream process flow production chart of CTP-modified FVII-CTP$_3$.

Upstream Process:

A stable clone of CHO cells expressing MOD-5014 was inoculated from a single vial of the master cell Bank (MCB) (Step 1 of FIG. 16 and step-wise expanded to 1000 L or 2000 L bioreactors, in serum free chemically defined media supplemented with vitamin K and using a fed-batch approach (Steps 2-4 of FIG. 16).

The production cell culture supernatant was tested for bioburden, bacterial endotoxin, productivity and adventitious virus. The process was performed using 50 L and 200 L bioreactors for seeding bioreactors (Step 3 of FIG. 16) and a 1000 or 2000 Liter bioreactor for scaling-up (Step 4 of FIG. 16). All product contact surfaces were disposable, while non-disposable product contact equipment were product dedicated. These pieces of equipment were cleaned and sanitized between batches. The culture was expanded to 50 L and 200 L bioreactors prior to inoculation in a 1000 L or 2000 L bioreactor. Final scale-up and fed-batch bioreactor production was performed in disposable bioreactors of 2000 L. Removal of the cells was accomplished using a disposable filter system (Millipore depth filter).

Cell propagation was carried out in a production bioreactor, 1000 or 2000 Liter (Step 4, FIG. 16).

The culture was incubated in the bioreactor for about 11 days (dependent on the viability of the cells) at 37° C., 50% dissolved oxygen (DO) and pH 7.1. During the run, the pH was shifted to 6.9 until the harvest, Feed (Cell Boost 6) was added, and vitamin $K_3$ was added. Further, DMSO was added to the bioreactor. Glucose feed solution was added to the culture in order to maintain a desired concentration and a bolus of 1M of Sodium Bicarbonate was added in order to maintain a desired culture concentration. The harvest was performed using pre-defined criteria. During the first four days, the cell culture was sampled daily for cell count, viability and metabolic analysis. From day 5, the culture was sampled twice-daily for cell count, viability and metabolic analysis and from Day 9 also for specific productivity by Elisa or HPLC Affinity method.

The example presented herein used a fedbatch mode but one skilled in the art could develop a perfusion mode using in general, similar growth and purification schemes. Alternatively, one skilled in the art could develop a perfusion method wherein duration of incubation could be even up to 7-120 days.

Cell Harvest and Storage (Step 5 of FIG. 16)

The harvest was performed using a disposable filtration process train. To clarify the harvest a depth filtration and 0.2 μm filtration was performed. The clarification was followed by a 0.45/0.2 μm filtration. The depth filters were flushed and the residual liquid was blown out of the system with air. Filtration process was run with a pump speed of ≤15 L/min and a maximal defined pressure. Afterwards the filters were washed with Tris-HCl buffer and blown out with pressurized air to increase the product recovery.

The clarified harvest was tested for bioburden, bacterial endotoxin, specific protein content by ELISA or HPLC Affinity Method, SDS-PAGE, Western Blot, HCP ELISA assay, residual DNA, in vitro virus assay, Virus-like particles, S+L- and *Mycoplasma*.

Purification and Activation Process

Purification scheme is described in FIG. 17. The purification process was based on four chromatrographic columns. The protein was purified using affinity chromatography, mixed mode chromatography, hydrophobic interaction Chromatography, and anion-exchange chromatrography. The protein was activated at the step of anion-exchange chromatography. The purification process also included virus-inactivation and nano-filtration steps.

Ultrafiltration and Diafiltration 1—UFDF1 (Step 6)

The Clarified Harvest was concentrated and diafiltered using tangential flow filtration (TFF) based ultrafiltration and diafiltration (UF/DF) steps. The cartridge nominal molecular weight cutoff size was 30 kDa. The concentrated and diafiltered harvest was tested for specific protein content by ELISA, HPLC Affinity methods, and endotoxins and Bioburden were assessed using SDS-PAGE, Western blot, and/or HCP ELISA.

Viral Inactivation by Incubation (Step 7)

The material was filtered through a 0.22 μm filter into a sterile mixing bag. Next, a solution was added to inactivate viral content, for example Tris/10% Triton solution was added to the final filtrate volume bringing the Triton concentration to 1% (w/w). After incubation, before loading on the affinity column, the product solution was again filtered using a 0.2 μm filter unit. The filtrated viral inactivation product was tested for endotoxins and Bioburden using SDS-PAGE and Western blot analysis.

Affinity Chromatography (Step 8)

An affinity column was used for this step. The column was packed to a pre-defined bed height. This step was performed in 2-4 cycles depending on product quantity. The specific protein in the load was determined prior to the addition of Triton due to the interference caused by the Triton in the assay. The affinity column was equilibrated and loaded with the viral inactivated pool and then washed. A second wash was conducted and the material was eluted and then stored at 2-8° C. for processing the next day. All chromatography steps were conducted in down flow mode.

The eluate was tested for specific protein product, endotoxins, residual DNA, sialic acid content, gammacarboylation percent, charged N-glycans, residual leached affinity ligand and bioburden using techniques well known in the art including absorbance at 280 nm, RP-HPLC, AIEX HPLC, SEC-HPLC, HCP ELISA, SDS-PAGE, and Western blot.

Multimodel or Mixed-Mode Chromatography (Step 9)

A column packed with multimodel or mixed-mode chromatography resin was used for this step. The column was packed to a pre-defined bed height. The step was performed in 1-4 cycles depending on product quantity. The column was equilibrated and loaded with the diluted affinity eluate, washed, and the eluate was collected and stored at 2-8° C. until further processing. The eluate was tested for specific protein product, endotoxins, residual DNA, sialic acid content, gammacarboylation percent, charged N-glycans, residual leached affinity ligand and bioburden using techniques that included absorbance at 280 nm, RP-HPLC, AIEX HPLC, SEC-HPLC, HCP ELISA, SDS-PAGE, and Western blot.

Hydrophobic Interaction Chromatography (HIC) (Step 10)

An HIC Resin was used for this step. The column was packed to a pre-defined bed height. The HIC chromatography was performed in 1-4 cycles depending on product quantity. The HIC load was prepared by adjusting the multimodel or mixed mode protein column eluate with Ammonium Sulfate. The column was equilibrated and loaded with the adjusted and 0.2 μm filtered multimodel or mixed mode column eluate, and then washed. The product was eluted, and then stored at 2-8° C. until further processing. The eluate was tested for specific protein concentration by absorption at 280 nm and SEC-HPLC. As well the eluate was tested for endotoxins and bioburden.

Ultrafiltration and Diafiltration of HIC Eluate (Step 11)

The HIC eluate was concentrated and diafiltered to reduce the volume and prepare the material for the Anion Exchange Column Step. Once the pH and conductivity were determined to be in range, the system was drained and filtered into a sterile bag using 0.5/0.2 μm filtration steps. The final volume of concentrated, and the diafiltered HIC eluate was stored at 2-8° C. until further processing. The eluate was tested for specific protein product, endotoxins, residual DNA, sialic acid content, gammacarboylation percent, charged N-glycans, residual leached affinity ligand and bioburden using techniques that included absorbance at 280 nm, RP-HPLC, AIEX HPLC, SEC-HPLC, HCP ELISA, SDS-PAGE, and Western blot.

Anion Exchange Chromatography (Step 12)

A column packed with Anion-Exchange Resin was used for this step. The column was packed to a pre-defined bed height. The load was the concentrated, diafiltered HIC eluate fraction. Activation of FVII to FVIIa occurred on the anion exchange column. Following activation and a wash step, the product was eluated and collected for further processing. The eluate was pH adjusted, if necessary. The eluate was then filtered through a 0.45/0.2 μm filter. The material was stored at 2-8° C. until further processing. All chromatography steps are done in downflow mode. The eluate was tested for specific protein concentration, residual DNA, and bioburden by absorption at 280 nm, RP-HPLC, AIEX HPLC, SEC-HPLC, HCP ELISA, SDS-PAGE, and Western blot.

Viral Removal by Nanofiltration (Step 13)

Viral removal was performed using an Asahi Planova 20N Virus filter. A filter of 0.45/0.2 μm or 0.1 μm membrane was used as prefilter of the nanofilter (Planova 20N filter). The Asashi Planova 20N filter was pre-equilibrated and primed with anion exchange elution buffer or the final formulation made with the formulation buffer. The Anion Exchange eluate was passed through the filter train at a continuous pressure and collected in a sterile bioprocess bag. The filter train (planova filter) was flushed with Anion Exchange elution buffer or formulation buffer to maximize product recovery. The filter was integrity tested pre and post use per the manufacturer's recommended procedures. The Post use test includes a gold-particle test, also per the manufacturer's procedure. The viral filtrate was tested for specific protein by absorbtion at 280 nms, RP-HPLC, AIEX HPLC, SEC-HPLC, SDS-PAGE. As well, the viral filtrate was tested for endotoxins and bioburden.

UFDF-3 and Filtration and Storage of the Drug Substance (DS) (Step 14)

The Viral Filtrate was concentrated to a target DS concentration (which could vary from 2-100 mg/ml) in preparation for the Bulk Filtration and Fill. The last step included filtration through a sterile filtration through a 0.2 μm filter. A single-use or reusable cassette was used for this step with a cut-off of 3-30 KDa. The product was concentrated in a first step to 5-25 mg/ml protein and diafiltrated (DF) in to 20 mM Citrate, 150 mM NaCl, 13.3 mM Glycine, pH 6.4 or 20 mM Citrate, 100 mM Arginine, 2% Trehalose, pH 6.2 (≥7 DF volumes). The UFDF-3 pool was tested for specific protein by absorption at 280 nm. As well, the UFDF-3 pool was tested forendotoxins, and bioburden.

The final product concentration was adjusted and polysorbate-80 (PS-80) was added to a final concentration of 0.04%. Alternatively, no additions were made. The adjusted UFDF-3 product was filtered with a Millipak 100 or Millipak 200 filter. The filtered product solutions were aliquoted and frozen at a temperature of 70±5° C. Formulated pool was tested for product concentration by A280. The formulation buffer was 20 mM Citrate, 100 mM Arginine, 2% Trehelose, 0.04% PS80 at pH 6.2.

Results

The purification process used captured and purified the highly-gamma carboxylated MOD-5014 during the multimodel step (FIG. 21), highly glycosylated MOD-5014 product. Further, the initial percentage of the highly glycosylated MOD-5014 is effected from the upstream cell culture process and remains constant throughout the purification process (FIG. 19). The process showed a high capacity for removal of process related impurities such as oxidized forms and other related forms during multimodel and HIC purification steps (FIG. 20) and resulted in a high quality product.

Figure 18:
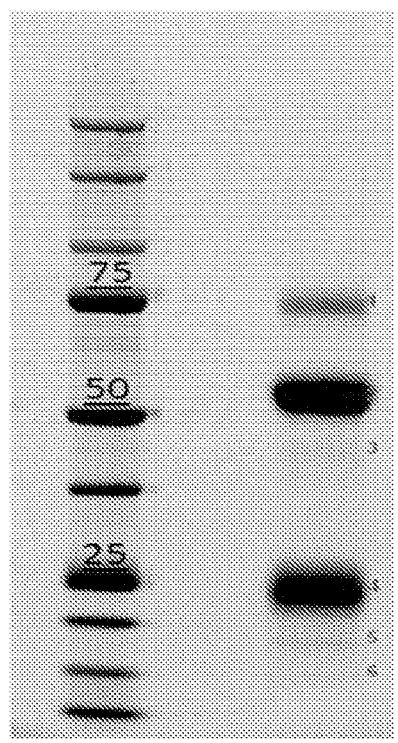
FIG. 18. Presents reduced SDS-PAGE results of purified CTP-modified FVII-CTP$_3$.

Reduced SDS-PAGE analysis of the purified MOD-5014 product is shown in FIG. 18. The following isolated products were identified (see numbering to the right): 75 kDa—non-activated form of MOD-5014 (1); 55 kDa-MOD-5014 heavy chain-CTP-CTP-CTP (2); 25 kDa-MOD-5014 light chain (4); low molecular weight (LMW) forms (3, 5, and 6).

Table 9 shows the results of production processes for an engineering run (ER), and different GMP runs (Good Manufacturing Process) in two different Contract Manufacturing Organizations (CMO). Details include potency, percent (%) non-activated MOD-5014, percent (%) oxidized form; percent (%) of glutamic acid residues that were not carboxylated (Gla domainless), sialic acid content (mol/mol), and O-glycan content (mol/mol).

TABLE 9

Purified MOD-5014 Quality Attributes

| Method | CMO-1 | | CMO-2 | |
| --- | --- | --- | --- | --- |
| | ER | GMP1 | GMP1 | GMP2 |
| Potency (U/mg) | 15,563 | 16,720 | 22,478 | 23,608 |
| Non activated FVII | 2.7 | 2.4 | 2.6 | 3.0 |
| Oxidized forms (%) | 4.0 | 4.9 | 2.9 | 3.9 |
| Gla domainless (%) | 5.4 | 5.5 | 0.6 | 0.6 |
| Sialic acid (mol/mol) | 17.1 | 17.1 | 18.4 | 17.2 |
| O-Glycans (mol/mol) | 12.3 | 13.2 | 13.2 | 12.5 |

In addition, CMO-1 results showed that the percent of charged N-glycans was 85.3 (ER) and 84.2 (GMP1).

Conclusion

In conclusion, the large-scale fed-batch manufacturing process suitable for supporting clinical development and commercial manufacturing of MOD-5014 was developed. The results support this process as a reproducible fed-batch manufacturing process for production of highly glycosylated long acting FVIIa-CTP (MOD-5014). The purified MOD-5014 product had high-content levels of O-glycans and sialic acid. The purified product had minimal levels of non-activated FVII and Gla domainless (Glu residues that were not carboxylated).

Example 4

Drug Product (DP) Manufacturing

The formulation of the drug product (DP) process starts with the thawing of Drug substance (DS). Drug Product is achieved by dilution of the Drug Substance (DS) to the required concentration using the formulation buffer or filling without dilution, aseptic filtration and filling in standard 2R vials or other primary packaging such as cartridges or pre-filled syringes. A skilled artisan would appreciate that the term "drug substance" (DS) may encompass or be equivalent to the active pharmaceutical ingredient (API). In one embodiment, a CTP-modified Factor VII, as set forth herein, is a drug substance (DS) comprising the bulk purified drug. The skilled artisan would also appreciate that the term "drug product" (DP) may encompass the finally formulated drug once dispensed into a final container, for example a vial, under aseptic conditions. In one embodiment, a CTP-modified Factor VII, as set forth herein, is a drug product (DP) comprising the finally formulated CTP-modified Factor VII.

Characterization of CTP-modified Factor VII

CTP-modified polypeptide content in the harvest and the percentage of the high glycosylated forms are determined by a specific RP-HPLC method. Total protein in the harvest is determined by Bradford analysis. The specific protein percentage in the harvest produced by a selected clone is above 70% relative to the total protein in the harvest. In addition, the manufacturing upstream process is developed to enable high percentage of the highly glycosylated CTP-modified protein compared to the low glycosylated form. The highly glycosylated form is the target form, as it results longer extension of the CTP-modified polypeptide half-life.

O-Glycan Content

Glycoprofiling is performed by releasing glycans followed by glycan labeling with 2-aminobenzamide (2AB), cleaned up and analyzed by NP-HPLC. Briefly, an O-glycan content assay is conducted to calculate the number of O-glycans mol per mol of a CTP-modified Factor VII. The terminal galactose units of the O-glycans are enzymatically cleaved from the protein by β-galactosidase. These free galactose units are separated on a CarboPac PA20-column and detected with pulsed amperometry. Galactose (Gal) is quantified using external calibration with a galactose reference standard. The content of galactose can be directly related to the content of O-glycan structure, Gal-GalNAc. Analysis of drug substance and drug product batches demonstrate a robust batch to batch consistency. This unexpected robust glycosylation content is significant, showing that the number of O-glycans per CTP is improved over that known in the art.

Intact Molecular Weight Analysis Samples

Molecular weight analysis of different DS batches is performed with the aim to obtain information on the number of O-linked glycosylation sites. Intact samples as well as de-sialylated samples using Neuramnidase, and de-O-glycosylated samples using O-glycosidase, are analyzed by on-line LC/ES-MS. The result showing a high % of serine occupancy is unexpected in comparison with levels known in the art (only 4 serines glycosylated compared with up to 6 in the CTP-modified Factor VII manufactured herein).

O-Linked Glycosylation Site Occupancy of CTP-Modified Protein Samples

O-glycosylation site occupancy of 4 different DS batches is performed at M-scan with the aim to obtain information on the number of O-linked glycosylation sites per molecule. Samples are de-sialylated using Neuramnidase followed by tryptic digestion of reduced/carboxymethylated samples. Finally an on line LC/ES-MS is carried out for the treated samples and interpretation of the MS data is conducted using a designated software. Evaluation of the data obtained from analysis of the tryptic digest mixtures leads to signals allowing 100% of the protein sequence being mapped. O-glycosylation may take place on both the N-terminal and C-terminal CTP region. Sites of occupancy are identified as serine residues following proline as well as two of the four serines in the regions of serine repeats. A total of up to 18 serine residues may serve as attachment sites for O-glycans. No significant differences between the batches are detected.

Purity

RP-HPLC separates molecules according to their polarity. A mobile phase gradient from a more polar to a less polar solvent is used to elute molecules with a strong polarity earlier than less polar molecules. The related forms are separated from the native protein using UV detection at 220 nm. The relative peak areas (area %) of the related forms and the main peak can be calculated by integrating the corresponding peak areas. The main peak of Drug Substance and Drug Product consists of more than 97% peak area, indicating a highly purified product and an effective purification process.

Size Exclusion HPLC is a chromatographic technique that separates molecules according to size. Within the fractionation range chosen, larger molecules elute earlier than smaller molecules. The separation mechanism is non-adsorptive and molecules are eluted under isocratic conditions. SEC enables monomers to be separated from higher molecular weight forms (such as dimers and polymers) of the target molecule. The SEC method is developed to analyze the content of dimers and polymers in Drug Substance and Drug Product.

RP-HPLC Content Method

This method is being used for the content determination of intermediate samples and the determination of %-unglycosylated CTP-modified polypeptide in intermediate samples by reversed phase chromatography. The reversed phase-HPLC separates molecules due to their polarity. Relatively non-polar molecules ligate to the column material while charged and polar molecules are eluted without accomplishing an interaction with the column.

The ligated molecules are eluted with the aid of a gradient from a polar to a less polar solution. Molecules of the strongest polarity eluted first followed by the less polar molecules. The detection is carried out via absorption at 214 nm.

Viral Clearance

The ability of the manufacturing process to address and mitigate contamination of final drug product with endogenous and adventitious virus has been the subject of a preliminary evaluation. A GLP-compliant study has been conducted according to applicable guidance for investigational products using three model viruses spiked into scaled down segments of the manufacturing process to quantify the ability of these steps to inactivate or clear the spiked virus population. With the amounts of virus expressed as log 10 Adjusted Titre, the log 10 clearance factor is determined simply by subtracting the value for output from the value for input. As log 10 numbers the clearance factors are additive to derive an overall clearance factor for all evaluated steps. A-MuLV is considered to be a model virus representing possible presence of CHO retroviruses, the measures taken to inactivate and remove contaminating A-MuLV virus achieved clearance factor of at least antilog 10, e.g. viral log reduction factor (LRF) of about 22, demonstrating that the overall process has an exceptional capacity for viral removal. For the PPV which is a resistant non-enveloped small virus, robust removal by the nanofiltration step is obtained.

While certain features of the disclosure have been illustrated and described herein, many modifications, substitutions, changes, and equivalents will now occur to those of ordinary skill in the art. It is, therefore, to be understood that the appended claims are intended to cover all such modifications and changes as fall within the true spirit of the disclosure.

What is claimed is:

1. A human chorionic gonadotropin carboxy terminal peptide (CTP)-modified human active Factor VII (FVIIa) polypeptide comprising three CTP molecules attached in tandem to the C-terminal end of FVIIa, wherein said CTP-modified FVIIa polypeptide is in a substantially pure and active form, said CTP-modified FVIIa polypeptide comprising:
   (a) a high sialic acid content of at least 15 mol/mol;
   (b) a high glycosylation form comprising an O-glycan content of at least 10 mol/mol;
   (c) a low oxidized form of said CTP-modified FVIIa consisting of less than 5% oxidized form;
   (d) a high percentage of carboxylated glutamic acid (Gla) residues consisting of at least 90% Gla residues;
   (e) at least 60% charged N-glycans; and
   (f) a potency of at least 10,500 U/mg;
   and, wherein said CTP-modified FVIIa comprises the amino acid sequence set forth in SEQ ID NO: 7, and wherein the purity of said substantially pure and active CTP-modified FVII polypeptide is at least 90%.

2. The CTP-modified FVIIa of claim 1, wherein the amino acid sequence of said CTP-modified FVIIa is structurally present as a disulfide-linked two chain heterodimer comprising a disulfide (S—S) bridge between cysteine residue 135 and cysteine residue 262 of SEQ ID NO: 7, and wherein said two chains comprise a light chain comprising amino acids 1-152 and a heavy chain comprising amino acids 153-490 of SEQ ID NO: 7.

3. The CTP-modified FVIIa of claim 1, wherein said substantially pure and active form comprises at least 60% of a high glycosylation form of said active CTP-modified FVIIa.

4. The CTP-modified FVIIa of claim 1, wherein at least 60% of the substantially pure and CTP-modified FVIIa form comprises a high percentage of carboxylated glutamic acid (Gla) residues.

5. The CTP-modified FVIIa of claim 1, wherein the purity is selected from the group consisting of 97.3%, 97.6%, 97.4% and 97.0% 11.

6. The CTP-modified FVIIa of claim 1, wherein said potency is selected from the group consisting of 15,563 U/mg 16,720 U/mg, 22,478 U/mg and 23,608 U/mg.

7. A human chorionic gonadotropin carboxy terminal peptide (CTP)-modified human active Factor VII (FVIIa) polypeptide according to claim 1, manufactured by a method comprising the steps of:
   stably transfecting a predetermined number of cells with an expression vector comprising a coding portion encoding said CTP-modified FVII,
   wherein said transfected cells express and secrete said CTP-modified FVII;
   obtaining cell clones that overexpress said CTP-modified FVII;
   expanding said clones in solution to a predetermined scale;
   harvesting said solution containing said clones;
   filtering said solution containing said clones to obtain a clarified harvest solution containing said CTP-modified FVII; and,
   purifying and activating CTP-modified FVII from said clarified harvest solution to obtain a purified protein solution having a desired concentration of the CTP-modified FVIIa.

8. The CTP-modified FVIIa of claim 7, wherein said expanding step comprises expanding clones obtained from a working cell bank (WCB) that optimally expresses and secretes said CTP-modified FVII or wherein said expanding step comprises expanding clones obtained from a master cell bank (MCB) that optimally express and secrete said CTP-modified FVII.

9. The CTP-modified FVIIa of claim 7, wherein said method of manufacturing is an animal-free process.

10. The CTP-modified FVIIa of claim 7, wherein said clones express and secrete CTP-modified FVII at a level of at least 40 mg/L.

11. The CTP-modified FVIIa of claim 7, wherein said clones are expanded in solution through a series of sub-cultivating steps up to production bioreactor level.

12. The CTP-modified FVIIa of claim 11, wherein said bioreactor comprises a disposable bioreactor or a stainless steel bioreactor or wherein said bioreactor is run as a fed-batch mode bioreactor.

13. The CTP-modified FVIIa of claim 7, wherein said purification of said clarified harvest comprises performing the following steps comprising:
   sequentially passing said clarified harvest solution through an affinity column, a multimodel or mixed mode column, a hydrophobic interaction column, and an anion exchange column, wherein the anion exchange eluate undergoes an ultrafiltration/diafiltration step;
   inactivating viruses present in the clarified harvest, or in the eluate collected following any of said chromatography columns, or any combination thereof, wherein inactivating viruses comprises incubating in a solution toxic to said viruses or nanofiltration, or any combination thereof;
   thereby arriving at a purified CTP-modified FVII.

14. The CTP-modified FVIIa of claim 13, wherein the purified CTP-modified FVII shows a viral log reduction factor (LRF) of about 22.

15. The CTP-modified FVIIa of claim 7, wherein said manufactured CTP-modified FVIIa is highly glycosylated or wherein said manufactured CTP-modified FVIIa comprises a high O-glycan content.

16. The CTP-modified FVIIa of claim 15, wherein the glycosylation pattern of the manufactured CTP-modified FVIIa comprises glycosylation of at least 4 O-linked glycosylation sites per CTP.

17. The CTP-modified FVIIa of claim 16, wherein the percentage of charged N-glycans out of the total N-Glycans is selected from the group consisting of 85.3% and 84.2%.

18. The CTP-modified FVIIa of claim 7, wherein said manufactured CTP-modified FVIIa is highly sialylated and comprises a content of sialic acid consisting of at least 15 mol/mol.

19. The CTP-modified FVIIa of claim 15, wherein said high O-glycan content comprises an O-glycan content consisting of at least 10 mol/mol.

20. The CTP-modified FVIIa of claim 7, wherein at least 60% of the CTP-modified FVIIa, comprises a high glycosylation form.

21. The CTP-modified FVIIa of claim 7, wherein at least 60% of the CTP-modified FVIIa, comprises a high percentage of carboxylated glutamic acid residues.

22. The CTP-modified FVIIa of claim 21, wherein the high percentage of carboxylated glutamic acid residues (Gla) of said CTP-modified FVIIa consists of at least 90% Gla.

23. The CTP-modified FVIIa of claim 7, wherein said CTP-modified FVIIa polypeptide comprises a low percentage of oxidized form of said CTP-modified FVIIa consisting of less than 5% oxidized form.

24. The CTP-modified FVIIa of claim 7, wherein said method achieves at least a 20% recovery rate of a highly glycosylated CTP-modified FVIIa.

25. The CTP-modified FVIIa of claim 7, wherein said method achieves a recovery rate of said CTP-modified FVIIa polypeptide of at least 90%.

26. The CTP-modified FVIIa of claim 25, wherein the recovery rate of said CTP-modified FVIIa polypeptide is selected from the group consisting of 97.3, 97.6, 97.4 and 97.0%.

27. The CTP-modified FVIIa of claim 26, wherein said CTP-modified FVIIa polypeptide comprises a potency selected from the group consisting of 15,563 U/mg 16,720 U/mg, 22,478 U/mg and 23,608 U/mg.

28. The CTP-modified FVIIa of claim 7, wherein the amino acid sequence of said manufactured CTP-modified FVIIa is structurally present as a disulfide-linked two chain heterodimer comprising a disulfide (S—S) bridge between cysteine residue 135 and cysteine residue 262 of SEQ ID NO: 7, and wherein said two chains comprise a light chain comprising amino acids 1-152 and a heavy chain comprising amino acids 153-490 of SEQ ID NO: 7.

29. A composition comprising the CTP-modified FVIIa of any one of claims 1-2, 3-4, and 5-6, and a pharmaceutically acceptable carrier.

* * * * *

SEQUENCE LISTING

<160> NUMBER OF SEQ ID NOS: 15

<210> SEQ ID NO 1
<211> LENGTH: 1356
<212> TYPE: DNA
<213> ORGANISM: Homo sapiens

<400> SEQUENCE: 1

```
ctcgaggaca tggtctccca ggccctcagg ctcctctgcc ttctgcttgg gcttcagggc      60
tgcctggctg cagtcttcgt aacccaggag gaagcccacg gcgtcctgca ccggcgccgg     120
cgcgccaacg cgttcctgga ggagctgcgg ccgggctccc tggagaggga gtgcaaggag     180
gagcagtgct ccttcgagga ggcccggag atcttcaagg acgcggagag gacgaagctg     240
ttctggattt cttacagtga tggggaccag tgtgcctcaa gtccatgcca gaatggggc      300
tcctgcaagg accagctcca gtcctatatc tgcttctgcc tccctgcctt cgagggccgg     360
aactgtgaga cgcacaagga tgaccagctg atctgtgtga cgagaacgg cggctgtgag      420
cagtactgca gtgaccacac gggcaccaag cgctcctgtc ggtgccacga ggggtactct     480
ctgctggcag acggggtgtc ctgcacaccc acagttgaat atccatgtgg aaaaatacct     540
attctagaaa aagaaatgc cagcaaaccc caaggccgaa ttgtgggggg caaggtgtgc     600
cccaaagggg agtgtccatg gcaggtcctg ttgttggtga atggagctca gttgtgtggg     660
gggaccctga tcaacaccat ctgggtggtc tccgcggccc actgtttcga caaaatcaag     720
aactggagga acctgatcgc ggtgctgggc gagcacgacc tcagcgagca cgacgggat      780
gagcagagcc ggcgggtggc gcaggtcatc atccccagca cgtacgtccc gggcaccacc     840
aaccacgaca tcgcgctgct ccgcctgcac cagcccgtgg tcctcactga ccatgtggtg     900
cccctctgcc tgcccgaacg gacgttctct gagaggacgc tggccttcgt gcgcttctca     960
ttggtcagcg gctggggcca gctgctggac cgtggcgcca cggccctgga gctcatggtc    1020
ctcaacgtgc cccggctgat gacccaggac tgcctgcagc agtcacggaa ggtgggagac    1080
tccccaaata tcacggagta catgttctgt gccggctact cggatggcag caaggactcc    1140
tgcaaggggg acagtggagg cccacatgcc acccactacc ggggcacgtg gtacctgacg    1200
ggcatcgtca gctggggcca gggctgcgca accgtgggcc actttggggt gtacaccagg    1260
gtctcccagt acatcgagtg gctgcaaaag ctcatgcgct cagagccacg cccaggagtc    1320
ctcctgcgag ccccatttcc ctgaggatgc ggccgc                              1356
```

<210> SEQ ID NO 2
<211> LENGTH: 444
<212> TYPE: PRT
<213> ORGANISM: Homo sapiens

<400> SEQUENCE: 2

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80
```

```
Ser Tyr Ser Asp Gly Asp Gln Cys Ala Ser Pro Cys Gln Asn Gly
                85              90              95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro
        435                 440

<210> SEQ ID NO 3
<211> LENGTH: 448
<212> TYPE: PRT
<213> ORGANISM: Homo sapiens

<400> SEQUENCE: 3

Met Val Ser Gln Ala Leu Arg Leu Leu Cys Leu Leu Leu Gly Leu Gln
1               5                   10                  15
```

```
Gly Cys Leu Ala Ala Val Phe Val Thr Gln Glu Ala His Gly Val
             20                  25                  30

Leu His Arg Arg Arg Ala Asn Ala Phe Leu Glu Glu Leu Arg Pro
         35                  40                  45

Gly Ser Leu Glu Arg Glu Cys Lys Glu Gln Cys Ser Phe Glu Glu
     50                  55                  60

Ala Arg Glu Ile Phe Lys Asp Ala Glu Arg Thr Lys Leu Phe Trp Ile
65                   70                  75                  80

Ser Tyr Ser Asp Gly Asp Gln Cys Ala Ser Ser Pro Cys Gln Asn Gly
                 85                  90                  95

Gly Ser Cys Lys Asp Gln Leu Gln Ser Tyr Ile Cys Phe Cys Leu Pro
             100                 105                 110

Ala Phe Glu Gly Arg Asn Cys Glu Thr His Lys Asp Asp Gln Leu Ile
             115                 120                 125

Cys Val Asn Glu Asn Gly Gly Cys Glu Gln Tyr Cys Ser Asp His Thr
130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                 165                 170                 175

Pro Ile Leu Glu Lys Arg Asn Ala Ser Lys Pro Gln Gly Arg Ile Val
             180                 185                 190

Gly Gly Lys Val Cys Pro Lys Gly Glu Cys Pro Trp Gln Val Leu Leu
             195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
             245                 250                 255

Asp Glu Gln Ser Arg Arg Val Ala Gln Val Ile Ile Pro Ser Thr Tyr
             260                 265                 270

Val Pro Gly Thr Thr Asn His Asp Ile Ala Leu Leu Arg Leu His Gln
             275                 280                 285

Pro Val Val Leu Thr Asp His Val Val Pro Leu Cys Leu Pro Glu Arg
             290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
             325                 330                 335

Val Leu Asn Val Pro Arg Leu Met Thr Gln Asp Cys Leu Gln Gln Ser
             340                 345                 350

Arg Lys Val Gly Asp Ser Pro Asn Ile Thr Glu Tyr Met Phe Cys Ala
             355                 360                 365

Gly Tyr Ser Asp Gly Ser Lys Asp Ser Cys Lys Gly Asp Ser Gly Gly
             370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                 405                 410                 415

Arg Val Ser Gln Tyr Ile Glu Trp Leu Gln Lys Leu Met Arg Ser Glu
             420                 425                 430
```

```
Pro Arg Pro Gly Val Leu Leu Arg Ala Pro Phe Pro Gly Cys Gly Arg
        435                 440                 445
```

<210> SEQ ID NO 4
<211> LENGTH: 1621
<212> TYPE: DNA
<213> ORGANISM: Artificial Sequence
<220> FEATURE:
<223> OTHER INFORMATION: CTP-Modified Factor VII

<400> SEQUENCE: 4

```
ctcgaggaca tggtctccca ggccctcagg ctcctctgcc ttctgcttgg gcttcagggc     60
tgcctggctg cagtcttcgt aacccaggag gaagcccacg gcgtcctgca ccggcgccgg    120
cgcgccaacg cgttcctgga ggagctgcgg ccgggctccc tggagaggga gtgcaaggag    180
gagcagtgct ccttcgagga ggcccgggag atcttcaagg acgcggagag gacgaagctg    240
ttctggattt cttacagtga tgggaccag tgtgcctcaa gtccatgcca gaatgggggc    300
tcctgcaagg accagctcca gtcctatatc tgcttctgcc tccctgcctt cgagggccgg    360
aactgtgaga cgcacaagga tgaccagctg atctgtgtga cgagaacgg cggctgtgag     420
cagtactgca gtgaccacac gggcaccaag cgctcctgtc ggtgccacga ggggtactct    480
ctgctggcag acggggtgtc ctgcacaccc acagttgaat atccatgtgg aaaaatacct    540
attctagaaa aagaaatgc cagcaaaccc caaggccgaa ttgtgggggg caaggtgtgc    600
cccaaggggg agtgtccatg caggtcctg ttgttggtga atggagctca gttgtgtggg    660
gggaccctga tcaacaccat ctgggtggtc tccgcggccc actgtttcga caaaatcaag    720
aactggagga acctgatcgc ggtgctgggc gagcacgacc tcagcgagca cgacggggat    780
gagcagagcc ggcgggtggc gcaggtcatc atccccagca cgtacgtccc gggcaccacc    840
aaccacgaca tcgcgctgct ccgcctgcac cagcccgtgg tcctcactga ccatgtggtg    900
cccctctgcc tgcccgaacg gacgttctct gagaggacgc tggccttcgt gcgcttctca    960
ttggtcagcg gctgggcca gctgctggac cgtggcgcca cggccctgga gctcatggtc    1020
ctcaacgtgc cccggctgat gacccaggac tgcctgcagc agtcacggaa ggtgggagac    1080
tccccaaata tcacggagta catgttctgt gccggctact cggatggcag caaggactcc    1140
tgcaaggggg acagtggagg cccacatgcc acccactacc ggggcacgtg gtacctgacc    1200
ggcatcgtga gctggggcca gggctgcgcc accgtgggcc acttcggcgt gtacaccagg    1260
gtgtcccagt acatcgagtg gctgcagaaa ctgatgagaa gcgagcccag accggcgtg    1320
ctgctgagag cccccttccc cagcagcagc tccaaggccc ctccccctag cctgcccagc    1380
cctagcagac tgcctgggcc cagtgacacc ctatcctgc ctcagtccag ctccagcaag    1440
gccccacccc ctagcctgcc ttctccttct cggctgcctg gccccagcga tactccaatt    1500
ctgccccagt cctccagcag taaggctccc cctccatctc tgccatcccc cagcagactg    1560
ccaggccctt ctgatacacc catcctccca cagtgatgag gatccgcggc cgcttaatta    1620
a                                                                   1621
```

<210> SEQ ID NO 5
<211> LENGTH: 528
<212> TYPE: PRT
<213> ORGANISM: Artificial Sequence
<220> FEATURE:
<223> OTHER INFORMATION: CTP-Modified Factor VII

<400> SEQUENCE: 5

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50              55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
            115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
            195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
            245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
            275                 280                 285

Pro Val Val Leu Thr Asp His Val Val Pro Leu Cys Leu Pro Glu Arg
            290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
            325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
            355                 360                 365

Gly Tyr Ser Asp Gly Ser Lys Asp Ser Cys Lys Gly Asp Ser Gly Gly
            370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
            405                 410                 415

Arg Val Ser Gln Tyr Ile Glu Trp Leu Gln Lys Leu Met Arg Ser Glu
```

```
                420                 425                 430
Pro Arg Pro Gly Val Leu Leu Arg Ala Pro Phe Pro Ser Ser Ser Ser
                435                 440                 445

Lys Ala Pro Pro Ser Leu Pro Ser Pro Ser Arg Leu Pro Gly Pro
        450                 455                 460

Ser Asp Thr Pro Ile Leu Pro Gln Ser Ser Ser Ser Lys Ala Pro Pro
465                 470                 475                 480

Pro Ser Leu Pro Ser Pro Ser Arg Leu Pro Gly Pro Ser Asp Thr Pro
                485                 490                 495

Ile Leu Pro Gln Ser Ser Ser Ser Lys Ala Pro Pro Ser Leu Pro
        500                 505                 510

Ser Pro Ser Arg Leu Pro Gly Pro Ser Asp Thr Pro Ile Leu Pro Gln
        515                 520                 525

<210> SEQ ID NO 6
<211> LENGTH: 38
<212> TYPE: PRT
<213> ORGANISM: Artificial Sequence
<220> FEATURE:
<223> OTHER INFORMATION: Signal Sequence

<400> SEQUENCE: 6

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
                20                  25                  30

Leu His Arg Arg Arg Arg
        35

<210> SEQ ID NO 7
<211> LENGTH: 490
<212> TYPE: PRT
<213> ORGANISM: Artificial Sequence
<220> FEATURE:
<223> OTHER INFORMATION: CTP- Modified Factor VII

<400> SEQUENCE: 7

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
                20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Gly Lys Val Cys Pro
145                 150                 155                 160
```

```
Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro Ser Ser Ser Lys Ala Pro Pro Pro Ser
                405                 410                 415

Leu Pro Ser Pro Ser Arg Leu Pro Gly Pro Ser Asp Thr Pro Ile Leu
            420                 425                 430

Pro Gln Ser Ser Ser Ser Lys Ala Pro Pro Pro Ser Leu Pro Ser Pro
        435                 440                 445

Ser Arg Leu Pro Gly Pro Ser Asp Thr Pro Ile Leu Pro Gln Ser Ser
    450                 455                 460

Ser Ser Lys Ala Pro Pro Pro Ser Leu Pro Ser Pro Ser Arg Leu Pro
465                 470                 475                 480

Gly Pro Ser Asp Thr Pro Ile Leu Pro Gln
                485                 490

<210> SEQ ID NO 8
<211> LENGTH: 152
<212> TYPE: PRT
<213> ORGANISM: Artificial Sequence
<220> FEATURE:
<223> OTHER INFORMATION: CTP-Modified Factor VII - Light Chain

<400> SEQUENCE: 8

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
                20                  25                  30
```

```
Asp Ala Glu Arg Thr Lys Leu Phe Trp Ile Ser Tyr Ser Asp Gly Asp
             35                  40                  45

Gln Cys Ala Ser Ser Pro Cys Gln Asn Gly Gly Ser Cys Lys Asp Gln
 50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                 85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
            115                 120                 125

Pro Thr Val Glu Tyr Pro Cys Gly Lys Ile Pro Ile Leu Glu Lys Arg
130                 135                 140

Asn Ala Ser Lys Pro Gln Gly Arg
145                 150

<210> SEQ ID NO 9
<211> LENGTH: 338
<212> TYPE: PRT
<213> ORGANISM: Artificial Sequence
<220> FEATURE:
<223> OTHER INFORMATION: CTP-Modified Factor VII - Heavy Chain

<400> SEQUENCE: 9

Ile Val Gly Gly Lys Val Cys Pro Lys Gly Glu Cys Pro Trp Gln Val
1               5                   10                  15

Leu Leu Leu Val Asn Gly Ala Gln Leu Cys Gly Gly Thr Leu Ile Asn
                 20                  25                  30

Thr Ile Trp Val Val Ser Ala Ala His Cys Phe Asp Lys Ile Lys Asn
             35                  40                  45

Trp Arg Asn Leu Ile Ala Val Leu Gly Glu His Asp Leu Ser Glu His
 50                  55                  60

Asp Gly Asp Glu Gln Ser Arg Arg Val Ala Gln Val Ile Ile Pro Ser
65                  70                  75                  80

Thr Tyr Val Pro Gly Thr Thr Asn His Asp Ile Ala Leu Leu Arg Leu
                 85                  90                  95

His Gln Pro Val Val Leu Thr Asp His Val Pro Leu Cys Leu Pro
            100                 105                 110

Glu Arg Thr Phe Ser Glu Arg Thr Leu Ala Phe Val Arg Phe Ser Leu
            115                 120                 125

Val Ser Gly Trp Gly Gln Leu Leu Asp Arg Gly Ala Thr Ala Leu Glu
130                 135                 140

Leu Met Val Leu Asn Val Pro Arg Leu Met Thr Gln Asp Cys Leu Gln
145                 150                 155                 160

Gln Ser Arg Lys Val Gly Asp Ser Pro Asn Ile Thr Glu Tyr Met Phe
                165                 170                 175

Cys Ala Gly Tyr Ser Asp Gly Ser Lys Asp Ser Cys Lys Gly Asp Ser
            180                 185                 190

Gly Gly Pro His Ala Thr His Tyr Arg Gly Thr Trp Tyr Leu Thr Gly
            195                 200                 205

Ile Val Ser Trp Gly Gln Gly Cys Ala Thr Val Gly His Phe Gly Val
210                 215                 220

Tyr Thr Arg Val Ser Gln Tyr Ile Glu Trp Leu Gln Lys Leu Met Arg
225                 230                 235                 240
```

```
Ser Glu Pro Arg Pro Gly Val Leu Leu Arg Ala Pro Phe Pro Ser Ser
            245                 250                 255

Ser Ser Lys Ala Pro Pro Pro Ser Leu Pro Ser Pro Ser Arg Leu Pro
        260                 265                 270

Gly Pro Ser Asp Thr Pro Ile Leu Pro Gln Ser Ser Ser Ser Lys Ala
            275                 280                 285

Pro Pro Pro Ser Leu Pro Ser Pro Ser Arg Leu Pro Gly Pro Ser Asp
        290                 295                 300

Thr Pro Ile Leu Pro Gln Ser Ser Ser Ser Lys Ala Pro Pro Pro Ser
305                 310                 315                 320

Leu Pro Ser Pro Ser Arg Leu Pro Gly Pro Ser Asp Thr Pro Ile Leu
                325                 330                 335

Pro Gln

<210> SEQ ID NO 10
<211> LENGTH: 2413
<212> TYPE: DNA
<213> ORGANISM: Homo sapiens

<400> SEQUENCE: 10
tctagagtcg accccgccat ggagctgagg ccctggttgc tatgggtggt agcagcaaca       60
ggaaccttgg tcctgctagc agctgatgct cagggccaga aggtcttcac caacacgtgg      120
gctgtgcgca tccctggagg cccagcggtg gccaacagtg tggcacggaa gcatgggttc      180
ctcaacctgg gccagatctt cggggactat taccacttct ggcatcgagg agtgacgaag      240
cggtccctgt cgcctcaccg cccgcggcac agccggctgc agaggagcc tcaagtacag       300 tggctggaac agcaggtggc aaagcgacgg actaaacggg acgtgtacca ggagcccaca      360
gaccccaagt tcctcagca gtggtacctg tctggtgtca ctcagcggga cctgaatgtg       420
aaggcggcct gggcgcaggg ctacacaggg cacggcattg tggtctccat tctggacgat      480
ggcatcgaga gaaccaccc ggacttggca ggcaattatg atcctgggc cagttttgat        540 gtcaatgacc aggaccctga ccccagcct cggtacacac agatgaatga caacaggcac       600
ggcacacggt gtgcggggga gtggctgcg gtggccaaca cggtgtctg tggtgtaggt        660 gtggcctaca cgcccgcat ggaggggtg cgcatgctgg atggcgaggt gacagatgca        720
gtggaggcac gctcgctggg cctgaacccc aaccacatcc acatctacag tgccagctgg      780
ggccccgagg atgacggcaa gacagtggat gggccagccc gcctcgccga ggaggccttc      840
ttccgtgggg ttagccaggg ccgaggggg ctgggctcca tctttgtctg ggcctcgggg       900 aacggggcc gggaacatga cagctgcaac tgcgacggct acaccaacag tatctacacg       960
ctgtccatca gcagcgccac gcagtttggc aacgtgccgt ggtacagcga ggcctgctcg     1020
tccacactgg ccacgaccta cagcagtggc aaccagaatg agaagcagat cgtgacgact     1080
gacttgcggc agaagtgcac ggagtctcac acgggcacct cagcctctgc ccccttagca     1140
gccggcatca ttgctctcac cctggaggcc aataagaacc tcacatggcg ggacatgcaa     1200
cacctggtgg tacagaccatc gaagccagcc cacctcaatg ccaacgactg gccaccaat     1260 ggtgtgggcc ggaaagtgag ccactcatat ggctacgggc ttttggacgc aggcgccatg     1320
gtggccctgg cccagaattg accacagtg gccccagc ggaagtgcat catcgacatc        1380
ctcaccgagc caaagacat cgggaaacgg ctcgaggtgc ggaagaccgt gaccgcgtgc     1440
ctgggcgagc caaccacat cactcggctg gagcacgctc aggcgcggct caccctgtcc     1500
tataatcgcc gtggcgacct ggccatccac ctggtcagcc ccatgggcac ccgctccacc     1560
```

```
ctgctggcag ccaggccaca tgactactcc gcagatgggt ttaatgactg ggccttcatg    1620
acaactcatt cctgggatga ggatccctct ggcgagtggg tcctagagat tgaaaacacc    1680
agcgaagcca acaactatgg gacgctgacc aagttcaccc tcgtactcta tggcaccgcc    1740
cctgaggggc tgcccgtacc tccagaaagc agtggctgca agaccctcac gtccagtcag    1800
gcctgtgtgg tgtgcgagga aggcttctcc ctgcaccaga gagctgtgt ccagcactgc     1860 cctccaggct tcgcccccca gtcctcgat acgcactata gcaccgagaa tgacgtggag     1920
accatccggg ccagcgtctg cgcccctgc cacgcctcat gtgccacatg ccaggggccg    1980
gccctgacag actgcctcag ctgccccagc cacgcctcct tggaccctgt ggagcagact    2040
tgctcccggc aaagccagag cagccgagag tccccgccac agcagcagcc acctcggctg    2100
cccccggagg tggaggcggg gcaacggctg cgggcagggc tgctgccctc acacctgcct    2160
gaggtggtgg ccggcctcag ctgcgccttc atcgtgctgg tcttcgtcac tgtcttcctg    2220
gtcctgcagc tgcgctctgg ctttagtttt cggggggtga aggtgtacac catggaccgt    2280
ggcctcatct cctacaaggg gctgccccct gaagcctggc aggaggagtg cccgtctgac    2340
tcagaagagg acgagggccg gggcgagagg accgccttta tcaaagacca gagcgccctc    2400
tgaacgcggc cgc                                                        2413
```

<210> SEQ ID NO 11
<211> LENGTH: 793
<212> TYPE: PRT
<213> ORGANISM: Homo sapiens

<400> SEQUENCE: 11

Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
            20                  25                  30

Thr Trp Ala Val Arg Ile Pro Gly Gly Pro Ala Val Ala Asn Ser Val
        35                  40                  45

Ala Arg Lys His Gly Phe Leu Asn Leu Gly Gln Ile Phe Gly Asp Tyr
    50                  55                  60

Tyr His Phe Trp His Arg Gly Val Thr Lys Arg Ser Leu Ser Pro His
65                  70                  75                  80

Arg Pro Arg His Ser Arg Leu Gln Arg Glu Pro Gln Val Gln Trp Leu
                85                  90                  95

Glu Gln Gln Val Ala Lys Arg Arg Thr Lys Arg Asp Val Tyr Gln Glu
            100                 105                 110

Pro Thr Asp Pro Lys Phe Pro Gln Gln Trp Tyr Leu Ser Gly Val Thr
        115                 120                 125

Gln Arg Asp Leu Asn Val Lys Ala Ala Trp Ala Gln Gly Tyr Thr Gly
    130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
            180                 185                 190

Arg His Gly Thr Arg Cys Ala Gly Glu Val Ala Ala Val Ala Asn Asn
        195                 200                 205

Gly Val Cys Gly Val Gly Val Ala Tyr Asn Ala Arg Ile Gly Gly Val

```
              210                 215                 220
Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
                245                 250                 255

Glu Asp Asp Gly Lys Thr Val Asp Gly Pro Ala Arg Leu Ala Glu Glu
                260                 265                 270

Ala Phe Phe Arg Gly Val Ser Gln Gly Arg Gly Gly Leu Gly Ser Ile
            275                 280                 285

Phe Val Trp Ala Ser Gly Asn Gly Gly Arg Glu His Asp Ser Cys Asn
290                 295                 300

Cys Asp Gly Tyr Thr Asn Ser Ile Tyr Thr Leu Ser Ile Ser Ser Ala
305                 310                 315                 320

Thr Gln Phe Gly Asn Val Pro Trp Tyr Ser Glu Ala Cys Ser Ser Thr
                325                 330                 335

Leu Ala Thr Thr Tyr Ser Ser Gly Asn Gln Asn Glu Lys Gln Ile Val
                340                 345                 350

Thr Thr Asp Leu Arg Gln Lys Cys Thr Glu Ser His Thr Gly Thr Ser
                355                 360                 365

Ala Ser Ala Pro Leu Ala Ala Gly Ile Ile Ala Leu Thr Leu Glu Ala
            370                 375                 380

Asn Lys Asn Leu Thr Trp Arg Asp Met Gln His Leu Val Val Gln Thr
385                 390                 395                 400

Ser Lys Pro Ala His Leu Asn Ala Asn Asp Trp Ala Thr Asn Gly Val
                405                 410                 415

Gly Arg Lys Val Ser His Ser Tyr Gly Tyr Gly Leu Leu Asp Ala Gly
                420                 425                 430

Ala Met Val Ala Leu Ala Gln Asn Trp Thr Thr Val Ala Pro Gln Arg
            435                 440                 445

Lys Cys Ile Ile Asp Ile Leu Thr Glu Pro Lys Asp Ile Gly Lys Arg
            450                 455                 460

Leu Glu Val Arg Lys Thr Val Thr Ala Cys Leu Gly Glu Pro Asn His
465                 470                 475                 480

Ile Thr Arg Leu Glu His Ala Gln Ala Arg Leu Thr Leu Ser Tyr Asn
                485                 490                 495

Arg Arg Gly Asp Leu Ala Ile His Leu Val Ser Pro Met Gly Thr Arg
                500                 505                 510

Ser Thr Leu Leu Ala Ala Arg Pro His Asp Tyr Ser Ala Asp Gly Phe
            515                 520                 525

Asn Asp Trp Ala Phe Met Thr Thr His Ser Trp Asp Glu Asp Pro Ser
530                 535                 540

Gly Glu Trp Val Leu Glu Ile Glu Asn Thr Ser Glu Ala Asn Asn Tyr
545                 550                 555                 560

Gly Thr Leu Thr Lys Phe Thr Leu Val Leu Tyr Gly Thr Ala Pro Glu
                565                 570                 575

Gly Leu Pro Val Pro Pro Glu Ser Ser Gly Cys Lys Thr Leu Thr Ser
                580                 585                 590

Ser Gln Ala Cys Val Val Cys Glu Glu Gly Phe Ser Leu His Gln Lys
            595                 600                 605

Ser Cys Val Gln His Cys Pro Pro Gly Phe Ala Pro Gln Val Leu Asp
            610                 615                 620

Thr His Tyr Ser Thr Glu Asn Asp Val Glu Thr Ile Arg Ala Ser Val
625                 630                 635                 640
```

```
Cys Ala Pro Cys His Ala Ser Cys Ala Thr Cys Gln Gly Pro Ala Leu
                645                 650                 655

Thr Asp Cys Leu Ser Cys Pro Ser His Ala Ser Leu Asp Pro Val Glu
            660                 665                 670

Gln Thr Cys Ser Arg Gln Ser Ser Arg Glu Ser Pro Pro Gln
        675                 680                 685

Gln Gln Pro Pro Arg Leu Pro Pro Glu Val Glu Ala Gly Gln Arg Leu
    690                 695                 700

Arg Ala Gly Leu Leu Pro Ser His Leu Pro Glu Val Val Ala Gly Leu
705                 710                 715                 720

Ser Cys Ala Phe Ile Val Leu Val Phe Val Thr Val Phe Leu Val Leu
                725                 730                 735

Gln Leu Arg Ser Gly Phe Ser Phe Arg Gly Val Lys Val Tyr Thr Met
                740                 745                 750

Asp Arg Gly Leu Ile Ser Tyr Lys Gly Leu Pro Pro Glu Ala Trp Gln
            755                 760                 765

Glu Glu Cys Pro Ser Asp Ser Glu Asp Gly Arg Gly Glu Arg
    770                 775                 780

Thr Ala Phe Ile Lys Asp Gln Ser Ala
785                 790

<210> SEQ ID NO 12
<211> LENGTH: 32
<212> TYPE: PRT
<213> ORGANISM: Homo sapiens

<400> SEQUENCE: 12

Asp Pro Arg Phe Gln Asp Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30

<210> SEQ ID NO 13
<211> LENGTH: 28
<212> TYPE: PRT
<213> ORGANISM: Homo sapiens

<400> SEQUENCE: 13

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 14
<211> LENGTH: 12
<212> TYPE: PRT
<213> ORGANISM: Homo sapiens

<400> SEQUENCE: 14

Ser Ser Ser Ser Lys Ala Pro Pro Pro Ser Leu Pro
1               5                   10
```

```
<210> SEQ ID NO 15
<211> LENGTH: 10
<212> TYPE: PRT
<213> ORGANISM: Homo sapiens

<400> SEQUENCE: 15

Ser Ser Ser Ser Lys Ala Pro Pro Pro Ser
1               5                   10
```